US010500047B2

(12) United States Patent
Olson et al.

(10) Patent No.: US 10,500,047 B2
(45) Date of Patent: Dec. 10, 2019

(54) METHODS FOR DELIVERING PROSTHETIC VALVES TO NATIVE HEART VALVES

(71) Applicant: Edwards Lifesciences Corporation, Irvine, CA (US)

(72) Inventors: Christopher J. Olson, Aliso Viejo, CA (US); Glen Thomas Rabito, Lake Forest, CA (US); Dustin P. Armer, Costa Mesa, CA (US); Minh T. Ma, Santa Ana, CA (US); Devin H. Marr, Newport Beach, CA (US); Cheng-Tung Huang, Laguna Niguel, CA (US); Hiroshi Okabe, Irvine, CA (US); Kevin M. Stewart, Newport Beach, CA (US); Alison S. Curtis, Irvine, CA (US); Philip P. Corso, Jr., Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/130,402

(22) Filed: Apr. 15, 2016

(65) Prior Publication Data
US 2016/0228240 A1 Aug. 11, 2016

Related U.S. Application Data

(63) Continuation of application No. 13/188,988, filed on Jul. 22, 2011, now Pat. No. 9,326,853.
(Continued)

(51) Int. Cl.
*A61F 2/24* (2006.01)

(52) U.S. Cl.
CPC ............ *A61F 2/2439* (2013.01); *A61F 2/243* (2013.01); *A61F 2/2418* (2013.01);
(Continued)

(58) Field of Classification Search
CPC ...... A61F 2002/9505; A61F 2002/9511; A61F 2/2427; A61F 2/2439; A61F 2/95; A61F 2/962; A61F 2/2436
See application file for complete search history.

(56) References Cited

U.S. PATENT DOCUMENTS

| 3,755,823 A | 9/1973 | Hancock |
| 4,035,849 A | 7/1977 | Angell et al. |

(Continued)

FOREIGN PATENT DOCUMENTS

| DE | 19532846 A1 | 3/1997 |
| DE | 19546692 A1 | 6/1997 |

(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3, pp. 305-311, 1989.
(Continued)

*Primary Examiner* — Christopher L Templeton
(74) *Attorney, Agent, or Firm* — Thomas C. Richardson; Brandon J. Johnson; Hans P. Smith

(57) ABSTRACT

Representative embodiments of methods, apparatus, and systems used to deliver a prosthetic heart valve to a deficient valve are disclosed. In one embodiment, for instance, a support structure and an expandable prosthetic valve are delivered to a position on or adjacent to the surface of the outflow side of the aortic valve (the support structure defining a support-structure interior) via a delivery system. The expandable prosthetic valve is delivered into the aortic valve and into the support-structure interior. The expandable, prosthetic heart valve is expanded while the expandable prosthetic heart valve is in the support-structure interior and while the support structure is at the position on or
(Continued)

adjacent to the surface of the outflow side of the aortic valve, thereby causing one or more native leaflets of the aortic valve to be frictionally secured between the support structure and the expanded prosthetic heart valve.

20 Claims, 82 Drawing Sheets

Related U.S. Application Data

(60) Provisional application No. 61/426,407, filed on Dec. 22, 2010, provisional application No. 61/367,293, filed on Jul. 23, 2010.

(52) U.S. Cl.
CPC .......... *A61F 2/2433* (2013.01); *A61F 2/2436* (2013.01); *A61F 2/2427* (2013.01); *A61F 2220/005* (2013.01); *A61F 2220/0016* (2013.01); *A61F 2220/0075* (2013.01); *A61F 2230/0054* (2013.01); *A61F 2230/0076* (2013.01); *A61F 2250/006* (2013.01)

(56) References Cited

U.S. PATENT DOCUMENTS

| | | |
|---|---|---|
| 4,777,951 A | 10/1988 | Cribier et al. |
| 4,787,899 A | 11/1988 | Lazarus |
| 4,790,843 A | 12/1988 | Carpentier et al. |
| 4,796,629 A | 1/1989 | Grayzel |
| 4,856,516 A | 8/1989 | Hillstead |
| 4,878,495 A | 11/1989 | Grayzel |
| 4,966,604 A | 10/1990 | Reiss |
| 4,994,077 A | 2/1991 | Dobben |
| 5,059,177 A | 10/1991 | Towne et al. |
| 5,192,297 A | 3/1993 | Hull |
| 5,282,847 A | 2/1994 | Trescony et al. |
| 5,370,685 A | 12/1994 | Stevens |
| 5,411,552 A | 5/1995 | Andersen et al. |
| 5,545,214 A | 8/1996 | Stevens |
| 5,554,185 A | 9/1996 | Block et al. |
| 5,558,644 A | 9/1996 | Boyd et al. |
| 5,584,803 A | 12/1996 | Stevens et al. |
| 5,591,195 A | 1/1997 | Taheri et al. |
| 5,607,464 A | 3/1997 | Trescony et al. |
| 5,665,115 A | 9/1997 | Cragg |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,925,063 A | 7/1999 | Khosravi |
| 6,027,525 A | 2/2000 | Suh et al. |
| 6,168,614 B1 | 1/2001 | Andersen et al. |
| 6,221,091 B1 | 4/2001 | Khosravi |
| 6,245,102 B1 | 6/2001 | Jayaraman |
| 6,302,906 B1 | 10/2001 | Goicoechea et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,454,799 B1 | 9/2002 | Schreck |
| 6,458,153 B1 | 10/2002 | Bailey et al. |
| 6,461,382 B1 | 10/2002 | Cao |
| 6,482,228 B1 | 11/2002 | Norred |
| 6,527,979 B2 | 3/2003 | Constantz et al. |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,767,362 B2 | 7/2004 | Schreck |
| 6,797,002 B2 | 9/2004 | Spence et al. |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,445,632 B2 | 11/2008 | McGuckin, Jr. et al. |
| 7,462,191 B2 | 12/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 7,637,946 B2 | 12/2009 | Solem et al. |
| 7,655,034 B2 | 2/2010 | Mitchell et al. |
| 7,708,775 B2 | 5/2010 | Rowe et al. |
| 7,737,060 B2 | 6/2010 | Strickler et al. |
| 7,785,366 B2 | 8/2010 | Maurer et al. |
| 7,951,195 B2 | 5/2011 | Antonsson et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,142,492 B2 | 3/2012 | Forster et al. |
| 8,167,932 B2 | 5/2012 | Bourang et al. |
| 8,236,049 B2 | 8/2012 | Rowe et al. |
| 8,323,335 B2 | 12/2012 | Rowe et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,685,086 B2 | 4/2014 | Navia et al. |
| 8,734,507 B2 | 5/2014 | Keranen |
| 8,801,776 B2 | 8/2014 | House et al. |
| 9,078,747 B2 | 7/2015 | Conklin |
| 9,095,434 B2 | 8/2015 | Rowe |
| 9,119,718 B2 | 9/2015 | Keranen |
| 9,192,471 B2 | 11/2015 | Bolling |
| 9,237,886 B2 | 1/2016 | Seguin et al. |
| 9,314,335 B2 | 4/2016 | Konno |
| 9,364,326 B2 | 6/2016 | Yaron |
| 9,463,268 B2 | 10/2016 | Spence |
| 9,474,599 B2 | 10/2016 | Keranen |
| 9,597,205 B2 | 3/2017 | Tuval |
| 9,622,863 B2 | 4/2017 | Karapetian et al. |
| 2002/0026094 A1 | 2/2002 | Roth |
| 2002/0032481 A1 | 3/2002 | Gabbay |
| 2002/0107535 A1 | 8/2002 | Wei et al. |
| 2002/0138135 A1 | 9/2002 | Duerig et al. |
| 2002/0151970 A1 | 10/2002 | Garrison et al. |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2003/0225420 A1 | 12/2003 | Wardle |
| 2004/0111006 A1 | 6/2004 | Alferness et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0096736 A1 | 5/2005 | Osse et al. |
| 2005/0119682 A1 | 6/2005 | Nguyen et al. |
| 2005/0119735 A1 | 6/2005 | Spence et al. |
| 2005/0137691 A1* | 6/2005 | Salahieh ............... A61F 2/2418 623/2.11 |
| 2005/0137699 A1 | 6/2005 | Saiahieh et al. |
| 2005/0182486 A1 | 8/2005 | Gabbay |
| 2005/0203617 A1 | 9/2005 | Forster et al. |
| 2005/0234546 A1 | 10/2005 | Nugent et al. |
| 2005/0251251 A1* | 11/2005 | Cribier ................. A61F 2/2412 623/2.11 |
| 2006/0025857 A1 | 2/2006 | Bergheim et al. |
| 2006/0058872 A1 | 3/2006 | Salahieh et al. |
| 2006/0149350 A1 | 7/2006 | Patel et al. |

(56) References Cited

U.S. PATENT DOCUMENTS

| | | |
|---|---|---|
| 2006/0195134 A1 | 8/2006 | Crittenden |
| 2007/0005131 A1 | 1/2007 | Taylor |
| 2007/0010877 A1 | 1/2007 | Salahieh et al. |
| 2007/0112422 A1 | 5/2007 | Dehdashtian |
| 2007/0203575 A1 | 8/2007 | Forster et al. |
| 2007/0265700 A1 | 11/2007 | Eliasen et al. |
| 2007/0293808 A1 | 12/2007 | Williams et al. |
| 2008/0033542 A1 | 2/2008 | Antonsson et al. |
| 2008/0114442 A1 | 5/2008 | Mitchell et al. |
| 2008/0125853 A1 | 5/2008 | Bailey et al. |
| 2008/0208330 A1 | 8/2008 | Keranen |
| 2009/0157175 A1 | 6/2009 | Benichou |
| 2009/0171456 A1 | 7/2009 | Kveen et al. |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2010/0049313 A1 | 2/2010 | Alon et al. |
| 2010/0145440 A1 | 6/2010 | Keranen |
| 2010/0198347 A1 | 8/2010 | Zakay et al. |
| 2010/0312333 A1 | 12/2010 | Navia et al. |
| 2010/0318184 A1 | 12/2010 | Spence |
| 2011/0015729 A1 | 1/2011 | Jimenez et al. |
| 2012/0059458 A1 | 3/2012 | Buchbinder et al. |
| 2012/0123529 A1 | 5/2012 | Levi et al. |
| 2012/0283820 A1 | 11/2012 | Tseng et al. |
| 2013/0023985 A1 | 1/2013 | Khairkhahan et al. |
| 2013/0317598 A1 | 11/2013 | Rowe et al. |
| 2014/0074299 A1 | 3/2014 | Endou et al. |
| 2014/0081394 A1 | 3/2014 | Keranen et al. |
| 2014/0172070 A1 | 6/2014 | Seguin |
| 2014/0358222 A1 | 12/2014 | Gorman, III et al. |
| 2014/0379074 A1 | 12/2014 | Spence et al. |
| 2015/0025623 A1 | 1/2015 | Granada et al. |
| 2015/0230921 A1 | 8/2015 | Chau et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |
| 2015/0374493 A1 | 12/2015 | Yaron et al. |
| 2016/0015514 A1 | 1/2016 | Lashinski et al. |
| 2016/0074165 A1 | 3/2016 | Spence et al. |
| 2016/0095705 A1 | 4/2016 | Keranen et al. |
| 2016/0143732 A1 | 5/2016 | Glimsdale |
| 2016/0184095 A1 | 6/2016 | Spence et al. |
| 2016/0199177 A1 | 7/2016 | Spence et al. |
| 2016/0256276 A1 | 9/2016 | Yaron |
| 2017/0007399 A1 | 1/2017 | Keranen |
| 2017/0007402 A1 | 1/2017 | Zerkowski et al. |
| 2017/0217385 A1 | 8/2017 | Rinkleff et al. |
| 2017/0273788 A1 | 9/2017 | O'Carroll et al. |
| 2017/0273789 A1 | 9/2017 | Yaron et al. |
| 2017/0281337 A1 | 10/2017 | Campbell |
| 2018/0000580 A1 | 1/2018 | Wallace et al. |
| 2018/0085217 A1 | 3/2018 | Lashinski et al. |
| 2018/0206074 A1 | 7/2018 | Tanasa et al. |
| 2018/0289481 A1 | 10/2018 | Dolan |
| 2018/0303606 A1 | 10/2018 | Rothstein et al. |
| 2018/0318073 A1 | 11/2018 | Tseng et al. |
| 2018/0318080 A1 | 11/2018 | Quill et al. |

FOREIGN PATENT DOCUMENTS

| | | |
|---|---|---|
| DE | 19857887 A1 | 7/2000 |
| DE | 19907646 A1 | 8/2000 |
| EP | 103546 A1 | 3/1984 |
| EP | 592410 A1 | 4/1994 |
| EP | 597967 A1 | 5/1994 |
| EP | 850607 A1 | 7/1998 |
| EP | 1432369 A1 | 6/2004 |
| EP | 1796597 A2 | 6/2007 |
| EP | 1296618 B1 | 1/2008 |
| EP | 2620125 A1 | 7/2013 |
| EP | 2806829 A2 | 12/2014 |
| FR | 2788217 A1 | 7/2000 |
| FR | 2815844 A1 | 5/2002 |
| SU | 1271508 A1 | 11/1986 |
| WO | 1991017720 A1 | 11/1991 |
| WO | 93001768 A1 | 2/1993 |
| WO | 1998029057 A1 | 7/1998 |
| WO | 1999040964 A1 | 8/1999 |
| WO | 1999047075 A1 | 9/1999 |
| WO | 2000041652 A1 | 7/2000 |
| WO | 2000047139 A1 | 8/2000 |
| WO | 0149213 A2 | 7/2001 |
| WO | 01049213 A2 | 7/2001 |
| WO | 0154625 A1 | 8/2001 |
| WO | 2001062189 A1 | 8/2001 |
| WO | 2001064137 A1 | 9/2001 |
| WO | 01076510 A2 | 10/2001 |
| WO | 0222054 A1 | 3/2002 |
| WO | 0236048 A1 | 5/2002 |
| WO | 0247575 A2 | 6/2002 |
| WO | 03028558 A2 | 4/2003 |
| WO | 0347468 A1 | 6/2003 |
| WO | 2005034812 A1 | 4/2005 |
| WO | 2005084595 A1 | 9/2005 |
| WO | 2005102015 A2 | 11/2005 |
| WO | 2006011127 A2 | 2/2006 |
| WO | 2006111391 A1 | 10/2006 |
| WO | 2006138173 A2 | 12/2006 |
| WO | 2007047488 A2 | 4/2007 |
| WO | 200767942 A1 | 6/2007 |
| WO | 2007097983 A2 | 8/2007 |
| WO | 2008005405 A2 | 1/2008 |
| WO | 2008091515 A2 | 7/2008 |
| WO | 2009033469 A1 | 3/2009 |
| WO | 2009155561 A2 | 12/2009 |
| WO | 2010121076 A2 | 10/2010 |
| WO | 2012063228 A1 | 5/2012 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |
| WO | 2017103833 A1 | 6/2017 |

OTHER PUBLICATIONS

Bailey, S. "Percutaneous Expandable Prosthetic Valves," Textbook of Interventional Cardiology vol. 2, 2nd Ed. pp. 1268-1276. 1994.

H.R. Andersen "History of Percutaneous Aortic Valve Prosthesis," Herz No. 34. pp. 343-346. 2009.

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Uchida, "Modifications of Gianturco Expandable Wire Stents," American Journal of Roentgenology, vol. 150. pp. 1185-1187. 1986.

Wheatley, "Valve Prostheses," Operative Surgery, 4th ed. pp. 415-424. 1986.

\* cited by examiner

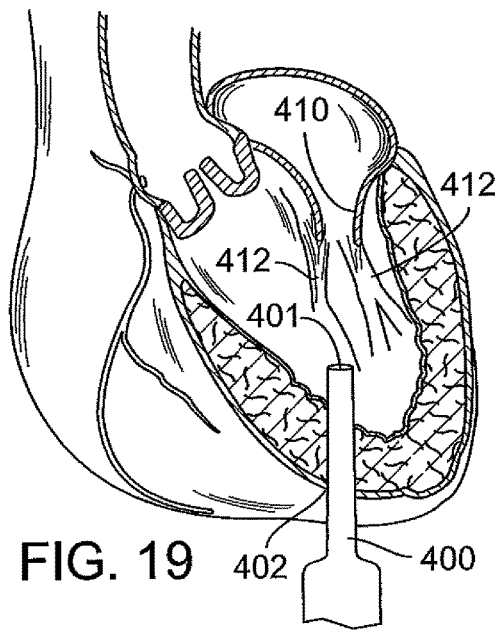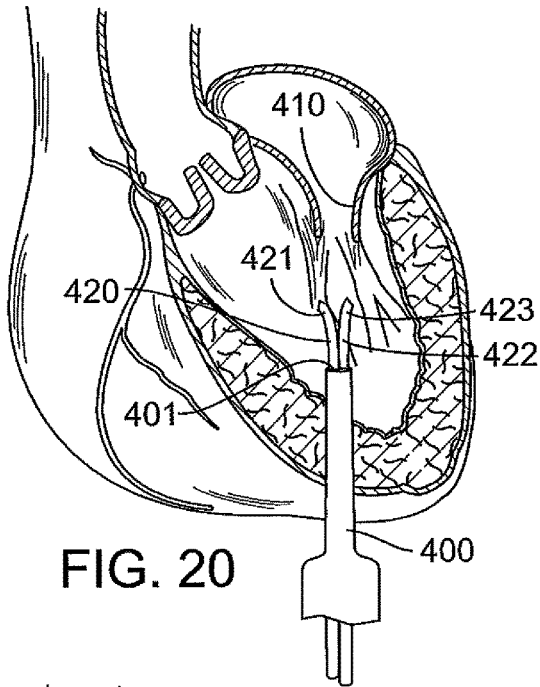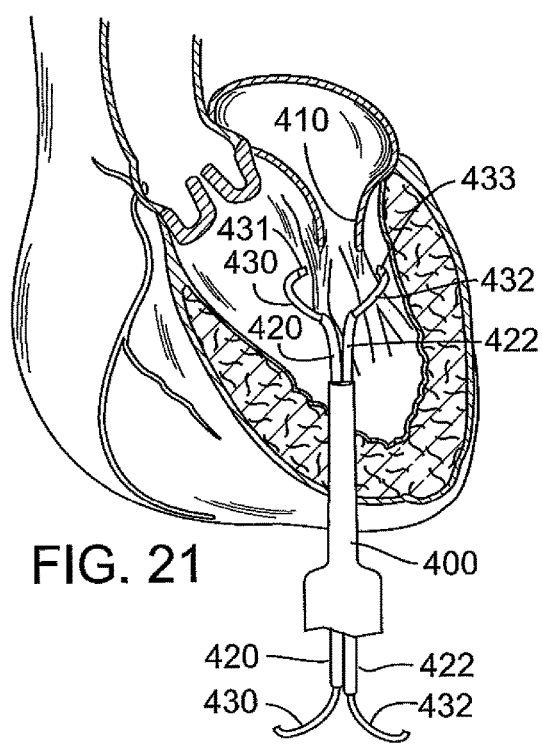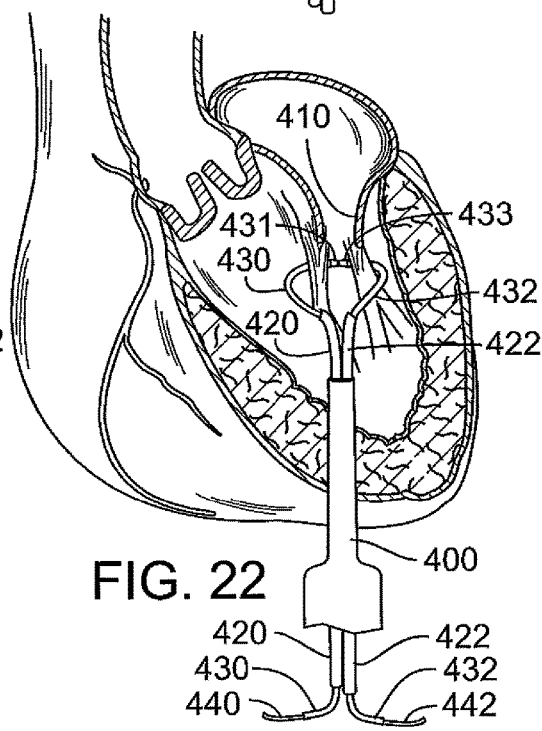

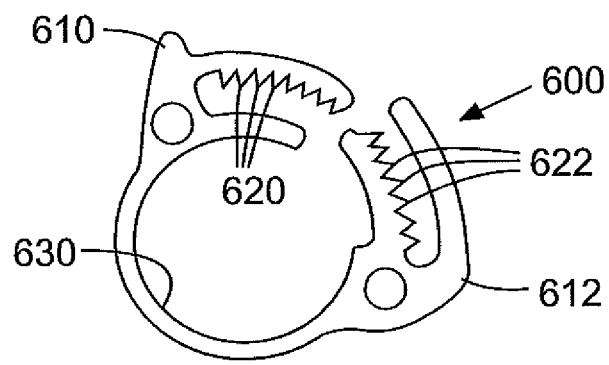
FIG. 29
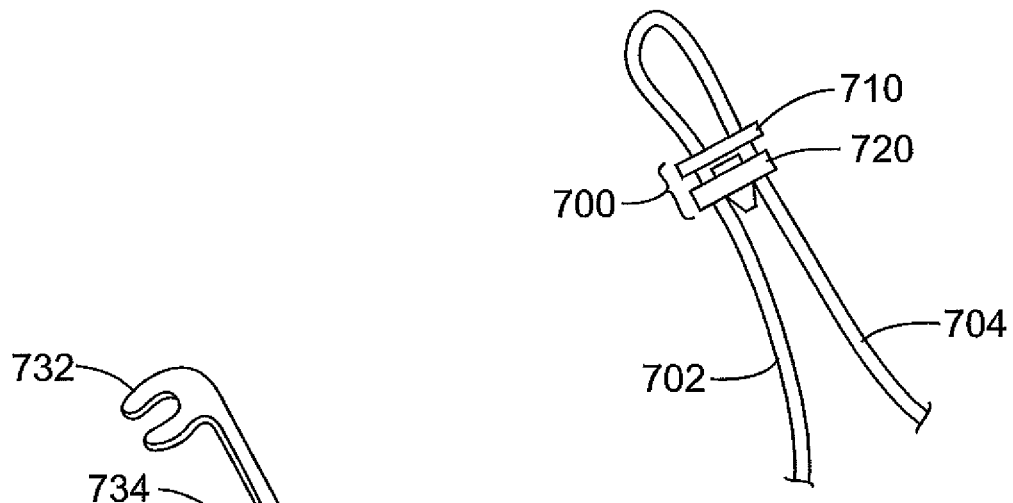
FIG. 30
FIG. 31

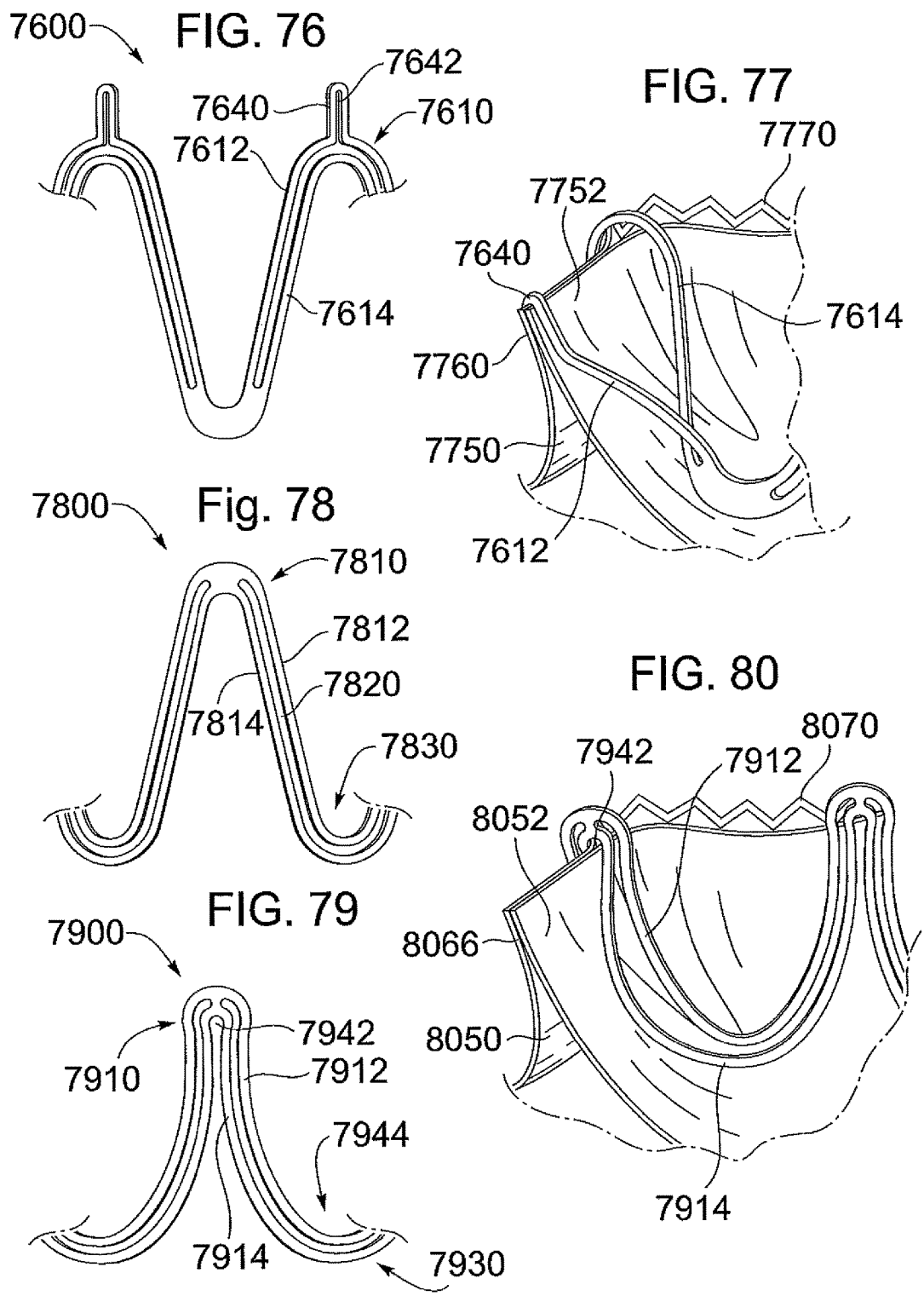

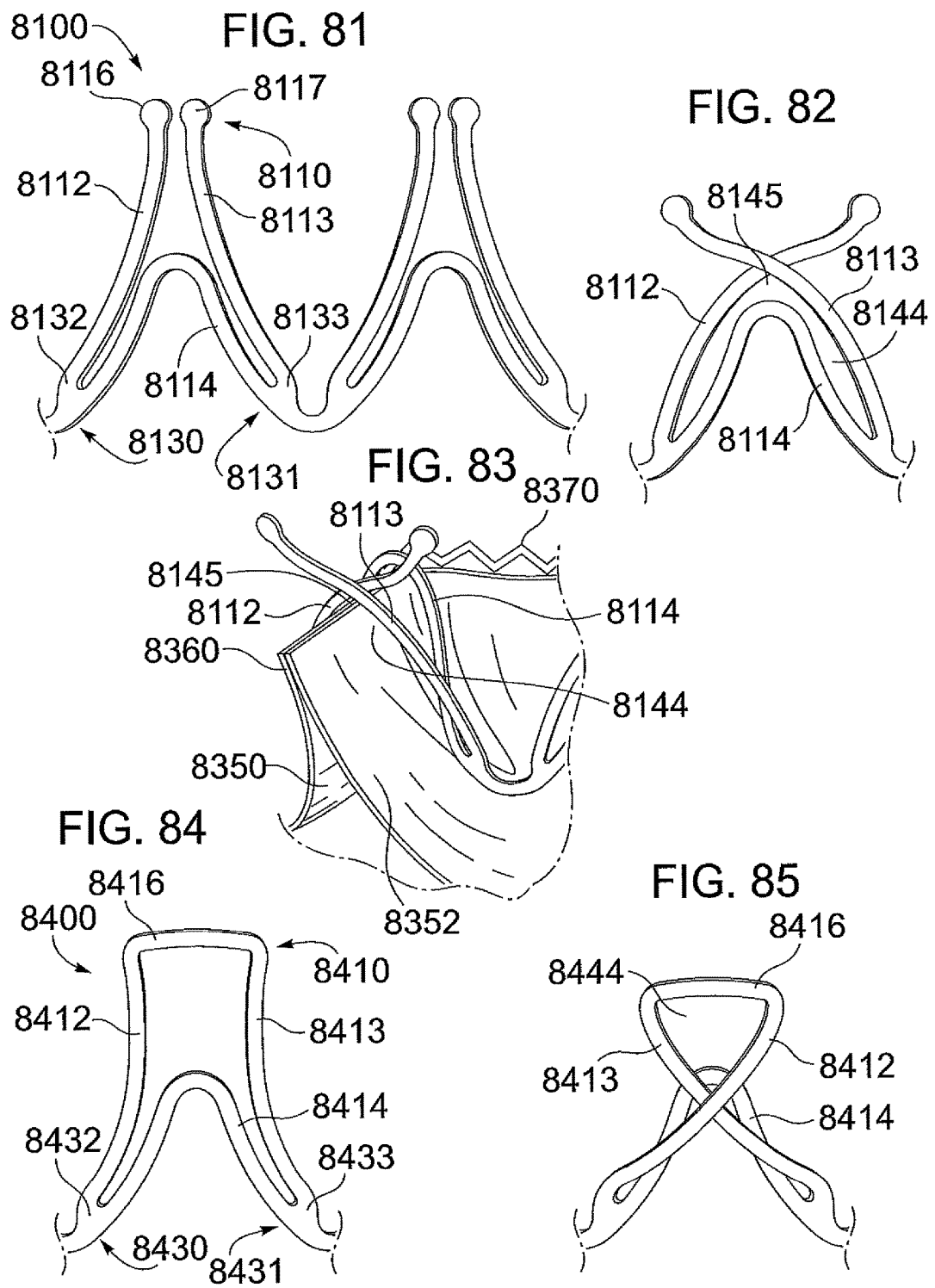

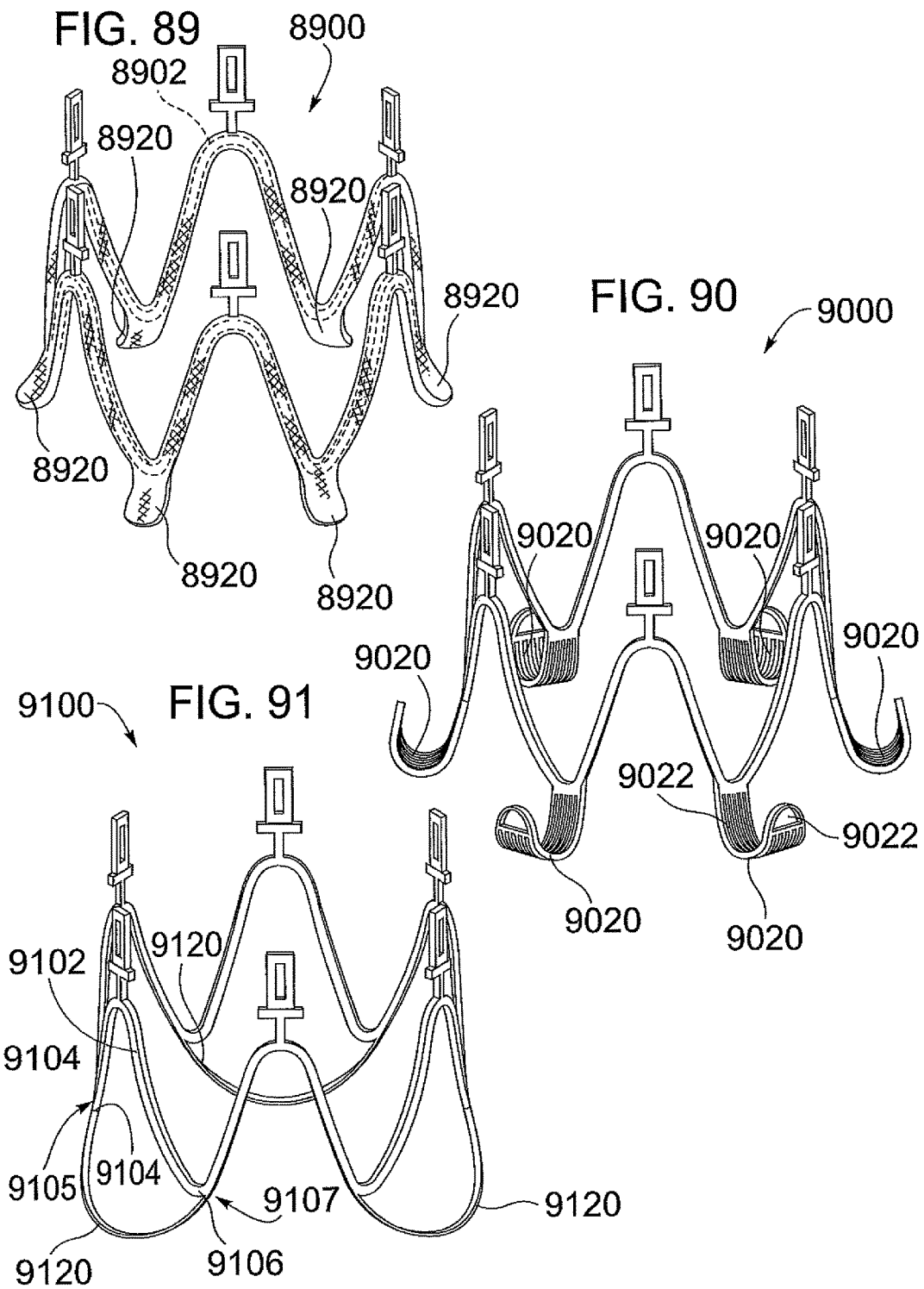

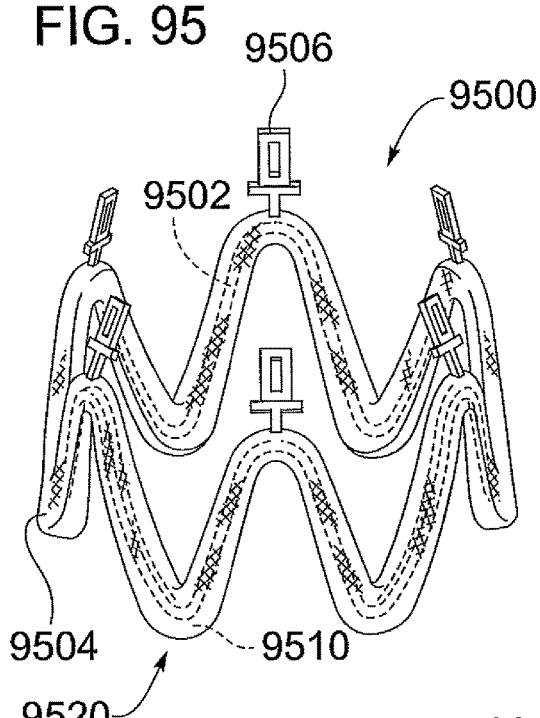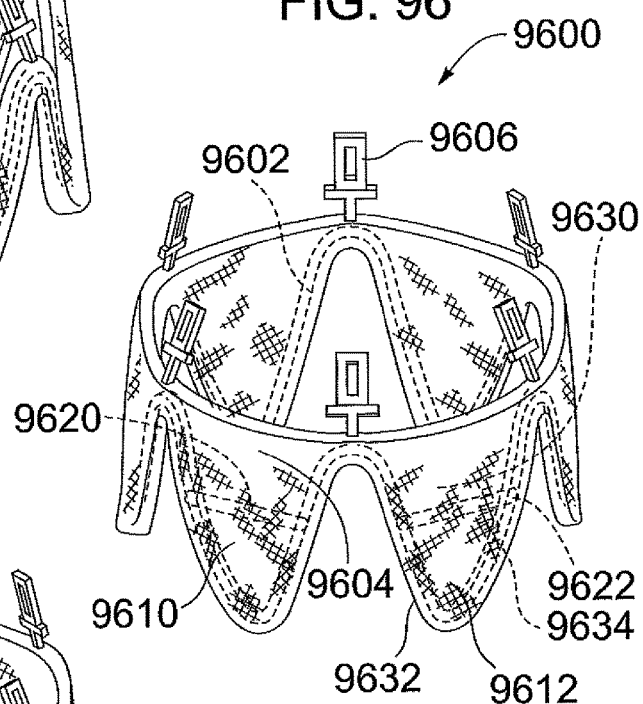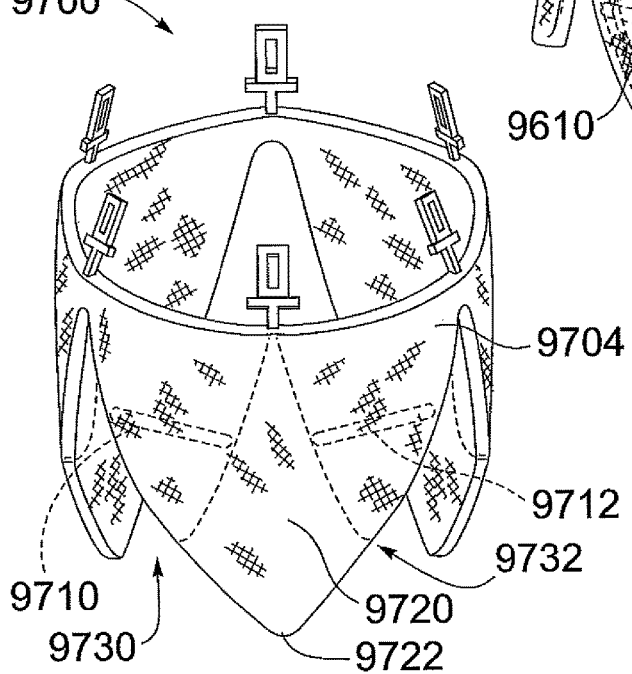

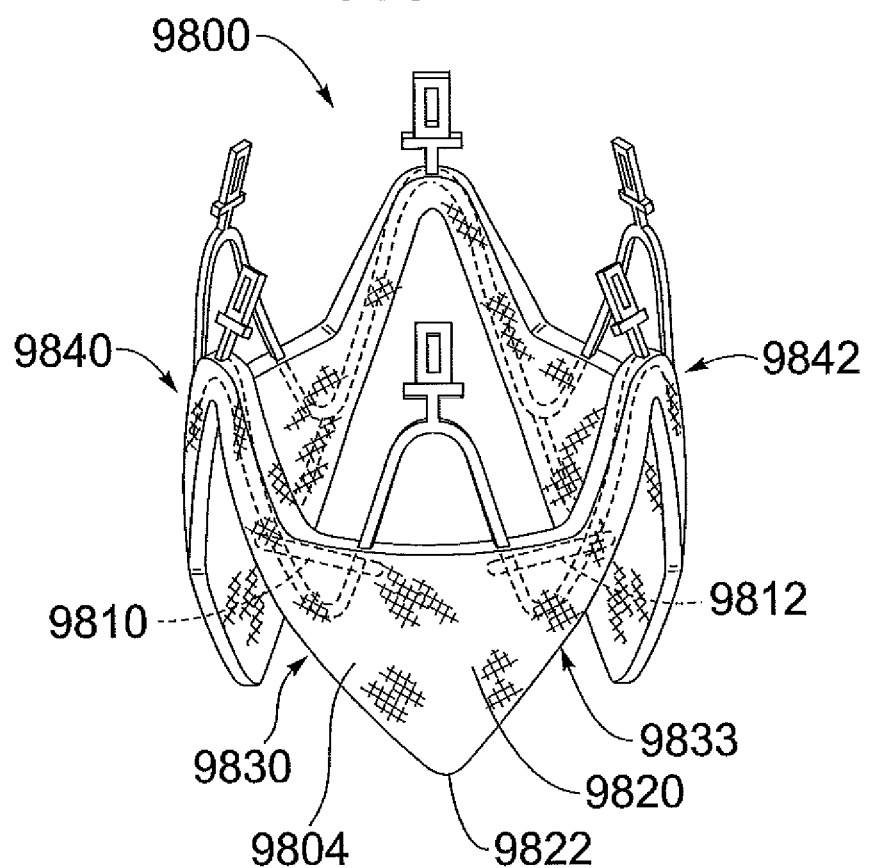

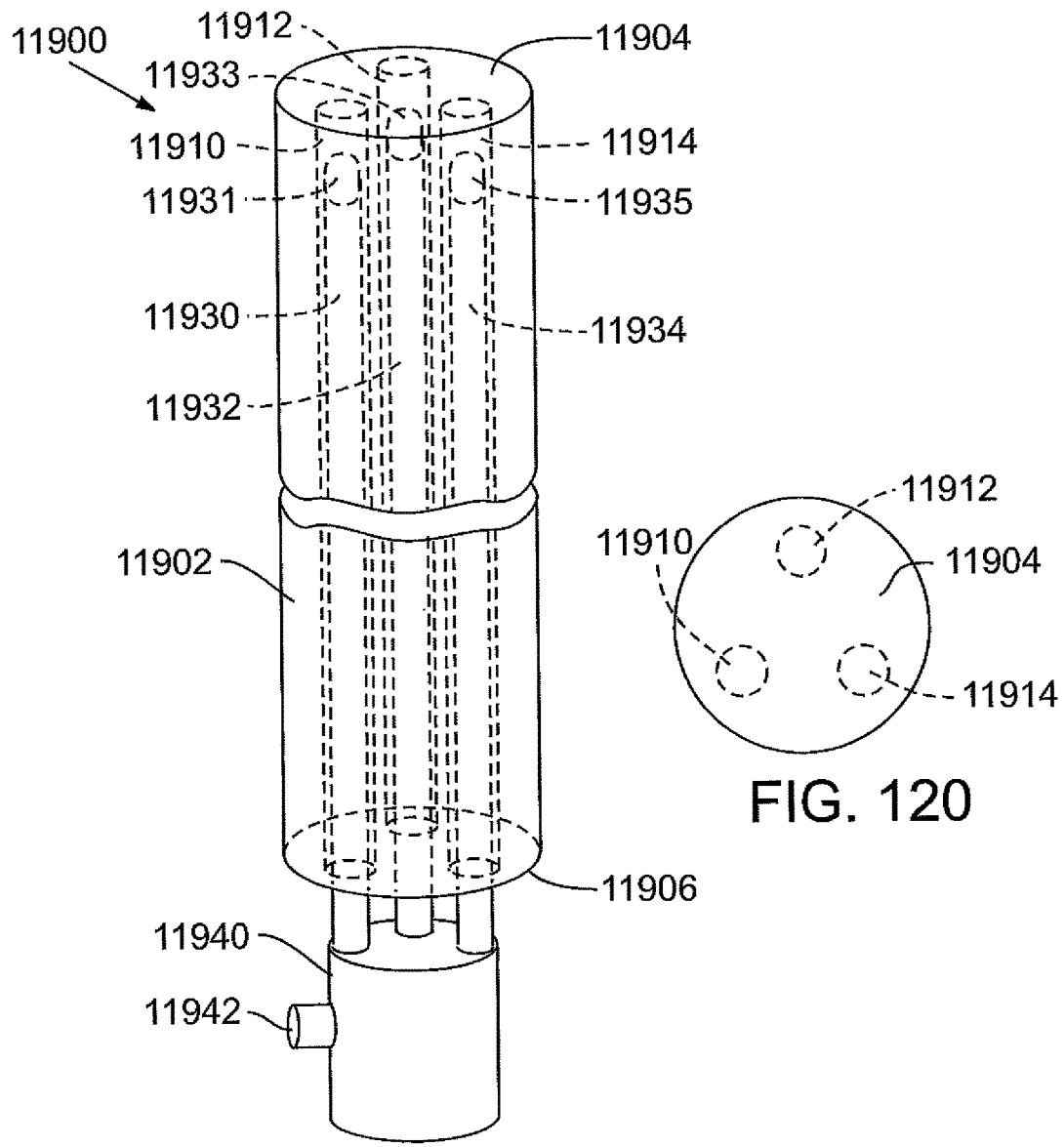

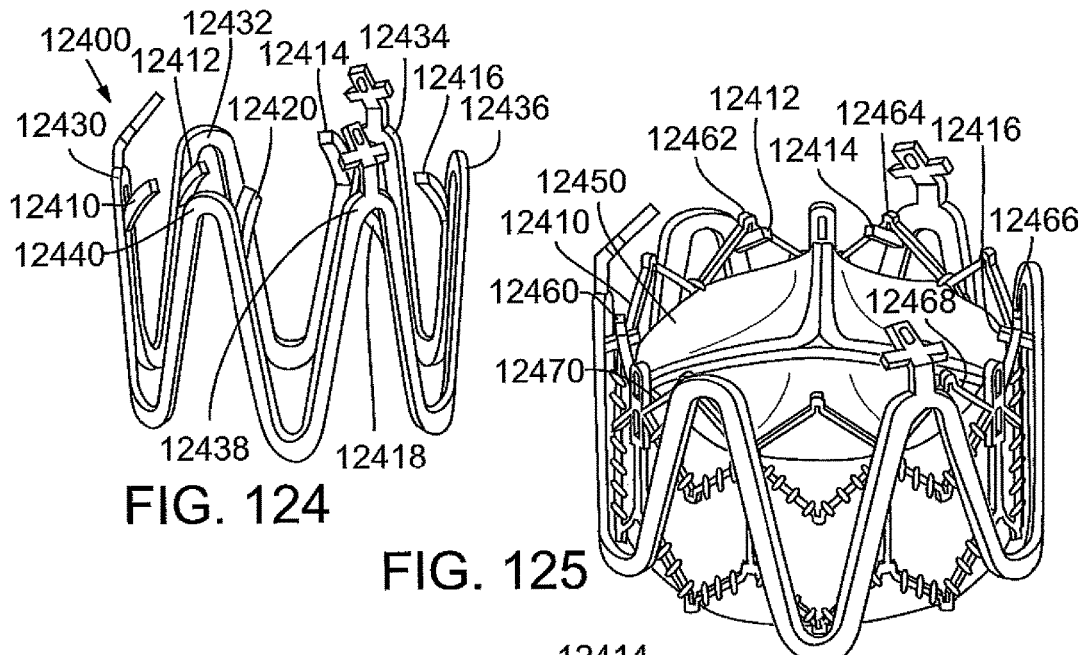
FIG. 124
FIG. 125
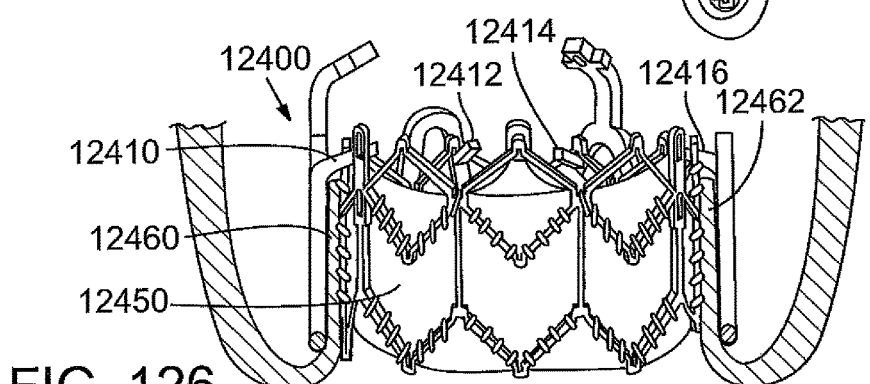
FIG. 126
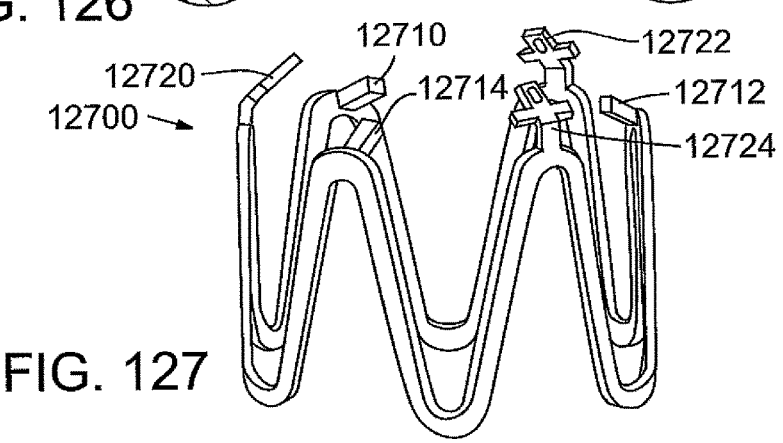
FIG. 127

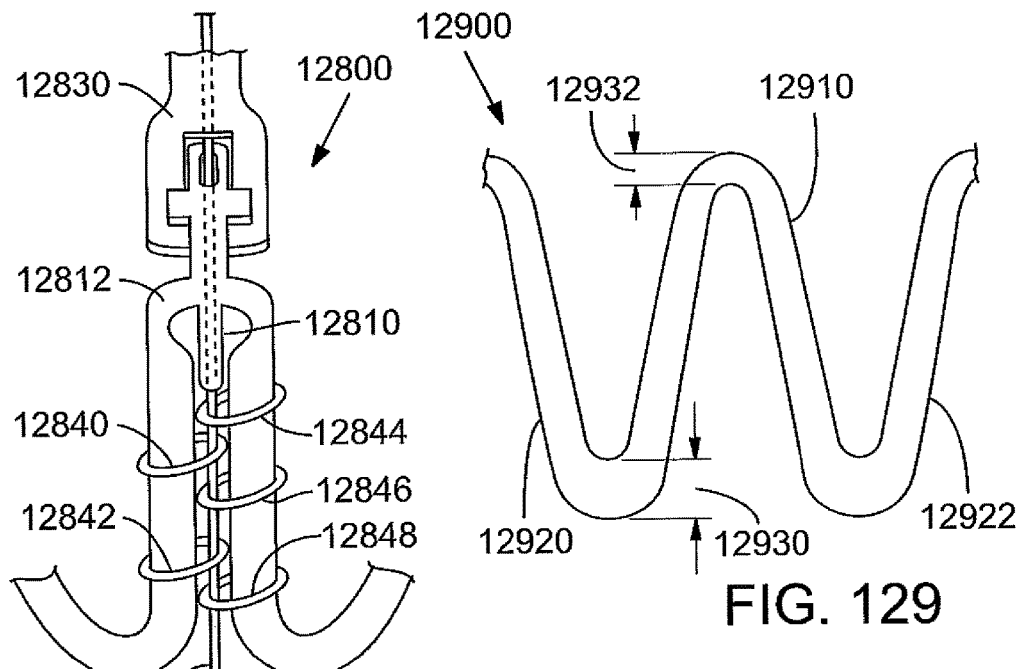
FIG. 128
FIG. 129
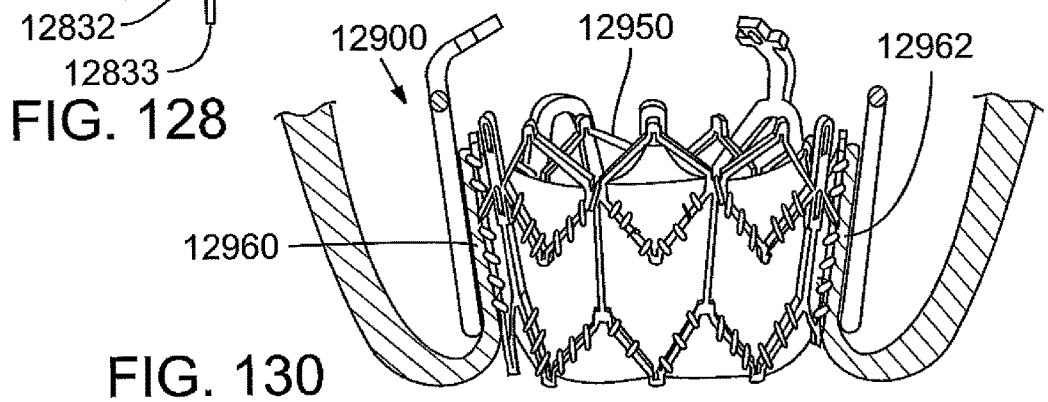
FIG. 130
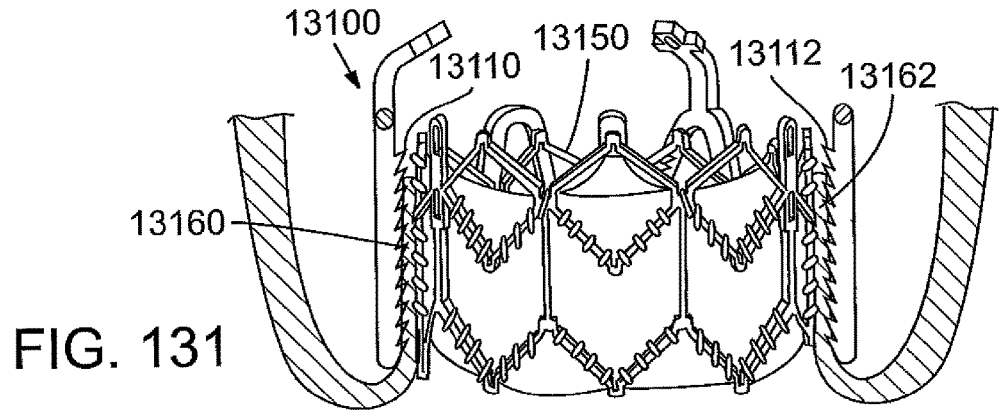
FIG. 131

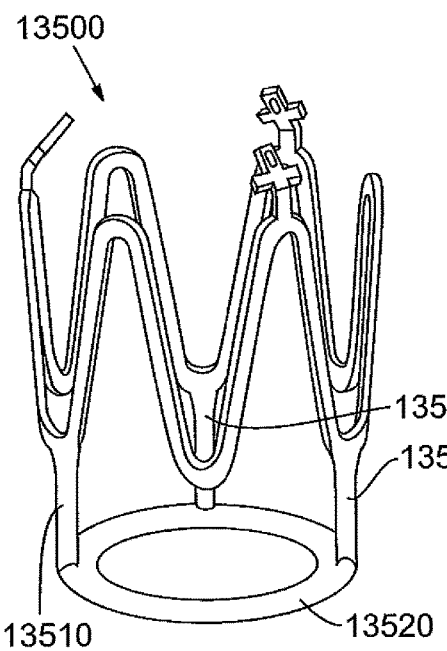
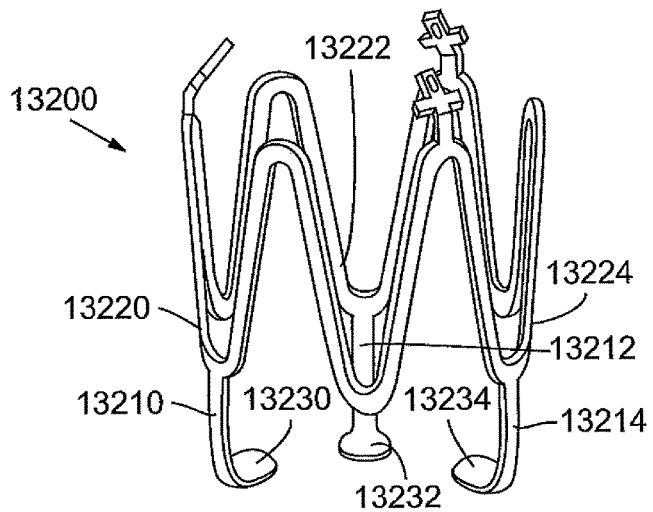
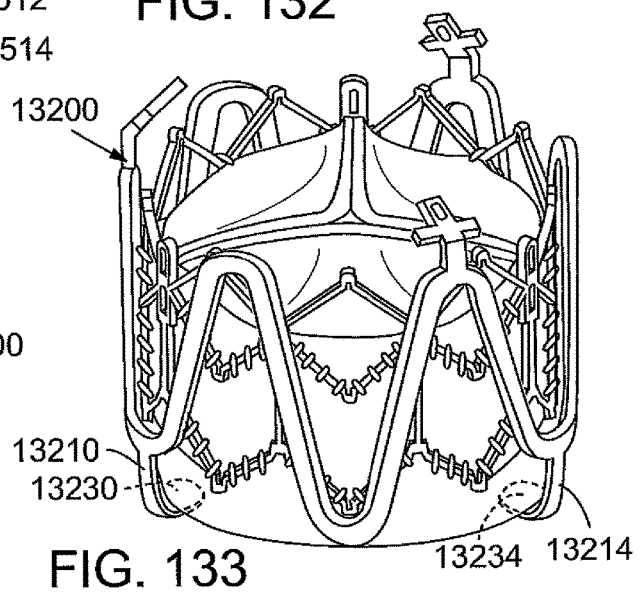
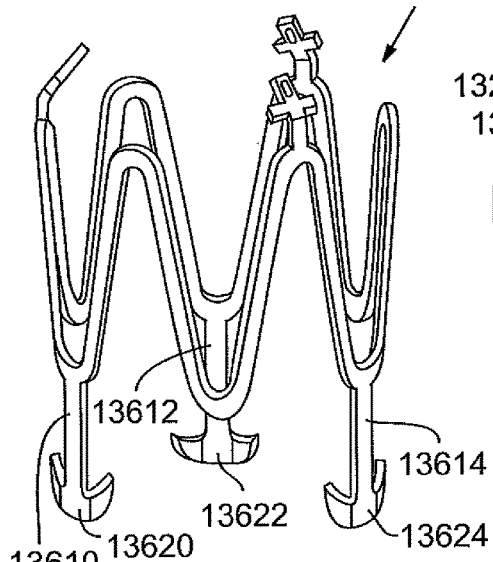
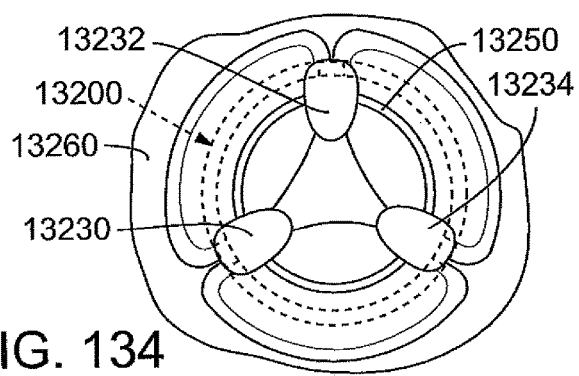
FIG. 135
FIG. 132
FIG. 133
FIG. 136
FIG. 134

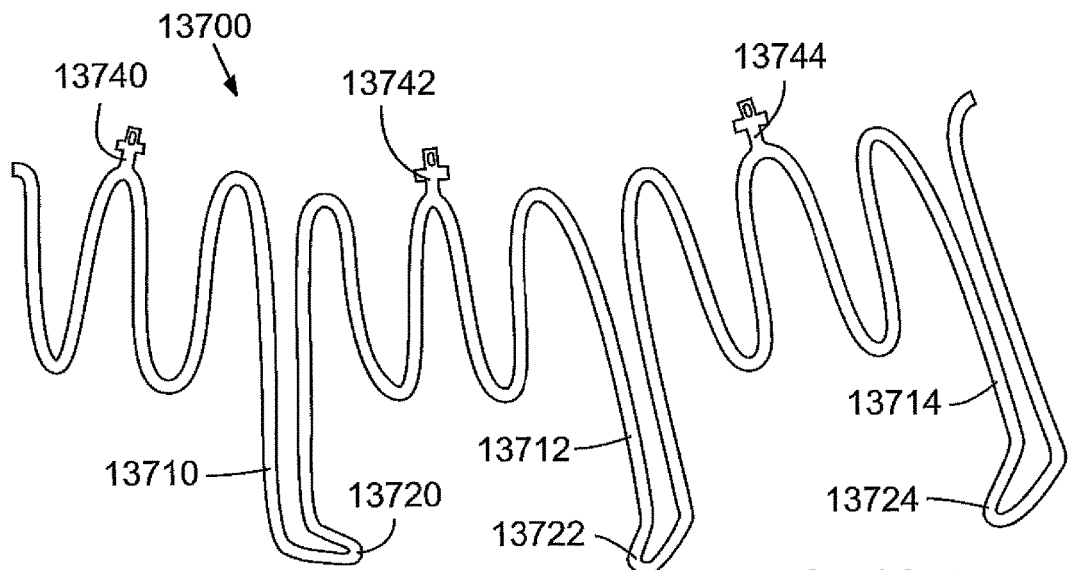
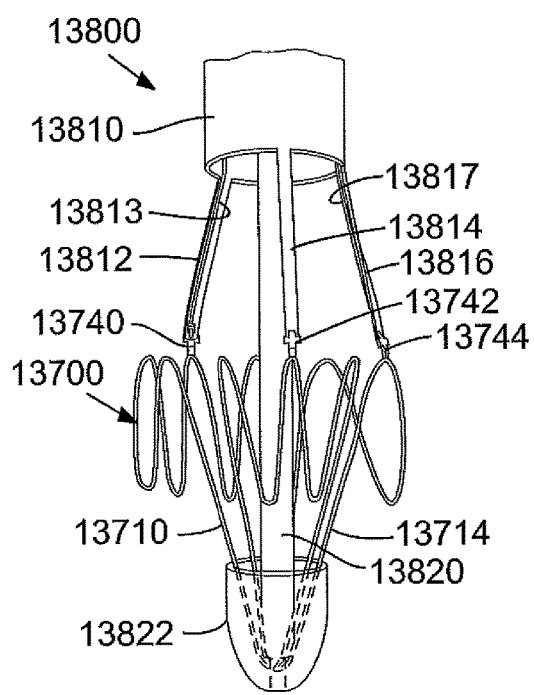
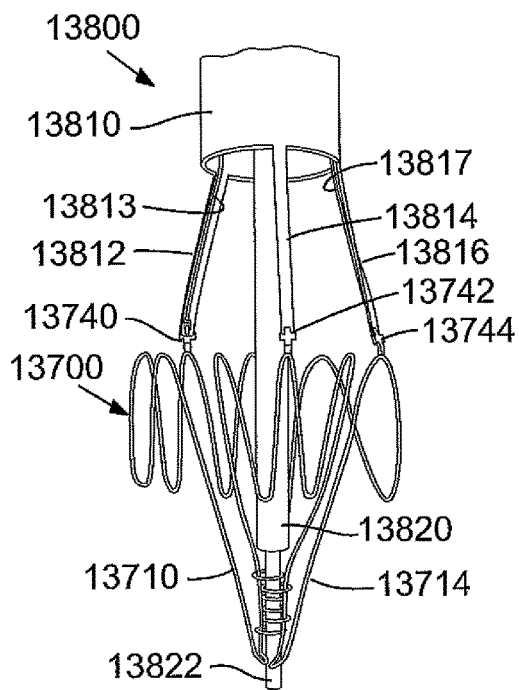
FIG. 137
FIG. 138
FIG. 139

METHODS FOR DELIVERING PROSTHETIC VALVES TO NATIVE HEART VALVES

CROSS-REFERENCE TO RELATED APPLICATIONS

This application is a continuation of U.S. patent application Ser. No. 13/188,988, now U.S. Pat. No. 9,326,853, filed Jul. 22, 2011, which claims the benefit of U.S. Provisional Application No. 61/367,293, filed Jul. 23, 2010, and U.S. Provisional Application No. 61/426,407, filed Dec. 22, 2010, both of which are incorporated herein by reference.

FIELD

This application relates to methods, systems, and apparatus for safely replacing native heart valves with prosthetic heart valves.

BACKGROUND

Prosthetic heart valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery, but such surgeries are dangerous and prone to complication.

More recently a transvascular technique has been developed for introducing and implanting a prosthetic heart valve using a flexible catheter in a manner that is less invasive than open heart surgery. In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter.

Balloon-expandable valves are commonly used for treating heart valve stenosis, a condition in which the leaflets of a valve (e.g., an aortic valve) become hardened with calcium. The hardened leaflets provide a good support structure on which the valve can be anchored within the valve annulus. Further, the catheter balloon can apply sufficient expanding force to anchor the frame of the prosthetic valve to the surrounding calcified tissue. There are several heart conditions, however, that do not involve hardened valve leaflets but which are still desirably treated by valve replacement. For example, aortic insufficiency (or aortic regurgitation) occurs when an aortic valve does not close properly, allowing blood to flow back into the left ventricle. One cause for aortic insufficiency is a dilated aortic annulus, which prevents the aortic valve from closing tightly. In such cases, the leaflets are usually too soft to provide sufficient support for a balloon-expandable prosthetic valve. Additionally, the diameter of the aortic annulus may continue to vary over time, making it dangerous to install a prosthetic valve that is not reliably secured in the valve annulus. Mitral insufficiency (or mitral regurgitation) involves these same conditions but affects the mitral valve.

Self-expanding prosthetic valves are sometimes used for replacing defective native valves with noncalcified leaflets. Self-expanding prosthetic valves, however, suffer from a number of significant drawbacks. For example, once a self-expanding prosthetic valve is placed within the patient's defective heart valve (e.g., the aorta or mitral valve), it continues to exert an outward force on the valve annulus. This continuous outward pressure can cause the valve annulus to dilate further, exacerbating the condition the valve was intended to treat. Additionally, when implanting a self-expanding valve, the outward biasing force of the valve's frame tends to cause the valve to be ejected very quickly from the distal end of a delivery sheath. This makes delivery of the valve very difficult and dangerous to the patient.

The size of the prosthetic valve to be implanted into a patient can also be problematic when treating aortic or mitral insufficiency. Specifically, the size of a prosthetic valve used to treat aortic or mitral insufficiency is typically larger than a prosthetic valve used to treat aortic or mitral stenosis. This larger valve size makes the delivery procedure much more difficult and dangerous to the patient.

Accordingly, there exists a need for improved methods, systems, and apparatus for delivering expandable prosthetic heart valves (e.g., balloon-expandable prosthetic valves). Embodiments of the methods, systems, and apparatus desirably can be used to replace native heart valves that do not have calcified leaflets (e.g., aortic valves suffering from aortic insufficiency). Furthermore, embodiments of the methods, systems, and apparatus desirably enable precise and controlled delivery of the prosthetic valves.

SUMMARY

Disclosed below are representative embodiments of methods, systems, and apparatus used to replace deficient native heart valves with prosthetic heart valves. Embodiments of the disclosed methods, systems, and apparatus can be used, for example, to replace an aortic valve suffering from aortic insufficiency or a mitral valve suffering from mitral insufficiency. These embodiments are not limiting, however, as the disclosed methods, systems, and apparatus can be more generally applied to replace any heart valve.

In certain embodiments, for example, a support structure is delivered to a position on or adjacent to the surface of the outflow side of a native heart valve of a patient, the support structure defining a support-structure interior. An expandable prosthetic heart valve is delivered into the native heart valve and into the support-structure interior. The expandable prosthetic heart valve can be expanded while the expandable prosthetic heart valve is in the support-structure interior and while the support structure is at the position on or adjacent to the surface of the outflow side of the native heart valve, thereby causing one or more native leaflets of the native heart valve to be frictionally secured between the support structure and the expanded prosthetic heart valve. The expandable prosthetic heart valve can be delivered from the inflow or the outflow side of the native heart valve. In certain embodiments, the native heart valve is an aortic valve, and the act of delivering the expandable prosthetic heart valve comprises delivering the prosthetic heart valve through the left ventricle of the patient's heart. In other embodiments, the native heart valve is an aortic valve, and the act of delivering the expandable prosthetic heart valve comprises delivering the prosthetic heart valve through the patient's aorta. In particular embodiments, the native heart valve is an aortic valve, the support structure is a support stent, and the act of delivering the support structure comprises advancing a first catheter through the aortic arch of the patient so that a distal end of the first catheter is near the aortic valve of the patient (the first catheter at least partially enclosing a stent-delivery catheter, an inner catheter, and the support stent in a compressed state) and advancing the stent-delivery catheter and the inner catheter through the first catheter, thereby causing the support stent to be deployed from the distal end of the first catheter and to expand into a decompressed state. In other particular embodiments, the native heart valve is a mitral valve, the support structure is a support band, and the act of delivering the support structure comprises advancing a first loop delivery catheter into the left ventricle of the patient so that a first distal end of the first loop delivery catheter extends around a first portion of the chordae tendineae, advancing a second loop delivery catheter into the left ventricle of the patient so that a second distal end of the second loop delivery catheter extends around a second portion of the chordae tendineae and so that the second distal end of the second loop delivery is adjacent to the first distal end of the first loop delivery catheter, advancing a support band material through an interior of the first loop delivery catheter and an interior of the second loop delivery catheter, attaching a locking member to portions of the support band material, and advancing the locking member along the portions of the support band material and into the left ventricle of the patient, thereby forming the support band around the chordae tendineae. In certain embodiments, the act of delivering the support structure comprises guiding the support structure to the position on or adjacent to the surface of the outflow side of the native heart valve and into a desired orientation, wherein the desired orientation aligns peaks of the support structure with either the tips or the commissures of the one or more native leaflets. In further embodiments, the support structure is disconnected from at least a delivery catheter once the one or more native leaflets of the native heart valve are frictionally secured between the support structure and the expanded prosthetic heart valve. The disconnecting can be performed by retracting an inner catheter relative to a stent-delivery catheter, thereby retracting inner prongs coupled to the inner catheter from corresponding apertures in retaining arms of the support stent. Alternatively, the disconnecting can be performed by cutting through material used to form the support structure, thereby releasing the support structure from a catheter. In certain embodiments, the act of expanding the expandable prosthetic heart valve comprises inflating a balloon of a balloon catheter, the expandable prosthetic heart valve being disposed around the balloon of the balloon catheter.

In certain embodiments, for example, a support structure is delivered to a position on or adjacent to the surface of the outflow side of a native heart valve of a patient, the support structure defining a support-structure interior. An expandable prosthetic heart valve is delivered into the native heart valve and into the support-structure interior. The expandable prosthetic heart valve can be expanded while the expandable prosthetic heart valve is in the support-structure interior and while the support structure is at the position on or adjacent to the surface of the outflow side of the native heart valve, thereby causing one or more native leaflets of the native heart valve to be frictionally secured between the support structure and the expanded prosthetic heart valve. The expandable prosthetic heart valve can be delivered from the inflow or the outflow side of the native heart valve. In certain embodiments, the native heart valve is an aortic valve, and the act of delivering the expandable prosthetic heart valve comprises delivering the prosthetic heart valve through the left ventricle of the patient's heart. In other embodiments, the native heart valve is an aortic valve, and the act of delivering the expandable prosthetic heart valve comprises delivering the prosthetic heart valve through the patient's aorta. In particular embodiments, the native heart valve is an aortic valve, the support structure is a support stent, and the act of delivering the support structure comprises advancing a first catheter through the aortic arch of the patient so that a distal end of the first catheter is near the aortic valve of the patient (the first catheter at least partially enclosing a stent-delivery catheter, an inner catheter, and the support stent in a compressed state) and advancing the stent-delivery catheter and the inner catheter through the first catheter, thereby causing the support stent to be deployed from the distal end of the first catheter and to expand into a decompressed state. In other particular embodiments, the native heart valve is a mitral valve, the support structure is a support band, and the act of delivering the support structure comprises advancing a first loop delivery catheter into the left ventricle of the patient so that a first distal end of the first loop delivery catheter extends around a first portion of the chordae tendineae, advancing a second loop delivery catheter into the left ventricle of the patient so that a second distal end of the second loop delivery catheter extends around a second portion of the chordae tendineae and so that the second distal end of the second loop delivery is adjacent to the first distal end of the first loop delivery catheter, advancing a support band material through an interior of the first loop delivery catheter and an interior of the second loop delivery catheter, attaching a locking member to portions of the support band material, and advancing the locking member along the portions of the support band material and into the left ventricle of the patient, thereby forming the support band around the chordae tendineae. In certain embodiments, the act of delivering the support structure comprises guiding the support structure to the position on or adjacent to the surface of the outflow side of the native heart valve and into a desired orientation, wherein the desired orientation aligns peaks of the support structure with either the tips or the commissures of the one or more native leaflets. In further embodiments, the support structure is disconnected from at least a delivery catheter once the one or more native leaflets of the native heart valve are frictionally secured between the support structure and the expanded prosthetic heart valve. The disconnecting can be performed by retracting an inner catheter relative to a stent-delivery catheter, thereby retracting inner prongs coupled to the inner catheter from corresponding apertures in retaining arms of the support stent. Alternatively, the disconnecting can be performed by cutting through material used to form the support structure, thereby releasing the support structure from a catheter. In certain embodiments, the act of expanding the expandable prosthetic heart valve comprises inflating a balloon of a balloon catheter, the expandable prosthetic heart valve being disposed around the balloon of the balloon catheter.

In other exemplary methods disclosed herein, a guide catheter is advanced through the aortic arch of a patient so that a distal end of the guide catheter is near the aortic valve of the patient. In these embodiments, the guide catheter at least partially encloses a stent-delivery catheter and a compressed support stent releasably connected to the stent-delivery catheter. The stent-delivery catheter is advanced through the guide catheter, thereby causing the support stent to be deployed from the distal end of the guide catheter and to become uncompressed. The uncompressed support stent is positioned adjacent to or on a surface of the aortic side of the aortic valve such that the leaflets of the aortic valve are circumscribed by the uncompressed support stent. The uncompressed support stent can then be disconnected from the stent-delivery catheter. In certain embodiments, to disconnect the support stent from the stent-delivery catheter, an inner catheter positioned in the interior of the stent-delivery catheter can be retracted, causing an inner prong attached to the inner catheter to withdraw from an aperture associated with the support stent, and/or at least one prong attached to the stent-delivery catheter can be disconnected from the support stent.

Other exemplary embodiments disclosed herein include apparatus for securing a prosthetic valve to a native heart valve. For example, certain embodiments comprise a support stent having an annular body that defines one or more peaks and one or more valleys along its circumference. The support stent can be radially compressible and self expandable. The support stent can be sized such that it can be positioned within the aorta of a patient at a location adjacent to the aortic valve and thereby circumscribe the aortic valve. The support stent can further comprise at least one retaining arm comprises an aperture at or near a respective one of the peaks. In particular embodiments, the support stent is formed from a single annular member. In some embodiments, the support stent consists of three peaks and three valleys. The shape formed by the three peaks and the three valleys can approximate the shape of the leaflets of the aortic valve when the aortic valve is fully opened. In certain embodiments, a projection of the annular body onto a first plane is ring shaped or starfish shaped, and the annular body defines the one or more peaks and the one or more valleys in a direction perpendicular to the first plane. For example, the annular body can be sinusoidal or saw-tooth shaped along its circumference. Certain embodiments further comprise a stent delivery catheter having an outer fork that includes one or more outer prongs. At least one of the outer prongs can comprise an aperture that is sized to receive at least a portion of one of the retaining arms of the support stent. An inner catheter can be positioned in an interior of the stent-delivery catheter and have an inner fork. The inner fork can comprise one or more inner prongs, and at least one of the inner prongs can be insertable through the aperture of the one of the retaining arms when the one of the retaining arms has been at least partially inserted through the aperture of a respective one of the outer prongs.

Other exemplary embodiments disclosed herein are systems for delivering a support frame for securing a prosthetic valve in a patient's native heart valve. Exemplary embodiments of the system comprise a guide catheter, a frame-delivery catheter positioned in the interior of the guide catheter, an inner catheter positioned in the interior of the frame-delivery catheter, and an expandable support frame positioned in the interior of the guide catheter in a radially compressed state. A distal end of the frame-delivery catheter can have an outer fork portion that comprises a plurality of flexible outer prongs. A distal end of the inner catheter can have an inner fork portion that comprises a plurality of flexible inner prongs. The expandable support frame can comprise a plurality of retaining arms, which can be releasably connected to corresponding ones of the outer prongs of the outer fork portion and corresponding ones of the inner prongs of the inner fork portion. The expandable support frame can be generally annular and comprise shaped portions configured to frictionally secure native leaflets of a patient's heart valve against an exterior surface of a prosthetic valve when the patient's heart valve has been replaced by the prosthetic valve. Alternatively, the expandable support frame can comprise a main body and a U-shaped lip that surrounds a bottom region of the support frame, the U-shaped lip having a diameter that is greater than a diameter of the main body. In particular embodiments, the guide catheter, frame-delivery catheter, and the inner catheter are axially slidable relative to one another. In some embodiments, the retaining arms of the expandable support frame comprise respective retaining arm apertures through which the corresponding ones of the inner prongs are inserted. The corresponding ones of the outer prongs can comprise, for example, respective outer prong apertures through which the respective retaining arms are inserted. In certain embodiments, the corresponding ones of the outer prongs and the corresponding ones of the inner prongs of the inner fork portion are configured such that relative retraction of either the corresponding ones of the inner prongs or the corresponding ones of the outer prongs causes release of the respective retaining arms.

Another disclosed embodiment is an apparatus comprising a support stent having an annular main body portion and a generally U-shaped rim portion at one end of the main body portion. The support stent of this embodiment is radially compressible into a compressed state and self expandable into an uncompressed state. Furthermore, the rim portion has a diameter that is greater than a diameter of the annular main body portion and that is sized so that an outer perimeter of the rim portion will engage the walls surrounding the aortic valve of a patient when the support stent is positioned within the aorta of the patient at a location adjacent to the aortic valve. In some embodiments, the support stent is made of a shape-memory alloy. In certain embodiments, the annular main body portion is sinusoidal or saw-tooth shaped along its circumference. In some embodiments, the rim portion is located around a bottom region of the main body portion. In certain embodiments, the support stent is made of multiple elements forming a criss-cross pattern. In particular embodiments, the apparatus further comprises at least one retaining arm at or near a top region of the main body portion.

In another disclosed embodiment, a distal end of a first delivery catheter is advanced into the left ventricle of a patient so that a distal portion of the first delivery catheter substantially circumscribes a first half of the patient's chordae tendineae. A distal end of a second delivery catheter is advanced into the left ventricle of the patient so that a distal portion of the second delivery catheter substantially circumscribes a second half of the patient's chordae tendineae and so that a distal end of the second delivery catheter contacts a distal end of the first delivery catheter, thereby forming a delivery catheter junction. A support band material is advanced through one of the first delivery catheter or the second delivery catheter, across the delivery catheter junction, and into the other one of the first delivery catheter or the second delivery catheter. The first delivery catheter and the second delivery catheter are retracted from the left ventricle of the patient. In certain embodiments, the distal end of the first delivery catheter and the distal end of the second delivery catheter are advanced through a puncture in the left ventricle. In other embodiments, the distal end of the first delivery catheter and the distal end of the second delivery catheter are advanced through the aorta of the patient. In some embodiments, the distal end of the first delivery catheter magnetically engages the distal end of the second delivery catheter. In some embodiments, a first steerable sheath and a second steerable sheath are advanced into the left ventricle. In these embodiments, the act of advancing the distal end of the first delivery catheter into the left ventricle comprises advancing the distal end of the first delivery catheter through an interior of the first steerable sheath, and the act of advancing the distal end of the second delivery catheter into the left ventricle comprises advancing the distal end of the second delivery catheter through an interior of the second steerable sheath. In certain embodiments, an introducer sheath is advanced into the left ventricle through a puncture in the left ventricle. In these embodiments, the act of advancing the first steerable sheath and the second steerable sheath into the left ventricle comprises advancing the first steerable sheath and the second steerable sheath through the introducer sheath. In some embodiments, a locking member is attached to portions of the support band material and advanced over the portions of the support band material, thereby adjusting a diameter of a loop formed by the support band material and the locking member and surrounding the chordae tendineae. The act of advancing the locking member over the portions of the support band material can be performed using a pusher tube. In some embodiments, the loop formed by the support band material and the locking member can be positioned around the outflow side of the mitral valve. An expandable prosthetic heart valve can be advanced into the mitral valve and the interior of the loop formed by the support band material and the locking member while the prosthetic heart valve is in a compressed state. The expandable prosthetic heart valve can be expanded into an uncompressed state, thereby causing one or more native leaflets of the mitral valve to be frictionally secured between the loop and the expandable prosthetic heart valve. Portions of the support band material that do not form part of the loop can be severed, thereby releasing the loop.

In another disclosed embodiment, a partial loop is formed around the chordae tendineae of a patient's heart with a cord of biocompatible material. A locking member is attached to portions of the cord of biocompatible material. The locking member is advanced toward the chordae tendineae along the portions of the cord of biocompatible material, thereby decreasing a diameter of a loop formed by the cord of biocompatible material and the locking member. In certain embodiments, an expandable prosthetic heart valve is positioned into the interior of the patient's mitral valve, the loop formed by the cord of biocompatible material and the locking member is positioned around an outflow side of the patient's mitral valve so that the native leaflets of the mitral valve open into the interior of the loop, and the expandable prosthetic heart valve is expanded, thereby causing an exterior surface of the expandable prosthetic heart valve to urge the native leaflets of the mitral valve against an interior surface of the loop and to frictionally secure the expandable prosthetic heart valve to the native leaflets of the mitral valve. In some embodiments, portions of the cord of biocompatible material are cut in order to release the loop formed by the cord of biocompatible material and the locking member. In certain embodiments, an expandable prosthetic heart valve is advanced into the interior of the patient's mitral valve and expanded. The exterior of the expandable prosthetic heart valve can comprise one or more fastening mechanisms configured to engage the native leaflets of the mitral valve and at least temporarily secure the expandable prosthetic heart to the native leaflets. In certain implementations of these embodiments, the loop formed by the cord of biocompatible material and the locking member is positioned around an outflow side of the patient's mitral valve so that the loop circumscribes the native leaflets of the mitral valve and the expanded prosthetic heart valve. In these embodiments, the act of advancing the locking member can decrease the diameter of the loop formed by the cord of biocompatible material and the locking member to a diameter that causes the expanded prosthetic heart valve to be frictionally secured to the native leaflets of the mitral valve. In certain particular embodiments, the locking member is locked at a desired position along the portions of the support band material, thereby forming a support band having a substantially fixed diameter. In some embodiments, the locking member can be unlocked, and the location of the locking member adjusted along the portions of the support band material. In certain embodiments, the act of forming the partial loop around the chordae tendineae of the patient's heart is performed using one or more delivery catheters inserted through the aortic arch of the patient. In other embodiments, the act of forming the partial loop around the chordae tendineae of the patient's heart is performed using one or more delivery catheters inserted through a puncture in the left ventricle of the patient.

Another disclosed embodiment is a system that comprises a first delivery catheter having a first distal end region and a first distal end, a second delivery catheter having a second distal end region and a second distal end, and an introducer sheath defining an interior that is configured to receive the first delivery catheter and the second delivery catheter. In these embodiments, the first distal end region is steerable into a first semi-circular shape, the second distal end region is steerable into a second semi-circular shape, the first distal end has a first magnetic polarity, and the second distal end has a second magnetic polarity opposite the first magnetic polarity. In certain embodiments, the introducer sheath is rigid and is sized for insertion through a puncture in the left ventricle of a patient. In other embodiments, the introducer sheath is bendable and is sized for insertion into the aortic arch of a patient. In some embodiments, the system further comprises a first catheter delivery sheath and a second catheter delivery sheath. In these embodiments, the first catheter delivery sheath defines a first interior configured to receive the first delivery catheter and has a first distal sheath region that naturally assumes a first arced shape. Further, the second catheter delivery sheath defines a second interior configured to receive the second delivery catheter and has a second distal sheath region that naturally assumes a second arced shape. In these embodiments, the interior of the introducer sheath is further configured to receive the first catheter delivery sheath, the second catheter delivery sheath, the first delivery catheter, and the second delivery catheter. In certain embodiments, the first catheter delivery sheath and the second catheter delivery sheath are manufactured at least in part from a shape-memory alloy.

Another disclosed embodiment is a system comprising a pusher tube defining a first pusher tube lumen and a second pusher tube lumen and a locking member defining a first locking member lumen and a second locking member lumen. In these embodiments, the first and second pusher tube lumens are sized to receive respective portions of a cord of material, and the first and second locking member lumens are also sized to receive the respective portions of the cord and are further configured to allow movement of the locking member in a first direction along the respective portions of the cord when pushed by the pusher tube but prevent movement of the locking member in a second direction opposite the first direction along the respective portions of the cord. In certain embodiments, the pusher tube further comprises a rotatable cutting element located at a distal end of the pusher tube, the rotatable cutting element being controllable from a proximal region of the pusher tube. In some embodiments, the first locking member lumen and the second locking member lumen each comprise one or more angled collars or teeth. In certain embodiments, the system further comprises an introducer sheath having an introducer sheath interior through which the pusher tube and the locking member are advanceable. In some embodiments, the system further comprises a prosthetic-heart-valve-delivery catheter. In these embodiments, the introducer sheath interior is further configured to simultaneously receive the pusher tube and the prosthetic-heart-valve-delivery catheter.

Another disclosed embodiment is a system comprising a locking member configured to receive two portions of a cord of biocompatible material and to secure the two portions in a desired position relative to one another, an adjustment tool configured to position the locking member into the desired position and to engage a locking mechanism in the locking member that secures the locking member to the two portions at the desired position, a balloon catheter on which an expandable prosthetic heart valve is disposed, and an introducer sheath defining an interior in which the adjustment tool and the balloon catheter can be simultaneously located. In certain embodiments, the adjustment tool is further configured to disengage the locking mechanism in the locking member, thereby unlocking the locking member from the two portions of the cord. In particular embodiments, the locking member comprises a pin member and a ring member. The pin member can have a first end, a second end, and openings for receiving the two portions of the cord, and the ring member can have openings for receiving the two portions of the cord and be configured to receive at least a portion of the first end of the pin member. In some embodiments, the adjustment tool comprises a fork member positioned at a distal end of the adjustment tool, an inner push member, and an outer push member. In these embodiments, the inner push member can be contained within a lumen of the adjustment tool and the outer push member can have a greater diameter than the inner push member and surround at least a portion of the inner push member.

Another disclosed embodiment comprises a support band having an annular body that defines a support band interior. The support band of this embodiment is formed from a biocompatible material having a first end that is secured to an opposite second end via a locking mechanism. The support band of this embodiment is sized such that it can be positioned adjacent to the outflow side of the mitral valve of a patient and thereby circumscribe the native leaflets of the mitral valve. Moreover, the support band interior has a fixed diameter when the first end is secured to the second end such that when an expandable prosthetic heart valve is expanded within the mitral valve and within the support band interior, the native leaflets of the mitral valve become pinched between the expandable prosthetic heart valve and the support band, thereby frictionally securing the expandable prosthetic heart valve to the mitral valve. In certain embodiments, the first end of the support band has a larger diameter than the second end, and the first end of the support band defines an interior into which the second end can be inserted and secured by the locking mechanism. In some embodiments, the locking mechanism comprises a snap-fit connection formed between the first end and the second end of the support band. In certain embodiments, the locking mechanism comprises a locking member having a first lumen configured to receive the first end of the support band and a second lumen configured to receive the second end of the support band, the first lumen and the second lumen each comprising one or more angled teeth or collars that allow movement of the locking mechanism along the support band in only a single direction. In some embodiments, the locking mechanism comprises a multi-element mechanism that can be selectively locked to and unlocked from the first end and the second end of the support band. In certain embodiments, one or more clamps are positioned on the support band.

In another disclosed embodiment, a prosthetic heart valve is delivered into an interior of a native heart valve and expanded. A support band is delivered to a position on or adjacent to the surface of the outflow side of the native heart valve such that an interior of the support band surrounds at least a portion of the prosthetic heart valve and at least a portion of one or more native leaflets of the native heart valve. The diameter of the support band is adjusted until the one or more native leaflets of the native heart valve are frictionally secured between the support band and the prosthetic heart valve. The prosthetic heart valve can be an expandable prosthetic heart valve and expanded once it is delivered into the interior of the native heart valve. The support band can be formed from a shape-memory metal or cord of support band material and an adjustable locking member through which portions of the cord extend. During delivery of the support band, the support band can be disconnected from at least a delivery catheter once the one or more native leaflets of the native heart valve are frictionally secured between the support band and the prosthetic heart valve (e.g., by cutting through material used to form the support band).

Other exemplary embodiments disclosed herein are integrated systems for delivering a support stent and a prosthetic valve to a patient's aortic valve. Exemplary embodiments of the system comprise one or more support stent delivery catheters, one or more prosthetic valve delivery catheters at least partially positioned in the interior of the one or more support stent delivery catheters, an expandable support stent releasably coupled to the one or more support stent delivery catheters, and an expandable prosthetic valve releasably coupled to the one or more prosthetic valve delivery catheters. The system can comprise a main catheter at least partially enclosing the one or more support stent delivery catheters and the one or more prosthetic valve delivery catheters. In certain implementations, the one or more support stent delivery catheters can comprise a stent delivery outer catheter (which can have a distal end with an outer fork portion that comprises a plurality of flexible outer prongs) and a stent delivery inner catheter at least partially positioned in the interior of the stent delivery outer catheter (the stent delivery inner catheter can have a distal end with an inner fork portion that comprises a plurality of flexible inner prongs). Furthermore, the expandable support stent can comprise a plurality of retaining arms that are releasably connected to corresponding ones of the outer prongs of the outer fork portion and corresponding ones of the inner prongs of the inner fork portion. In further implementations, the one or more prosthetic valve delivery catheters comprise a prosthetic valve delivery outer catheter (which can have a distal end with an outer fork portion that comprises a plurality of flexible outer prongs) and a prosthetic valve delivery inner catheter at least partially positioned in the interior of the prosthetic valve delivery outer catheter (the prosthetic valve delivery inner catheter can have a distal end with an inner fork portion that comprises a plurality of flexible inner prongs). Furthermore, the expandable prosthetic valve can comprise a plurality of retaining arms that are releasably connected to corresponding ones of the outer prongs of the outer fork portion and corresponding ones of the inner prongs of the inner fork portion. In some implementations, the one or more support stent delivery catheters comprise a stent delivery outer catheter (which can have a distal end with an outer fork portion that comprises a plurality of flexible outer prongs) and a plurality of wires at least partially positioned in the interior of the stent delivery outer catheter. Furthermore, the expandable support stent can comprise a plurality of retaining arms releasably connected to corresponding ones of the outer prongs of the outer fork portion and corresponding ones of the distal ends of the wires. In certain implementations, the one or more prosthetic valve delivery catheters comprise a prosthetic valve delivery outer catheter (which can have a distal end with an outer fork portion that comprises a plurality of flexible outer prongs) and a plurality of wires at least partially positioned in the interior of the prosthetic valve delivery outer catheter. Furthermore, the expandable prosthetic valve can comprise a plurality of retaining arms releasably connected to corresponding ones of the outer prongs of the outer fork portion and corresponding ones of the distal ends of the wires. In further implementations, the system further comprises a prosthetic valve sheath positioned in the interior of the one or more support stent delivery catheters but on an exterior of the one or more prosthetic valve delivery catheters. In these implementations, the expandable support stent can be a self-expanding support stent, and the self-expanding support stent can be positioned within and held in a compressed state by the prosthetic valve sheath. In some implementations, the one or more prosthetic valve delivery catheters comprises a prosthetic valve delivery catheter having a distal balloon portion on which the expandable prosthetic valve is disposed. In certain implementations, the expandable prosthetic valve is located distally of the expandable support stent, whereas in other implementations the expandable prosthetic valve is located concentrically within the expandable support stent. In further implementations, the system additionally comprises a nose cone (e.g., a collapsible nose cone) connected to a distal end of one of the one or more valve delivery catheters. In certain implementations, the system further comprises a nose cone catheter positioned in the interior of the one or more valve delivery catheters, and a nose cone (e.g., a collapsible nose cone) coupled to a distal end of the nose cone catheter. In further implementations, the expandable support stent is generally annular and comprises shaped portions configured to frictionally secure native leaflets of a patient's heart valve against an exterior surface of a prosthetic valve when the patient's heart valve has been replaced by the prosthetic valve.

Embodiments of another disclosed system comprise one or more prosthetic valve delivery catheters, one or more support stent delivery catheters at least partially positioned in the interior of the one or more prosthetic valve delivery catheters, an expandable prosthetic valve releasably coupled to the one or more prosthetic valve delivery catheters, and an expandable support stent releasably coupled to the one or more support stent delivery catheters. The system can further comprise a main catheter at least partially enclosing the one or more support stent delivery catheters and the one or more prosthetic valve delivery catheters. In certain implementations, the one or more support stent delivery catheters comprise a stent delivery inner fork catheter (which can have a distal end with an inner fork portion that comprises a plurality of flexible inner prongs) and a stent delivery outer fork catheter positioned in the interior of the stent delivery inner fork catheter (the stent delivery outer fork catheter can have a distal end with an outer fork portion that comprises a plurality of flexible outer prongs). The expandable support stent can comprise a plurality of retaining arms releasably connected to corresponding ones of the outer prongs of the outer fork portion and corresponding ones of the inner prongs of the inner fork portion. In further implementations, the system further comprises a nose cone catheter, and an elongated nose cone connected to a distal end of the nose cone catheter. In such implementations, the stent delivery inner fork catheter, the stent delivery outer fork catheter, and the expandable support stent can be selectively enclosable within the elongated nose cone. In some implementations, the system further comprises a nose cone catheter, and a nose cone (e.g., a collapsible nose cone) connected to a distal end of the nose cone catheter. In certain implementations, the one or more prosthetic valve delivery catheters comprise a prosthetic valve delivery outer catheter (which can have a distal end with an outer fork portion that comprises a plurality of flexible outer prongs) and a prosthetic valve delivery inner catheter at least partially positioned in the interior of the prosthetic valve delivery outer catheter (the prosthetic valve delivery inner catheter can have a distal end with an inner fork portion that comprises a plurality of flexible inner prongs). The expandable prosthetic valve can comprise a plurality of retaining arms releasably connected to corresponding ones of the outer prongs of the outer fork portion and corresponding ones of the inner prongs of the inner fork portion. In further implementations, the system additionally comprises a prosthetic valve sheath positioned in the interior of the expandable support stent but on an exterior of the one or more prosthetic valve delivery catheters and the one or more support stent delivery catheters. In such implementations, the expandable prosthetic valve can be a self-expanding prosthetic valve positioned within and held in a compressed state by the prosthetic valve sheath. In some implementations, the one or more prosthetic valve delivery catheters comprise a prosthetic valve delivery catheter having a distal balloon portion on which the expandable prosthetic valve is disposed. In certain implementations, the expandable prosthetic valve is located proximally of the expandable support stent, whereas in other implementations the expandable prosthetic valve is located concentrically within the expandable support stent. In further implementations, the expandable support stent is generally annular and comprises shaped portions configured to frictionally secure native leaflets of a patient's heart valve against an exterior surface of a prosthetic valve when the patient's heart valve has been replaced by the prosthetic valve.

Embodiments of another disclosed system comprise a main catheter, one or more support stent delivery catheters positioned in the interior of the main catheter, an expandable support stent positioned in the interior of the main catheter in a radially compressed state (the expandable support stent can comprise a plurality of retaining arms releasably connected to the one or more support stent delivery catheters), a nose cone catheter positioned in the interior of the one or more support stent delivery catheters, and a collapsible nose cone coupled to a distal end of the nose cone catheter. The nose cone catheter and the collapsible nose cone can be retracted into the interior of one of the one or more support stent delivery catheters. In certain implementations, the collapsible nose cone comprises a wire mesh structure (e.g., formed from a shape-memory alloy). In other implementations, the collapsible nose cone is formed of a collapsible foam.

Embodiments of another disclosed system comprise a main catheter, one or more delivery catheters positioned in the interior of the main catheter and configured to deliver an implantable device, a nose cone catheter positioned in the interior of the one or more support stent delivery catheters, and a collapsible nose cone coupled to a distal end of the nose cone catheter. The nose cone catheter and the collapsible nose cone can be retracted into the interior of one of the one or more support stent delivery catheters. The collapsible nose cone can comprise a wire mesh structure (e.g., wherein the wires of the wire mesh structure are formed from a shape-memory alloy) or be formed from a collapsible foam.

Exemplary methods for delivering a support structure together with the expandable prosthetic valve using a single dual-stage system are also disclosed. In certain embodiments, a support structure and an expandable prosthetic valve are advanced through the aortic arch of a patient using a delivery system, the support structure is delivered to a position on or adjacent to the surface of the outflow side of the aortic valve (the support structure defining a support-structure interior), the expandable prosthetic valve is delivered into the aortic valve and into the support-structure interior, and the expandable prosthetic heart valve is expanded while the expandable prosthetic heart valve is in the support-structure interior and while the support structure is at the position on or adjacent to the surface of the outflow side of the aortic valve, thereby causing one or more native leaflets of the aortic valve to be frictionally secured between the support structure and the expanded prosthetic heart valve. In certain implementations, the act of delivering the support structure comprises advancing a stent delivery outer catheter and a stent delivery inner catheter through a distal end of a guide catheter of the delivery system, thereby causing the support structure to expand into an expanded state. In such implementations, the act of delivering the support structure can further comprise, while the support structure is in the expanded state, guiding the support structure to the position on or adjacent to the surface of the outflow side of the aortic valve and into a desired orientation (e.g., an orientation that aligns peaks of the support structure with either the tips or the commissures of the one or more native leaflets). In further implementations, the act of delivering the support structure further comprises retracting the stent delivery inner catheter relative to the stent delivery outer catheter, thereby causing the support structure to be released from the stent delivery inner catheter and the stent delivery outer catheter. In some implementations, the act of delivering the expandable prosthetic valve comprises advancing a balloon portion of a balloon catheter into the aortic valve of the patient, the expandable prosthetic valve being disposed around the balloon portion of the balloon catheter. The expandable prosthetic valve can then be expanded by inflating the balloon portion of the balloon catheter. In certain implementations, the act of delivering the expandable prosthetic valve comprises advancing at least a portion of a prosthetic valve sheath into the aortic valve while the prosthetic valve sheath encloses one or more prosthetic valve delivery catheters. In such implementations, the act of expanding the expandable prosthetic valve can further comprise retracting the prosthetic valve sheath relative to the one or more prosthetic valve delivery catheters and the expandable prosthetic valve, thereby causing the expandable prosthetic valve to be advanced through a distal end of the prosthetic valve sheath and to expand within the aortic valve. A prosthetic valve delivery inner catheter can then be retracted relative to a prosthetic valve delivery outer catheter, thereby causing the prosthetic valve to be released from the prosthetic valve delivery inner catheter and the prosthetic valve delivery outer catheter. In some implementations, the act of delivering the expandable prosthetic heart valve comprises advancing or retracting one or more prosthetic valve delivery catheters relative to a surrounding one or more support stent delivery catheters. In further implementations, a nose cone catheter can be retracted, thereby causing a collapsible nose cone of the delivery system to be withdrawn into a catheter of the delivery system in a collapsed state.

In embodiments of another disclosed method, a support structure and an expandable prosthetic valve are advanced through a puncture in the left ventricle of a patient and toward the aortic valve of the patient using a delivery system, the support structure is delivered to a position on or adjacent to the surface of the outflow side of the aortic valve (the support structure defining a support-structure interior), the expandable prosthetic valve is delivered into the aortic valve and into the support-structure interior, and the expandable prosthetic heart valve is expanded while the expandable prosthetic heart valve is in the support-structure interior and while the support structure is at the position on or adjacent to the surface of the outflow side of the aortic valve, thereby causing one or more native leaflets of the aortic valve to be frictionally secured between the support structure and the expanded prosthetic heart valve. In certain implementations, the act of delivering the support structure comprises advancing one or more stent delivery catheters through a proximal end of an elongated nose cone of the delivery system, thereby causing the support structure to expand into an expanded state. In such implementations, the act of delivering the support structure can further comprise, while the support structure is in the expanded state, guiding the support structure to the position on or adjacent to the surface of the outflow side of the aortic valve and into a desired orientation (e.g., an orientation that aligns peaks of the support structure with either the tips or the commissures of the one or more native leaflets). The act of delivering the support structure can comprise advancing a stent delivery inner catheter distally relative to a stent delivery outer catheter, thereby causing the support structure to be released from the stent delivery inner catheter and the stent delivery outer catheter. The elongated nose cone can then be withdrawn through the expanded support structure. In certain implementations, the act of delivering the expandable prosthetic valve comprises advancing a balloon portion of a balloon catheter into the aortic valve of the patient, the expandable prosthetic valve being disposed around the balloon portion of the balloon catheter. In these implementations, the expandable prosthetic valve can be expanded by inflating the balloon portion of the balloon catheter. In further implementations, the act of delivering the expandable prosthetic valve comprises advancing at least a portion of a prosthetic valve sheath into the aortic valve while the prosthetic valve sheath encloses one or more prosthetic valve delivery catheters and the expandable prosthetic valve. In these implementations, the act of expanding the expandable prosthetic valve can further comprise retracting the prosthetic valve sheath relative to the one or more prosthetic valve delivery catheters and the expandable prosthetic valve, thereby causing the expandable prosthetic valve to be uncovered by the prosthetic valve sheath and to expand within the aortic valve. A prosthetic valve delivery inner catheter can then be retracted relative to a prosthetic valve delivery outer catheter, thereby causing the expandable prosthetic valve to be released from the prosthetic valve delivery inner catheter and the prosthetic valve delivery outer catheter. In some implementations, the act of delivering the expandable prosthetic heart valve comprises advancing or retracting one or more support stent delivery catheters relative to a surrounding one or more prosthetic valve delivery catheters. In further implementations, the support structure and the expanded prosthetic heart valve are disconnected from the delivery system once the one or more native leaflets of the native heart valve are frictionally secured between the support structure and the expanded prosthetic heart valve.

Exemplary embodiments of the support stent or support structure that can be used in the disclosed systems are also described. For example, certain embodiments comprise a support stent having an annular body that defines one or more peaks and one or more valleys along its circumference, where a peak or valley of the support stent comprises one or more outer strut members and one or more inner strut members, the one or more outer strut members being separated from the one or more inner strut members by an aperture and being outwardly angled from the one or more inner strut members. In certain implementations, each of the peaks or the valleys of the support stent comprise one or more of the outer strut members angled outwardly from one or more of the inner strut members. The support stent can consist of six peaks and six valleys. The support stent can be made of a shape-memory alloy. The annular body can be sinusoidal or saw-tooth shaped along its circumference. The biocompatible material can extend across the aperture between the one or more outer strut members and the one or more inner strut members. At least one of the one or more outer strut members can comprise a projection defining an interior space, the interior space being confluent with the aperture. The one or more outer strut members comprise a first outer strut member and a second outer strut member, the first outer strut member and the second outer strut member being configured to cross one another when the support stent is in the uncompressed state. A first distal end of the first outer strut member and a second distal end of the second outer strut member can be connected by a connecting member. One or more of the peaks of the support stent can include enlarged circular head members or enlarged clover-shaped head members.

Other embodiments comprise a support stent having an annular body that defines one or more peaks and one or more valleys along its circumference, and one or more covers that at least partially cover the annular body of the support stent, the one or more covers comprising a biocompatible material. Each of the one or more valleys of the support stent can be at least partially covered by respective ones of the one or more covers. The one or more covers can comprise a plurality of tubular covers that at least partially cover the annular body of the support stent. The one or more covers can comprise one or more covers that extend across one or more of the valleys defined by the support stent. The biocompatible material can be a biocompatible silicone, cloth, or foam. At least one of the one or more covers can be formed from at least a first material and a second material, the first material being thicker than the second material. The thicker first material can be positioned on an inward-facing side of the support stent, or the thicker first material can be positioned at or adjacent to respective nadirs of the one or more valleys of the support stent. Certain implementations further comprise a mechanism configured to allow one or more of the covers to hang below the support stent when the support stent is in the compressed state and to move the one or more of the covers into a final position on the support stent when the support stent is expanded into the uncompressed state. One or more of the peaks of the support stent can include enlarged circular head members or enlarged clover-shaped head members.

Other embodiments comprise a support stent having an annular body that defines one or more peaks and one or more valleys along its circumference, and one or more projections extending outwardly from the support stent at locations at or adjacent to respective nadirs of one or more of the valleys. The one or more projections can be U-shaped projections that curve upwards relative the one or more of the valleys. The one or more projections can alternatively be loop-shaped projections. Each of the loop-shaped projections can include a first end connected to a first one of the valleys and a second end connected to a second one of the valleys adjacent to the first one of the valleys. Certain implementations further comprise a coating of biocompatiable material that at least partially coats the annular body of the support stent or one or more covers that at least partially cover the annular body of the support stent.

Also disclosed herein are leaflet stabilizing systems that can be used when delivering embodiments of the disclosed support structures (support stents) to a native heart valve. Certain exemplary embodiments of such system comprise a main catheter, a leaflet stabilizer outer catheter positioned in the interior of the main catheter, a leaflet stabilizer inner catheter positioned in the interior of the leaflet stabilizer outer catheter, and one or more retractable leaflet stabilizer arms that are configured to extend radially outward from the leaflet stabilizer outer catheter and retract radially inward toward the leaflet stabilizer outer catheter based on relative motion between the leaflet stabilizer outer catheter and the leaflet stabilizer inner catheter. The one or more retractable leaflet stabilizer arms can include distal ends that form one of an open loop, a closed loop, a hook, a clover-shaped profile, or a leaf-shaped profile. The one or more retractable leaflet stabilizer arms can comprise three retractable leaflet stabilizer arms, each of the three retractable leaflet stabilizer arms being configured to engage respective native valve leaflets of an aortic valve. The system can further comprise a respective pivot arm for each of the one or more retractable leaflet stabilizer arms. Each of the pivot arms can have a first end pivotally coupled to a distal portion of the leaflet stabilizer outer catheter and a second end pivotally coupled to a portion of a respective retractable leaflet stabilizer arm. In certain implementations, the system comprises a nose cone coupled to a distal end of the leaflet stabilizer inner catheter. The nose cone can be at least partially hollow. Further, in particular embodiments, the one or more retractable leaflet stabilizer arms are configured to be retractable into the at least partially hollow nose cone in an un-deployed state and are further configured to be uncovered from the at least partially hollow nose cone in a deployed state. The one or more retractable leaflet stabilizer arms can be formed from a variety of materials, including a shape memory alloy. In certain implementations, each of the one or more retractable leaflet stabilizer arms includes a generally flat upper surface and an inwardly-angled lip portion.

Other exemplary embodiments of a leaflet retaining system comprises a main catheter, the main catheter comprising one or more stabilizer arm lumens and further comprising a distal end and a proximal end. In these embodiments, the systems further comprise one or more leaflet stabilizer arms, each of the one or more leaflet stabilizer arms being positioned in the interior of a respective one of the one or more stabilizer arm lumens, and each of the one or more leaflet stabilizer arms further having a respective leaflet stabilizer arm lumen. The one or more leaflet stabilizer arms can be configured to be retractable into the one or more stabilizer arm lumens in an undeployed state and to be extendable through the distal end of the main catheter in a deployed state. Some embodiments of the system further comprise one or more balloon portions, each of the one or more balloon portions being coupled to a distal end of a respective one of the one or more more leaflet stabilizer arms. The one or more balloon portions can be sized to engage native heart valve leaflets when expanded. The system can further comprise at least one inflation lumen fluidly coupled to the leaflet stabilizer arm lumens of the one or more leaflet stabilizer arms. In other embodiments, each of the one or more leaflet stabilizer arms comprises an inflation port. The one or more leaflet stabilizer arms can be formed from a variety of materials, including a shape-memory alloy. In certain implementations, the one or more leaflet stabilizer arms are configured to extend radially outwardly from the distal end of the main catheter and backward toward the proximal end of the main catheter when deployed from the main catheter. In some implementations, the system further comprises a handle at or adjacent to the proximal end of the main catheter, the handle being coupled to each of the one or more leaflet stabilizer arms such that the one or more leaflet stabilizer arms can be moved in unison with movement of the handle.

Also disclosed are exemplary methods for stabilizing leaflets (e.g., during delivery of a support structure or support stent to a native heart valve). In certain embodiments, for example, a leaflet stabilizing system including one or more leaflet stabilizing arms is advanced through a puncture in the left ventricle of a patient and through the aortic valve of the patient. The one or more leaflet stabilizing arms are caused to engage respective native heart valve leaflets of the aortic valve and urge the respective native heart valve leaflets radially inward toward a center of the leaflet stabilizing system. In some embodiments, a support structure is advanced through the aortic arch of the patient and toward the aortic valve using a support structure delivery system, and the support structure is delivered to a position on or adjacent to the surface of the outflow side of the aortic valve. The act of delivering the support structure can include advancing the support structure toward the one or more leaflet stabilizing arms so that the leaflet stabilizing arms contact the support structure. The contact between the support structure and the leaflet stabilizing arms can cause the support structure to rotate to a desired orientation relative to the aortic valve. In certain embodiments, the leaflet stabilizing system is removed from the aortic valve, thereby releasing the respective native heart valve leaflets such that at least a portion of the respective native heart valve leaflets are located in an interior of the support structure when the respective native heart valve leaflets are open. An expandable prosthetic valve can then be delivered into the aortic valve and into the support-structure interior. The expandable prosthetic heart valve can be expanded while the expandable prosthetic heart valve is in the support-structure interior and while the support structure is at the position on or adjacent to the surface of the outflow side of the aortic valve, thereby causing the one or more native heart valve leaflets to be frictionally secured between the support structure and the expanded prosthetic heart valve. In some embodiments, the one or more leaflet stabilizing arms are extended radially outward by moving a leaflet stabilizer outer catheter relative to a leaflet stabilizer inner catheter, distal ends of the extended leaflet stabilizing arms are positioned against the surfaces of the respective native heart valve leaflets on the outflow side of the aortic valve, and the one or more leaflet stabilizing arms are retracted radially inward by moving the leaflet stabilizer outer catheter relative to the leaflet stabilizer inner catheter, thereby causing the leaflet stabilizing arms to urge the respective native heart valve leaflets radially inward toward the center of the leaflet stabilizing system. In other embodiments, the one or more leaflet stabilizing arms are extended radially outward by advancing an at least partially hollow nose cone distally relative to the one or more leaflet stabilizing arms, thereby revealing at least a portion of the leaflet stabilizing arms from an interior of the at least partially hollow nose cone, and distal ends of the extended leaflet stabilizing arms are positioned against the outflow side surfaces of the respective native heart valve leaflets. In still other embodiments, the one or more leaflet stabilizing arms are advanced through lumens of the leaflet stabilizing system so that distal ends of the leaflet stabilizing arms extend outwardly from a distal end of the leaflet stabilizing system and are positioned near or adjacent to surfaces of the respective native heart valve leaflets on the outflow side of the aortic valve. In such embodiments, one or more balloons located at the distal ends of the leaflet stabilizing arms can be inflated so that the inflated balloons contact and urge the respective native heart valve leaflets radially inward toward the center of the leaflet stabilizing system Other disclosed embodiments include embodiments of support stents or support structures that include one or more additional mechanisms for securing the support stent to a prosthetic heart valve. For example, certain embodiments disclosed herein comprise a support stent having an annular body that defines one or more peaks and one or more valleys along its circumference, the support stent being radially compressible into a compressed state and self expandable into an uncompressed state, the support stent being sized such that it can be positioned within the aorta of a patient at a location adjacent to the aortic valve and thereby circumscribe the aortic valve, the support stent further comprising one or more projections extending inwardly toward an interior of the support stent from locations at or adjacent to respective apices of one or more of the peaks. In some embodiments, the one or more projections are projections that project upwardly relative to the horizontal plane of the support stent. In certain embodiments, the one or more projections are configured to engage a frame of a prosthetic heart valve when the one or more projections extend through one or more opposing apertures in the frame. In some embodiments, each of the one or more projections is bendable. In certain embodiments, at least one respective peak of the support stent includes a retaining arm, and the at least one respective peak further includes a respective one of the projections positioned at a bottom edge of the at least one respective peak. In such embodiments, the at least one respective peak of the support stent can further include a first set of one or more sutures on a first side of the at least one respective peak and a second set of one or more sutures on a second side of the at least one respective peak. Further, a wire can extend through an aperture of the retaining arm of the at least one respective peak, through the first set of one or more sutures, and through the second set of one or more sutures, the wire further engaging the respective one of the projections and restraining the respective one of the projections so that the respective one of the projections does not protrude inward.

Other exemplary embodiments disclosed herein comprise a support stent having an annular body that defines one or more peaks and one or more valleys along its circumference, the support stent being radially compressible into a compressed state and self expandable into an uncompressed state, the support stent being sized such that it can be positioned within the aorta of a patient at a location adjacent to the aortic valve and thereby circumscribe the aortic valve, the body of the support stent having a diameter or width along at least a portion of the bottom half of the support stent that is greater than a diameter or width along at least a portion of the upper half of the support stent. In some embodiments, the top half of the support stent is more flexible than the bottom half. In certain embodiments, the support stent is formed from a shape-memory alloy. In some embodiments, the support stent has a generally frustoconical shape in an expanded state.

Further exemplary embodiments disclosed herein comprise a support stent having an annular body that defines one or more peaks and one or more valleys along its circumference, the support stent being radially compressible into a compressed state and self expandable into an uncompressed state, the support stent being sized such that it can be positioned within the aorta of a patient at a location adjacent to the aortic valve and thereby circumscribe the aortic valve, the support stent further comprising one or more extension portions extending longitudinally downward from a bottom edge of the support stent. In some embodiments, the support stent further comprises one or more inward-facing projections located at a distal end of one or more of the extension portions. The inward-facing projections can be hook-shaped projections, platform-shaped projections, or spoon-shaped projections. Additionally, the inward-facing projections can be configured to engage a bottom edge of a frame of a prosthetic heart valve. Certain embodiments further comprise a ring-shaped member coupled to distal ends of the one or more extension portions. In some embodiments, the one or more extension portions extend from the bottom edges of respective valleys of the support stent. In particular embodiments, the one or more extension portions are formed from respective valleys of the support stent. In some embodiments, the one or more extension portions comprise three extension portions, each of the extension portions being configured to extend through the aortic valve at respective commissures between native valve leaflets of the aortic valve. Any of the extension portions in the disclosed embodiments can be bendable.

Other exemplary embodiments disclosed herein comprise a support stent having an annular body that defines one or more peaks and one or more valleys along its circumference, the support stent being radially compressible into a compressed state and self expandable into an uncompressed state, the support stent being sized such that it can be positioned within the aorta of a patient at a location adjacent to the aortic valve and thereby circumscribe the aortic valve, the body of the support stent having an hourglass profile such that the diameter of the interior of the support stent at a middle portion of the support stent is less than the diameter of the interior of the support stent at an upper portion and at a lower portion of the support stent.

Further exemplary embodiments disclosed herein comprise a support stent having an annular body that defines one or more peaks and one or more valleys along its circumference, the support stent being radially compressible into a compressed state and self expandable into an uncompressed state, the support stent being sized such that it can be positioned within the aorta of a patient at a location adjacent to the aortic valve and thereby circumscribe the aortic valve, the body of the support stent having an outwardly bowed portion located between an upper portion of the support stent and a lower portion of the support stent, the diameter of the interior of the support stent at the outwardly bowed portion of the support stent being greater than the diameter of the interior of the support stent at the upper portion and at the lower portion of the support stent.

Other exemplary embodiments disclosed herein comprise a support stent having an annular body that defines one or more peaks and one or more valleys along its circumference, the support stent being radially compressible into a compressed state and self expandable into an uncompressed state, the support stent being sized such that it can be positioned within the aorta of a patient at a location adjacent to the aortic valve and thereby circumscribe the aortic valve, the support stent further comprising one or more protrusions integrally formed from respective valleys of the annular body, the protrusions being formed to extend inwardly toward an interior of the support stent. The one or more protrusions can further include respective apertures. In such embodiments, one or more wires can extend through the respective apertures of the protrusions. Any of the one or more protrusions can be bendable.

Further exemplary embodiments disclosed herein comprise a support stent having an annular body that defines one or more peaks and one or more valleys along its circumference, the support stent being radially compressible into a compressed state and self expandable into an uncompressed state, the support stent being sized such that it can be positioned within the aorta of a patient at a location adjacent to the aortic valve and thereby circumscribe the aortic valve, the support stent further comprising one or more protrusions configured to extend inwardly toward an interior of the support stent in a natural state, the one or more protrusions originating at locations adjacent to the bottom edges of respective valleys of the support stent or at locations along the body of the support stent between the one or more peaks and valleys of the support stent. The one or more protrusions can further include respective apertures. In such embodiments, one or more wires can extend through the respective apertures of the protrusions. In certain embodiments, the one or more protrusions are configured to engage a frame of a prosthetic heart valve when the one or more protrusions extend through one or more opposing apertures in the frame. Further, the one or more protrusions can be bendable. In particular embodiments, the one or more protrusions are shaped such that the protrusions are angled upward toward a top edge of the support stent.

Other exemplary embodiments disclosed herein comprise a support stent having an annular body that defines one or more peaks and one or more valleys along its circumference, the support stent being radially compressible into a compressed state and self expandable into an uncompressed state, the support stent being sized such that it can be positioned within the aorta of a patient at a location adjacent to the aortic valve and thereby circumscribe the aortic valve, the support stent further comprising one or more spherical members attached to or formed integrally with the annular body of the support stent, the spherical members being positioned at locations adjacent to the bottom edges of respective valleys of the support stent.

Also disclosed herein are embodiments of prosthetic heart valves that comprise mechanisms for self securing themselves to an interior of a native heart valve. In certain exemplary embodiments, for instance, a prosthetic heart valve comprises a radially expandable and compressible support frame comprising a plurality of strut members interconnected to each other to form a mesh structure, plural prosthetic leaflets secured to the inside of the support frame, and one or more native valve leaflet retaining arms attached to or formed integrally with the support frame, each of the one or more native valve leaflet retaining arms having a deployed state in which at least a portion of the respective native valve leaflet retaining arm presses against an exterior surface of the support frame. In certain embodiments, one or more of the native valve leaflet retaining arms originate at or adjacent to an outflow end of the support frame, extend radially outward from the support frame, and loop back toward an inflow end of the support frame. In some embodiments, each of the one or more native valve leaflet retaining arms includes a respective aperture. In such embodiments, one or more wires can extend through the respective apertures of the one or more native valve leaflet retaining arms. In some embodiments, one or more of the native leaflet retaining arms includes a distal end portion that defines a larger surface area than a remainder of the respective one or more of the native leaflet retaining arms. In certain embodiments, one or more of the native leaflet retaining arms originate at a location between an outflow end of the support frame and an inflow send of the support frame, and wherein the one or more native leaflet retaining arms extend laterally across the exterior surface of the support frame. In some embodiments, the support frame has an intermediate portion located between an outflow end and an inflow end of the support frame, the intermediate portion of the support stent defining a diameter of the prosthetic heart valve greater than the diameter of the prosthetic heart valve at the outflow end and the inflow end of the support frame.

Also disclosed herein are exemplary methods for mechanically securing a support structure (support stent) to a prosthetic heart valve. In certain exemplary methods disclosed herein a support structure is delivered to a position on or adjacent to the surface of the outflow side of the aortic valve, the support structure defining a support-structure interior, the support structure further comprising one or more protrusions that are configured to extend into the support-structure interior when the protrusions are in a natural state; an expandable prosthetic valve is delivered into the aortic valve and into the support-structure interior; and the expandable prosthetic heart valve is expanded while the expandable prosthetic heart valve is in the support-structure interior and while the support structure is at the position on or adjacent to the surface of the outflow side of the aortic valve, thereby causing one or more native leaflets of the aortic valve to be frictionally secured between the support structure and the expanded prosthetic heart valve. In certain embodiments, the expansion of the prosthetic heart valve causes one or more of the protrusions of the support structure to mechanically engage a frame of the expandable prosthetic valve, the mechanical engagement creating resistance to movement of the expanded heart valve toward an inflow side of the aortic valve relative to the support structure. In some embodiments, the one or more protrusions are held in an undeployed position during delivery of the support structure to the position on or adjacent to the surface of the outflow side of the aortic valve, and the method further comprises releasing the one or more protrusions after the prosthetic heart valve has been expanded into the support-structure interior, thereby allowing the protrusions to move toward the natural state and thereby causing the protrusions to mechanically engage a frame of the expandable prosthetic valve, the mechanical engagement creating resistance to movement of the expanded heart valve toward an inflow side of the aortic valve relative to the support structure. In certain implementations, the releasing is performed by retracting one or more releases wires threaded through respective apertures of the protrusions.

Other exemplary methods disclosed herein comprise delivering a main body of a support structure to a position on or adjacent to the surface of the outflow side of the aortic valve, wherein the support structure defines a support-structure interior and comprises one or more extension portions that extend longitudinally downward from a bottom edge of the support structure, the one or more extension portions comprising distal ends having one or more inward-facing projections. The act of delivering can comprise orienting the support structure during delivery so that the extension portions are generally aligned with commissures of the aortic valve, and advancing the extension portions to an inflow side of the aortic valve through commissures. Such embodiments can further comprise delivering an expandable prosthetic valve into the aortic valve and into the support-structure interior, and expanding the expandable prosthetic heart valve while the expandable prosthetic heart valve is in the support-structure interior and while the main body of the support structure is at the position on or adjacent to the surface of the outflow side of the aortic valve, thereby causing one or more native leaflets of the aortic valve to be frictionally secured between the support structure and the expanded prosthetic heart valve and causing a bottom edge of the expandable prosthetic heart valve to be adjacent to or engaged with one or more of the inward-facing projections at the distal ends of the extension portions.

Also disclosed herein are methods of delivering a support structure and a prosthetic valve at least partially simultaneously using two separate delivery systems. In certain exemplary methods, for example, a support structure is delivered to a position on or adjacent to the surface of the outflow side of the aortic valve using a first delivery system that is advanced through the ascending aorta toward the outflow side of the aortic valve of a patient, and an expandable prosthetic heart valve is delivered into the aortic valve and into the support-structure interior using a second delivery system separate from the first delivery system, the second delivery system also being advanced through the ascending aorta toward the outflow side of the aortic valve of the patient. The expandable prosthetic heart valve can be expanded while the expandable prosthetic heart valve is in the support-structure interior and while the support structure is at the position on or adjacent to the surface of the outflow side of the aortic valve and while both the first delivery system and the second delivery system are at least partially positioned in the ascending aorta, the expanding of the expandable prosthetic heart valve causing one or more native leaflets of the aortic valve to be frictionally secured between the support structure and the expanded prosthetic heart valve. In particular embodiments, the act of delivering the support stent comprises advancing the first delivery system through a carotid artery or subclavian artery, and wherein the delivering the expandable prosthetic heart valve comprises advancing the second delivery system through a femoral artery. In other embodiments, the act of delivering the expandable prosthetic heart valve comprises advancing the second delivery system through a carotid artery or subclavian artery, and wherein the delivering the support structure comprises advancing the first delivery system through a femoral artery. In still other embodiments, the method further comprises (a) advancing the first delivery system through a left femoral artery and advancing the second delivery system through a right femoral artery, or (b) advancing the first delivery system through the right femoral artery and advancing the second delivery system through the left femoral artery The foregoing and other objects, features, and advantages of the disclosed technology will become more apparent from the following detailed description, which proceeds with reference to the accompanying figures.

BRIEF DESCRIPTION OF THE DRAWINGS

FIG. 3 shows the delivery system before the support structure is deployed, and FIG. 4 shows the delivery system after the support structure is deployed.

FIGS. 19-27 are cross-sectional view of a patient's heart illustrating how an exemplary support band can be deployed around the native leaflets of a patient's mitral valve and used to secure a THV to the native leaflets of the mitral valve. In FIGS. 19-27, the support band is deployed using a transapical approach.

FIG. 29 is a top view of an exemplary locking member that can be used to secure portions of a cord of support band material to one another and thereby form a loop.

FIG. 30 is a top view of another exemplary locking member that can be used to secure portions of a cord of support band material to one another and thereby form a loop.

FIG. 31 is a perspective view of an exemplary adjustment tool (or pusher tube) that can be used in connection with the locking member of FIG. 30.

FIG. 40 shows the delivery system before the support structure is deployed, and FIG. 41 shows the delivery system after the support structure is deployed.

In FIGS. 42-46, the support structure is deployed using a transfemoral approach.

FIG. 48 shows the delivery system before the support structure is deployed, and FIG. 49 shows the delivery system after the support structure is deployed.

In FIGS. 50-55, the support structure is deployed using a transapical approach.

FIG. 56 shows the delivery system before the support structure is deployed.

In FIGS. 57-61, the support structure is deployed using a transfemoral approach.

FIG. 63 shows the delivery system before the support structure is deployed.

In FIGS. 64-70, the support structure is deployed using a transapical approach.

FIG. 71A shows the delivery system before the support structure is deployed, and FIG. 71B shows the delivery system after the support structure is deployed.

FIG. 76 is a front view of a portion of an alternative support stent design having one or more projection extending from a support stent strut member.

FIG. 77 is a perspective view of the support stent of FIG. 76 engaging leaflets of a native heart valve.

FIG. 78 is front view of a portion of another alternative support stent design having spaced-apart support stent strut members.

FIG. 79 is a front view of a portion of a further alternative support stent design having spaced-apart support stent strut members.

FIG. 80 is a perspective view of the support stent of FIG. 79 engaging leaflets of a native heart valve.

FIG. 81 is a front view of a flattened-out alternative support stent design having a separate upper strut arms.

FIG. 82 is a front view of the support stent design of FIG. 81 after the support stent has been shape set so that the upper strut arms cross.

FIG. 83 is a perspective view of the support stent of FIG. 82 engaging leaflets of a native heart valve.

FIG. 84 is a front view of a portion of a flattened-out alternative support stent design having a upper strut arms that are connected by a connecting member.

FIG. 85 is a front view of the support stent design of FIG. 84 after the support stent has been shape set so that the upper strut arms cross.

FIG. 89 is a perspective view of a support stent that includes a biocompatible coating and projections at the base of the valleys of the support stent.

FIG. 90 is a perspective view of a support stent that includes U-shaped projections at the base of the valleys of the support stent.

FIG. 91 is a perspective view of a support stent that includes loop-shaped projections at the base of the valleys of the support stent.

FIG. 95 is a perspective view of a support stent that is covered by a cover or coating having thicker portion at or near the bases of the valleys of the support stent.

FIG. 96 is a perspective view of a support stent that includes an integrated cover that covers the valleys of the support stent.

FIG. 97 is a perspective view of a support stent that includes an integrated cover that covers the valleys of the support stent and has portions that extend below the support stent.

FIG. 98 is a perspective view of another support stent that includes an integrated cover that covers the valleys of the support stent and has portions that extend below the support stent.

FIG. 119 is a perspective front view of a fourth exemplary embodiment of a leaflet stabilizing system.

FIG. 120 is a cross-sectional view of the main catheter of the leaflet stabilizing system of FIG. 119.

FIG. 124 is a perspective front view of a first exemplary support stent having inward-facing projections.

FIG. 125 is a perspective front view of the support stent of FIG. 124 coupled to the frame a prosthetic heart valve using the inward-facing projections.

FIG. 126 is a cross-sectional side view of a patient's aortic valve showing the support stent of FIG. 124 mechanically secured to the aortic valve and to the frame of the prosthetic heart valve.

FIG. 127 is a perspective front view of a second exemplary support stent having inward-facing projections.

FIG. 128 is a partial side view of a third exemplary support stent having an inward-facing projection.

FIG. 129 is a partial side view of a portion of an exemplary support stent having an increased diameter or width in its bottom portion.

FIG. 130 is a cross-sectional side view of a patient's aortic valve showing the support stent of FIG. 129 frictionally secured to the aortic valve and to the frame of a prosthetic heart valve.

FIG. 131 is a cross-sectional side view of a patient's aortic valve showing an exemplary support stent having one or more interior ridges. The support stent in FIG. 131 is frictionally secured to the aortic valve and to the frame of the prosthetic heart valve.

FIG. 132 is a perspective front view of a first exemplary support stent having extension portions that include inward-facing projections.

FIG. 133 is a perspective front view of the support stent of FIG. 132 coupled to the frame of a prosthetic heart valve.

FIG. 134 is a bottom cross-sectional view of a patient's aortic valve in which the support stent of FIG. 132 is located and secures a prosthetic heart valve.

FIG. 135 is a perspective front view of a second exemplary support stent having extension portions that include inward-facing projections.

FIG. 136 is a perspective front view of a third exemplary support stent having extension portions that include inward-facing projections.

FIG. 137 is a side view of a laid out, or unrolled, support stent with valleys that are formed into extension portions having inward-facing projections.

FIG. 138 is a perspective front view of a first system for delivering the support stent of FIG. 137.

FIG. 139 is a perspective front view of a second system for delivering the support stent of FIG. 138.

DETAILED DESCRIPTION

General Considerations

Figure 1:
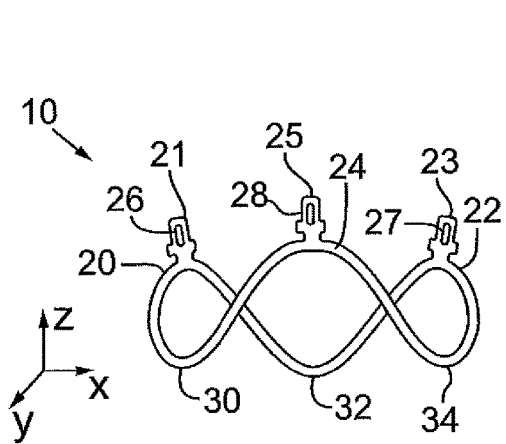
FIG. 1 is a perspective view of an exemplary embodiment of a support structure according to the disclosed technology.

Disclosed below are representative embodiments of a support structure (sometimes referred to as a "support stent," "support frame," "support band," or "support loop") that can be used to secure a prosthetic heart valve within a native heart valve. For illustrative purposes, embodiments of the support structure are described as being used to secure a transcatheter heart valve ("THV") in the aortic valve or the mitral valve of a heart. It should be understood that the disclosed support structure and THV can be configured for use with any other heart valve as well. Also disclosed herein are exemplary methods and systems for deploying the support structure and corresponding THV. Although the exemplary methods and systems are mainly described in connection with replacing an aortic or mitral valve, it should be understood that the disclosed methods and systems can be adapted to deliver a support structure and THV to any heart valve.

For illustrative purposes, certain embodiments of the support structure are described as being used in connection with embodiments of the balloon-expandable THV described in U.S. Patent Application Publication Nos. 2007/0112422 (U.S. application Ser. No. 11/280,063) and 2010/0049313 (U.S. application Ser. No. 12/429,040), which is hereby expressly incorporated herein by reference. It should be understood, however, that this particular usage is for illustrative purposes only and should not be construed as limiting. Instead, embodiments of the disclosed support structure can be used to secure a wide variety of THVs delivered through a variety of mechanisms (e.g., self-expanding heart valves, other balloon-expanding heart valves, and the like). For instance, any of the embodiments described in U.S. Pat. No. 6,730,118 can be used with embodiments of the disclosed support structure. U.S. Pat. No. 6,730,118 is hereby expressly incorporated herein by reference.

The specification and claims sometimes refer to a first catheter being "advanced" relative to a second catheter. It should be noted that this language not only encompasses situations where the first catheter is physically moved by an operator relative to the second catheter but also encompasses situations where the second catheter is physically moved by the operator relative to the first catheter (e.g., the second catheter is withdrawn over the first catheter, thereby causing the first catheter to be advanced relative to the second catheter). Likewise, the specification and claims sometimes refer to a first catheter being "withdrawn" relative to a second catheter. It should be noted that this language not only encompasses situations where the first catheter is physically moved by an operator relative to the second catheter but also encompasses situations where the second catheter is physically moved by the operator relative to the first catheter (e.g., the second catheter is advanced over the first catheter, thereby causing the first catheter to be withdrawn relative to the second catheter).

The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

Exemplary Embodiments for Replacing Aortic Valves

FIG. 1 is a perspective view showing an exemplary embodiment of a support stent or frame 10. Support stent 10 has a generally annular or toroidal body formed from a suitable shape-memory metal or alloy, such as spring steel, Elgiloy®, or Nitinol. Desirably, the material from which the support stent 10 is fabricated allows the support stent to automatically expand to its functional size and shape when deployed but also allows the support stent to be radially compressed to a smaller profile for delivery through the patient's vasculature. In other embodiments, however, the stent is not self expanding. In these embodiments, and as more fully explained below, other mechanisms for expanding the stent can be used (e.g., a balloon catheter).

In the illustrated embodiment, the projection of the support stent 10 onto an x-y plane has a generally annular or toroidal shape. The illustrated support stent 10 further defines a number of peaks and valleys (or crests and troughs) along its circumference. For example, the support stent 10 is sinusoidally shaped in the z direction. In other embodiments, the support stent 10 is shaped differently in the z direction (e.g., sawtooth-shaped, ringlet-shaped, square-wave shaped, or otherwise shaped to include peaks and valleys).

The illustrated support stent 10 includes three peaks 20, 22, 24 and three valleys 30, 32, 34. In the illustrated embodiment, the peaks 20, 22, 24 are positioned above the valleys 30, 32, 34 in the z direction. In some embodiments, the peaks have greater radii than the valleys 30, 32, 34, or vice versa. For instance, in some embodiments, the projection of the support stent 10 onto an x-y plane forms a closed shape having a variable radius (e.g., a starfish shape).

The size of the support stent 10 can vary from implementation to implementation. In particular embodiments, the support stent 10 is sized such that the support stent can be positioned within the aorta of a patient at a location adjacent to the aortic valve, thereby circumscribing the aortic valve. Furthermore, in order to frictionally secure a prosthetic heart valve in its interior, certain embodiments of the support stent 10 have a diameter that is equal to or smaller than the diameter of the prosthetic heart valve when fully expanded. In particular embodiments, for instance, the support stent can have an inner or outer diameter between 10 and 50 mm (e.g., between 17 and 28 mm) and a height between 5 and 35 mm (e.g., between 8 and 18 mm). Furthermore, the thickness of the annular body of the support stent 10 may vary from embodiment to embodiment, but in certain embodiments is between 0.3 and 1.2 mm.

Figure 2:
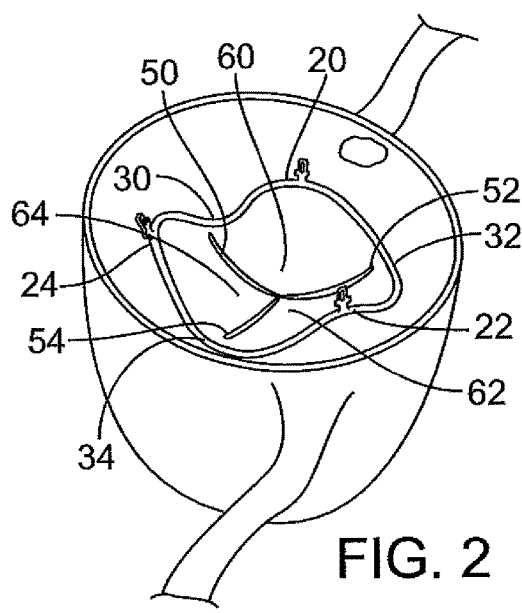
FIG. 2 is a cross-sectional view of a native aortic valve with the support structure of FIG. 1 positioned therein.

FIG. 2 is a perspective view of the exemplary support stent 10 positioned on the surface of an outflow side of a native aortic valve and further illustrates the shape of the support stent. In particular, it can be seen from FIG. 2 that the valleys 30, 32, 34 of the support stent 10 are shaped so that they can be placed adjacent to commissures 50, 52, 54 of the native leaflets 60, 62, 64 of the aortic valve. Furthermore, in the illustrated embodiment, the peaks 20, 22, 24 are shaped so that they generally approximate or mirror the size and shape of the leaflets 60, 62, 64 but are slightly smaller and lower than the height of the leaflets 60, 62, 64 at their tips when the aortic valve is fully opened. In other embodiments, the peaks 20, 22, 24 are oriented so that they are adjacent to the commissures 50, 52, 54 of the native leaflets 60, 62, 64 and the valleys are opposite the apexes of the leaflets 60, 62, 64. The support stent 10 can be positioned in any other orientation within the aortic valve as well.

It should be understood that the shape of the support stent or frame 10 can vary from implementation to implementation. For example, in some embodiments, the support stent is not sinusoidal or otherwise shaped in the z-plane. In other embodiments, the support stent is shaped as a cylindrical band or sleeve. In general, the support stent or frame can be any shape that defines an interior through which a THV can be inserted, thereby causing the native leaflets of the aortic valve (or other heart valve) to be pinched or securely held between the support stent and the THV. Furthermore, the support stent can have a more complex structure. For example, although the support stent illustrated in FIGS. 1 and 2 is formed from a single annular member (or strut), the support stent can comprise multiple annular elements that interlock or are otherwise connected to one another (e.g., via multiple longitudinal members).

Returning to FIG. 1, the illustrated support stent 10 also include retaining arms 21, 23, 25 that can be used to help position and deploy the support stent 10 into its proper location relative to the native aortic valve. The retaining arms 21, 23, 25 can have respective apertures 26, 27, 28. An exemplary deployment system and procedure for deploying the support stent 10 using the retaining arms 21, 23, 25 are described in more detail below. The support stent 10 can also have one or more barbs located on its surface. Such barbs allow the support stent 10 to be more securely affixed to the tissue surrounding the stent or the leaflets of the aorta.

Figure 3:
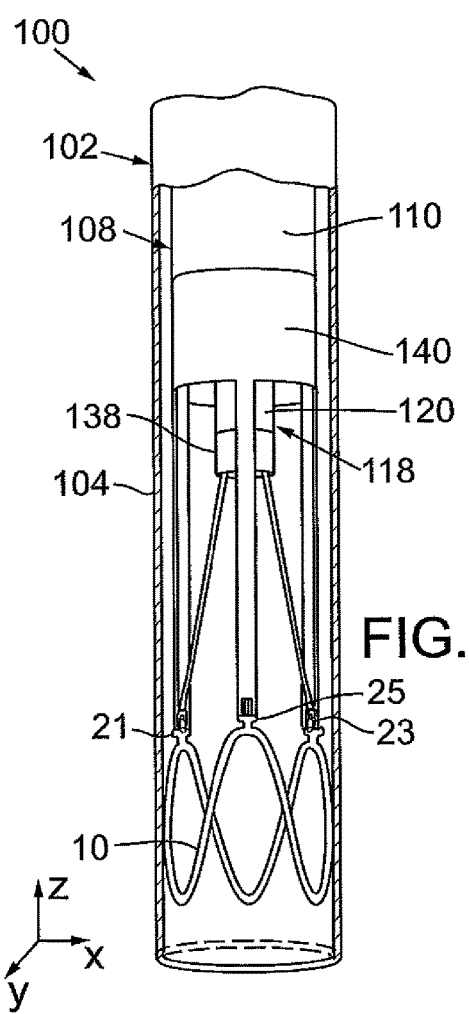
FIGS. 3 and 4 are perspective views of an exemplary delivery system for the support structure of FIG. 1. In particular.
Figure 4:
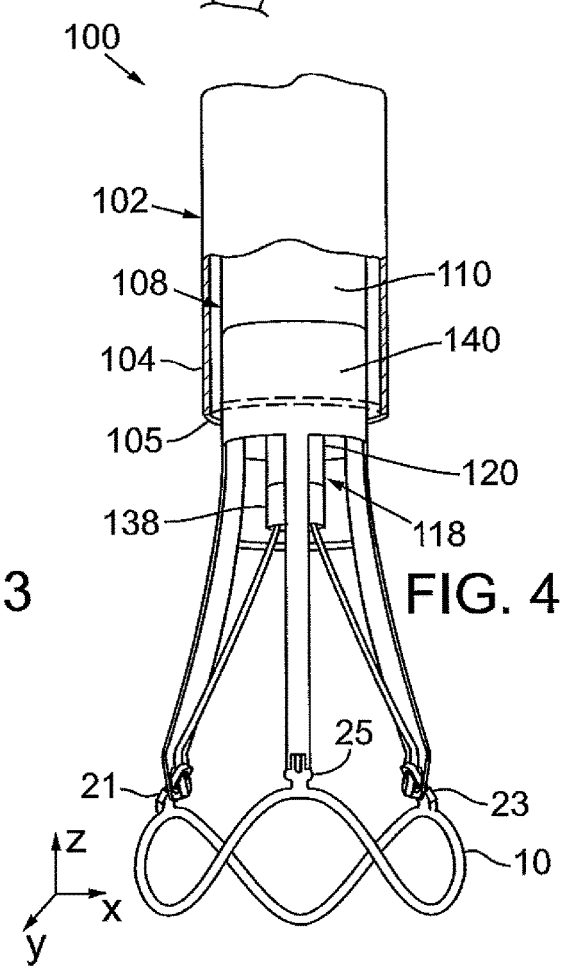

FIGS. 3 and 4 are side views of the distal end portion of an exemplary delivery apparatus 100 for delivering the support stent 10 to its location adjacent the native aortic valve through a patient's vasculature. In particular, FIG. 3 shows the delivery apparatus when the support stent 10 is in a compressed, predeployed state, whereas FIG. 4 shows the delivery apparatus when the support stent 10 is in a decompressed, deployed state. The delivery apparatus 100 comprises a guide catheter 102 having an elongated shaft 104, whose distal end 105 is open in the illustrated embodiment. In other embodiments, the distal end 105 of the guide catheter 102 can be tapered into a conical shape comprising multiple "flaps" forming a protective nose cone that can be urged apart when the support stent 10 and any interior catheters are advanced therethrough. Furthermore, for illustrative purposes, the guide catheter 102 is shown as being partially cut away, thus revealing the catheters in its interior.

A proximal end (not shown) of the guide catheter 102 is connected to a handle of the delivery apparatus 100. During delivery of a support stent, the handle can be used by a clinician to advance and retract the delivery apparatus through the patient's vasculature. In a particular use, the delivery apparatus 100 is advanced through the aortic arch of a patient's heart in the retrograde direction after having been percutaneously inserted through the femoral artery. The guide catheter can be configured to be selectively steerable or bendable to facilitate advancement of the delivery system 100 through the patient's vasculature. An exemplary steerable guide catheter as can be used in embodiments of the disclosed technology is described in detail in U.S. Patent Application Publication No. 2007/0005131 (U.S. patent application Ser. No. 11/152,288), which is hereby expressly incorporated herein by reference.

The delivery apparatus 100 also includes a stent delivery catheter 108 positioned in the interior of the guide catheter 102. The stent delivery catheter 108 has an elongated shaft 110 and an outer fork 140 connected to a distal end portion of the shaft 110. The shaft 110 of the stent delivery catheter 108 can be configured to be moveable axially relative to the shaft 104 of the guide catheter 102. Furthermore, the shaft 110 of the stent delivery catheter 108 can be sized so that its exterior wall is adjacent to or in contact with the inner wall of the shaft 104 of the guide catheter 102.

The delivery apparatus 100 can also include an inner catheter 118 positioned in the interior of the stent deliver catheter 108. The inner catheter 118 can have an elongated shaft 120 and an inner fork 138 secured to the distal end portion of the shaft 120. The shaft 120 of the inner catheter 118 can be configured to be moveable axially relative to the shaft 104 of the guide catheter 102 and relative to the shaft 110 of the stent delivery catheter 108. Furthermore, the shaft 120 of the inner catheter 118 can be sized so that its exterior wall is adjacent to or in contact with the inner wall of the shaft 110 of the stent delivery catheter 108. A guide wire (not shown) can be inserted into the interior of the inner catheter 118. The guide wire can be used, for example, to help ensure proper advancement of the guide catheter 102 and its interior catheters through the vasculature of a patient.

Figure 5:
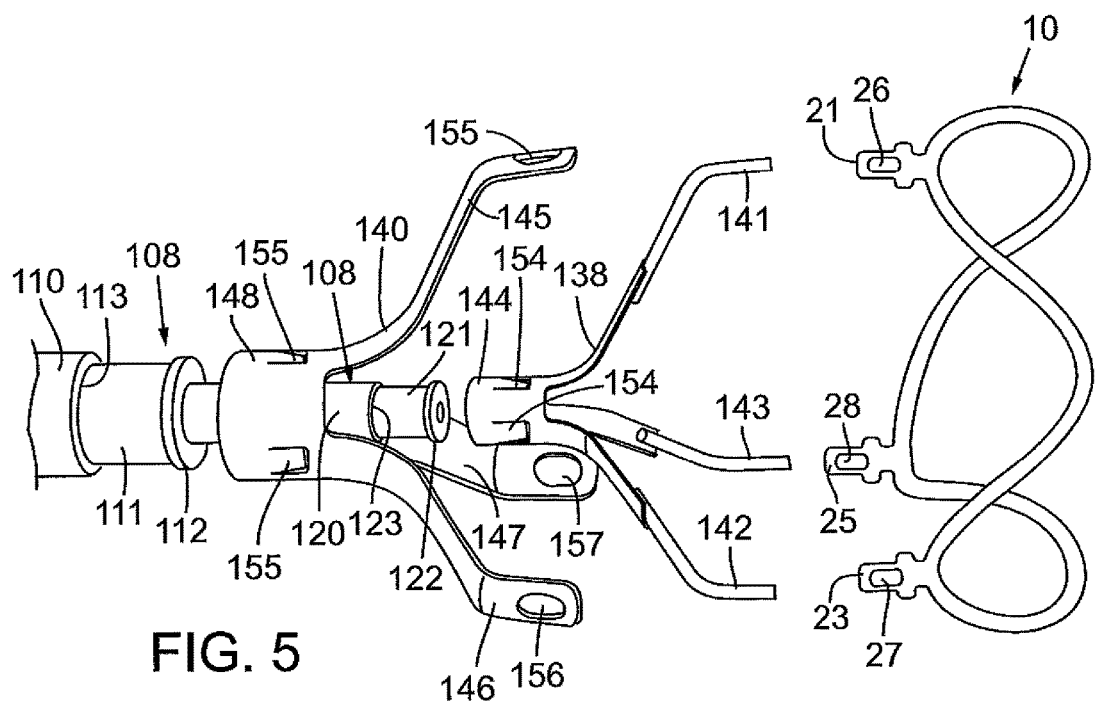
FIG. 5 is an exploded view of the components of the exemplary delivery system shown in FIGS. 3 and 4.

As best shown in FIG. 5, a stent retaining mechanism is formed from the inner fork 138 attached to the distal end portion of the shaft 120 of the inner catheter 118 and the outer fork 140 attached to the distal end portion of the shaft 110 of the stent delivery catheter 108. The inner fork 138 includes a plurality of flexible inner prongs 141, 142, 143 (three in the illustrated embodiment) at is distal end corresponding to the retaining arms 21, 23, 25 of the support stent 10, and a head portion 144 at its proximal end. The outer fork 140 includes a plurality of flexible outer prongs 145, 146, 147 (three in the illustrated embodiment) at its distal end corresponding to the retaining arms 21, 23, 25 of the stent 10, and a head portion 148 at its proximal end. The distal end portions of the outer prongs 145, 146, 147 are formed with respective apertures 155, 156, 157 sized to receive the retaining arms 21, 23, 25.

Figure 6:
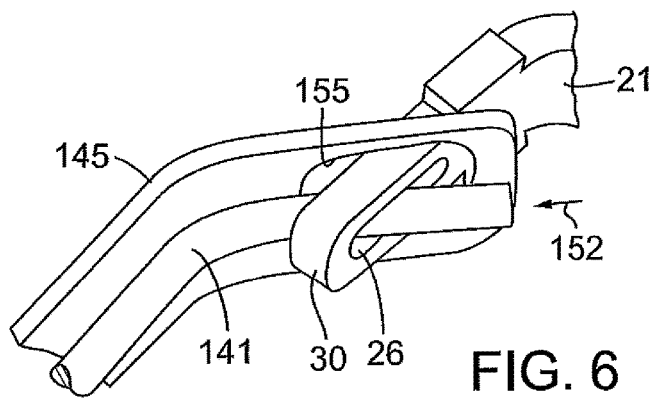
FIG. 6 is a zoomed-in perspective view showing the mechanism for releasably connecting the support structure to the exemplary delivery system of FIGS. 3 and 4.

FIG. 6 is a zoomed-in view of one of the retaining arms 21, 23, 25 as it interfaces with corresponding prongs of the outer fork 140 and the inner fork 138. In this example, retaining arm 21 is shown, though it should be understood that the retaining mechanism is similarly formed for the retaining arms 23, 25. The distal end portion of the outer prong 145 is formed with the aperture 155. When assembled, the retaining arm 21 of the stent is inserted through the aperture 155 of the prong 145 of the outer fork and the prong 141 of the inner fork is inserted through the aperture 26 of the retaining arm 21 so as to retain the retaining arm 21 in the aperture 155.

Retracting the inner prong 141 proximally (in the direction of arrow 152) to remove the prong from the aperture 26 allows the retaining arm 21 to be removed from the aperture 155, effectively releasing the retaining arm from the retaining mechanism. For instance, the outer prong 145 and the retaining arm 21 can be formed such that when the inner prong 141 is withdrawn from the aperture 26, the outer prong 145 flexes radially inward (downward in FIG. 7) and/or the retaining arm 21 of the support stent flexes radially outward (upward in FIG. 7), thereby causing the retaining arm 21 to be removed from the aperture 155. In this manner, the retaining mechanism formed by the inner fork 138 and the outer fork 140 create a releasable connection with the support stent 10 that is secure enough to retain the support stent to the stent delivery catheter 108 and to allow the user to adjust the position of the support stent after it is deployed. When the support stent 10 is positioned at the desired location adjacent to the leaflets of the aortic valve, the connection between the support stent and the retaining mechanism can be released by retracting the inner fork 138 relative to the outer fork 140, as further described below. In other embodiments, the function of the inner fork and the outer fork can be reversed. For example, the prongs of the inner fork can be formed with apertures sized to receive the corresponding retaining arms of the support stent and the prongs of the outer fork can be inserted through the apertures of the retaining arms when the retaining arms are placed through the apertures of the prongs of the inner fork.

As best shown in the exploded view in FIG. 5, the head portion 144 of the inner fork can be connected to the distal end portion of the shaft 120 of the inner catheter 118. In the illustrated embodiment, for example, the head portion 144 of the inner fork is formed with a plurality of angularly spaced, inwardly biased retaining flanges 154. An end piece of the shaft 120 can be formed as a cylindrical shaft having an annular groove 121. On the distal side of the annular groove 121, the shaft 120 can have a collar 122 with an outer diameter that is slightly greater than the diameter defined by the inner free ends of the flanges 154. Thus, the inner fork 138 can be secured to the end piece by inserting head portion 144 of the inner fork onto the end piece of the shaft 120 until the flanges 154 flex inwardly into the annular groove 121 adjacent the collar 122, thereby forming a snap-fit connection between the head portion 144 and the shaft 120. The head portion 144 can have a proximal end that engages an annular shoulder 123 of the shaft 120 that is slightly larger in diameter so as to prevent the head portion from sliding longitudinally along the shaft 120 in the proximal direction.

The head portion 148 of the outer fork can be secured to a distal end portion of the shaft 110 of the stent delivery catheter 108 in a similar manner. As shown in FIG. 5, the head portion 148 can be formed with a plurality of angularly spaced, inwardly biased retaining flanges 155. An end piece of the shaft 110 can be formed as a cylindrical shaft having an annular groove 111. On the distal side of the annular groove 111, the shaft 110 can have a collar 112 with an outer diameter that is slightly greater than the diameter defined by the free ends of the flanges 155. Thus, the outer fork 140 can be secured to the end piece of the shaft 110 by inserting the shaft 110 onto the head portion 148 until the flanges flex inwardly into the groove 111, thereby forming a snap-fit connection between the head portion 148 and the shaft 110. The head portion 148 can have a proximal end that engages an annular shoulder 123 of the shaft 110 that is slightly larger so as to prevent the head portion from sliding longitudinally along the shaft 110 in the proximal direction.

In FIG. 3, the support stent 10 is shown in a radially compressed state in the interior of the elongated shaft 104 of the guide catheter 102. In the radially compressed state, the distance along the z axis between a peak and an adjacent valley of the support stent is greater than the distance along the z axis between the peak and the adjacent valley when the support stent is in it uncompressed state. The distal end portion of the shaft 104 can also be referred to as a delivery sheath for the stent 10. In this undeployed and compressed state, the prongs of the outer fork 140 and the inner fork 138 of the stent delivery catheter 108 and the inner catheter 118 engage the retaining arms 21, 23, 25 of the support stent 10 in the manner described above with respect to FIGS. 5 and 6. To deploy the support stent 10 in the illustrated embodiment (advance the stent from the delivery system), the stent delivery catheter 108 and the inner catheter 118 are advanced toward the distal end 105 of the guide catheter 102 using one or more control handles or mechanisms (not shown) located at the proximal end of the guide catheter 102. This action causes the support stent 10 to be advanced outwardly through the distal end 105 of the guide catheter 102 and expand into its relaxed, uncompressed state (shown, for example, in FIGS. 1 and 2).

FIG. 4 is a perspective view showing the support stent 10 after it has been advanced from the distal end of the guide catheter 102. As seen in FIG. 4, the support stent 10 now assumes its relaxed, uncompressed shape but remains connected to the outer fork 140 and the inner fork 138 at its retaining arms 21, 23, 25. In this configuration, the support stent 10 can be rotated (in the clockwise or counter-clockwise directions) or repositioned (in the proximal and distal directions and/or into a different position in the x-y plane) into a proper orientation adjacent to its intended target area. For example, the support stent 10 can be positioned against the upper surfaces of leaflets of the aortic valve in the manner illustrated in FIG. 2 while the support stent 10 remains connected to the delivery system 100 via the retaining arms 21, 23, 25. As more fully illustrated below in FIGS. 7-12, a prosthetic valve (e.g., a THV) can be delivered to the aortic valve through a transapical approach (e.g., through the apex of the heart and through the left ventricle) and deployed within the native valve such that the prosthetic valve is secured in place by frictional engagement between the support stent, the native leaflets, and the prosthetic valve.

In particular embodiments, the support stent 10 is shaped so that the THV can be positioned in the interior of the support stent along with the native leaflets of the aortic valve. More specifically, the support stent 10 can be shaped such that the native leaflets become trapped or pinched between the support stent 10 and the exterior of the THV when the THV is installed. For instance, the diameter of the support stent 10 can be equal to or smaller than the maximum diameter of the THV when fully expanded, thus causing the THV to be frictionally fit to the leaflets of the aortic valve and the support stent 10. This friction fit creates a solid foundation for the THV that is independent of the state or condition of the leaflets in the aortic valve. For example, THVs are most commonly used for treating aortic stenosis, a condition in which the leaflets of the aortic valve become hardened with calcium. The hardened leaflets typically provide a good support structure for anchoring the THV within the aortic annulus. Other conditions may exist, however, in which it is desirable to implant a THV into the aortic valve and which do not result in a hardening of the leaflets of the aortic valve. For instance, the support stent 10 can be used as a foundation for a THV when treating patients with aortic insufficiency. Aortic insufficiency results when the aortic annulus dilates such that the aortic valve does not close tightly. With this condition, the aortic annulus is larger than normal and would otherwise require a large THV. Using a support stent or frame (such as the support stent or frame 10), however, a smaller THV can be used, thereby making the THV delivery process easier and safer. Furthermore, the use of a support stent protects against displacement of the THV if there is any further dilation of the aortic valve.

A support stent can be used to secure a THV in any situation in which the aorta or aortic valve may not be in condition to help support the THV and is not limited to cases of aortic insufficiency. For example, a support stent 10 can be used in cases in which the aortic annulus is too dilated or in which the leaflets of the aorta are too weak or soft. The support stent can be used to create an anchor for the THV, for instance, in cases in which the native leaflet tissue is too soft because of excess collagen in the aorta.

Figure 7:
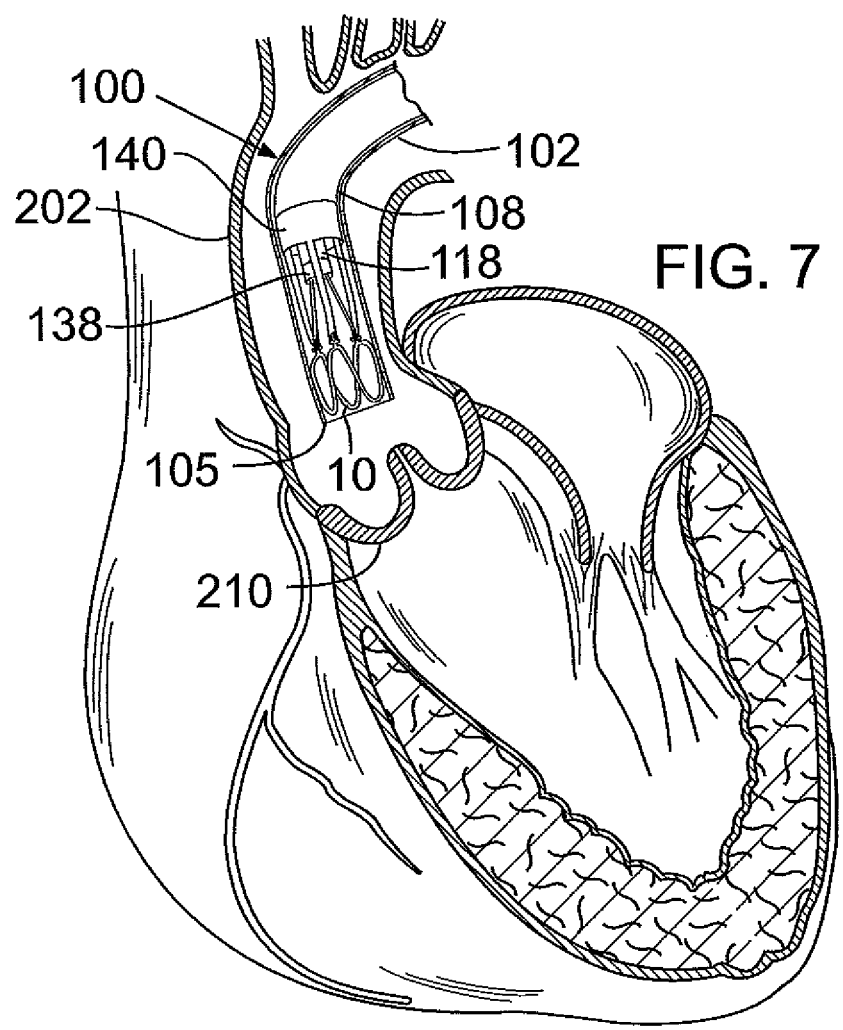
FIGS. 7 and 8 are cross-sectional views of a patient's heart illustrating how the delivery system of FIGS. 3 and 4 can operate to deploy the support structure of FIG. 1 to a desired position on the patient's aortic valve.
Figure 8:
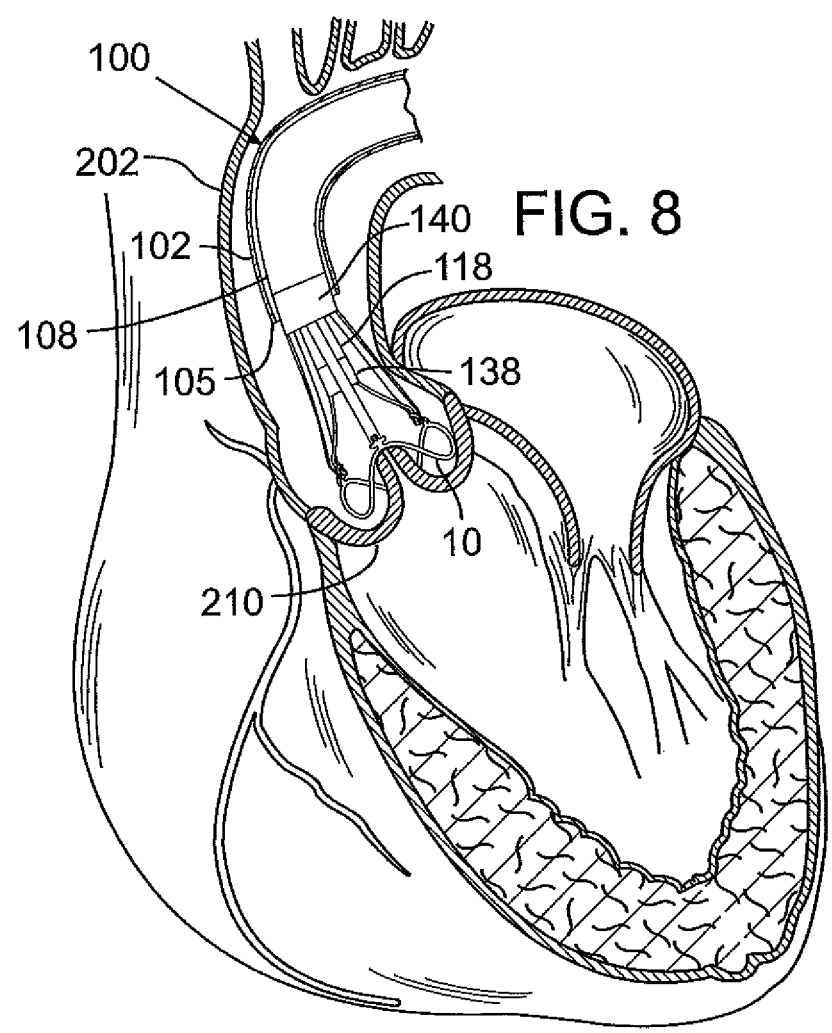

FIGS. 7-13 illustrate one exemplary procedure for deploying the support stent and securing a THV to the support stent. In particular, FIGS. 7-8 are cross-sectional views through the left side of a patient's heart showing the acts performed in delivering the support stent 10 through the aortic arch to the aortic valve. FIGS. 9-13 are cross-sectional views through the left side of a patient's heart showing the acts performed in deploying a THV 250 and having it engage the support stent 10. In order to better illustrate the components of the delivery system 100, the guide catheter 102 is shown partially cut away in FIGS. 7-13. For the sake of brevity, certain details concerning the delivery system of the THV 250 are omitted. Additional details and alternative embodiments of the delivery system for the THV 250 that may be used with the support stent described herein are discussed in U.S. Patent Application Publication No. 2007/0112422 (U.S. application Ser. No. 11/280,063), which is hereby expressly incorporated herein by reference.

FIG. 7 shows the guide catheter 102 of the delivery system 100 as it is advanced through the aortic arch 202 into a position near the surface of the outflow side of the aortic valve 210. The delivery system 100 can be inserted through the femoral artery of the patient and advanced into the aorta in the retrograde direction. FIG. 7 also shows the stent delivery catheter 108, the inner catheter 118, and the support stent 10. In FIG. 7, the support stent 10 is in its radially compressed, predeployment state. Also seen in FIG. 7 are the outer fork 140 and the inner fork 138, which couple the radially compressed support stent 10 to the distal ends of the stent delivery catheter 108 and the inner catheter 118, respectively.

FIG. 8 shows the support stent 10 after it has been advanced through the distal end of the guide catheter 102 and assumes its final, uncompressed shape in a position above and adjacent to the aortic valve 210. The support stent 10 can also be placed directly on the surface of the outflow side of the aortic valve. FIG. 8 shows that the stent delivery catheter 108 and the inner catheter 118 have been advanced though the distal end of the guide catheter 102, thereby pushing the support stent 10 out of the guide catheter and allowing it to expand into its natural shape. In particular embodiments, the support stent 10 is rotated and positioned as necessary so that the support stent generally circumscribes the aortic valve and so that the peaks of the support stent are aligned with the tips of the natural leaflets of the aortic valve 210. Therefore, when the THV is inserted and expanded within the aortic valve 210, the leaflets of the aortic valve will engage at least the majority of the surface in the interior of the support stent 10. This alignment will create an overall tighter fit between the support stent 10 and the THV. In other embodiments, the support stent 10 is rotated and positioned as necessary so that the peaks of the support stent 10 are aligned with the commissures or other portions of the aortic valve. The position of the guide catheter 102 and the support stent 10 relative to the aortic valve 210, as well as the position of other elements of the system, can be monitored using radiopaque markers and fluoroscopy, or using other imaging systems such as transesophageal echo, transthoracic echo, intravascular ultrasound imaging ("IVUS"), or an injectable dye that is radiopaque.

Also seen in FIG. 8 are the prongs of the outer fork 140 and the prongs of the inner fork 138. In the exemplary procedure, the prongs of the outer fork 140 and the inner fork 138 remain secured to the support stent 10 until the THV is deployed and frictionally engaged to the support stent. The inner and outer forks desirably form a connection between the stent 10 and the delivery system that is secure and rigid enough to allow the clinician to hold the stent 10 at the desired implanted position against the flow of blood while the THV is being implanted.

In FIG. 8, the support stent 10 is self-expanding. In other embodiments, however, the support stent may not be self-expanding. In such embodiments, the support stent can be made of a suitable ductile material, such as stainless steel. In addition, a mechanism for expanding the support stent can be included as part of the delivery system 100. For example, the support stent can be disposed around a balloon of a balloon catheter in a compressed state. The balloon catheter can have a shaft that is interior to the inner catheter 118. Because the stent 10 is not self-expanding, the distal end portion of the guide catheter 102 need not extend over the compressed support stent. During delivery of the support stent, the support stent, balloon catheter, inner catheter 118, and stent delivery catheter 108 can be advanced from the distal end of the guide catheter 102. The balloon portion of the balloon catheter can be inflated, causing the support stent to expand. The balloon portion can subsequently be deflated and the balloon catheter withdrawn into the delivery system 100 to remove the balloon from the interior of the support stent while the support stent remains connected to the inner catheter for positioning of the support stent. The delivery of the support stent otherwise proceeds as in the illustrated embodiment using the self-expanding support stent 10.

Figure 9:
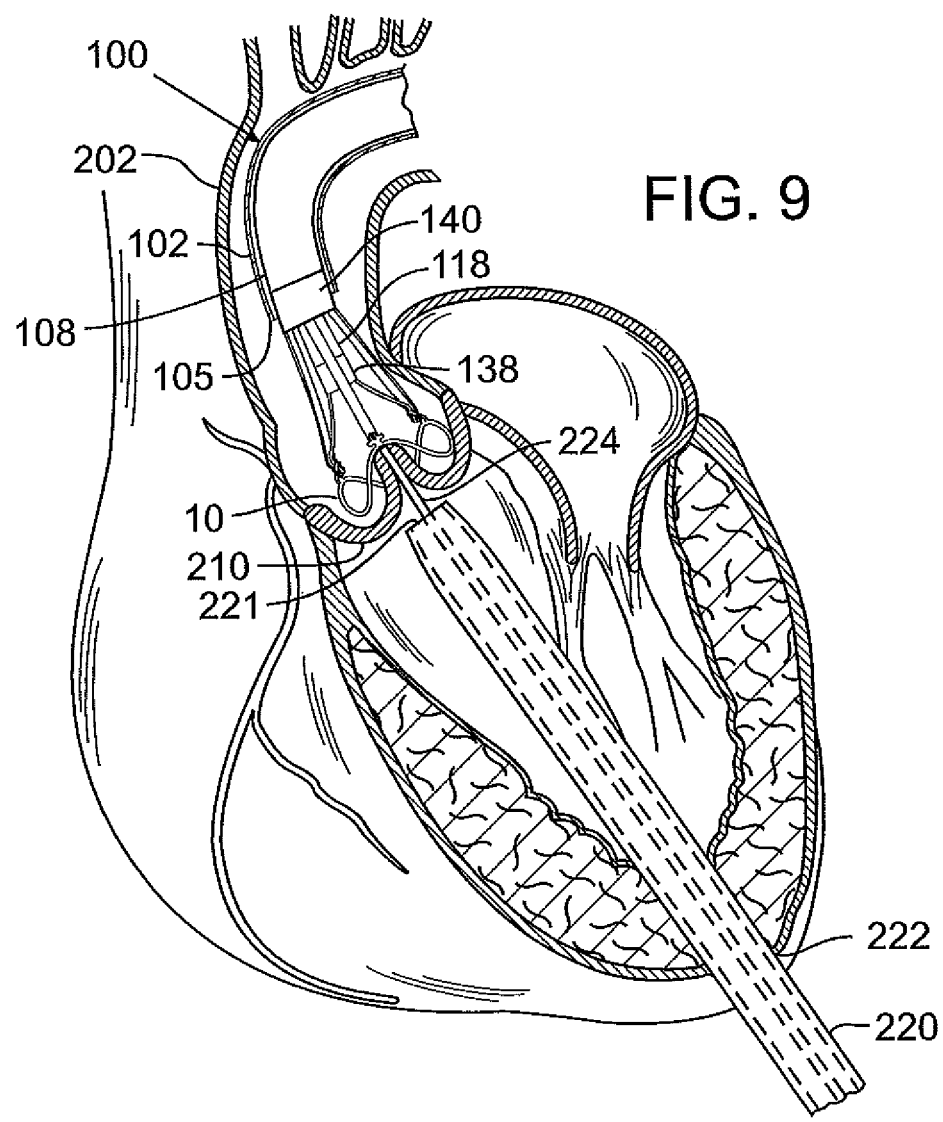
FIGS. 9-13 are cross-sectional views of a patient's heart illustrating how an exemplary transcatheter heart valve ("THV") can be deployed to the patient's aortic valve and frictionally secured to the native leaflets using the support structure of FIG. 1.

FIG. 9 shows an introducer sheath 220 passing into the left ventricle through a puncture 222 and over a guidewire 224 that extends upward through the aortic valve 210. The clinician locates a distal tip 221 of the introducer sheath 220 just to the inflow side of the aortic valve 210. The position of the introducer sheath 220 relative to the aortic valve 210, as well as the position of other elements of the system, can be monitored using radiopaque markers and fluoroscopy, or using other imaging systems.

Figure 10:
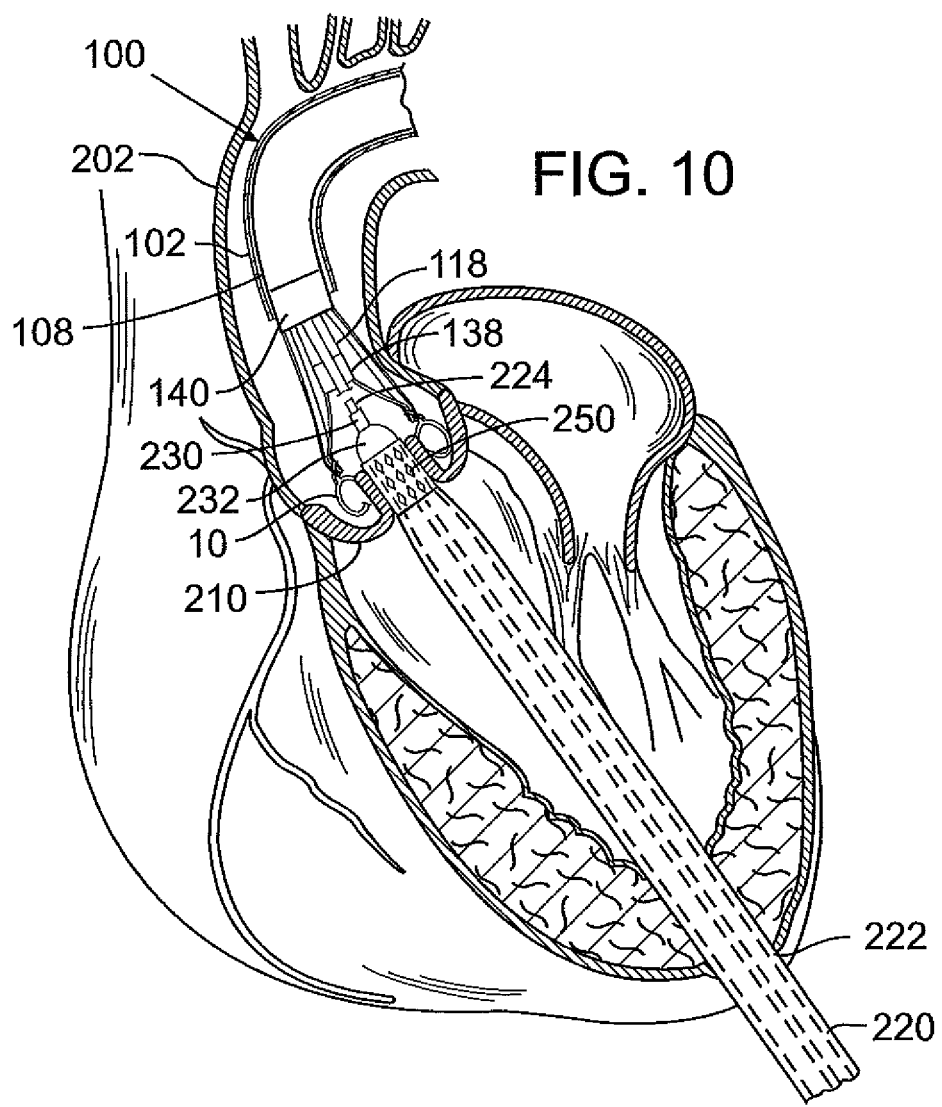
Figure 11:
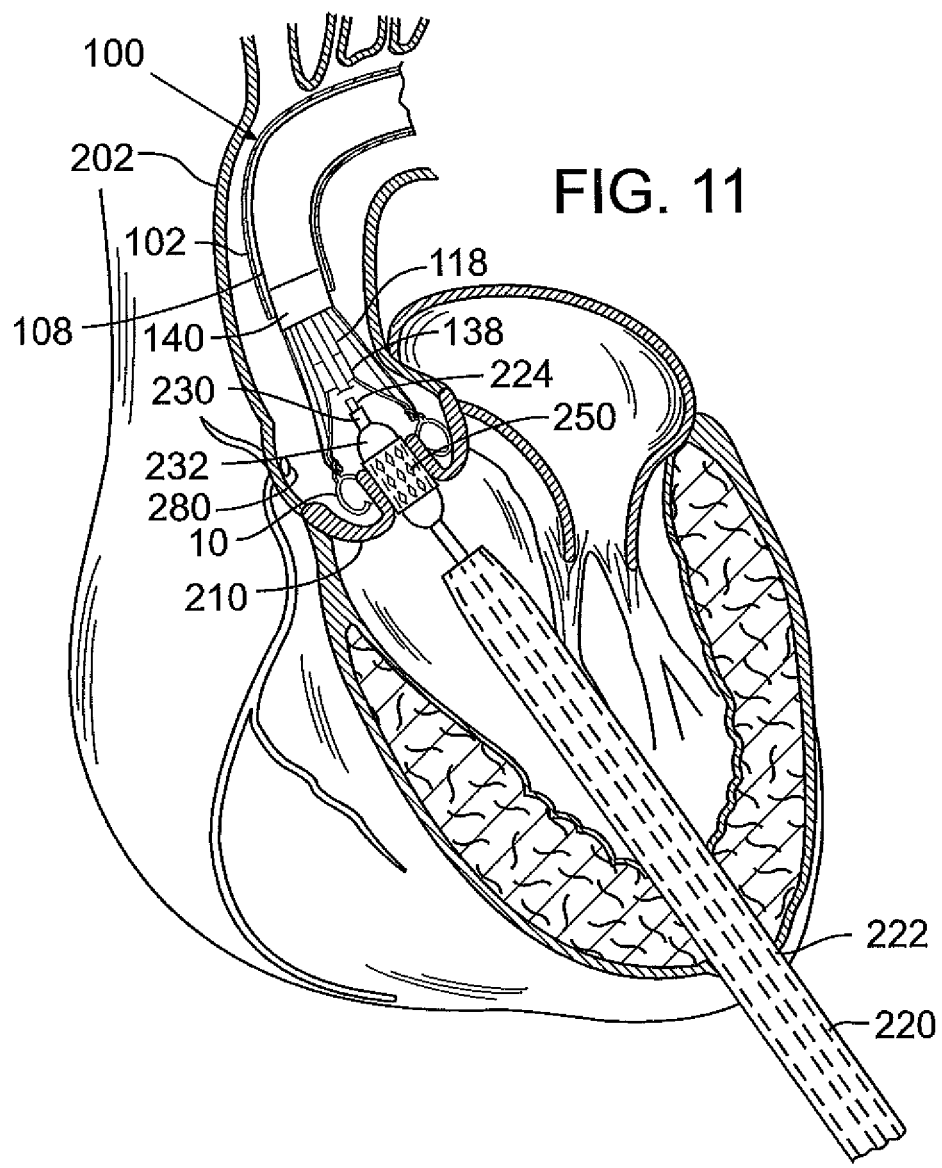
Figure 12:
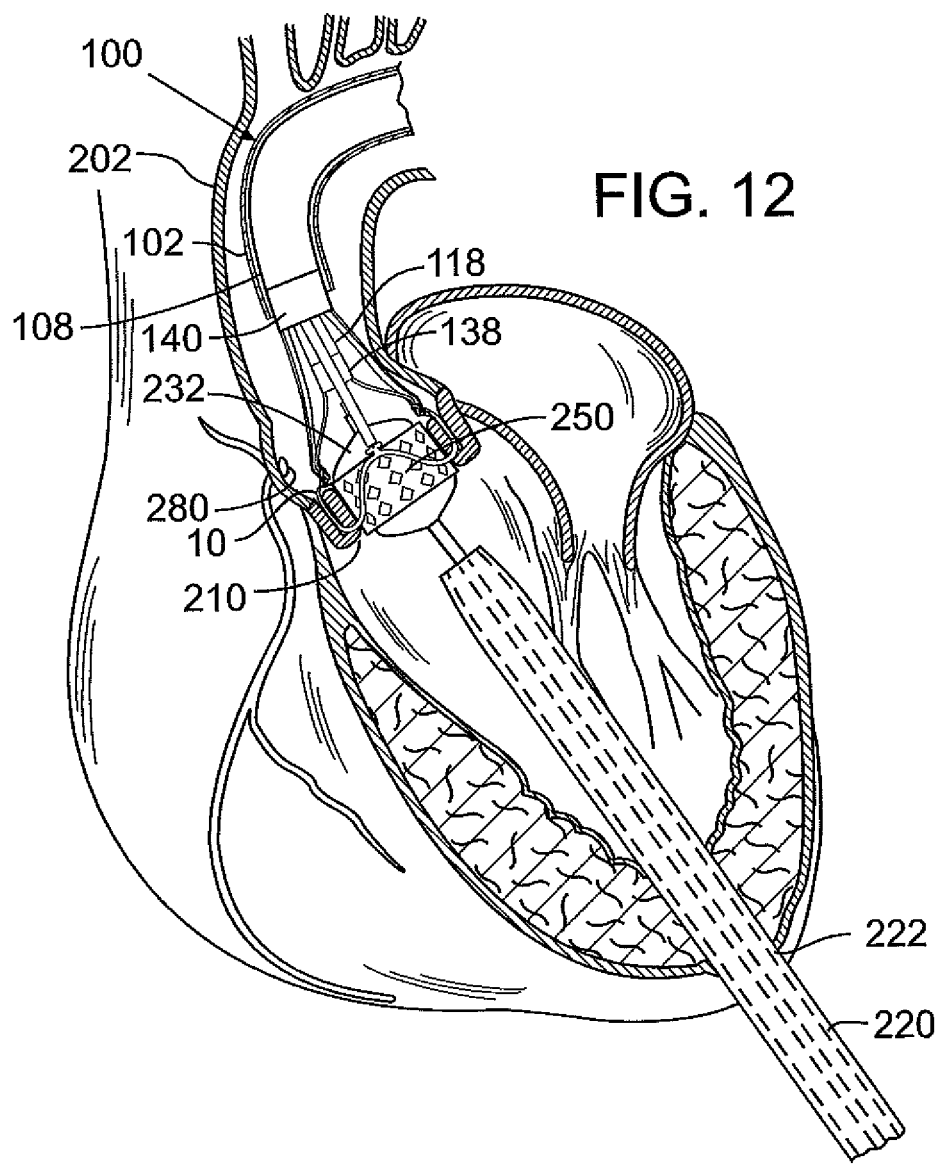
Figure 13:
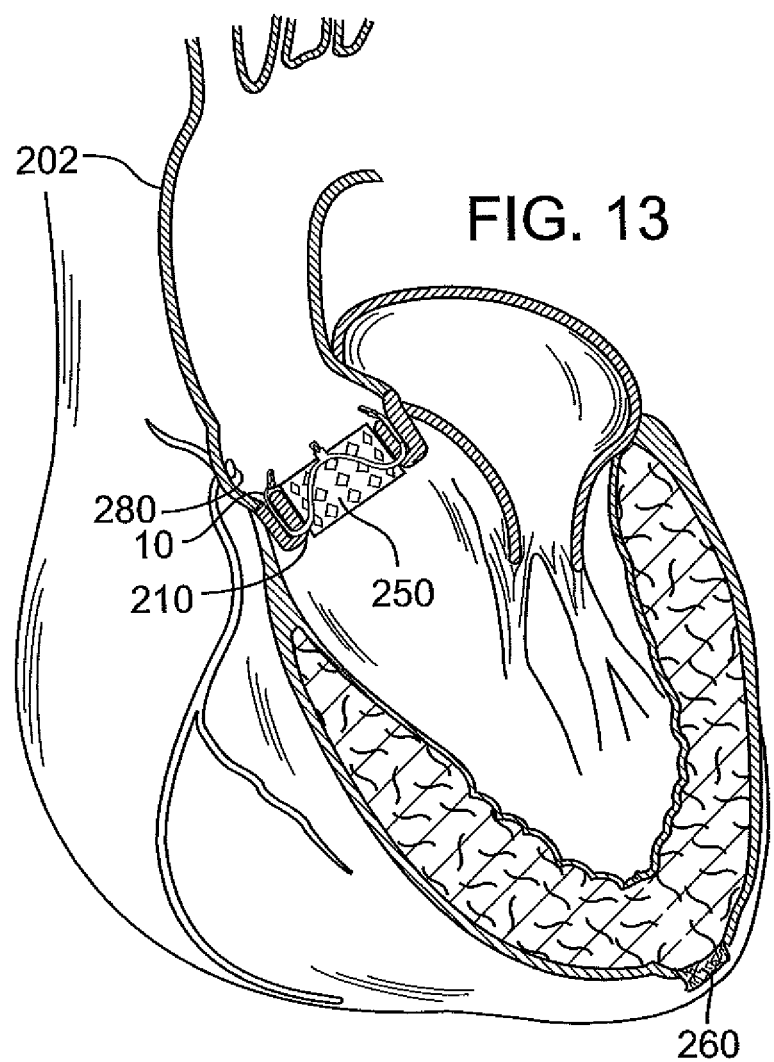

FIG. 10 shows the advancement of the balloon catheter 230 over the guidewire 224 and through the introducer sheath 220. Ultimately, as seen in FIG. 11, the THV 250 is located at the aortic annulus and between the native aortic leaflets. FIG. 11 also illustrates retraction of the introducer sheath 220 from its more distal position in FIG. 10. Radiopaque markers may be provided on the distal end of the introducer sheath 220 to more accurately determine its position relative to the valve 210 and balloon 232. In order to better illustrate the components of the delivery system for the THV, FIGS. 10-11 do not show the front third of the support stent 10 or the corresponding outer and inner prong of the outer fork and the inner fork, respectively. Furthermore, for purpose of illustrating the relative position of the support stent 10 on the THV 250, FIGS. 12-13 show the front third of the support stent 10 and the front of the THV 250, but do not show the portions of the native heart valve that would be secured by the front of the support stent 10. It is to be understood, however, that a corresponding leaflet of the native heart valve would be secured between the support stent 10 and the THV 250.

Again, the precise positioning of the THV 250 may be accomplished by locating radiopaque markers on its distal and proximal ends. In some embodiments, the clinician can adjust the position of the valve 250 by actuating a steering or deflecting mechanism within the balloon catheter 230. Furthermore, the rotational orientation of the valve 250 can be adjusted relative to the cusps and commissures of the native aortic valve by twisting the balloon catheter 230 from its proximal end and observing specific markers on the valve (or balloon catheter) under fluoroscopy. One of the coronary ostia 280 opening into one of the sinuses of the ascending aorta is also shown in FIG. 11, and those of skill in the art will understand that it is important not to occlude the two coronary ostia with the prosthetic valve 250.

FIG. 11 shows the THV 250 in its contracted or unexpanded state crimped around the balloon 232. When the clinician is satisfied of the proper positioning and rotational orientation of the valve 250, the balloon 232 is expanded to engage the support stent 10 as seen in FIG. 12. The engagement of the support stent 10 to the exterior of the THV 250 pinches the leaflets of the aortic valve between the support stent and the THV 250, and thereby secures the THV within the annulus of the aortic valve. Once secured into this position, the inner catheter 118 of the delivery system 100 can be retracted, thereby causing the prongs of the inner fork 138 to become disengaged from the retaining arms of the support stent 10. Once the prongs of the inner fork 138 are disengaged, the prongs of the outer fork 140 can be disengaged from the retaining arms by retracting the stent delivery catheter 108. Once disengaged from the support stent, the delivery system 100 can be retracted from the aortic arch and removed from the patient.

It should be noted that the valve 250 can take a variety of different forms and may comprise an expandable stent portion that supports a valve structure. The stent portion desirably has sufficient radial strength to hold the valve at the treatment site and to securely engage the support stent 10. Additional details regarding balloon expandable valve embodiments that can be used in connection with the disclosed technology are described in U.S. Pat. Nos. 6,730, 118 and 6,893,460, both of which are hereby expressly incorporated herein by reference.

Once the valve 250 is properly implanted, as seen in FIG. 13, the balloon 232 is deflated, and the entire delivery system including the balloon catheter 230 is withdrawn over the guidewire 224. The guidewire 224 can then be withdrawn, followed by the introducer sheath 220. Ultimately, purse-string sutures 260 at the left ventricular apex can be cinched tight and tied to close the puncture.

Figure 14:
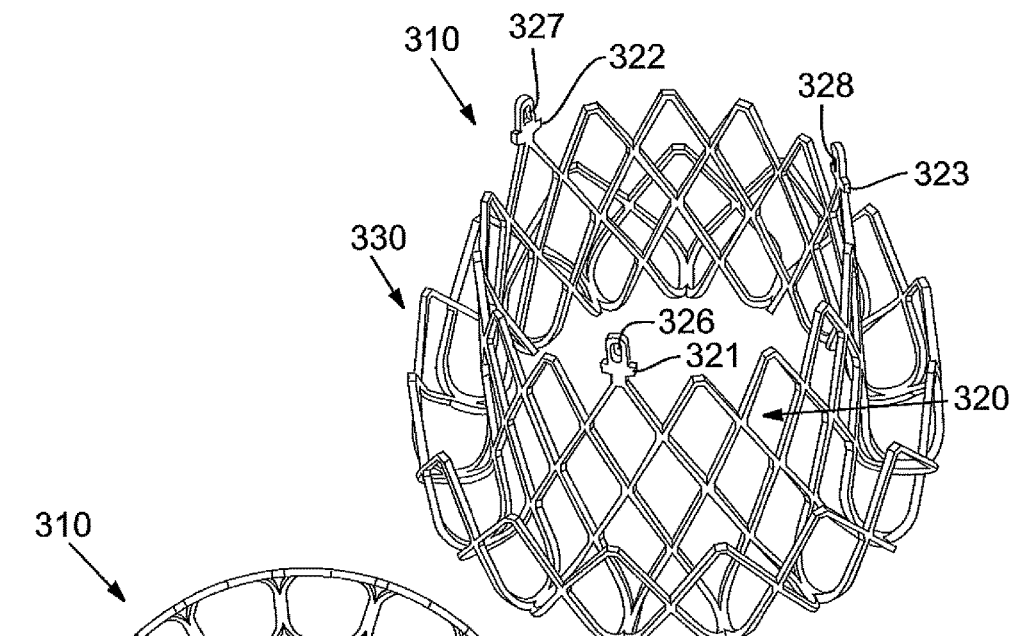
FIG. 14 is a perspective view of another exemplary embodiment of a support structure according to the disclosed technology.
Figure 15:
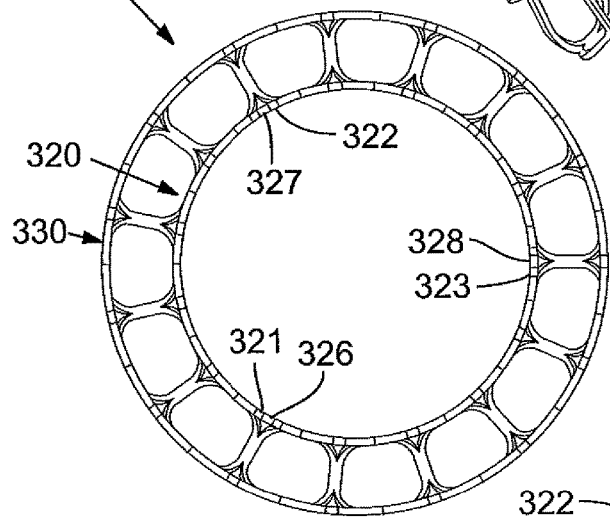
FIG. 15 is a top view of the support structure embodiment shown in FIG. 14
Figure 16:
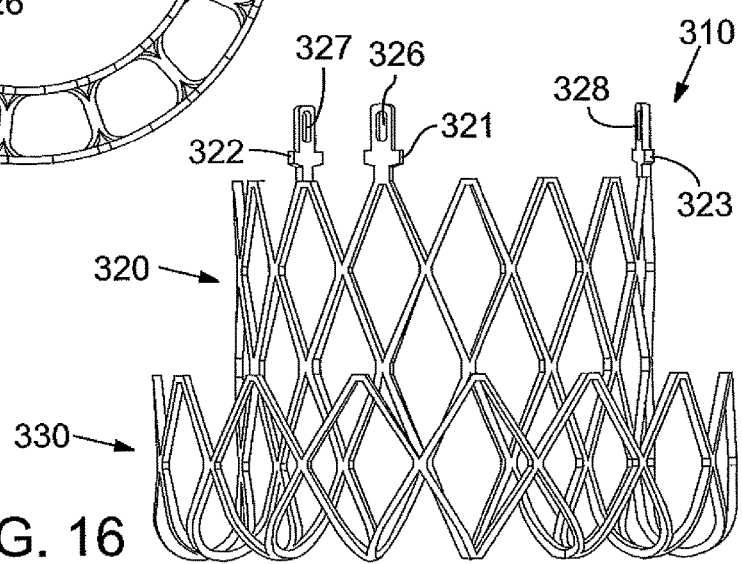
FIG. 16 is a side view of the support structure embodiment shown in FIG. 14.

FIGS. 14-16 shows another embodiment of a support stent or frame 310 that can be used to help secure a THV into the interior of a native heart valve, such as the aortic valve. In particular, FIG. 14 is a perspective view of the support stent 310, FIG. 15 is a top view of the support stent 310, and FIG. 16 is a side view of the support stent 310. Like support stent 10, support stent 310 has a generally annular or toroidal body formed from a suitable shape-memory metal or alloy, such as spring steel, Elgiloy®, or Nitinol. The support stent 310 is also radially compressible to a smaller profile and can self expand when deployed into its functional size and shape. In other embodiments, however, the support stent 310 is not self expanding.

The support stent 310 includes a generally cylindrical main body portion 320 and a rim portion 330. The support stent 310 can be a mesh structure, which can be formed, for example, from multiple elements in which approximately half of the elements are angled in a first direction and approximately half of the elements are angled in a second direction, thereby creating a criss-cross or diamond-shaped pattern. In the illustrated embodiment, the rim portion 330 has a greater diameter than the main body portion 320 and is formed as an extension at a bottom region of the main body portion that is folded outwardly from the main body portion and back toward a top region of the main body portion. The rim portion 330 thus forms a U-shaped rim or lip around the bottom region of the support stent 310. In general, the rim portion 330 is designed to have a diameter that is slightly larger than the walls of the aortic arch that surround the aortic valve. Thus, when the support stent 310 is delivered to the aortic valve and deployed at the aorta, the rim portion 330 expands to engage the surrounding aorta wall and frictionally secures the support stent 310. At the same time, the main body portion 320 defines an interior into which an expandable THV can be expanded and which further engages the native leaflets of the aortic valve. Thus, the main body portion 320 operates in the same manner as the support stent 10 described above and illustrated in FIGS. 1-12, whereas the rim portion 330 of the support stent 310 operates to secure the support stent in place by engaging the walls of the aorta that surround the aortic valve.

As best seen in FIGS. 14 and 16, the support stent 310 further includes retaining arms 321, 322, 323 that can be used to help position and deploy the support stent 310 into its proper location relative to the native aortic valve. The retaining arms 321, 322, 323 can have respective apertures 326, 327, 328. In general, the retaining arms 321, 322, 323 are constructed and function in a similar manner as retaining arms 21, 23, 25 described above in the embodiment illustrated in FIGS. 1-12.

Figure 17:
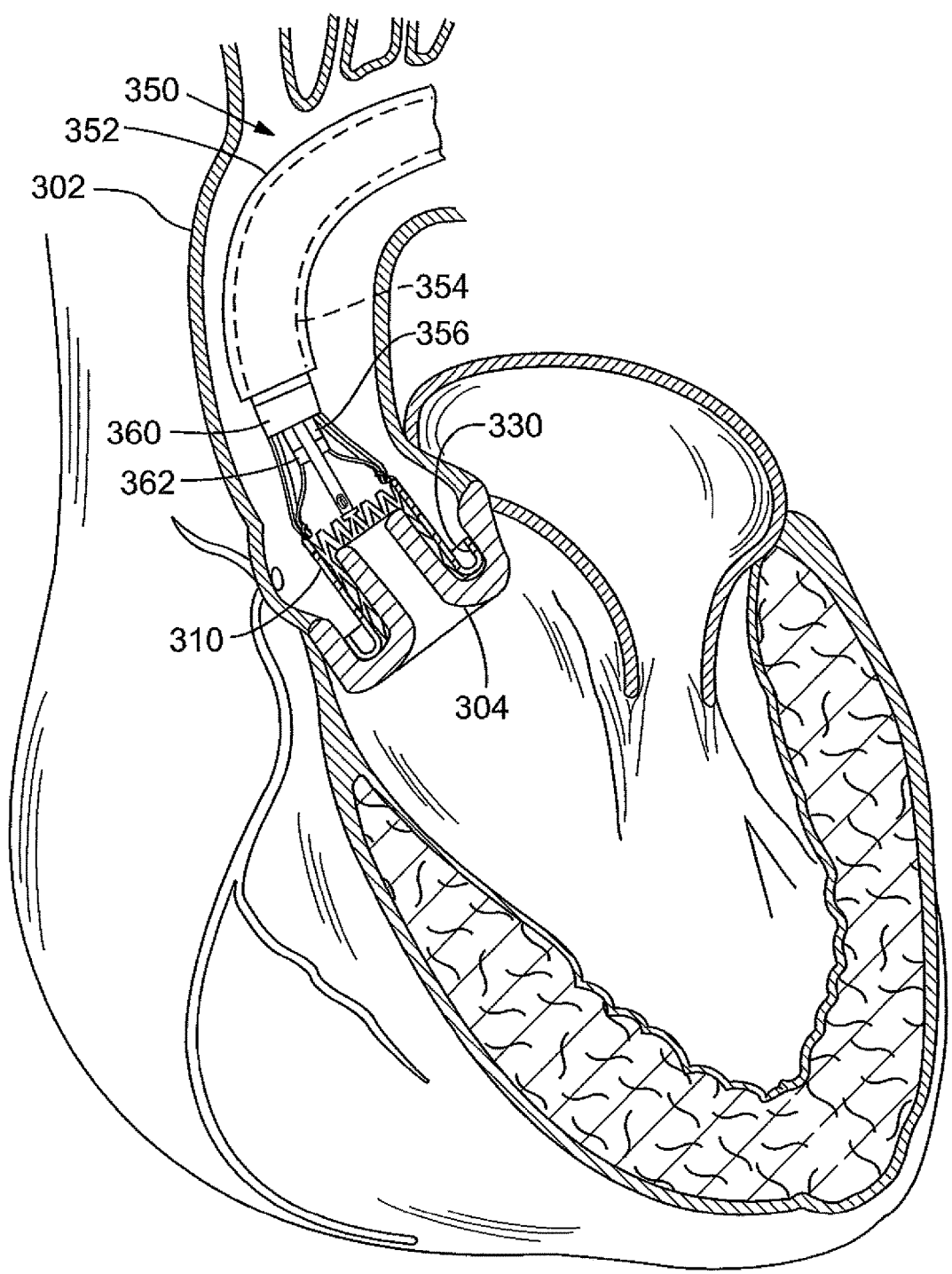
FIG. 17 is a cross-sectional view of a patient's heart illustrating how a delivery system can operate to deploy the support structure of FIG. 14 to a desired position on the patient's aortic valve.
Figure 18:
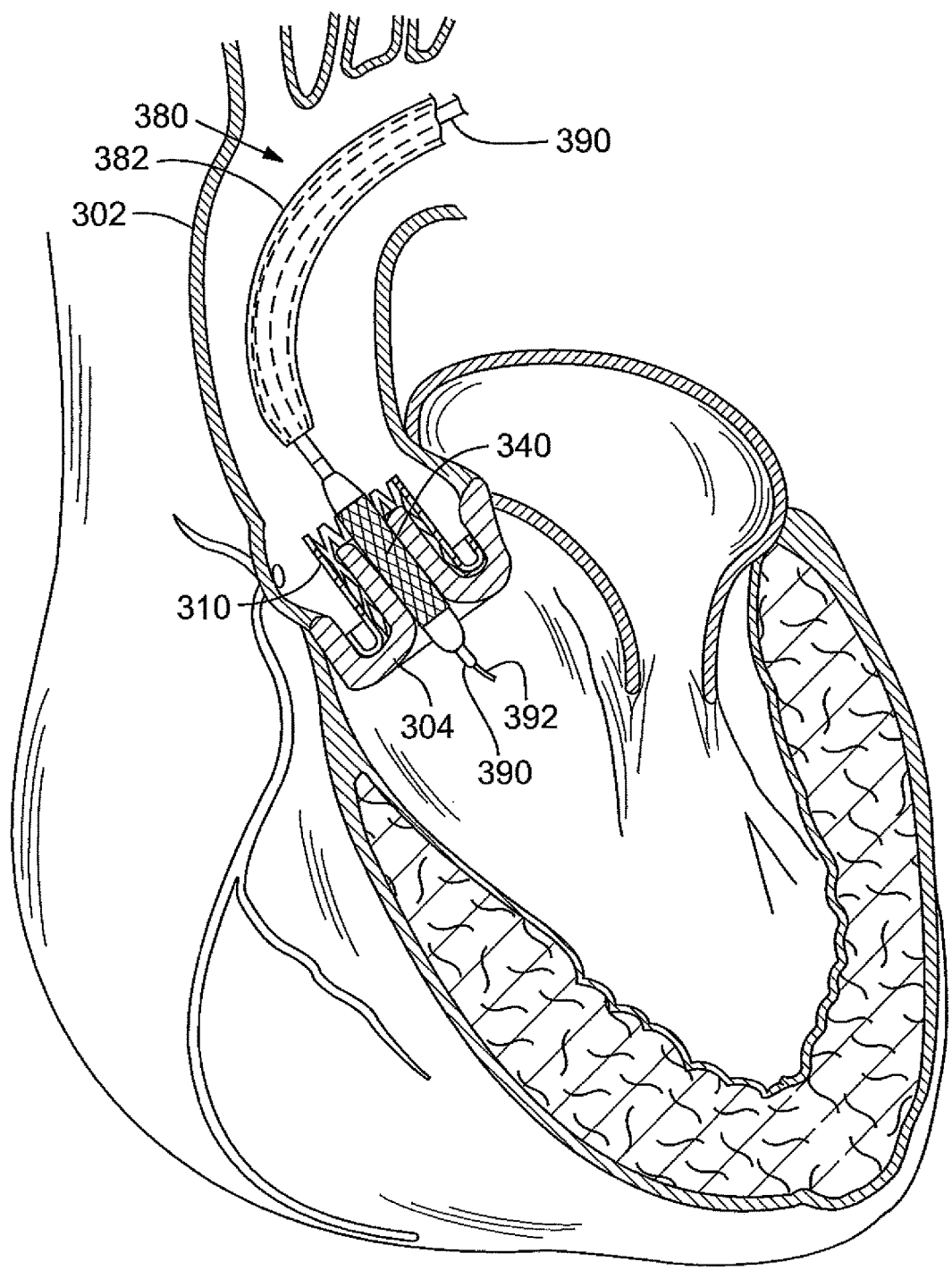
FIG. 18 is a cross-sectional view of a patient's heart illustrating how an exemplary THV can be deployed through the aortic arch and into the patient's aortic valve, where it can be frictionally secured to the native leaflets using the support structure of FIG. 14.

FIGS. 17-18 illustrate one exemplary procedure for deploying the support stent 310 and securing a THV 340 within an interior of the support stent. In particular, FIGS. 17-18 are cross-sectional views through the left side of a patient's heart showing the acts performed in delivering the support stent 310 through the aortic arch to the aortic valve. For the sake of brevity, certain details concerning the delivery system of the THV 340 are omitted. Additional details and alternative embodiments of the delivery system for the THV 340 that may be used with the support stent described herein are discussed in U.S. Patent Application Publication No. 2008/0065011 (U.S. application Ser. No. 11/852,977) and U.S. Patent Application Publication No. 2007/0005131 (U.S. application Ser. No. 11/152,288), which are hereby expressly incorporated herein by reference.

FIG. 17 shows an outer catheter 352 (which can be a guide catheter) of a delivery system 350 as it is advanced through the aortic arch 302 into a position near the surface of the outflow side of the aortic valve 304. The delivery system 350 can be inserted through the femoral artery of the patient and advanced into the aorta in the retrograde direction. FIG. 17 also shows a stent delivery catheter 354, an inner catheter 356, and the support stent 310. Also seen in FIG. 17 are the outer fork 360 and the inner fork 362, which couple the support stent 310 to the distal ends of the stent delivery catheter 354 and the inner catheter 356, respectively.

More specifically, FIG. 17 shows the support stent 310 after it has been advanced through the distal end of the guide catheter 352 and assumes its final, uncompressed shape in a position adjacent to the aortic valve 304. In order to better illustrate the components of the delivery system for the THV, FIGS. 17-18 do not show the entire front side of the support stent 310 or the corresponding valve leaflet that would be secured by the front side of the support stent 310. It is to be understood, however, that in practice the entire support stent 310 would exist and engage a corresponding leaflet of the native heart valve.

The support stent 310 can be positioned adjacent to the aortic valve 304 so that the rim portion 330 of the support stent engages the walls surrounding the aortic valve 304 and exerts an outward force against those walls, thereby securing the support stent 310 within the aorta. This positioning can be achieved, for example, by advancing the guide catheter 352 to a position directly adjacent the aortic valve 304 while the stent delivery catheter 354 and the inner catheter 356 are undeployed and while the support stent 310 remains in its compressed state. The guide catheter 352 can then be retracted while the stent delivery catheter 354 and the inner catheter 356 are held in place, thereby allowing the support stent 310 to expand toward its natural shape. As with the delivery system 100 described above, the position of the guide catheter 352 and the support stent 310 relative to the aortic valve 304, as well as the position of other elements of the system, can be monitored using radiopaque markers and fluoroscopy, or using other imaging systems such as transesophageal echo, transthoracic echo, IVUS, or an injectable dye that is radiopaque.

Once the support stent 310 is positioned into the desired location adjacent the aortic valve 304, the prongs of the inner fork 362 can be disengaged from the corresponding apertures of the retaining arms of the support stent 310. For example, the inner catheter 356 can be retracted into the interior of the stent delivery catheter 354, thereby releasing the support stent 310 from the outer fork 360 and the inner fork 362. The delivery system 350 can then be retracted from the aorta and removed from the patient's body.

With the support stent 310 secured to the aortic valve, a THV (such as any of the THVs discussed above) can be introduced. In contrast to the procedure illustrated in FIGS. 7-13, a delivery system having a delivery catheter that is advanced through the patient's aorta can be used to deliver the THV. In other words, a transfemoral approach can be used. For instance, any of the exemplary systems and methods described in U.S. Patent Application Publication No. 2008/0065011 (U.S. application Ser. No. 11/852,977) or U.S. Patent Application Publication No. 2007/0005131 (U.S. application Ser. No. 11/152,288) can be used with the support stent 310. Alternatively, the transapical approach shown in FIGS. 7-13 can be used.

FIG. 18 shows delivery system 380 comprising an outer catheter 382 (which can be a guide catheter) and a balloon catheter 390 extending through the guide catheter. The balloon catheter 390 has a balloon at its distal end on which the THV is mounted. As with the delivery system 350, the delivery system 380 can be inserted through the femoral artery of the patient and advanced into the aorta in the retrograde direction. FIG. 18 further shows a guidewire 392 that has been first inserted into the patient's vasculature and advanced into the left ventricle. The delivery system can then be inserted into the body and advanced over the guidewire 392 until the THV is positioned within the interior of the aortic valve. As shown, the THV is not only in the interior of the aortic valve 304 but also in the interior of the main body portion of the support stent 310.

FIG. 18 shows the THV 340 in its contracted (or unexpanded) state crimped around the balloon portion of the balloon catheter 390. When the clinician is satisfied of the proper positioning, the balloon of the balloon catheter 390 can be expanded such that the THV 340 expands and urges the native leaflets of the aortic valve against the support stent 310, thereby securing the THV within the annulus of the aortic valve. Once the THV 340 is properly implanted, the balloon of the balloon catheter 390 is deflated, and the entire delivery system 380 including the balloon catheter is withdrawn over the guidewire 392. The guidewire 392 can then be withdrawn.

Other methods of delivering a support stent and THV to the aortic valve or any other heart valve are also possible. For example, in certain embodiments, the support stent and the THV are delivered surgically to the desired heart valve (e.g., in an open-heart surgical procedure). Furthermore, in certain embodiments in which the support stent and THV are delivered surgically, non-compressible support stents and/or THVs are used.

Exemplary Embodiments for Replacing Mitral Valves

The mitral valve can also suffer from valve insufficiency, which may be desirably treated through the implantation of a prosthetic valve. As with aortic valve insufficiency, mitral valve insufficiency often causes the valve annulus to be dilated and the valve leaflets to be too soft to provide reliable support for securing a prosthetic valve. Accordingly, and according to certain exemplary embodiments of the disclosed technology, it is desirable to use a support structure to help secure a transcatheter heart valve ("THV") within a patient's mitral valve. As with the support stents and frames described above, the mitral valve support structure is desirably positioned on the outflow side of the mitral valve. The THV can be inserted into the interiors of the native mitral valve and the support structure and then expanded such that the mitral valve leaflets are frictionally engaged between the exterior surface of the THV and the interior surface of the support structure. Alternatively, the support structure can be deployed after the THV is positioned and expanded within the mitral valve. The diameter of the support structure can then be adjusted such that the valve leaflets are frictionally engaged against the exterior of the THV. By using a support structure to secure the THV, a smaller THV can be used, thereby making the THV delivery process easier and safer. Furthermore, the use of a support structure protects against displacement of the THV if there is any further dilation of the aortic valve. Moreover, when a support structure is used to secure the THV, the native leaflets function as a sealing ring around the valve that prevents paravalvular leaks.

The support structure for the mitral valve can have a variety of shapes. For example, in some embodiments, the support structure has a sinusoidal shape as with the support stent 110, but in other embodiments does not have a sinusoidal shape or is not otherwise shaped in the z-plane. In further embodiments, the support stent is shaped as a cylindrical band or sleeve. The support frame can also have a more complex structure. In general, any of the shapes and materials used for embodiments of the aortic valve support structures described above can be used for embodiments of the mitral valve support structures and vice versa.

In one exemplary embodiment, the mitral valve support structure is made of a suitable biocompatible material that can be delivered through one or more delivery catheters and formed into a band or loop. For this reason, the structure is sometimes referred to herein as a "support band" or "support loop." The biocompatible material may comprise, for example, nylon, silk, polyester, or other synthetic biocompatible material. The biocompatible material may alternatively comprise a natural material, such as catgut. In still other embodiments, the support structure is formed of a biocompatible shape-memory metal or alloy, such as spring steel, Elgiloy®, or Nitinol.

Figure 23:
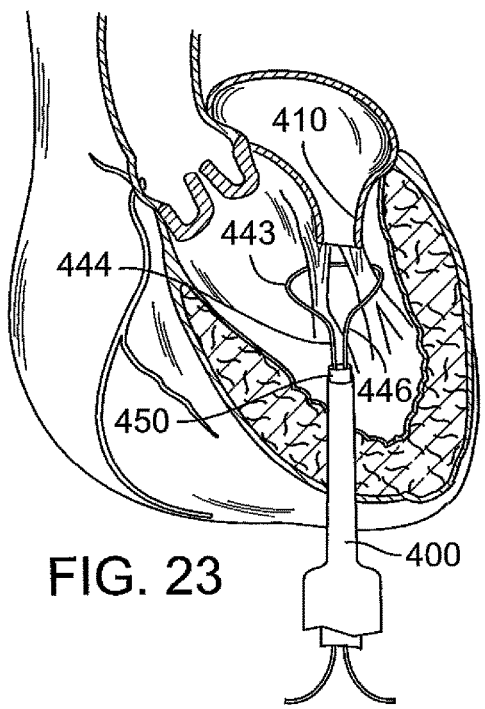
Figure 24:
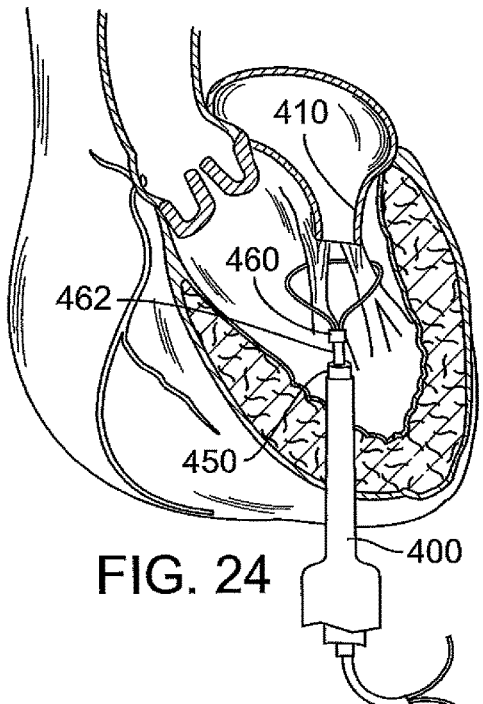
Figure 25:
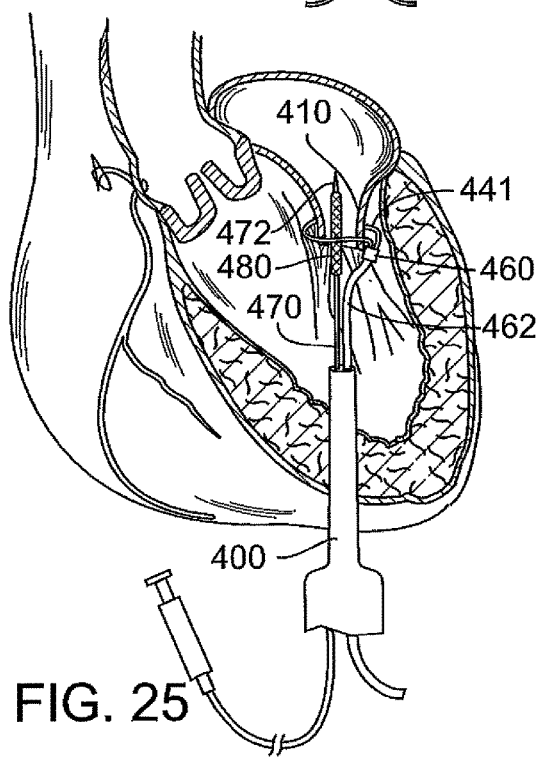
Figure 26:
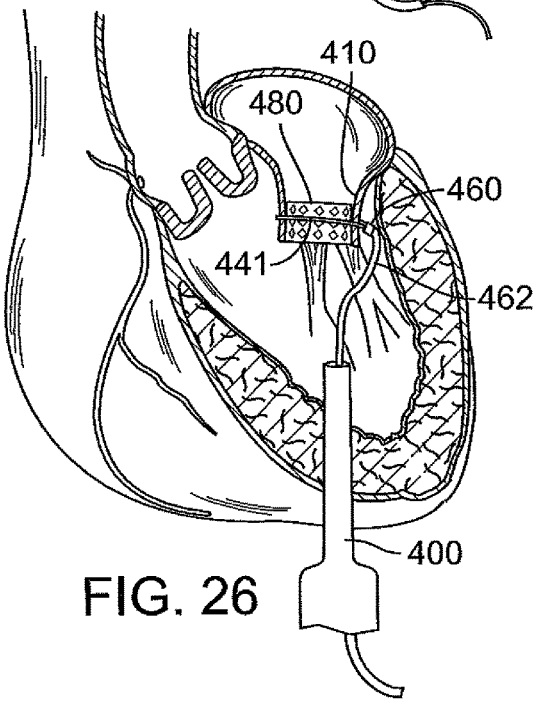
Figure 27:
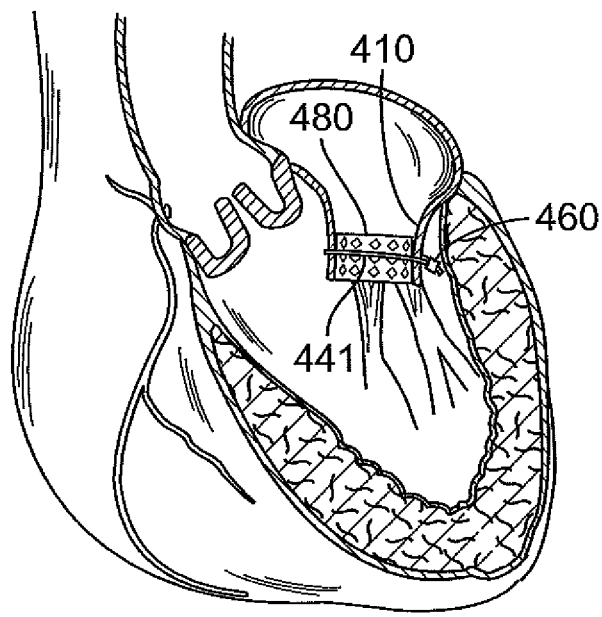

FIGS. 19-27 show one exemplary procedure for delivering a support structure to the mitral valve and having it secure a THV into its desired position within the mitral valve. In particular, FIGS. 19-24 are cross-sectional views through the left side of a patient's heart showing the acts performed in delivering the support structure using a transapical approach. FIGS. 25-27 are cross-sectional views through the left side of a patient's heart showing the acts performed in deploying a THV and having it engage the mitral valve leaflets and the interior of the support structure. It should be noted that FIGS. 19-27 are schematic in nature and thus do not necessarily depict a precise representation of the delivery process. For example, the patient's ribcage is not shown for illustrative purposes and the size of the sheaths used with the delivery system have been altered somewhat in order to better illustrate the procedure. One of ordinary skill in the art, however, will readily understand the range and types of sheaths and catheters that can be used to implement the depicted procedure.

FIG. 19 shows an introducer sheath 400 inserted into the left ventricle of a patient's heart through a puncture 402. In particular implementations, the introducer sheath 400 is positioned so that it is not directly centered about the outflow side of the mitral valve, but rather is offset from the center. In particular, the introducer sheath 400 can be positioned so that it is on the exterior side of the space enclosed by chordae tendineae 412. It should be noted that in FIGS. 19-27, the chordae tendineae 412 of the left ventricle are only partially shown. It is to be understood, however, that the chordae tendineae 412 are respectively attached to each of the mitral valve leaflets and to the papillary muscles of the left ventricle. A clinician can locate a distal tip 401 of the introducer sheath 400 near the outflow side of the mitral valve (e.g., within 1-10 millimeters).

FIG. 20 shows a first catheter delivery sheath 420 and a second catheter delivery sheath 422 being advanced through the interior of the introducer sheath 400. The introducer sheath 400 can define two or more separate lumens through which the first and the second catheter delivery sheaths 420, 422 can be inserted or can define a single lumen sufficiently large to receive both the first and the second catheter delivery sheaths 420, 422. The first and second catheter delivery sheaths 420, 422 can be shaped so that they arc outwardly from each other when advanced out of the distal tip 401 of the introducer sheath 400. For example, in the illustrated embodiment, the first and second catheter delivery sheaths 420, 422 have end regions 421, 423 that arch about 90 degrees (or some other amount, such as between 45-90 degrees) when they are in their natural state. The amount of arching may vary from implementation to implementation but is desirably selected so that the tips of the end portions 421, 423 are in approximately the same plane. In other embodiments, the catheter delivery sheaths 420, 422 are not used as part of the support structure delivery procedure.

In FIG. 21, a first loop delivery catheter 430 is advanced through the interior of the first catheter delivery sheath 420 and extended substantially around the exterior of one half of the chordae tendineae (e.g., the medial half of the chordae tendineae). Similarly, a second loop deliver catheter 432 is advanced through the interior of the second catheter delivery sheath 422 and extended substantially around the exterior of the other half of the chordae tendineae (e.g., the lateral half of the chordae tendineae). The loop delivery catheters 430, 432 can be steerable catheters having end regions that can be selectively deformed or arched by an operator. Such steerable catheters are well known in the art. The loop delivery catheters 420, 432 can additionally be magnetic or have magnetic distal end portions. For example, in the illustrated embodiment, the first loop delivery catheter 430 has a magnetic distal end portion 431 with a first polarity, and the second loop delivery catheter 432 has a magnetic distal end portion 433 with a second polarity opposite the first polarity. As a result of their magnetization, the end portions 431, 433 are attracted to one another and will form a contiguous junction when in sufficient proximity to each other. Other mechanisms for engaging the end portions 431, 433 to one another are also possible (e.g., a hook mechanism, an adhesive, an enlarged diameter of one end portion, and other such mechanisms). When the end portions 431, 433 are engaged to one another, the first and the second loop delivery catheters 430, 432 form a single interior or lumen through which a support band material can be advanced. Furthermore, when the end portions 431, 433 are engaged to one another, the first and the second loop delivery catheters 430, 432 create a partial loop that circumscribes the chordae tendineae.

FIG. 22 shows the magnetic distal end portions 431, 433 after the first and second loop delivery catheters 430, 432 are arched around the chordae tendineae and after the distal end portions have been magnetically engaged to one another. In this configuration, a cord 440 of biocompatible material can be advanced through the interior of one of the loop delivery catheters 430, 432 and into the interior of the other one of the loop delivery catheters. As used herein, the term "cord" refers to a slender length of material that can be formed from a single strand, fiber, or filament, or can comprise multiple strands, fibers, or filaments. In one particular implementation, an end 442 of the cord 440 can be advanced from a proximal end of the first loop delivery catheter 430, through the interior of the first loop delivery catheter, through the junction formed by the distal end portions 431, 433, and through the interior of the second loop delivery catheter 432 until it appears on the proximate end of the second loop delivery catheter 432. In one particular embodiment, the cord 440 is a guidewire (e.g., a guidewire made of stainless steel or other suitable metal). The guidewire can then be attached to another cord of biocompatible material used to form the support band and pulled through the interior of the first and the second loop delivery catheters 430, 432, thereby positioning the cord of biocompatible material around the chordae tendineae in a partial loop. With the cord of biocompatible material delivered around the chordae tendineae, the first and second loop delivery catheters 430, 432 and the first and second catheter delivery sheaths 420, 422 can be retracted from the introducer sheath 400.

FIG. 23 shows a cord 443 of biocompatible material used to form the support band positioned around the chordae tendineae after the first and second loop delivery catheters 430, 432 and the first and second catheter delivery sheaths 430, 422 have been withdrawn. In FIG. 23, a sheath 450 is inserted over both ends of the cord 443 and over a first portion 444 and a second portion 446 of the cord 443, which run through the length of the sheath 450.

As shown in FIG. 24, a locking member 460 can be advanced over the first and second portions 444, 446 of the cord 443 and into the left ventricle. The locking member 460 can be advanced, for example, by a pusher tube 462 that pushes the locking member 460 over the portions 444, 446 of the cord 440. In one particular embodiment, the locking member 460 includes lumens or other openings configured to receive each of the two portions 444, 446 and permits movement along the portions 444, 446 in only a single direction. In certain other embodiments, the locking member 460 can be unlocked from the portions 444, 446 of the cord 440 and advanced in both directions along the cord 440. In the illustrated embodiment, the pusher tube 462 is further configured to sever the portions of the cord 440 that extend through a proximal side of the locking member 460, thereby releasing a support band 441 formed by the locking member 460 and the loop-shaped portion of the cord 443 from the pusher tube 462. As more fully shown in FIG. 25, the pusher tube 462 can further be formed of a shape memory material or include a deflection mechanism that allows the pusher tube to have an arched shape toward its distal end. On account of this arched shape, the pusher tube 462 can be used to better position the support band 441 formed by the loop-shaped portion of the cord 443 and the locking member 460 adjacent to the outflow side of the mitral valve such that the native leaflets of the mitral valve open into an interior of the support band 441.

As shown in FIG. 25, the sheath 450 can be withdrawn from the introducer sheath 400 once the locking member 460 and the pusher tube 462 are advanced into the left ventricle. A balloon catheter 470 can be advanced through the introducer sheath 400 and into the interior of the mitral valve 410 of the patient. Although not shown in the illustrated embodiment, the balloon catheter may be guided by a guidewire into the center of the mitral valve. Ultimately, and as seen in FIG. 25, a balloon portion 472 of the balloon catheter 470 around which a THV 480 is crimped can be located within the mitral annulus. Radiopaque markers or other imaging enhancers may be provided on the distal end of the introducer sheath 400 and the balloon catheter 470 to more accurately determine the position of the THV 480 relative to the native valve 410. In some embodiments, a clinician can adjust the position of the THV 480 by actuating a steering or deflecting mechanism within the balloon catheter 470.

As also shown in FIG. 25, the locking member 460 and the pusher tube 462 can be positioned so as not to interfere with the balloon catheter 470. Furthermore, with the THV 480 properly positioned within the mitral valve 410, the pusher tube 462 can be used to position the support band 441 formed by the loop-shaped remaining portion of the cord 443 around the native valve leaflets of the mitral valve. Radiopaque markers or other suitable imaging enhancers can be provided on the pusher tube 462, the locking member 460, and/or the loop-portion of the cord to allow for the proper positioning of the support band 441 relative to the valve leaflets. With the THV 480 in its desired position, the balloon portion 472 of the balloon catheter 470 can be inflated, thereby expanding the THV 480 against the native valve leaflets and causing the leaflets to frictionally engage the interior surface of the support band 441. This expansion secures the THV 480 to the native valve leaflets. In other words, the expansion pinches the native leaflets of the mitral valve between the support band 441 and the THV 480, and thereby secures the THV within the annulus of the mitral valve.

As shown in FIG. 26, with the THV 480 secured against the native mitral valve leaflets and the support band 441, the balloon portion 472 of the balloon catheter 470 can be deflated and the balloon catheter withdrawn from the introducer sheath 400. The pusher tube 462 can then be disengaged from the loop 441. For example, the pusher tube 462 can comprise a cutting element at its distal end that can be activated by the clinician from the proximal end. An example of one suitable cutting element is shown below with respect to FIG. 39. Alternatively, a separate cutting device (e.g., a cutting catheter or catheter having a controllable cutting element) can be inserted through the introducer sheath 400 and used to cut the portions of the cord 443 that extend through the proximal side of the locking member 460 and do not form part of the support band 441.

FIG. 27 shows the THV 480 secured within the native mitral valve after the support band 441 has been released from the pusher tube 462 and the pusher tube has been retracted from the introducer sheath 400. It should be noted that the THV 480 can take a variety of different forms and may comprise an expandable stent portion that supports a valve structure. The stent portion desirably has sufficient radial strength to hold the valve at the treatment site and to securely engage the support band 441.

It will be understood by those of ordinary skill in the art that the above-described loop deployment technique can be modified in a number of manners without departing from the disclosed technology. For example, in some embodiments, the THV is delivered and expanded into the mitral valve before the support band is delivered to the left ventricle. In these embodiments, the THV can be temporarily secured within the mitral valve. For example, the THV can be temporarily secured to the mitral valve using one or more anchoring members on the exterior of the THV (e.g., anchoring members having a main body and one or more hook-shaped or umbrella-shaped barbs). The THV can also be temporarily secured within the mitral valve through the use of one or more spring-loaded clamps, rivets, clasps, or other such fastening mechanisms. With the THV temporarily secured, the support band can be delivered around the native leaflets as described above and the diameter of the support band reduced until a desired frictional fit is created between the support band, the leaflets, and the THV. Any of the locking members described herein that allow the diameter of the support band to be adjusted can be used to achieve the desired diameter.

Figure 28:
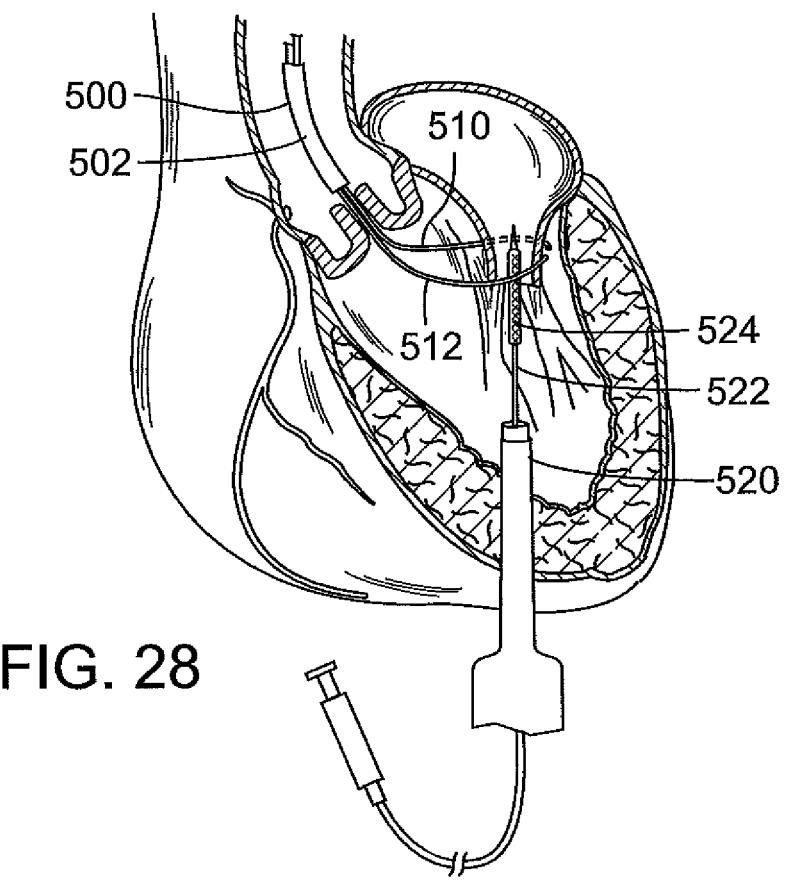
FIG. 28 is a cross-sectional view of a patient's heart illustrating how an exemplary support band as in FIGS. 19-27 can be deployed through the aortic arch.

Further, although the delivery method shown in FIGS. 19-27 uses a transapical approach, a delivery system adapted for introduction through the patient's aortic arch can alternatively be used. FIG. 28 shows an example of such a delivery system 500. In particular, FIG. 28 shows the delivery system 500 after a delivery catheter has been advanced through the aortic arch to a position adjacent the aortic valve and as a first loop deliver catheter 510 and a second loop deliver catheter 512 are deployed through the distal end of a delivery catheter 502. As with the procedure described above, the first and second loop delivery catheters 510, 512 can be steerable and comprise magnetic distal end portions that allow the catheters 510, 512 to engage one another on a distal side of the chordae tendineae, thereby forming a delivery lumen through which biocompatible material for the support band or loop can be deployed. Also shown in FIG. 28 is an introducer sheath 520 and a balloon delivery catheter 522 for deploying a THV 524. Besides the adaptations for aortic delivery, the delivery procedure can otherwise be substantially similar or identical to the procedure shown in FIGS. 19-27.

Still other delivery variations are possible. For instance, the support band may be formed of a shape-memory material that assumes a C-shape when not acted on by any external forces. The support band can be further configured such that one end of the C-shaped member is hollow and has a slightly larger diameter than the opposite end. To deliver the C-shaped support band, the support band can be stretched into a linear form and advanced through a delivery catheter (e.g., using a pusher element). In particular, the distal end of the delivery catheter can be positioned adjacent the chordae tendineae such that when the support band is advanced out of the distal end, it wraps around the chordae tendineae. After the support band is deployed from the distal end of the delivery catheter, a clamping device that is designed to engage the C-shaped support band and urge the ends of the support band together can be inserted into the heart (e.g., through the delivery catheter, the introducer sheath, or through a separate catheter). The clamping device can be used to urge one end of the support band into the hollow opposite end of the band. The ends can be crimped so that the support band forms a ring-shaped support band (e.g., using the clamping device or other device). In other embodiments, the hollow end of the support band can comprise a shoulder that engages an angled collar on the other end of the support band when the ends are urged together, thereby form a snap-fit connection. With the ends of the support band secured to one another, the support band can be positioned around the native leaflets of the mitral valve (e.g., using the clamping device or other positioning device) as a balloon catheter delivers a THV. Upon expansion, the THV will pinch the native valve leaflets between the outer surface of the THV and the interior surface of the support band, thereby securing the THV within the mitral valve.

In still another embodiment, the support band includes one or more clamping or fastening devices that can be used to clamp or fasten the support band to the native leaflets of the mitral leaflets. For example, the clamping or fastening devices can comprise spring-loaded clamps, anchoring members having one or more hook or umbrella-shaped barbs, clasps, or other such clamping or fastening mechanisms. In this embodiment, the support band still has a substantially fixed diameter such that when the THV is expanded into the interior of the mitral valve, the THV causes the native valve leaflets to be pinched against the interior surface of the support band, thereby securing the THV within the mitral valve. In still other embodiments, the THV itself can include one or more clamping or fastening devices designed to clamp or fasten the THV to the native leaflets of the mitral valve (e.g., any of the clamping or fastening mechanisms described above). In this embodiment, the THV can be secured directly to the native leaflets without the use of a support band or other support structure.

FIG. 29 shows one exemplary embodiment of a locking member that can be used for locking member 460 shown in FIGS. 19-27. In particular, FIG. 29 shows locking member 600, which can be a clamp, such as an adjustable, C-shaped clamp with interlocking teeth around a portion of the clamp. The locking member 600 has two arms 610, 612, each formed with interlocking teeth 620, 622. Interlocking teeth 620, 622 are configured to lock the clamp in one or more positions of varying circumference when pressure is applied to the two arms 610, 612 and pushes the arms together. Referring to FIG. 23, the cord portions (such as portions 446, 446) can be inserted into the interior 630 of the locking member 600. The arms 610, 612 can be pushed together and tightened so that the portions 444, 446 are secured in place (e.g., using a clamping device inserted into the left ventricle through the introducer sheath or using the pusher tube 462 modified to include a clamping mechanism). The interior 630 can additionally have grooves to increase the friction and decrease the slippage between the locking member 600 and the portions of the cord secured therein.

Figure 32:
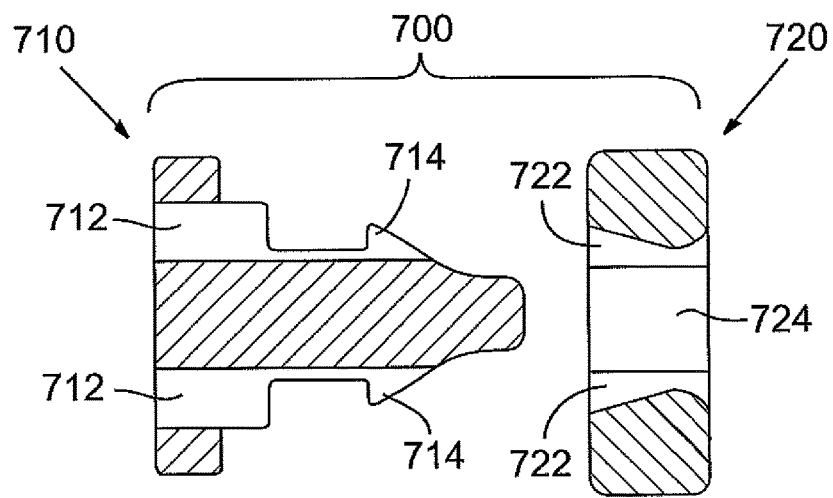
FIG. 32 is a cross-sectional side view of the exemplary locking member of FIG. 30.

FIGS. 30-37 depict another exemplary embodiment of a locking member that can be used for locking member 460 shown in FIGS. 19-27. In particular, FIGS. 30-37 show an adjustable locking member 700, which can be attached to two portions of a cord, thereby forming the support band. As best seen in FIGS. 30 and 32, the adjustable locking member 700 comprises a tapered, plastic pin 710 that fits into a tapered, plastic snap ring 720. When pin 710 and ring 720 are locked together, the adjustable locking member 700 is prevented from moving relative to the portions of the cord that are captured within the adjustable locking member 700 (e.g., cord portions 702, 704 in FIG. 30).

FIG. 31 illustrates an exemplary pusher tube (or adjustment catheter) 730 that can be used to introduce, position, and lock the adjustable locking member 700 in a desired position. The exemplary pusher tube 730 in the illustrated configuration has a fork member 732, an unlocking push member 734 that is extendable through the fork member 732, and a locking push member 736 that is extendable over the unlocking push member 734. Fork member 732 is configured so that it can move the adjustable locking member 700 over the cord portions to which it is connected. In particular, fork member 732 can engage the adjustable locking member 700 when it is positioned along the cord portions (but not yet in a locked position) such that by moving the pusher tube 730 in one direction along the length of the cord portions, adjustable locking member 700 is also moved. By moving the adjustable locking member 700 in this manner, the effective diameter of the support band formed by the cord and the adjustable locking member 700 can be modified.

Push members 734, 736 are slidably movable relative to each other and the fork member 732 to effect locking and unlocking of the adjustable locking member 700, as further described below. The unlocking push member 734 unlocks the adjustable locking member 700 from the locked position and the locking push member 736 locks the adjustable locking member 700 from the unlocked position.

FIG. 32 depicts the adjustable locking member 700, according to one embodiment, in more detail. The pin 710 comprises pin slots or holes 712 (which accept the cord portions) and locking members or flanges 714 (which extend outward to secure the pin to the ring in a locked position). Ring 720 comprises ring slots or holes 722 (which accepts the cord portions) and pin receiving hole 724 (which receives the pin to secure the pin to the ring in a locked position). The locking members 714 are deformable to allow the pin member to be inserted throughout ring member and form a snap-fit connection sufficient to hold the ring member on the pin member.

Figure 33:
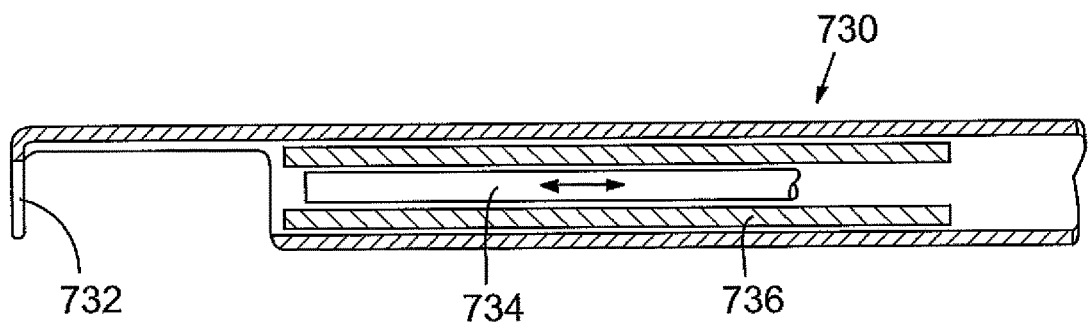
FIG. 33 is a cross-sectional side view of the exemplary adjustment tool of FIG. 31.

FIGS. 33-37 depict the relationship between the adjustable locking member 700 and the pusher tube 730, according to one embodiment, and their functions relative to one another. As discussed above, the pusher tube 730 comprises fork member 732, unlocking push member 734, and locking push member 736. FIG. 33 shows the pusher tube 730 in more detail. Both the unlocking push member 734 and the locking push member 736 are slidably movable within the pusher tube 730 along the longitudinal direction identified by the arrows shown in FIG. 33. The unlocking push member 734 is desirably a solid member that is sized to fit within the locking push member 736, which is desirably cylindrical with a longitudinally extending hollow section or lumen for receiving the unlocking push member 734.

Figure 34:
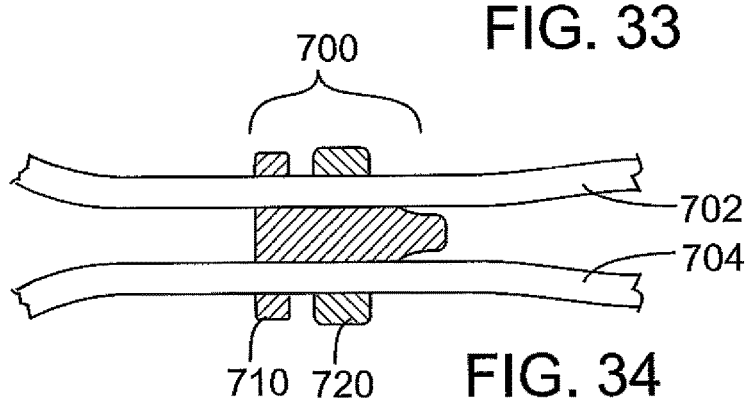
FIGS. 34-37 are cross-sectional views illustrating how the exemplary adjustment tool of FIG. 31 can be used to adjust, lock, and unlock the exemplary locking member of FIG. 30.

FIG. 34 shows the adjustable locking member 700 with the pin 710 and the ring 720 locked together. In the locked position, the cord portions 702, 704 pass inside the ring 720 and around the pin 710 (through the ring holes and pin holes) and are captured between these two components. The cord portions 702, 704 are held in place relative to each other, and the pin 710 and the ring 720 are held in place relative to the cord portions 702, 704 by the friction created at the surface interfaces.

Figure 35:
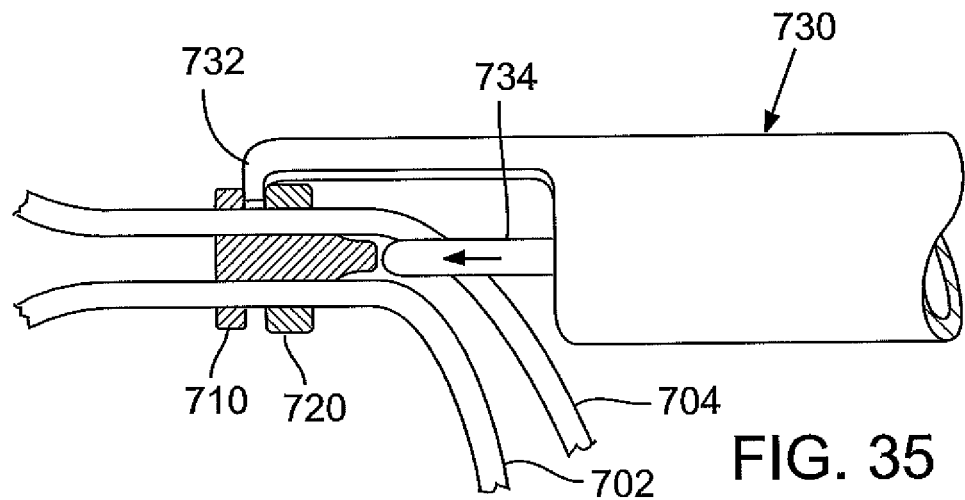
Figure 36:
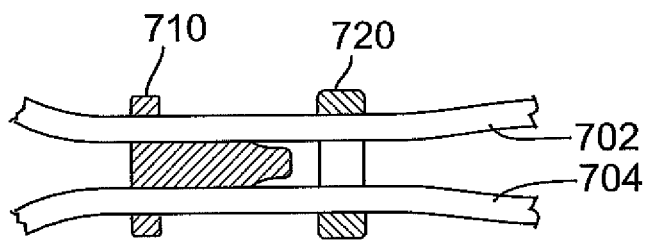

Referring to FIGS. 35 and 36, to unlock the adjustable locking member 700, the fork member 732 is inserted between the pin 710 and the ring 720, and the unlocking push member 734 is extended from the pusher tube 730 to push the pin 710 and the ring 720 apart. The fork member 732 holds the ring 720 in place, while the unlocking push member 734 applies longitudinal pressure against the tip of the pin 710, forcing it out of the ring 720. The unlocking push member 734 is desirably sized so that it can fit at least partially through the pin receiving hole 724 to assist in unlocking the pin 710 and the ring 720 from one another. Once the pin 710 and the ring 720 are separated, the adjustable locking member 700 can be moved relative to the cord portions 702, 704 in order to adjust the diameter of the support band formed by the cord portions 702, 704.

Figure 37:
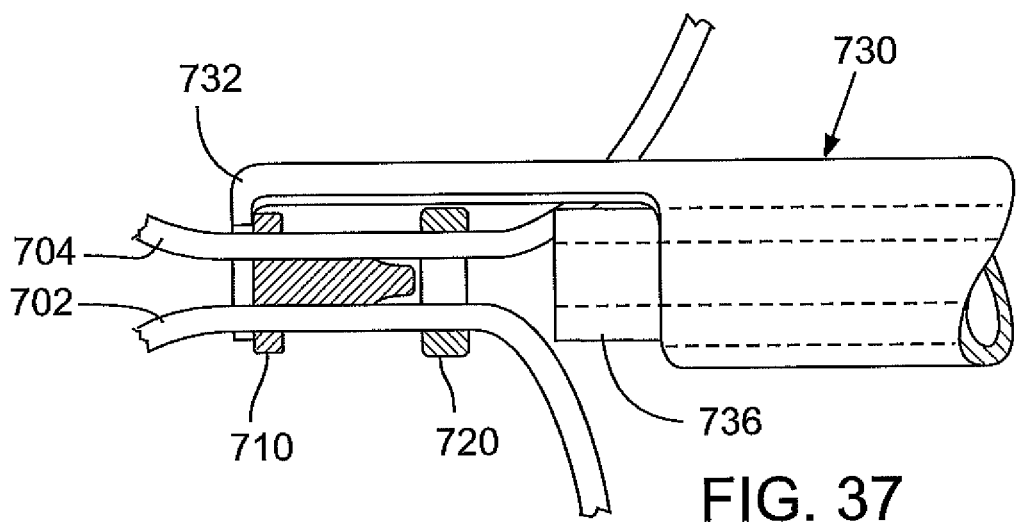

Referring to FIG. 37, the manner in which the pusher tube 730 can be used to secure the pin 710 and the ring 720 together is shown. The fork member 732 is placed at the far (distal) end of the pin 710 and the locking push member 736 is extended from the pusher tube 730. The locking push member 736 is configured with a cylindrical surface that is sized to mate with the area of the ring 720 that surrounds the pin receiving hole. While the fork member 732 holds the pin 710 in place, the locking push member 736 forces the ring 720 onto the pin 710 and locks the pin and the ring together. Once the adjustable locking member 700 is locked, the frictional engagement of the adjustable locking member with the cord portions maintains the position of the adjustable locking member relative to the cord portions 702, 704. The three-point connection system described above permits a clinician to perform fine adjustments of the diameter of the support band around the chordae tendineae and around the outflow side of the native leaflets of the mitral valve.

Figure 38:
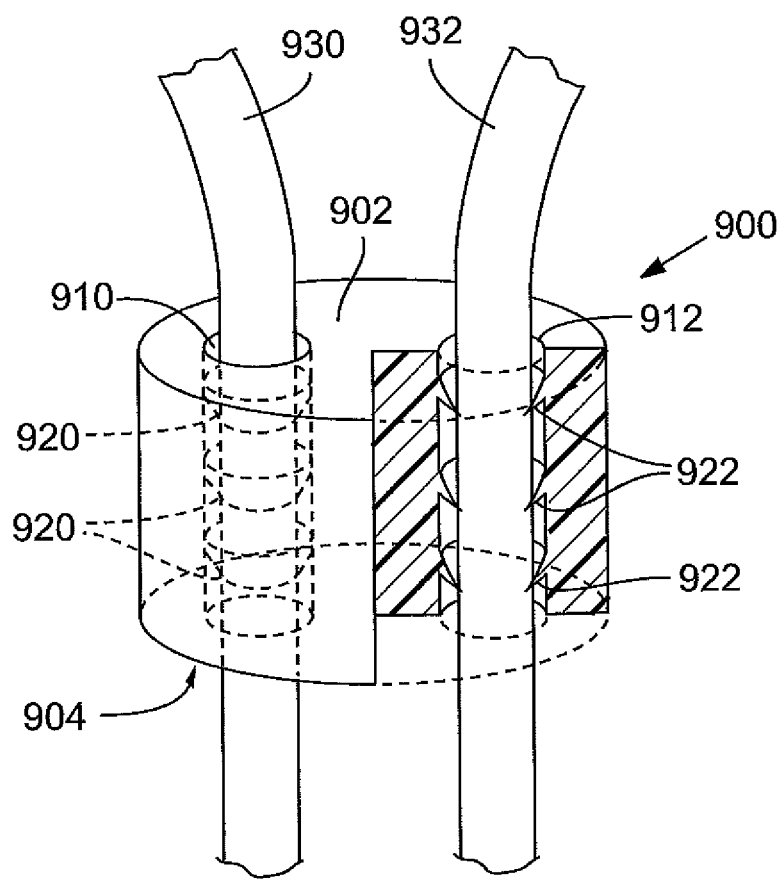
FIG. 38 is a cross-sectional perspective view of another exemplary locking member that can be used to secure portions of a cord of support band material to one another and thereby form a loop.
Figure 39:
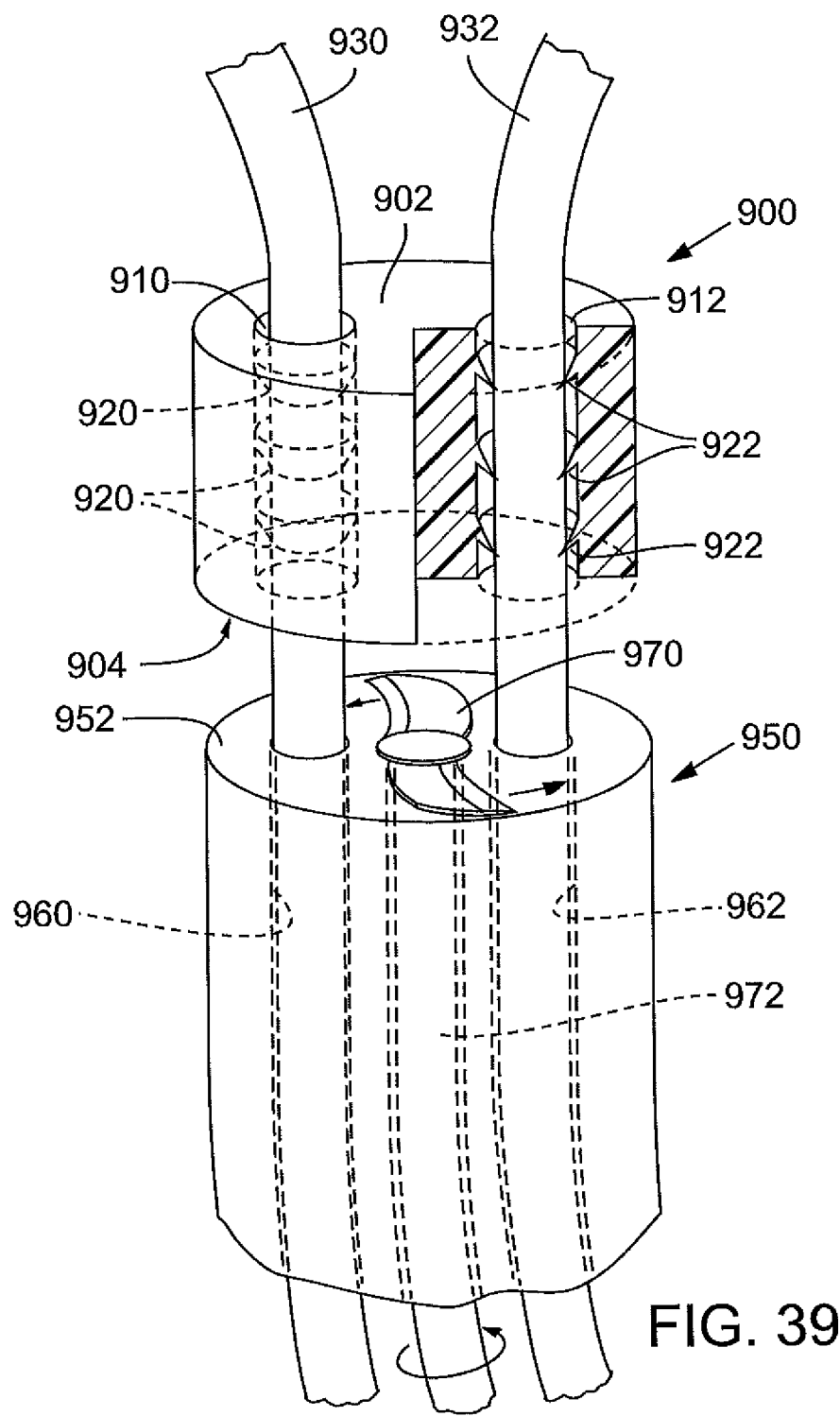
FIG. 39 is a cross-sectional perspective view of an exemplary pusher tube that can be used in connection with the exemplary locking member of FIG. 38.

FIGS. 38-39 depict another exemplary embodiment of a locking member that can be used for locking member 460 shown in FIGS. 19-27. In particular, FIG. 38 shows an adjustable locking member 900 having a generally cylindrical body with two lumens (or apertures) 910, 912 formed therein that extend from a top surface 902 to a bottom surface 904 of the body. In the illustrated embodiment, and as best seen in the cut-away portion of FIG. 38 showing the lumen 912, the interior of the lumens 910, 912 comprises a plurality of teeth (or collars) 920, 922 that are angled toward the bottom surface 904. The teeth 920 can have some flexibility and be formed to allow a cord portion, such as cord portion 930 or cord portion 932, to slide through the lumens 910, 912 in a first direction, but not in an opposite second direction. In other words, the teeth 920, 922 of the adjustable locking member 900 allow for one-way movement of the locking member 900 along the cord portions 930, 932. In this way, the adjustable locking member 900 can be used to securely form the support band and allows for the diameter of the support band to be adjusted to its desired size.

FIG. 39 shows an exemplary embodiment of a pusher tube 950 that can be used with the adjustable locking member 900 (e.g., the pusher tube 950 can be used as the pusher tube 462 shown in FIGS. 19-27). The exemplary pusher tube 950 includes lumens 960, 962 through which the cord portions 930, 932 can extend. In a particular embodiment, the lumens 960, 962 have a sufficiently large diameter and a smooth interior that allows the cord portions 930, 932 to more easily slide therethrough. In the illustrated embodiment, the pusher tube 950 further includes a rotatable blade 970 at its distal end 902. The rotatable blade 970 can be rotatable about a central axis of the pusher tube 950 and connected to an interior rod member 972 that extends through a central lumen of the pusher tube 950. A handle (not shown) can be attached to the interior rod member 972 at its proximal end and allow for an operator to manually rotate the rotatable blade 970 in order to sever the pusher tube 950 from the adjustable locking member 900.

Other methods of delivering a support band and THV to the mitral valve or any other heart valve are also possible. For example, in certain embodiments, the support band and the THV are delivered surgically to the desired heart valve (e.g., in an open-heart surgical procedure). Furthermore, in certain embodiments in which the support band and THV are delivered surgically, non-compressible THVs are used.

Exemplary Embodiments for Replacing an Aortic Valve Using Integrated Delivery Systems In this section, embodiments of integrated delivery systems capable of delivering both a prosthetic valve and a support stent to a desired location are described. The integrated delivery systems can help reduce the trauma experienced by a patient during valve implantation since the systems can use a single point of entry. For example, the embodiments shown in FIGS. 40-47 and 56-62 can be used to perform a transfemoral valve delivery, whereas the embodiments shown in FIGS. 48-55 and 63-70 can be used to perform a transapical valve delivery.

Figure 40:
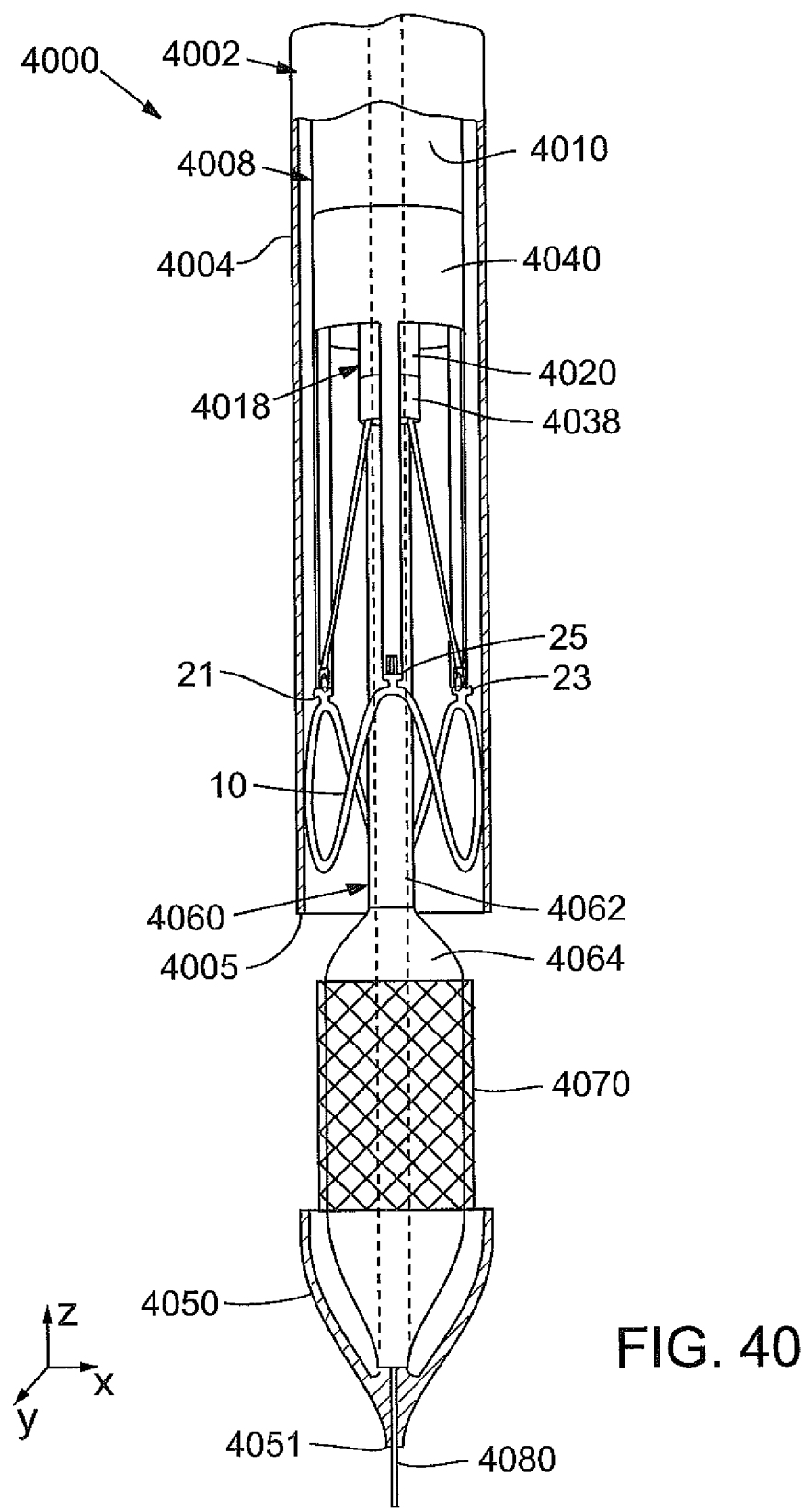
FIGS. 40 and 41 are front views of an exemplary integrated delivery system for delivering embodiments of the disclosed support structures. In particular.
Figure 41:
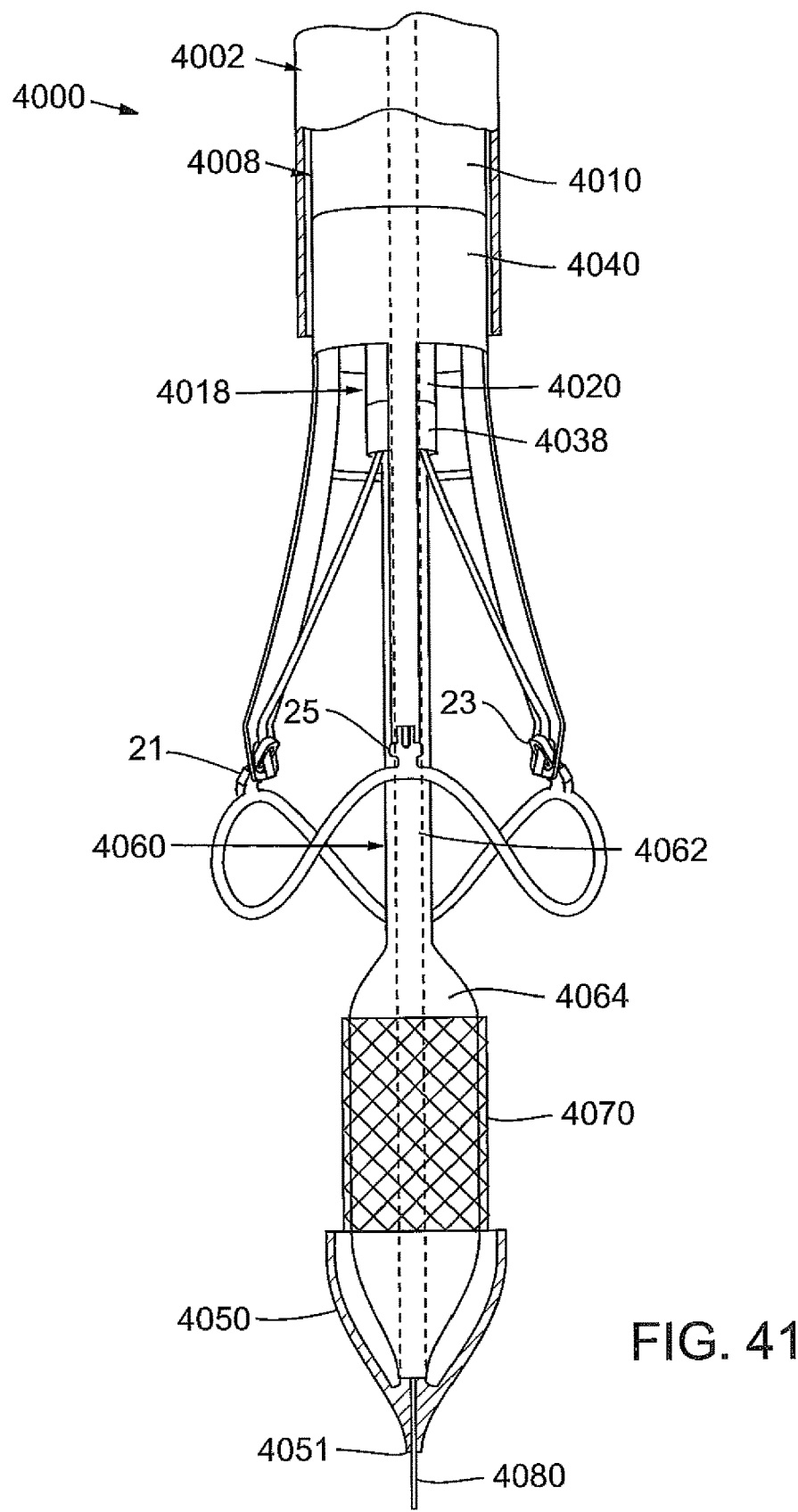

FIGS. 40 and 41 are front views of the distal end portion of an exemplary delivery system 4000 for delivering the support stent 10 to its location adjacent the native aortic valve through a patient's vasculature (e.g., transfemorally). In particular, FIG. 40 shows the delivery system when the support stent 10 is in a compressed, predeployed state, whereas FIG. 41 shows the delivery system when the support stent 10 is in a decompressed, deployed state. The delivery system 4000 comprises a main catheter 4002 (which can be a steerable guide catheter) having an elongated shaft 4004, whose distal end 4005 is open. In other embodiments, the distal end 4005 of the main catheter 4002 can be tapered (e.g., tapered into a conical shape comprising multiple "flaps" forming a protective nose cone that can be urged apart when the support stent 10 and any interior catheters are advanced therethrough or tapered into a conically shaped solid profile with only a thru lumen for the placement of a guidewire). The nose cone can be configured to have a variety of different profiles, including, but not limited to, a bullet-tipped, blunt-tipped, triangular, or other such tapered profile. Furthermore, for illustrative purposes, the main catheter 4002 is shown as being partially cut away, thus revealing the catheters in its interior.

A proximal end (not shown) of the main catheter 4002 is connected to a handle of the delivery system 4000. During delivery of a support stent, the handle can be used by a clinician to advance and retract the delivery system through the patient's vasculature. In a particular use, the delivery system 4000 is advanced through the aortic arch of a patient's heart in the retrograde direction after having been percutaneously inserted through the femoral artery. The main catheter can be configured to be selectively steerable or bendable to facilitate advancement of the delivery system 4000 through the patient's vasculature. An exemplary steerable catheter as can be used in embodiments of the disclosed technology is described in detail in U.S. Patent Application Publication No. 2007/0005131 (U.S. patent application Ser. No. 11/152,288), which is hereby expressly incorporated herein by reference.

The delivery system 4000 also includes a stent delivery outer catheter 4008 positioned in the interior of the main catheter 4002. The stent delivery outer catheter 4008 has an elongated shaft 4010 and an outer fork 4040 connected to a distal end portion of the shaft 4010. The shaft 4010 of the stent delivery outer catheter 4008 can be configured to be moveable axially relative to the other shafts of the delivery system 4000 (e.g., using a handle or lever (such as a lockable handle or lever) located at or near a proximal end of the delivery system 4000 as is known in the art). Furthermore, the shaft 4010 of the stent delivery outer catheter 4008 can be sized so that its exterior wall is adjacent to or in contact with the inner wall of the shaft 4004 of the main catheter 4002.

The delivery system 4000 can also include a stent delivery inner catheter 4018 positioned in the interior of the stent deliver outer catheter 4008. The stent delivery inner catheter 4018 can have an elongated shaft 4020 and an inner fork 4038 secured to the distal end portion of the shaft 4020. The shaft 4020 of the inner catheter 4018 can be configured to be moveable axially relative to the other shafts of the delivery system 4000 (e.g., using a handle or lever (such as a lockable handle or lever) located at or near a proximal end of the delivery system 4000 as is known in the art). Furthermore, the shaft 4020 of the inner catheter 4018 can be sized so that its exterior wall is adjacent to or in contact with the inner wall of the shaft 4010 of the stent delivery outer catheter 4008.

The delivery system 4000 further includes a prosthetic valve delivery catheter 4060. The prosthetic valve delivery catheter 4060 comprises an elongated shaft 4062 positioned in the interior of the stent delivery inner catheter 4018 and a balloon portion 4064 located near a distal end of the elongated shaft 4062. The shaft 4062 of the prosthetic valve delivery catheter 4060 can be configured to be moveable axially relative to the other shafts of the delivery system 4000 (e.g., using a handle or lever (such as a lockable handle or lever) located at or near a proximal end of the delivery system 4000 as is known in the art). Furthermore, the shaft 4062 of the prosthetic valve delivery catheter 4060 can be sized so that its exterior wall is adjacent to or in contact with the inner wall of the shaft 4020 of the stent delivery inner catheter 4018. In the illustrated embodiment, a nose cone 4050 is attached to the distal end of the balloon portion 4064, though in other embodiments, the elongated shaft 4062 can continue beyond the balloon portion and the nose cone can be attached to a distal end of the elongated shaft. In still other embodiments, the nose cone 4050 is absent. A prosthetic valve 4070 (e.g., a THV) is positioned around the balloon portion 4064 in a crimped or unexpanded state. The prosthetic valve 4070 can be any suitable expandable prosthetic heart valve, such as those described in U.S. Patent Application Publication No. 2007/0112422 (U.S. application Ser. No. 11/280,063), which is expressly incorporated herein by reference. The prosthetic valve delivery catheter 4060 can include one or more fluid lumens (not shown) through which a suitable liquid or gas can be inserted to cause the balloon portion 4064 to expand, thereby expanding the prosthetic valve 4070 into its expanded state. In other words, the prosthetic valve delivery catheter 4060 can be a balloon catheter. The one or more fluid lumens of the prosthetic valve delivery catheter 4060 can comprise an annular lumen or a non-concentric (or offset) lumen that allows a further lumen to be defined within the prosthetic valve delivery catheter 4060. In certain embodiments, the prosthetic valve delivery catheter 4060 itself comprises multiple catheters, including an outer catheter to which the balloon is attached and an inner catheter that is coupled to the balloon only at the balloon's distal end. With such a design, fluid can be inserted in the annular space between the outer catheter and the inner catheter. Furthermore, the prosthetic valve delivery catheter 4060 can define a guidewire lumen through which a guide wire 4080 can be inserted. The guide wire can extend through a distal end 4051 of the nose cone 4050 and can be used, for example, to help ensure proper advancement of the main catheter 4002 and its interior catheters through the vasculature of a patient. In FIG. 40, the prosthetic valve 4070 is shown as not being enclosed by the main catheter 4002. However, in other embodiments, the main catheter 4002 can be configured to enclose the prosthetic valve 4070 during insertion of the delivery system 4000 into the vasculature of the patient.

In FIG. 40, the support stent 10 is shown in a radially compressed state in the interior of the elongated shaft 4004 of the main catheter 4002. In the radially compressed state, the distance along the z axis between a peak and an adjacent valley of the support stent is greater than the distance along the z axis between the peak and the adjacent valley when the support stent is in it uncompressed state. The distal end portion of the shaft 4004 can also be referred to as a delivery sheath for the stent 10. In this undeployed and compressed state, the prongs of the outer fork 4040 and the inner fork 4038 of the stent delivery outer catheter 4008 and the stent delivery inner catheter 4018 engage the retaining arms 21, 23, 25 of the support stent 10 in the manner described above with respect to FIGS. 5 and 6. To deploy the support stent 10 in the illustrated embodiment (advance the stent from the delivery system), the stent delivery outer catheter 4008 and the stent delivery inner catheter 4018 are advanced toward the distal end 4005 of the main catheter 4002 using one or more control handles or mechanisms (not shown) located at the proximal end of the main catheter 4002. This action causes the support stent 10 to be advanced outwardly through the distal end 4005 of the main catheter 4002 and expand into its relaxed, uncompressed state (shown, for example, in FIGS. 1 and 2).

FIG. 41 is a front view showing the support stent 10 after it has been advanced from the distal end of the main catheter 4002. As seen in FIG. 41, the support stent 10 now assumes its relaxed, uncompressed shape but remains connected to the outer fork 4040 and the inner fork 4038 at its retaining arms 21, 23, 25. In this configuration, the support stent 10 can be rotated (in the clockwise or counter-clockwise directions) or repositioned (in the proximal and distal directions and/or into a different position in the x-y plane) into a proper orientation adjacent to its intended target area. For example, the support stent 10 can be positioned against the upper surfaces of leaflets of the aortic valve in the manner illustrated in FIG. 2 while the support stent 10 remains connected to the delivery system 4000 via the retaining arms 21, 23, 25.

As more fully illustrated below in FIGS. 42-46, a prosthetic valve (e.g., a THV) can be delivered to the aortic valve entirely through a tranfemoral approach (e.g., through the aortic arch of the heart) using the deployment system 4000. The prosthetic valve 4070 can be deployed transfemorally such that the prosthetic valve is secured in place by frictional engagement between the support stent, the native leaflets, and the prosthetic valve. As explained above with reference to FIGS. 4 and 5, the support stent 10 can be shaped so that the native leaflets of the aortic valve become trapped or pinched between the support stent 10 and the exterior of the prosthetic valve 4070 when the prosthetic valve is expanded and deployed within the native valve. The deployment system 4000 can be used, for example, to deliver a support stent 10 to treat aortic insufficiency, as well as any other condition in which the aorta or aortic valve may not be in condition to help support the prosthetic valve (e.g., when the aortic annulus is too dilated or in which the leaflets of the aorta are too weak or soft to support the prosthetic valve).

FIGS. 42-46 illustrate one exemplary procedure for deploying the support stent and securing a prosthetic valve (e.g., a THV) to the support stent. In particular, FIGS. 42-46 are cross-sectional views through the left side of a patient's heart showing the acts performed in delivering the support stent 10 through the aortic arch to the aortic valve. In order to better illustrate the components of the delivery system 4000, the main catheter 4002 is shown partially cut away in FIGS. 42-36.

Figure 42:
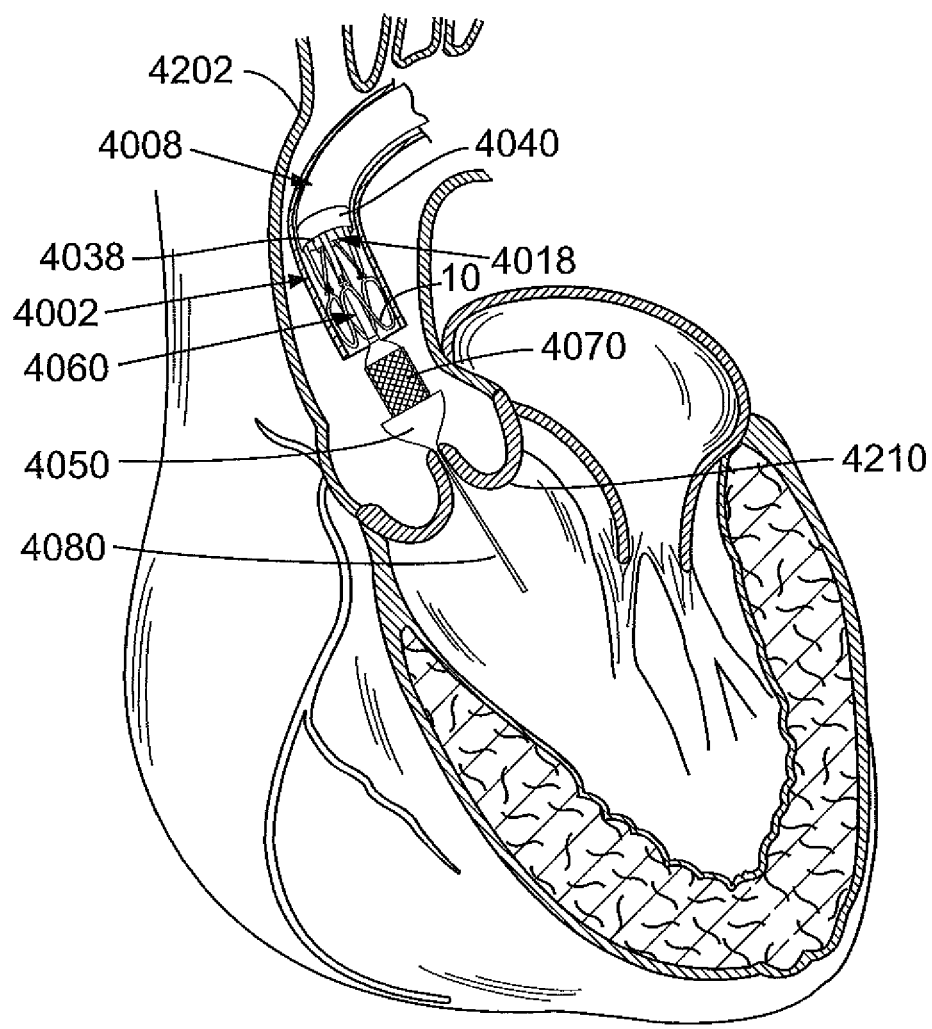
FIGS. 42-46 are cross-sectional views of a patient's heart illustrating how the delivery system of FIGS. 40 and 41 can operate to deploy the support structure of FIG. 1 to a desired position on the patient's aortic valve.

FIG. 42 shows the main catheter 4002 of the delivery system 4000 as it is advanced through the aortic arch 4202 into a position near the surface of the outflow side of the aortic valve 4210. The delivery system 4000 can be inserted through the femoral artery of the patient and advanced into the aorta in the retrograde direction. FIG. 42 also shows the outer fork 4040 of the stent delivery outer catheter 4008, the inner fork 4038 of the stent delivery inner catheter 4018, the prosthetic valve delivery catheter 4060, nose cone 4050, and the support stent 10. In FIG. 42, the main catheter 4002 is advanced in the direction of guidewire 4080, which is shown as being extended through the aortic valve 4210. The delivery system 4000 is advanced to the point where the nose cone 4050 is located adjacent to the native leaflets of the aortic valve when the valve is closed. In FIG. 42, the support stent 10 is in its radially compressed, predeployment state. Also seen in FIG. 42 are the outer fork 4040 and the inner fork 4038, which releasably couples the radially compressed support stent 10 to the distal ends of the stent delivery outer catheter 4008 and the stent delivery inner catheter 4018, respectively. In FIG. 40, the prosthetic valve 4070 is shown as not being enclosed by the main catheter 4002. However, in other embodiments, the main catheter 4002 can be configured to enclose the prosthetic valve 4070 during insertion of the delivery system 4000 into the vasculature of the patient.

Figure 43:
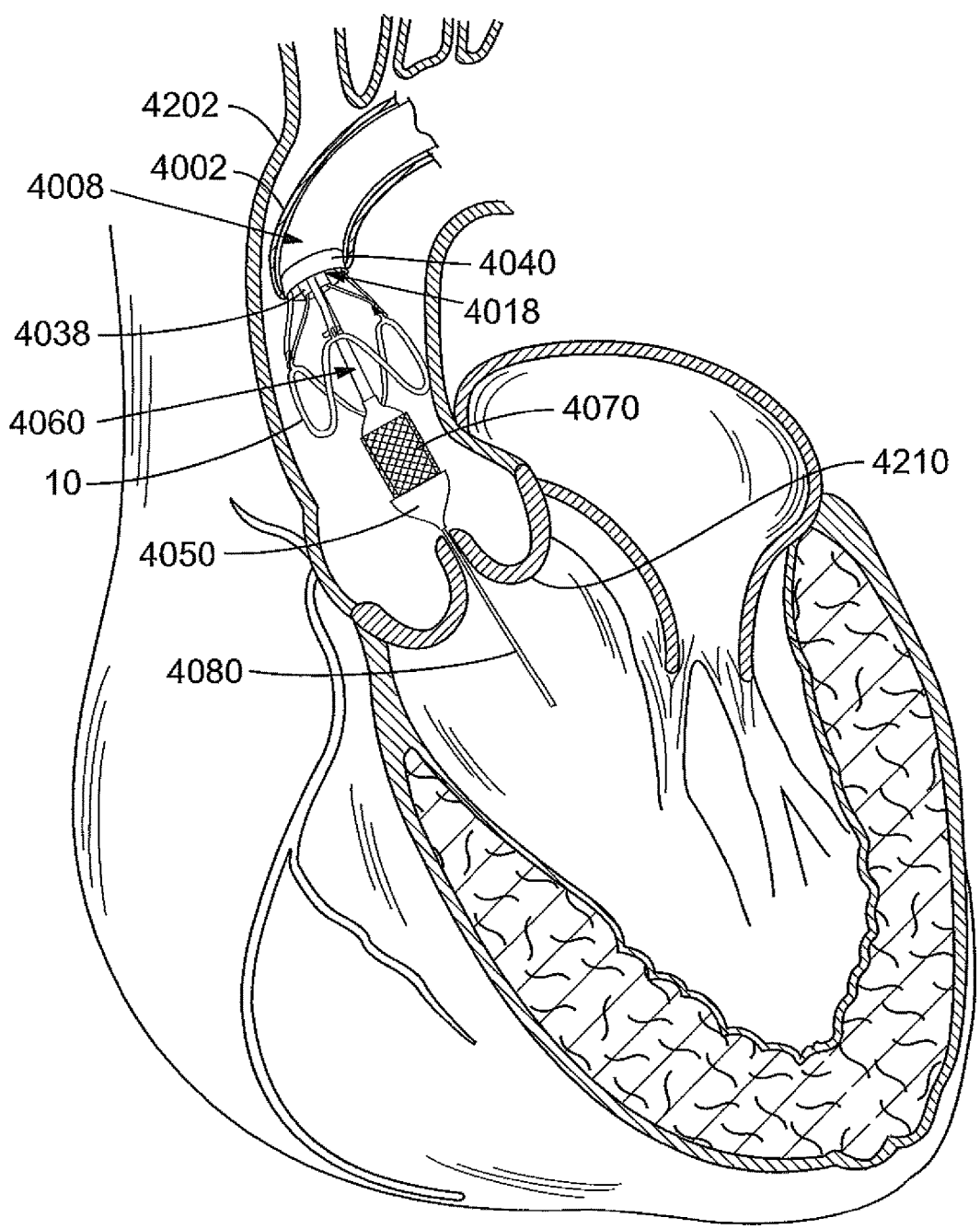

In FIG. 43, the main catheter 4002 is withdrawn from the stent delivery outer catheter 4008, the stent delivery inner catheter 4018, and the support stent 10. When the main catheter 4002 is withdrawn, the support stent 10 is no longer held within the inner walls of the main catheter and expands into its uncompressed, natural shape in a position above the aortic valve 4210. In FIG. 43, the support stent 10 is self-expanding. In other embodiments, however, the support stent may not be self-expanding. In such embodiments, the support stent can be made of a suitable ductile material, such as stainless steel. In addition, a mechanism for expanding the support stent can be included as part of the delivery system 4000. For example, and as explained above with respect to FIG. 8, the support stent can be disposed around a balloon of a balloon catheter in a compressed state. At this point in the exemplary procedure, portions of the delivery system 4000 are ready to be advanced further into the aortic valve, led by the nose cone 4050.

Figure 44:
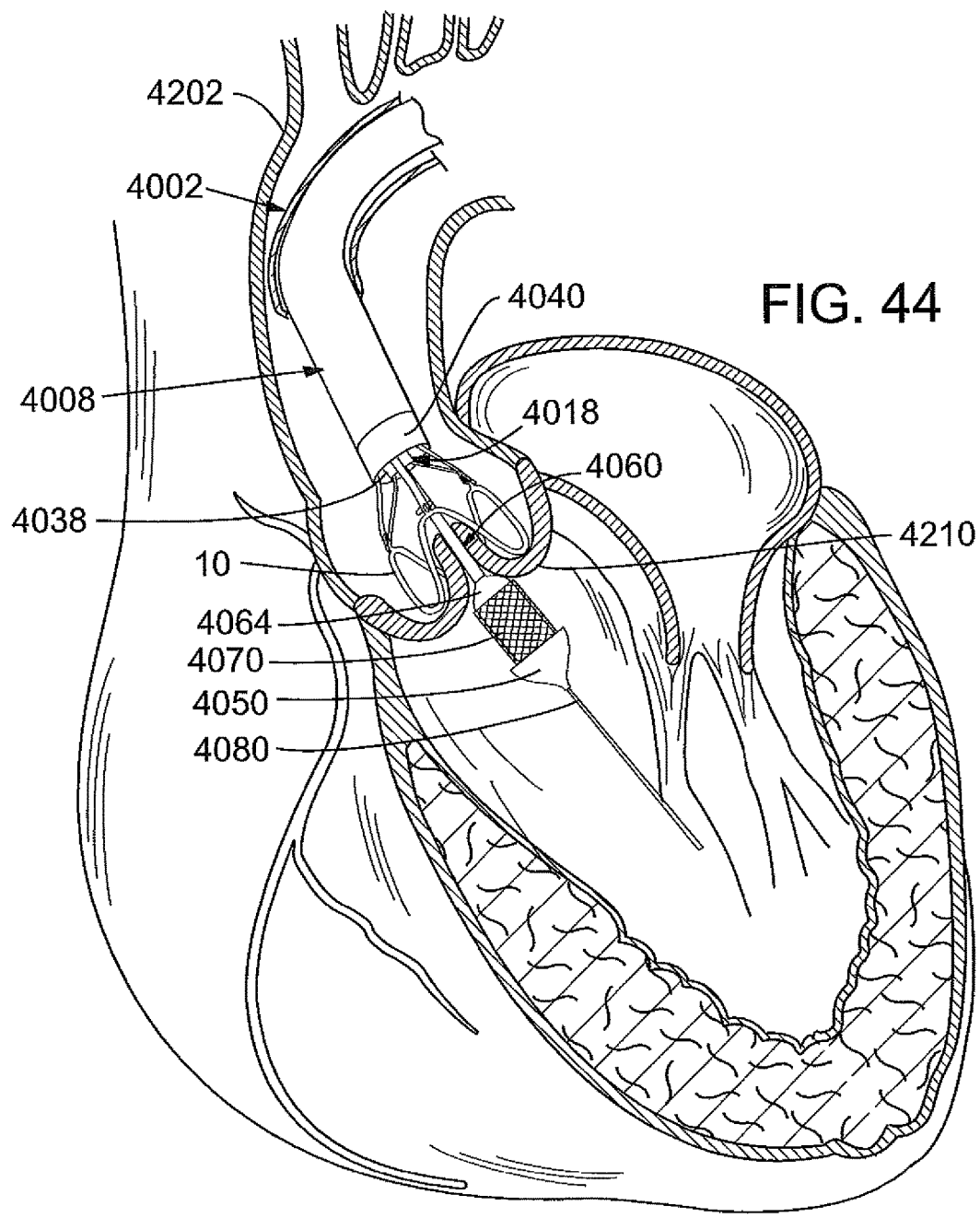

In FIG. 44, the prosthetic valve delivery catheter 4060 is advanced through the aortic valve 4210 led by the nose cone 4050. In the illustrated position, the prosthetic valve delivery catheter 4060 is advanced to a point where the balloon portion 4064 and compressed prosthetic valve 4070 are located on the inflow side of the aortic valve 4210. In FIG. 44, the stent delivery outer catheter 4008 and the stent delivery inner catheter 4018 are also advanced toward the aortic valve 4210 but remain on the outflow side of the aortic valve 4210. In particular, the stent delivery outer catheter 4008 and the stent delivery inner catheter 4018 are positioned so that the support stent 10 is placed adjacent to or directly on the surface of the outflow side of the aortic valve. The support stent 10 is rotated and positioned as necessary so that the support stent generally circumscribes the aortic valve and so that the peaks of the support stent are aligned with the tips of the natural leaflets of the aortic valve 4210. Therefore, when the prosthetic valve 4070 is inserted and expanded within the aortic valve 4210, the leaflets of the aortic valve will engage at least the majority of the surface in the interior of the support stent 10. This alignment will create an overall tighter fit between the support stent 10 and the prosthetic valve. In other embodiments, the support stent 10 is rotated and positioned as necessary so that the peaks of the support stent 10 are aligned with the commissures or other portions of the aortic valve 4210. The position of the main catheter 4002 and the support stent 10 relative to the aortic valve 4210, as well as the position of other elements of the system, can be monitored using radiopaque markers and fluoroscopy, or using other imaging systems such as transesophageal echo, transthoracic echo, intravascular ultrasound imaging ("IVUS"), or an injectable dye that is radiopaque. Additionally, longitudinal alignment of the two implants can be engineered via "hard stops" or locking mechanisms designed into the proximal handle system.

Also seen in FIG. 44 are the prongs of the outer fork 4040 and the prongs of the inner fork 4038. In the exemplary procedure, the prongs of the outer fork 4040 and the inner fork 4038 remain secured to the support stent 10 until the prosthetic valve is deployed and frictionally engaged to the support stent. The inner and outer forks desirably form a connection between the stent 10 and the delivery system 4000 that is secure and rigid enough to allow the clinician to hold the stent 10 at the desired implanted position against the flow of blood while the prosthetic valve is being implanted. The inner and outer forks are also desirably flexible enough to allow for balloon inflation of the prosthetic valve within the fork prong area.

Figure 45:
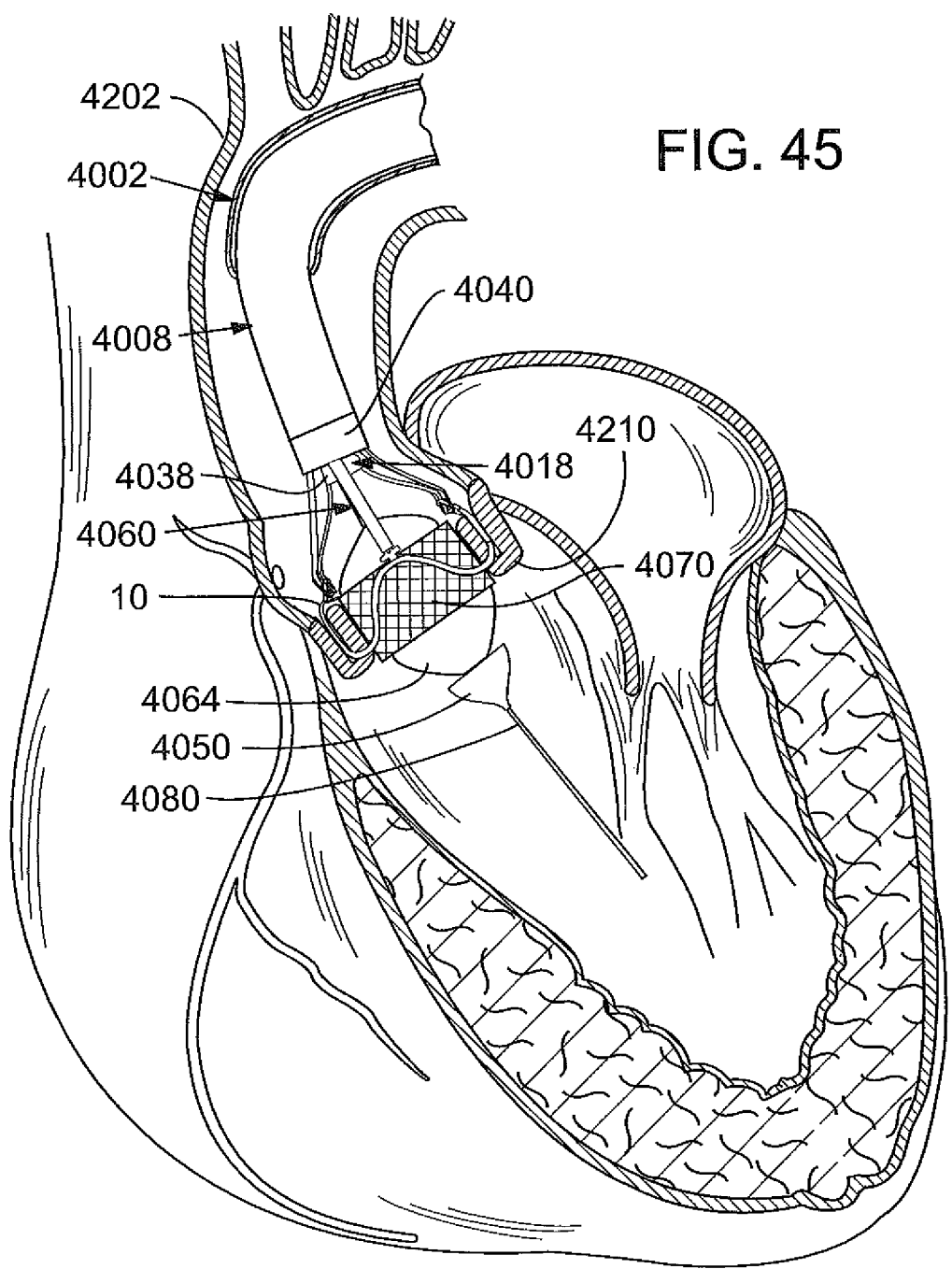
Figure 46:
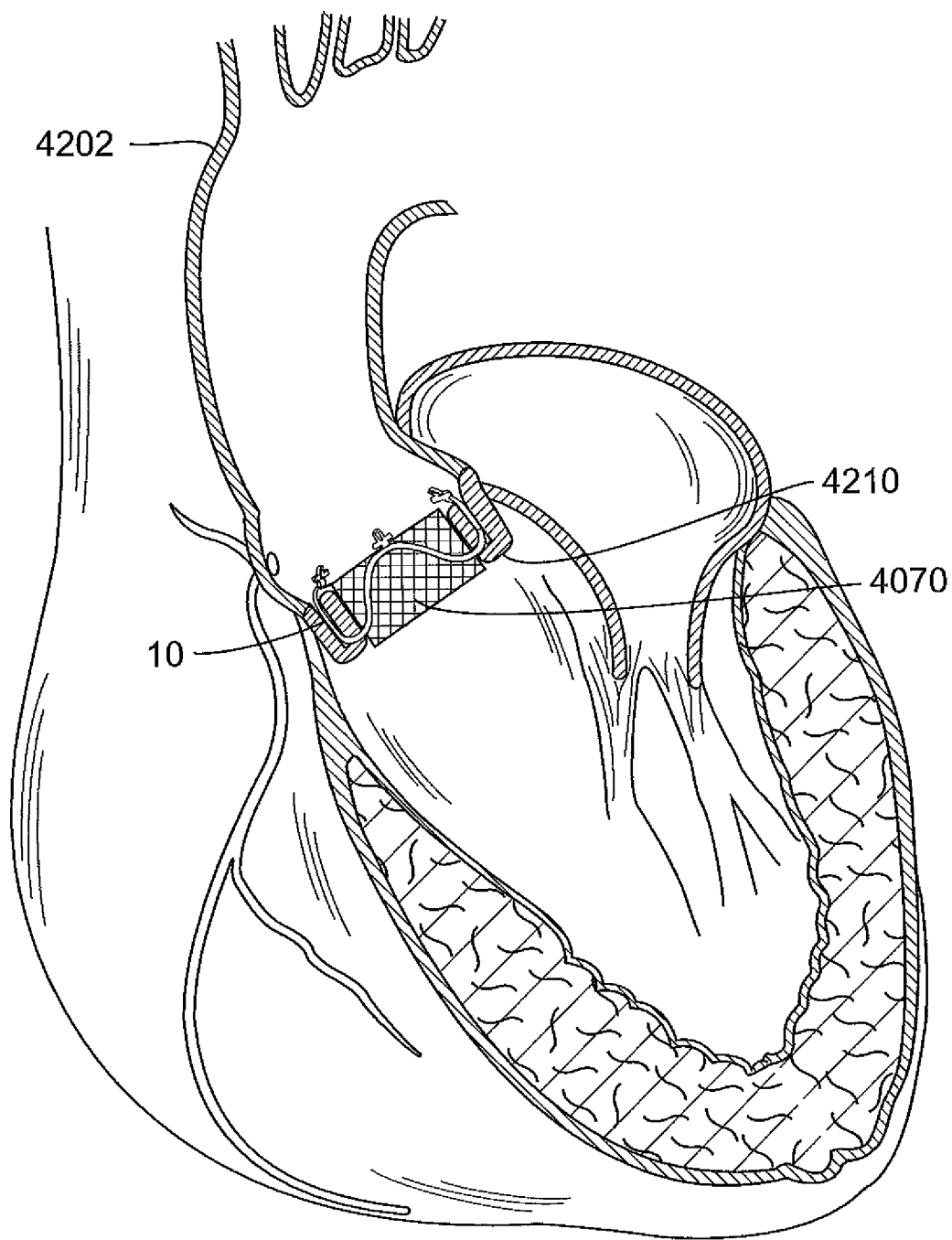

In FIG. 45, the prosthetic valve delivery catheter 4060 is retracted so that the balloon portion 4064 and the prosthetic valve 4070 are located in the aortic annulus and between the native aortic leaflets. In particular, the compressed prosthetic valve 4070 is located concentrically within the aortic valve and within the interior of the support stent 10. Furthermore, the balloon portion 4064 is expanded to expand the prosthetic valve 4070, thereby causing the exterior of the prosthetic valve to engage the leaflets of the aortic valve 4210, and in turn cause the leaflets of the aortic valve to engage the interior of the support stent 10. In other words, the expansion of the prosthetic valve 4070 pinches the leaflets of the aortic valve 4210 between the support stent 10 and the prosthetic valve, thereby securing the prosthetic valve within the annulus of the aortic valve. In order to better illustrate the components of the delivery system for the prosthetic valve, FIGS. 44-46 show the front third of the support stent 10 and the front of the prosthetic valve 4070, but do not show the portions of the native heart valve that would be secured by the front of the support stent 10. It is to be understood, however, that a corresponding leaflet of the native heart valve would be secured between the support stent 10 and the prosthetic valve 4070.

Radiopaque or other imaging markers may be provided on the prosthetic valve delivery catheter 4060 to more accurately determine the position of the valve 4070 and the balloon portion 4064 relative to the support stent 10 and the aortic valve 4210. In some embodiments, the clinician can adjust the position of the valve 4070 by actuating a steering or deflecting mechanism within the prosthetic valve delivery catheter 4060. Furthermore, the rotational orientation of the valve 4070 can be adjusted relative to the cusps and commissures of the native aortic valve by twisting the prosthetic valve delivery catheter 4060 from its proximal end and observing specific markers on the valve (or prosthetic valve delivery catheter) using fluoroscopy or other imaging technology.

Once the prosthetic valve 4070 is secured into its desired position, the balloon portion 4064 can be deflated so that the prosthetic valve delivery catheter 4060 becomes disengaged from the expanded prosthetic valve 4070. The prosthetic valve delivery catheter 4060 can then be withdrawn. The stent delivery inner catheter 4018 of the delivery system 4000 can be retracted, thereby causing the prongs of the inner fork 4038 to become disengaged from the retaining arms of the support stent 10. Once the prongs of the inner fork 4038 are disengaged, the prongs of the outer fork 4040 can be disengaged from the retaining arms by retracting the stent delivery outer catheter 4008. Once the support stent 10 and the prosthetic valve 4070 are disengaged from the delivery system 4000, the stent delivery outer catheter 4018, the stent delivery inner catheter 4018, and the prosthetic valve delivery catheter 4060 can be retracted (at least partially) into the main catheter 4002. The delivery system 4000 can then be retracted from the aortic arch 4202 over the guide wire 4080 and removed from the patient. The guide wire can then be withdrawn from the patient as well, leaving the prosthetic valve 4070 securely positioned within the aortic valve 4210 by the support stent 10 as shown by FIG. 46.

Figure 47:
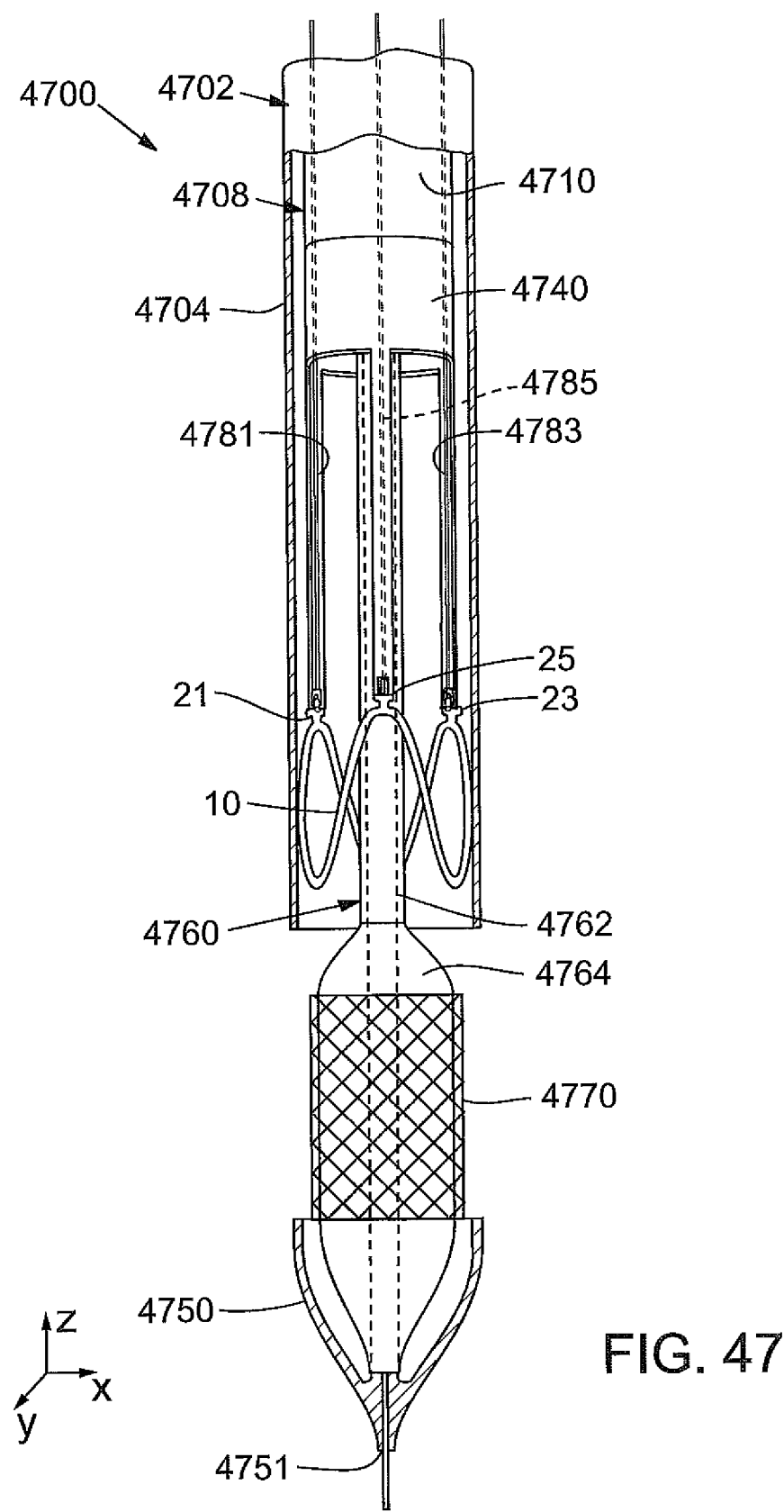
FIG. 47 is a front view of another exemplary integrated delivery system for embodiments of the disclosed support structures.

FIG. 47 is a front view of an embodiment of a delivery system 4700 that is similar to the embodiment shown in FIG. 40 but in which the inner fork catheter is replaced by one or more cables or wires. In particular, FIG. 47 shows the delivery system when the support stent 10 is in a compressed, predeployed state. The delivery system 4700 comprises a main catheter 4702 (which can be a steerable guide catheter) having an elongated shaft 4704. The delivery system 4700 also includes a stent delivery outer catheter 4708 positioned in the interior of the main catheter 4702. The stent delivery outer catheter 4708 has an elongated shaft 4710 and an outer fork 4740 connected to a distal end portion of the shaft 4710. The shaft 4710 of the stent delivery outer catheter 4708 can be configured to be moveable axially relative to the other shafts of the delivery system 4700 (e.g., using a handle or lever (such as a lockable handle or lever) located at or near a proximal end of the delivery system 4700 as is known in the art). Furthermore, the shaft 4710 of the stent delivery outer catheter 4708 can be sized so that its exterior wall is adjacent to or in contact with the inner wall of the shaft 4704 of the main catheter 4702.

Instead of a stent delivery inner catheter, the delivery system 4700 includes threads or wires 4781, 4783, 4785 having distal ends that form a hook, slip knot, suture loop, or other shape that allows the threads or wires to be releasably engage the retaining arms 21, 23, 25 of the support stent. The wires 4781, 4783, and 4785 can alternatively include a fastening mechanism at their distal end that allows the wires to be releasably coupled to the retaining arms 21, 23, 25. In general, the wires 4781, 4783, and 4785 operate in substantially the same fashion as the prongs of the inner fork 4038 shown in FIG. 40. For example, each of the wires 4881, 4783, and 4785 can include a suture loop at its distal end that is configured to be threaded through the eyelets (not shown) of the retaining arms 21, 23, 25, thereby securing the prongs of the outer fork 4740 to the retaining arms in the fashion shown in FIG. 6. The wires 4781, 4783, 4785 can extend through the interior of the stent delivery outer catheter 4708 (e.g., through an annular lumen or one or more interior lumens of the stent delivery outer catheter 4708) to proximal ends at or near the proximal end of the main catheter 4702. The proximal ends of the wires 4781, 4783, 4785 can be coupled to a handle or other control mechanism configured to allow for the wires to be retracted relative to the stent delivery outer catheter 4708. When retracted, the distal ends of the wires 4781, 4783, 4785 become disengaged from the retaining arms 21, 23, 25 (e.g., by releasing a slip-knot or suture loop, by causing a hooked portion of the wires to be straightened and pulled through the eyelet of a retaining arm, or by another such releasing mechanism). Once the wires 4781, 4783, 4785 are disengaged, the prongs of the outer fork 4740 become disengaged, thereby releasing the support stent in its desired position.

As with the delivery system 4000, the delivery system 4700 further includes a prosthetic valve delivery catheter 4760. The prosthetic valve delivery catheter 4760 comprises an elongated shaft 4762 positioned in the interior of the stent delivery inner catheter 4718 and a balloon portion 4764 located near a distal end of the elongated shaft 4762. The shaft 4762 of the prosthetic valve delivery catheter 4760 can be configured to be moveable axially relative to the other shafts of the delivery system 4700 (e.g., using a handle or lever (such as a lockable handle or lever) located at or near a proximal end of the delivery system 4700 as is known in the art). As with the delivery system 4000, a prosthetic valve 4770 (e.g., a THV) is positioned around the balloon portion 4764 in a crimped or unexpanded state. The delivery system 4700 can be used to deliver the prosthetic valve 4770 to its desired location adjacent to or on the outflow side of the aortic valve in the manner described above with respect to FIGS. 42-46.

Figure 48:
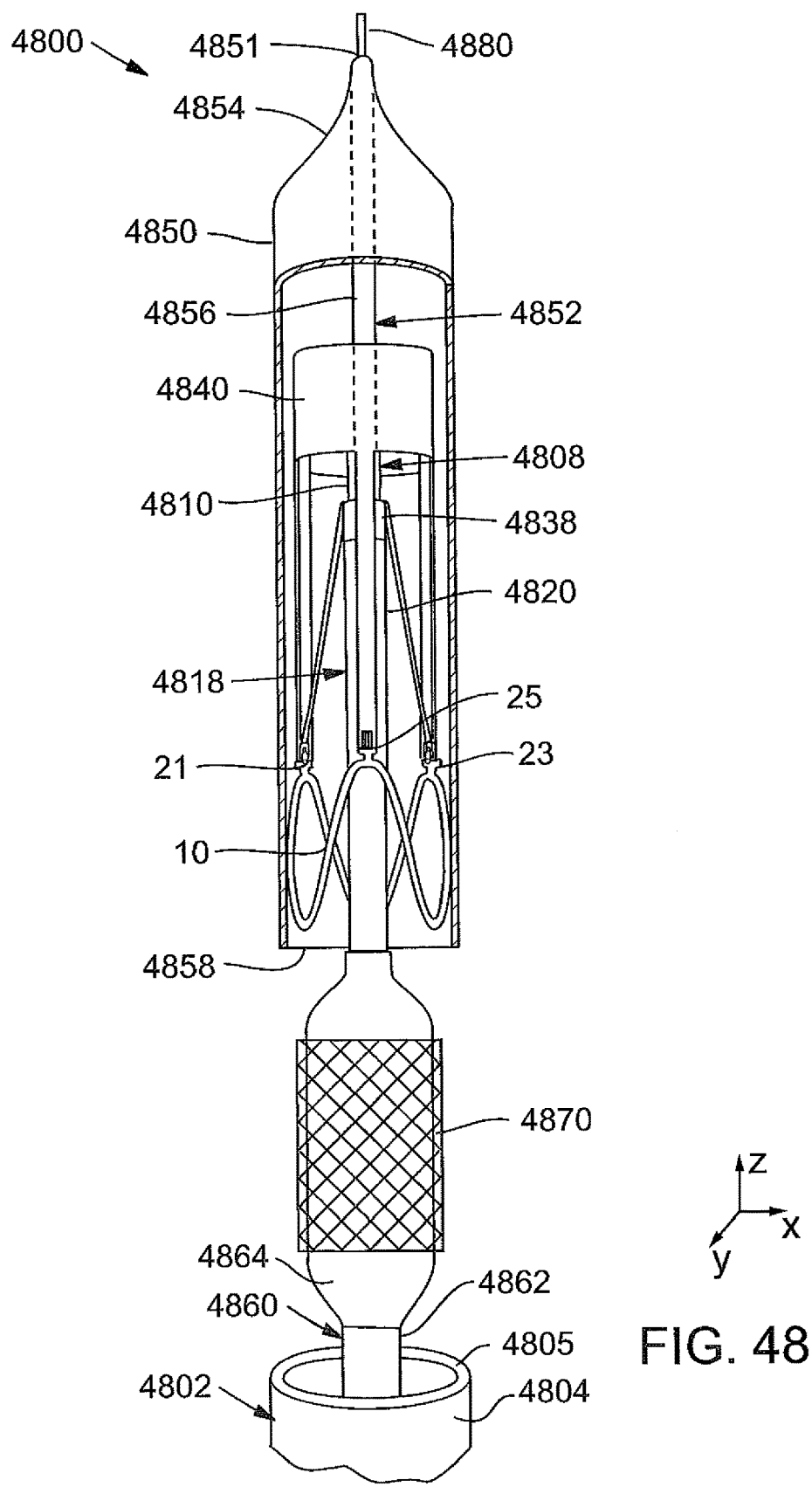
FIGS. 48 and 49 are front views of an exemplary integrated delivery system for delivering embodiments of the disclosed support structures. In particular.
Figure 49:
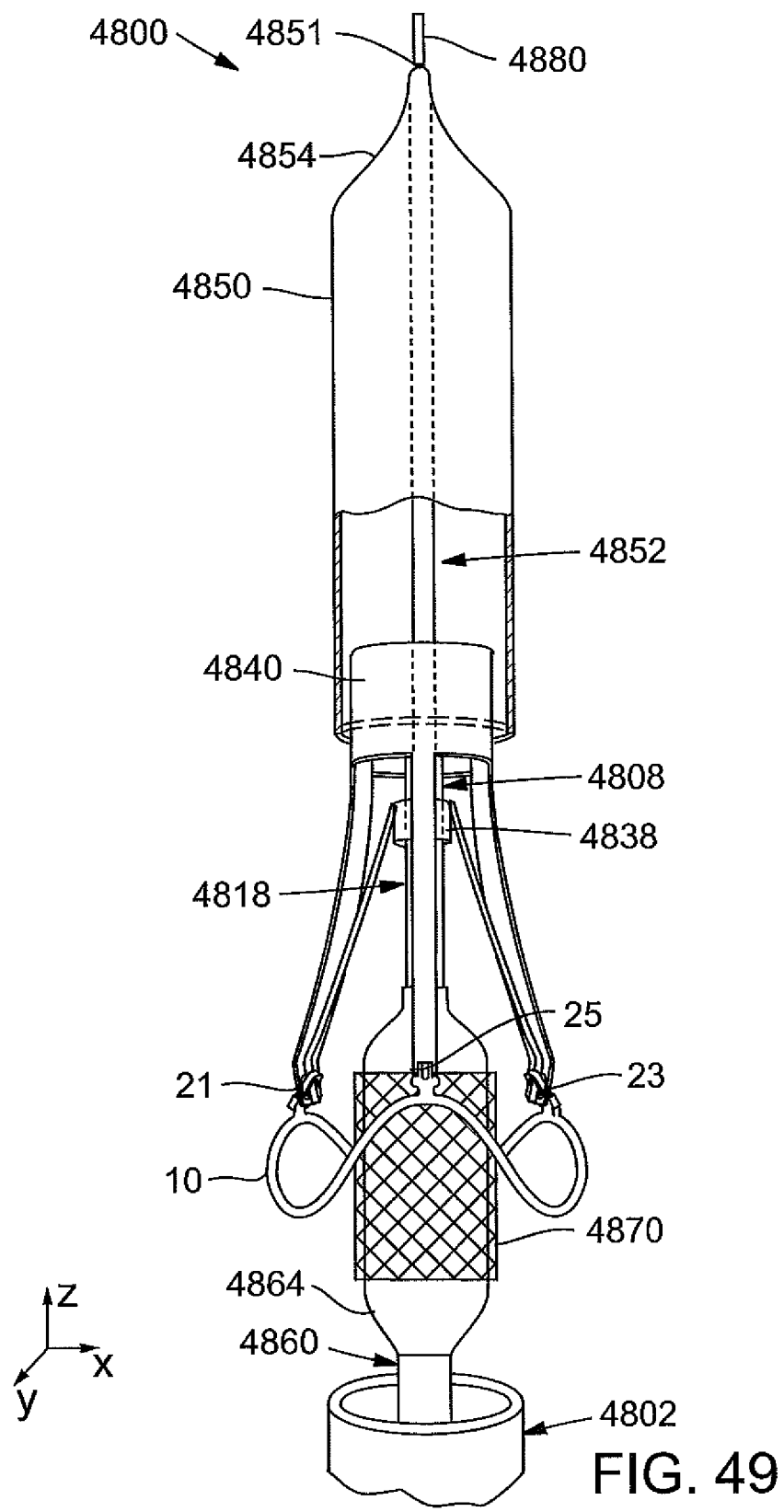

FIGS. 48 and 49 are front views of the distal end portion of an exemplary delivery system 4800 for delivering the support stent 10 to its location adjacent the native aortic valve through a patient's left ventrical (e.g., transapically). In particular, FIG. 48 shows the delivery system 4800 when the support stent 10 is in a compressed, predeployed state, whereas FIG. 48 shows the delivery system 4800 when the support stent 10 is in a decompressed, deployed state. The delivery system 4800 comprises an introducer sheath 4802 (which can alternatively be a steerable guide catheter) having an elongated shaft that is axially and rotatably movable relative to the other shafts of the delivery system 4800 (e.g., using a handle or lever (such as a lockable handle or lever) located at or near a proximal end of the delivery system 4800 as is known in the art). The introducer sheath 4802 of the illustrated embodiment is further configured to have the same or approximately the same circumference as an elongated nose cone 4850. The elongated nose cone 4850 includes a tapered distal portion 4854 and a distal end 4851 that can include a small lumen through which a guide wire can be inserted and further forms a housing circumferentially surrounding a stent delivery outer fork catheter 4808, a stent delivery inner fork catheter 4818, and a compressed support stent 10. For illustrative purposes, the nose cone 4850 is shown as being partially cut away, thus revealing the catheters in its interior.

A proximal end (not shown) of the introducer sheath 4802 is connected to a handle of the delivery system 4800. During delivery of the support stent, the handle can be used by a clinician to advance and retract the delivery system through the patient's heart. In a particular use, the delivery system 4800 is advanced transapically over a guide wire through the left ventricle of a patient's heart after having been inserted through a puncture in the left ventricle.

The delivery system 4800 includes a prosthetic valve delivery catheter 4860. The prosthetic valve delivery catheter 4860 comprises an elongated shaft 4862 positioned in the interior of the introducer sheath 4802 and a balloon portion 4864 located near a distal end of the elongated shaft 4862. The shaft 4862 of the prosthetic valve delivery catheter 4860 can be configured to be moveable axially relative to the other shafts of the delivery system 4800 (e.g., using a handle or lever (such as a lockable handle or lever) located at or near a proximal end of the delivery system 4800 as is known in the art). In some embodiments, the shaft 4862 is configured to be sized so that its exterior wall is adjacent to or in contact with the inner wall of the shaft 4804 of the introducer sheath 4802. In the illustrated embodiment, the shaft 4862 is the outermost catheter within the introducer sheath 4802. Furthermore, the balloon portion 4864 defines a lumen through which one or more additional catheters are placed. A prosthetic valve 4870 (e.g., a THV) is positioned around the balloon portion 4864 in a crimped or unexpanded state. The prosthetic valve 4870 can be any suitable expandable prosthetic heart valve, such as those described in U.S. Patent Application Publication No. 2007/0112422 (U.S. application Ser. No. 11/280,063) and 2010/0049313 (U.S. application Ser. No. 12/429,040), which are expressly incorporated herein by reference. The prosthetic valve delivery catheter 4860 can include one or more fluid lumens (not shown) through which a suitable liquid or gas can be inserted to cause the balloon portion to expand, thereby expanding the prosthetic valve 4870 into its expanded state (e.g., the prosthetic valve delivery catheter 4860 can be a balloon catheter). The one or more fluid lumens of the prosthetic valve delivery catheter 4860 can be an annular lumen or a non-concentric (or offset) lumen that allows one or more further lumens to be defined within the prosthetic valve delivery catheter 4860. In certain embodiments, the prosthetic valve delivery catheter 4860 itself comprises multiple catheters, including an outer catheter to which the balloon is attached and an inner catheter that is coupled to the balloon only at the balloon's distal end. With such a design, fluid can be inserted in the annular space between the outer catheter and the inner catheter. In FIG. 48, the prosthetic valve 4870 is shown as not being enclosed by the introducer sheath 4802. However, in other embodiments, the introducer sheath 4802 can be configured to enclose the prosthetic valve 4870 during insertion of the delivery system 4800 into the vasculature of the patient.

As noted, the delivery system 4800 also includes a stent delivery outer fork catheter 4808 and a stent delivery inner fork catheter 4818. In the illustrated embodiment, the stent delivery inner fork catheter 4818 comprises a stent delivery inner fork 4838 positioned in the interior of the elongated nose cone 4850 and secured to a distal end of an elongated shaft 4820. The shaft 4820 can be sized to fit within the lumen of the prosthetic valve delivery catheter 4860. In particular, the shaft 4820 can be configured to be moveable axially relative to the other shafts of the delivery system

4800 (e.g., using a handle or lever (such as a lockable handle or lever) located at or near a proximal end of the delivery system 4800 as is known in the art). Furthermore, the shaft 4820 can be sized so that its exterior wall is adjacent to or in contact with the inner wall of the lumen of the prosthetic valve delivery catheter 4860.

The stent delivery outer fork catheter 4808 comprises a stent delivery outer fork 4840 positioned in the interior of the nose cone 4850 and secured to a distal end of an elongated shaft 4810. In this embodiment, the shaft 4810 of the stent delivery outer fork catheter 4808 is sized to fit within the stent delivery inner fork catheter 4818. In particular, the shaft 4810 of the stent delivery outer fork catheter 4808 can be configured to be moveable axially relative to the other shafts of the delivery system 4800 (e.g., using a handle or lever (such as a lockable handle or lever) located at or near a proximal end of the delivery system 4800 as is known in the art). Furthermore, the shaft 4810 of the stent delivery outer catheter 4808 can be sized so that its exterior wall is adjacent to or in contact with the inner wall of the shaft 4820 of the stent delivery inner fork catheter 4818. (Note that this is in contrast to the delivery system 4000 described above in which the shaft 4010 of the stent delivery outer catheter 4008 has a larger circumference than the shaft 4020 of the stent delivery inner catheter 4018 and encloses the shaft 4020.)

The stent delivery system 4800 further includes a nose cone catheter 4852 having a shaft 4856 and a distal end to which the nose cone 4850 is secured. For example, the distal portion 4854 of the nose cone 4850 can be attached to the distal end of the nose cone catheter 4852. The nose cone 4850 can be attached to the nose cone catheter 4852, for instance, using a suitable adhesive, a frictional engagement mechanism (e.g., a snap-fit or threaded collar attachment), by forming the nose cone 4850 and the nose cone catheter 4852 as part of a single unibody element (e.g., using suitable molding techniques), or other such attachment mechanisms. In the illustrated embodiment, shaft 4856 of the nose cone catheter 4852 can be sized so that its exterior wall is adjacent to or in contact with the inner wall of the shaft 4810 of the stent delivery outer fork catheter 4818. In particular, the shaft 4856 of the nose cone catheter 4852 can be configured to be moveable axially relative to the other shafts of the delivery system 4800 (e.g., using a handle or lever (such as a lockable handle or lever) located at or near a proximal end of the delivery system 4800 as is known in the art). Additionally, the nose cone catheter 4852 can define an interior lumen through a guide wire can extend. For instance, a guide wire 4880 can be inserted through the nose cone catheter 4852 such that it extends through a distal end 4851 of the elongated nose cone 4850.

In FIG. 48, the support stent 10 is shown in a radially compressed state in the interior of the elongated nose cone 4850. In this undeployed and compressed state, the prongs of the outer fork 4840 and the inner fork 4838 of the stent delivery outer fork catheter 4808 and the stent delivery inner fork catheter 4818 engage the retaining arms 21, 23, 25 of the support stent 10 in the manner described above with respect to FIGS. 5 and 6. To deploy the support stent 10 in the illustrated embodiment (advance the stent from the delivery system 4800), the nose cone catheter and the elongated nose cone 4850 are advanced distally relative to the stent delivery outer fork catheter 4808 and the stent delivery inner fork catheter 4818 using one or more control handles or mechanisms (not shown) located at the proximal end of the delivery system 4800. This action causes the stent 10 to be revealed through a proximal end 4858 of the elongated nose cone 4850. When the wall of the elongated nose cone 4850 extends beyond the support stent 10, the support stent can expand into its relaxed, uncompressed state (shown, for example, in FIGS. 1 and 2).

FIG. 49 is a front view showing the support stent 10 after the nose cone 4850 has been advanced to reveal the support stent to the exterior of the delivery system 4800. As seen in FIG. 49, the support stent 10 now assumes its relaxed, uncompressed shape but remains connected to the outer fork 4840 and the inner fork 4838 at its retaining arms 21, 23, 25. In this configuration, the support stent 10 can be rotated (in the clockwise or counter-clockwise directions) or repositioned (in the proximal and distal directions and/or into a different position in the x-y plane) into a proper orientation adjacent to its intended target area. For example, the support stent 10 can be positioned against the upper surfaces of leaflets of an aortic valve in the manner illustrated in FIG. 2 while the support stent 10 remains connected to the delivery system 4800 via the retaining arms 21, 23, 25.

As more fully illustrated below in FIGS. 50-55, a prosthetic valve (e.g., a THV) can be delivered to the aortic valve entirely through a transapical approach (e.g., through the apex of the heart through the left ventricle) using the delivery system 4800. The prosthetic valve 4870 can be deployed transapically within the native valve such that the prosthetic valve is secured in place by frictional or mechanical engagement between the support stent 10, the native leaflets, and the prosthetic valve. As explained above with reference to FIGS. 4 and 5, the support stent 10 can be shaped so that the native leaflets of the aortic valve become trapped or pinched between the support stent 10 and the exterior of the prosthetic valve 4870 when the prosthetic valve is expanded and deployed within the native valve. The deployment system 4800 can be used, for example, to deliver a support stent 10 to treat aortic insufficiency, as well as any other condition in which the aorta or aortic valve may not be in condition to help support the prosthetic valve (e.g., when the aortic annulus is too dilated or in which the leaflets of the aorta are too weak or soft to support the prosthetic valve).

FIGS. 50-55 illustrate one exemplary procedure for deploying the support stent and securing the prosthetic valve 4870 (e.g., a THV) to the support stent 10 using the delivery system 4800 or other such transapical delivery system. In particular, FIGS. 50-55 are cross-sectional views through the left side of a patient's heart showing the acts performed in delivering the support stent 10 through the left ventricle and into the annulus of the aortic valve. In order to better illustrate the components of the delivery system 4800, the introducer sheath 4802 is shown partially cut away in FIGS. 50-55.

Figure 50:
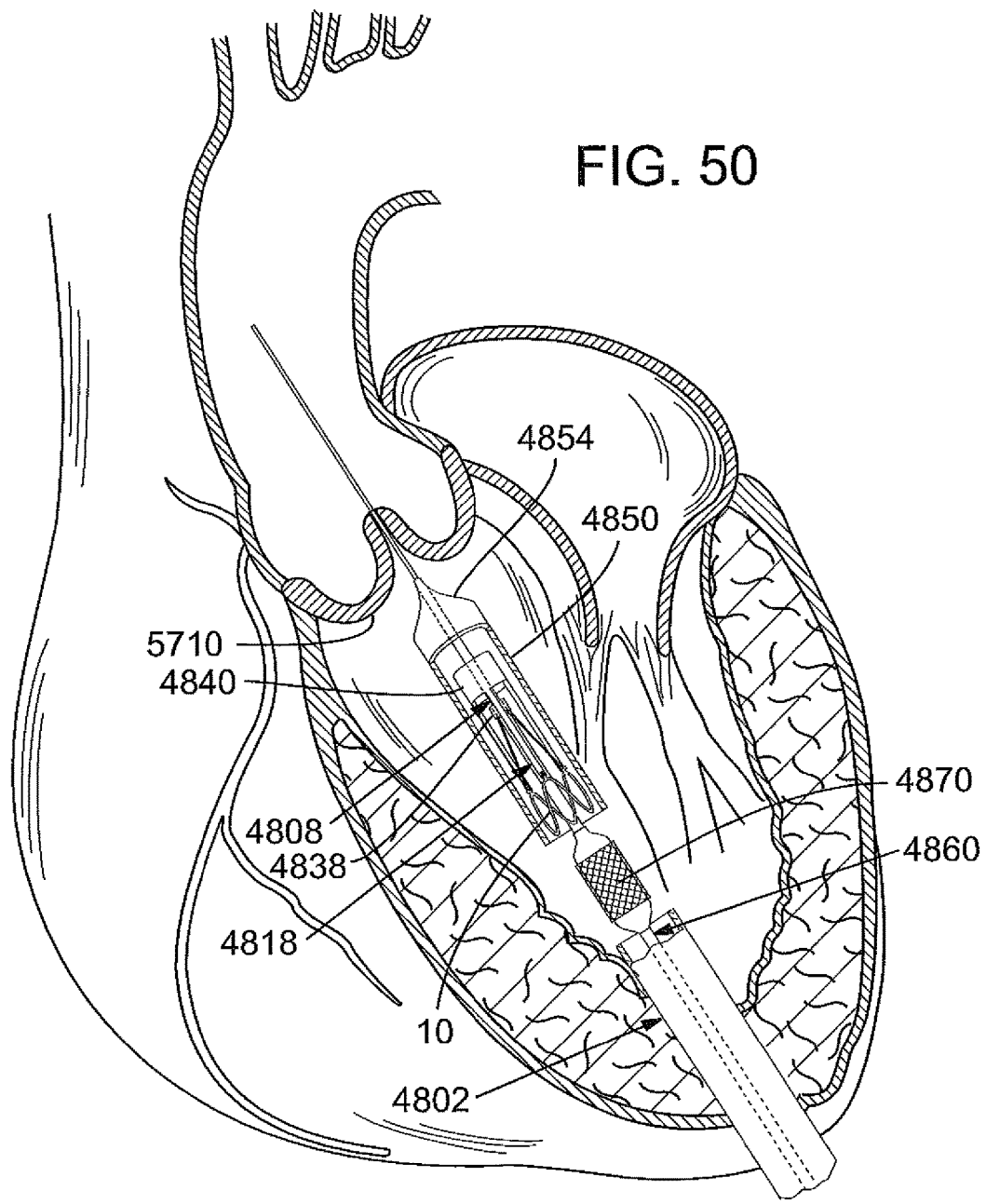
FIGS. 50-55 are cross-sectional views of a patient's heart illustrating how the delivery system of FIGS. 48 and 49 can operate to deploy the support structure of FIG. 1 to a desired position on the patient's aortic valve.

FIG. 50 shows the introducer sheath 4802 and the nose cone 4850 of the delivery system 4800 as they are advanced toward the aortic valve 5010. FIG. 50 also shows the outer fork 4840 of the stent delivery outer fork catheter 4808, the inner fork 4838 of the stent delivery inner fork catheter 4818, the prosthetic valve delivery catheter 4860, and the support stent 10. In FIG. 50, the introducer sheath 4802 is advanced in the direction of guidewire 4880, which is shown as being extended through the aortic valve 5010. In FIG. 50, the prosthetic valve 4870 is shown as not being enclosed by the introducer sheath 4802. However, in other embodiments, the introducer sheath 4802 can be configured to enclose the prosthetic valve 4870 during insertion of the delivery system 4800 into the vasculature of the patient.

Figure 51:
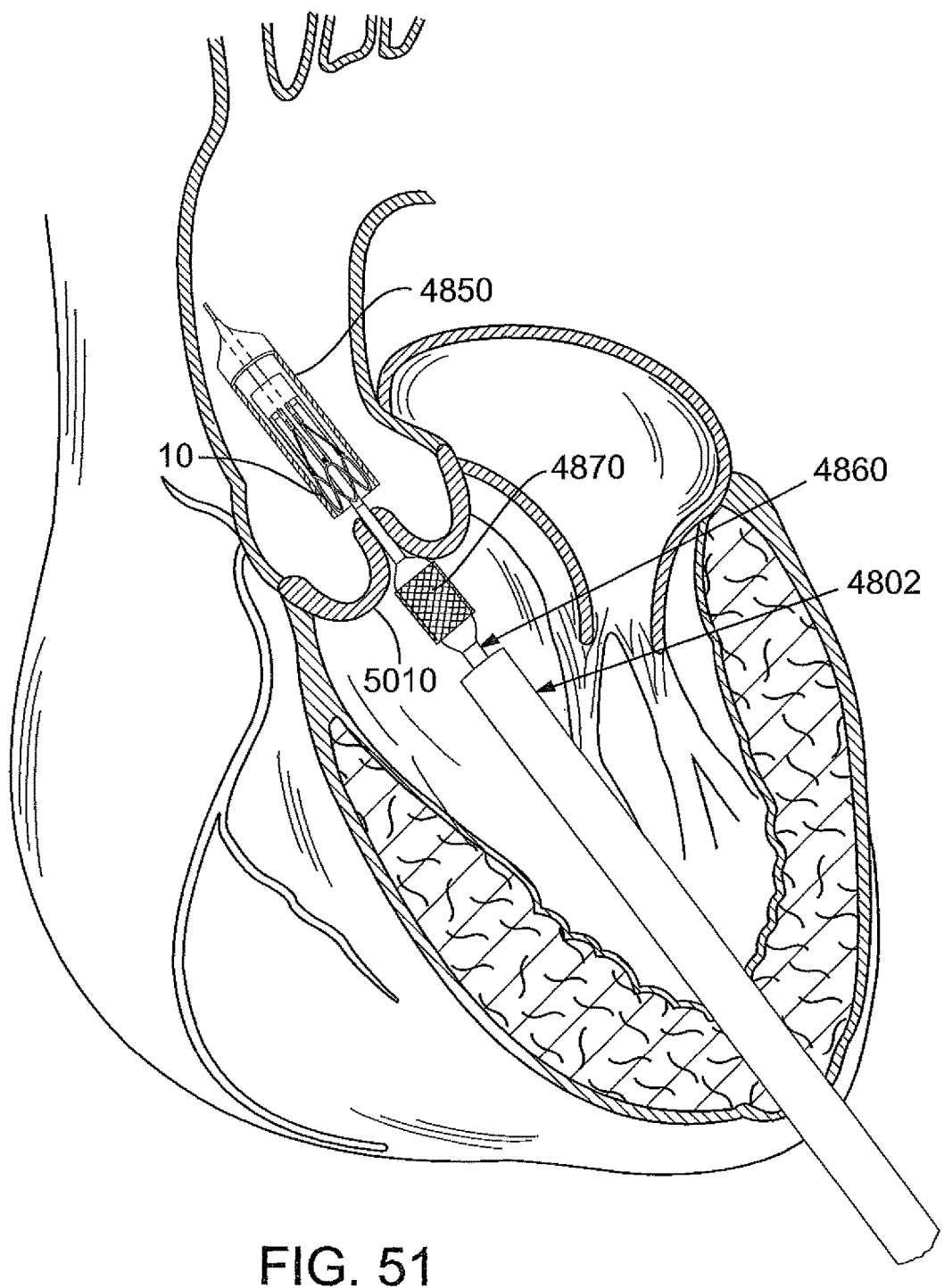

In FIG. 51, the introducer sheath 4802 and the nose cone 4850 are advanced over the guidewire 4880 through the annulus of the aortic valve 5010. In particular, the nose cone 4850 is advanced so that the support stent 10 is located in a position that is above the native leaflets of the aortic valve when the valve is open.

Also seen in FIG. 51 is the valve delivery catheter 4870, which is positioned adjacent or near to the inflow side of the aortic valve 5010. This positioning allows the operator of the delivery system 4800 to position the support stent 10 into its proper location without any interference in the aortic valve 5010 caused by the presence of the prosthetic valve 4870 in the interior of the native valve.

Figure 52:
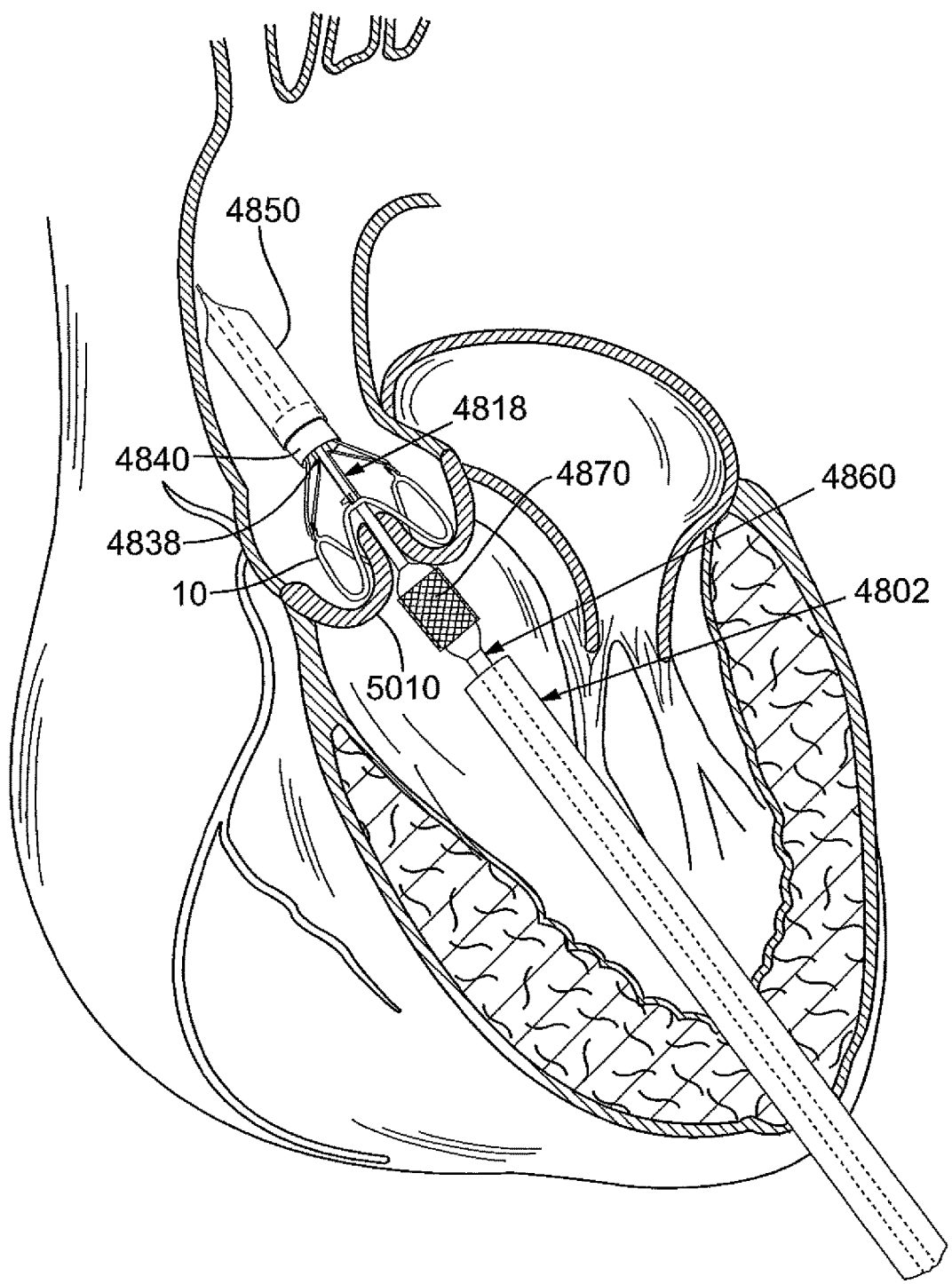

In FIG. 52, the nose cone 4850 is advanced distally relative to the outer fork 4840 of the stent delivery outer fork catheter 4808 (not visible in FIG. 52) and the inner fork 4838 of the stent delivery inner fork catheter 4818. With the nose cone 4850 advanced, the support stent 10 is no longer held within the inner walls of the nose cone 4850 and expands into its uncompressed, natural shape in a position on the outflow side of the aortic valve 5010. In FIG. 51, the support stent 10 is self-expanding. In other embodiments, however, the support stent may not be self-expanding. In such embodiments, the support stent can be made of a suitable ductile material, such as stainless steel. In addition, a mechanism for expanding the support stent can be included as part of the delivery system 4800. For example, and as explained above with respect to FIG. 8, the support stent can be disposed around a balloon of a balloon catheter in a compressed state In FIG. 52, the stent delivery outer fork catheter 4808 (not visible in FIG. 52) and the stent delivery inner fork catheter 4818 are positioned so that the support stent 10 is placed adjacent to or directly on the surface of the outflow side of the aortic valve. The support stent 10 is rotated and positioned as necessary so that the support stent generally circumscribes the aortic valve and so that the peaks of the support stent are aligned with the tips of the natural leaflets of the aortic valve 5010. Therefore, when the prosthetic valve 4870 is inserted and expanded within the aortic valve 5010, the leaflets of the aortic valve will engage at least the majority of the surface in the interior of the support stent 10. In other embodiments, the support stent 10 is rotated and positioned as necessary so that the peaks of the support stent are aligned with the commissures or other portions of the aortic valve. The position of the introducer sheath 4802, the nose cone 4850, the prosthetic valve 4870, and the support stent 10 relative to the aortic valve 5010, as well as the position of other elements of the system, can be monitored using radiopaque markers and fluoroscopy, or using other imaging systems such as transesophageal echo, transthoracic echo, intravascular ultrasound imaging ("IVUS"), or an injectable dye that is radiopaque.

Also seen in FIG. 52 are the prongs of the outer fork 4840 and the prongs of the inner fork 4838. In the exemplary procedure, the prongs of the outer fork 4840 and the inner fork 4838 remain secured to the support stent 10 until the prosthetic valve is deployed and frictionally engaged to the support stent. The inner and outer forks 4838, 4840 desirably form a connection between the stent 10 and the delivery system that is secure and rigid enough to allow the clinician to hold the stent 10 at the desired implanted position against the flow of blood while the prosthetic valve is being implanted.

Also seen in FIG. 52 is the valve delivery catheter 4860, which is positioned adjacent or near to the inflow side of the aortic valve 5010. This positioning allows the operator of the delivery system 4800 to position the support stent 10 into its proper location without any interference in the aortic valve 5010 caused by the presence of the prosthetic valve 4870 in the interior of the native valve.

Figure 53:
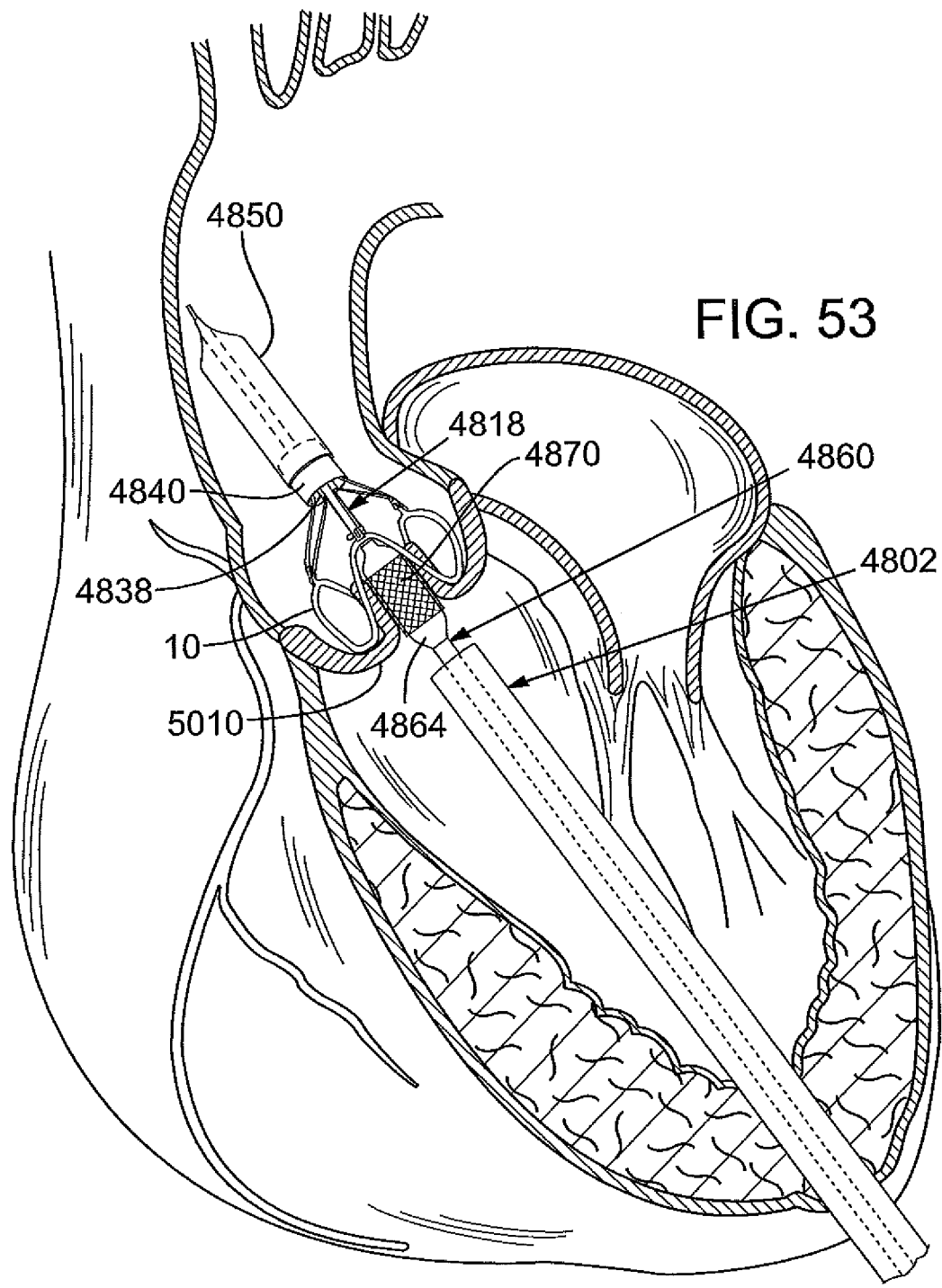

In FIG. 53, the support stent 10 is properly positioned and oriented on the outflow side of the aortic valve 5010. The valve delivery catheter 4860 is then advanced into the aortic valve 5010 so that the prosthetic valve 4870 is located within the interior of the annulus of the aortic valve and within the interior of the expanded support stent 10 (e.g., concentrically with the annulus of the aortic valve and the expanded support stent 10).

At the point in the exemplary procedure illustrated in FIG. 53, the compressed prosthetic vlave 4870 is ready to be expanded into the aortic valve 5010. The balloon portion 4864 is then inflated to expand the prosthetic valve 4870, thereby causing the exterior of the prosthetic valve to engage the leaflets of the aortic valve 5010, and in turn cause the leaflets of the aortic valve to engage the inner wall of the support stent 10. In other words, the expansion of the prosthetic valve 4870 pinches the leaflets of the aortic valve 5010 between the support stent and the prosthetic valve 4870, thereby securing the prosthetic valve within the annulus of the aortic valve.

In order to better illustrate the components of the delivery system for the prosthetic valve, FIGS. 52 through 55 show the front third of the support stent 10 and the front of the prosthetic valve 4870, but do not show the portions of the native heart valve that would be secured by the front of the support stent 10. It is to be understood, however, that a corresponding leaflet of the native heart valve would be secured between the support stent 10 and the prosthetic valve 4870.

Radiopaque markers may be provided on the prosthetic valve delivery catheter 4860 to more accurately determine the position of the valve 4870 and the balloon portion 4864 relative to the support stent 10 and the aortic valve 5010. In some embodiments, the clinician can adjust the position of the valve 4870 by actuating a steering or deflecting mechanism within the prosthetic valve delivery catheter 4860. Furthermore, the rotational orientation of the valve 4870 can be adjusted relative to the cusps and commissures of the native aortic valve by twisting the prosthetic valve delivery catheter 4860 from its proximal end and observing specific markers on the valve (or prosthetic valve delivery catheter) under fluoroscopy.

Figure 54:
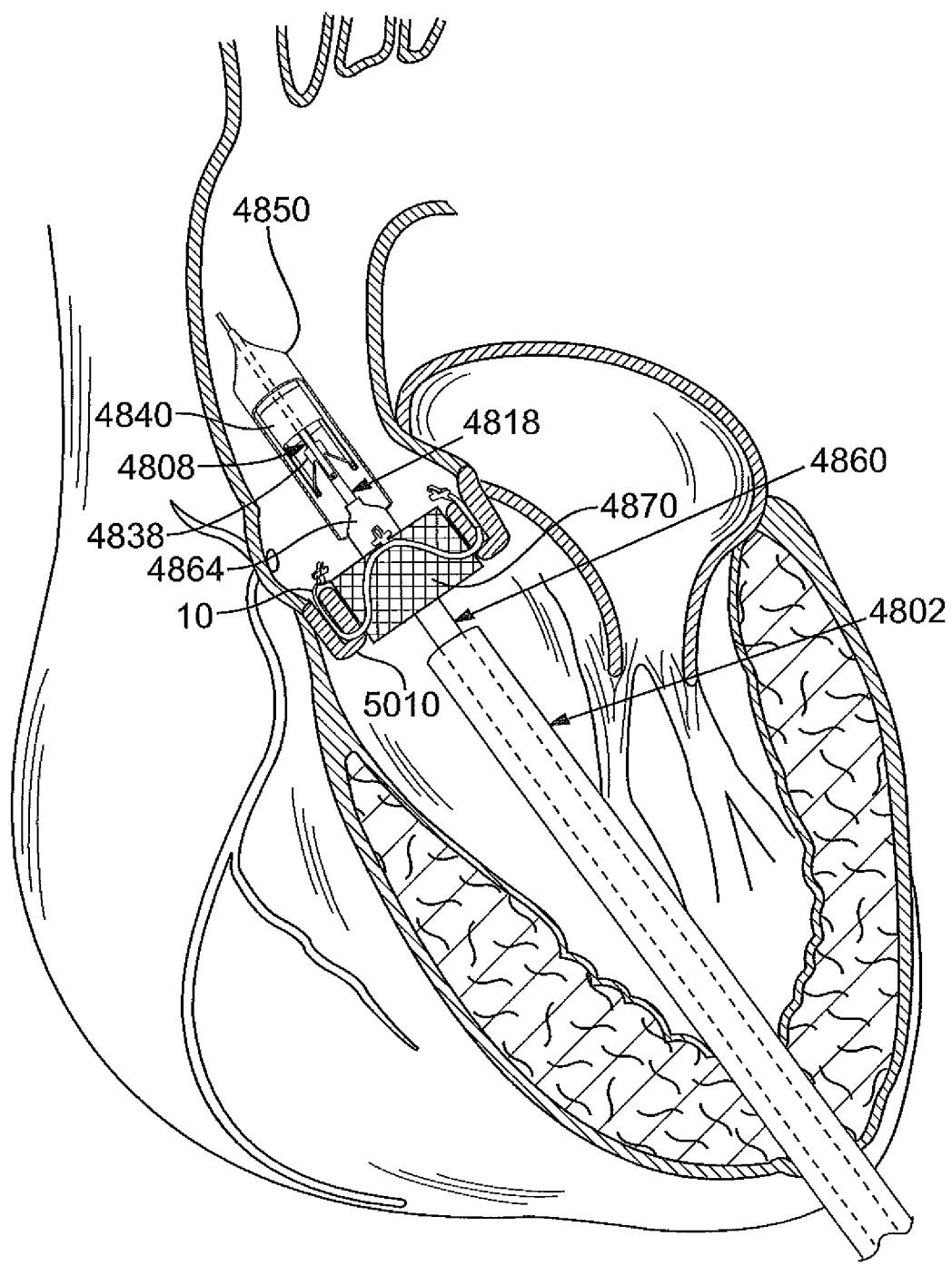
Figure 55:
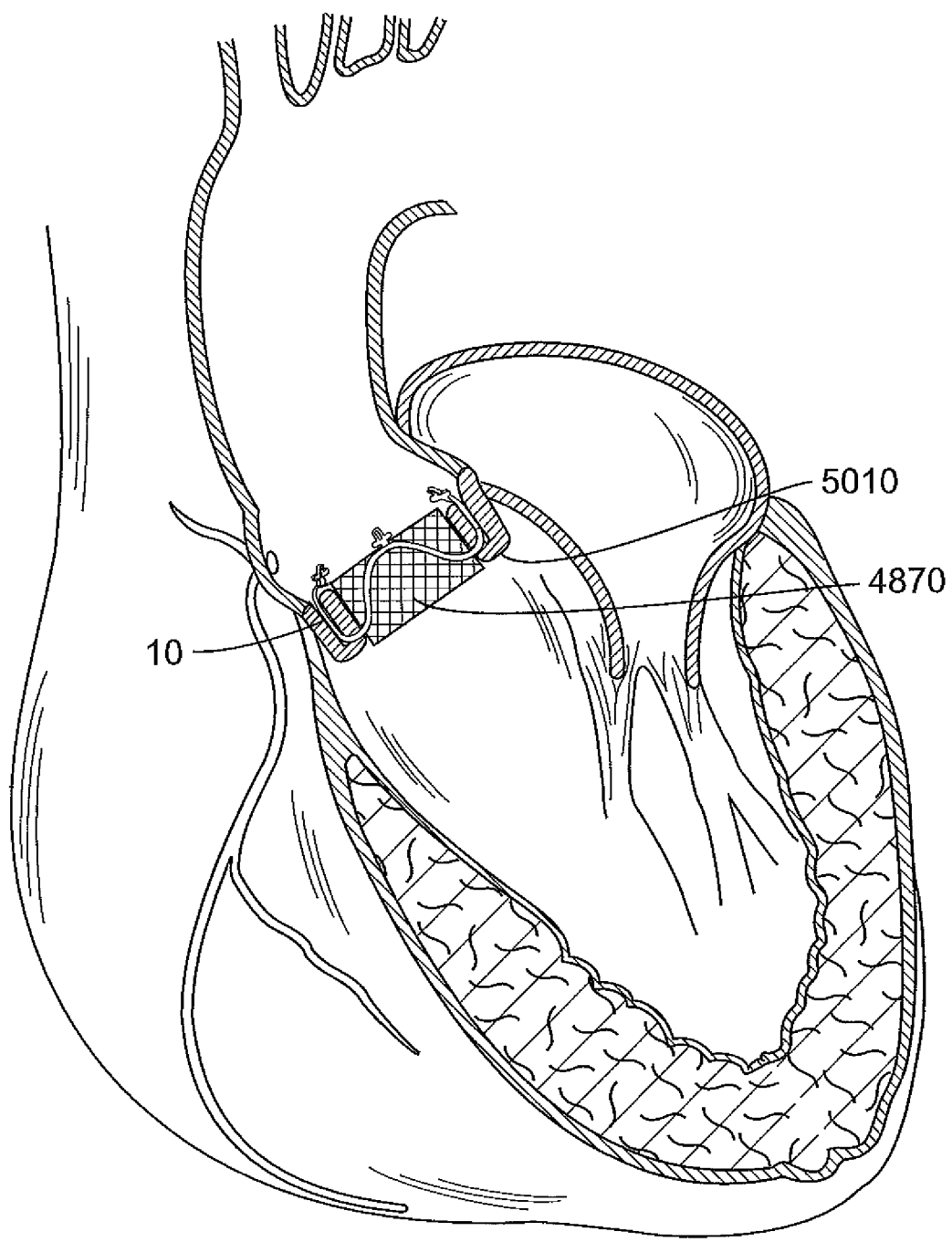

As shown in FIG. 54, once the prosthetic valve 4870 is secured into its desired position, the balloon portion 4864 can be deflated and the stent delivery inner fork catheter 4818 of the delivery system 4800 can be advanced distally while the stent delivery outer fork catheter 4808 is held in a constant position, thereby causing the prongs of the inner fork 4838 to become disengaged from the retaining arms of the support stent 10. Once the prongs of the inner fork 4838 are disengaged, the prongs of the outer fork 4840 become disengaged from the retaining arms. The stent delivery outer fork catheter 4808 is then advanced distally. Furthermore, and as also illustrated in FIG. 54, the stent delivery inner fork catheter 4818 and the stent delivery outer fork catheter 4808 can be advanced into the elongated nose cone 4850 so that the prongs of the inner fork 4838 and the prongs of the outer fork 4840 are enclosed within the walls of the nose cone. With the balloon portion 4864 deflated and the stent delivery inner fork catheter 4818 and the stent delivery outer fork catheter 4808 (as well as the prongs of their associated forks) being enclosed by the nose cone, the nose cone 4850 and the prosthetic valve delivery catheter 4860 can be retracted into the introducer sheath 4802. The delivery system 4800 can then be retracted from the left ventricle over the guide wire and removed from the patient, leaving the prosthetic valve 4870 securely positioned within the aortic valve 5010 by the support stent 10 as shown in FIG. 55.

It should be noted that the balloon-expandable prosthetic valve used in the above embodiments can take a variety of different forms and may comprise an expandable stent portion that supports a valve structure. The stent portion desirably has sufficient radial strength to hold the valve at the treatment site and to securely engage the support stent 10. Additional details regarding balloon expandable valve embodiments that can be used in connection with the disclosed technology are described in U.S. Pat. Nos. 6,730,118 and 6,893,460, both of which are hereby expressly incorporated herein by reference.

Figure 56:
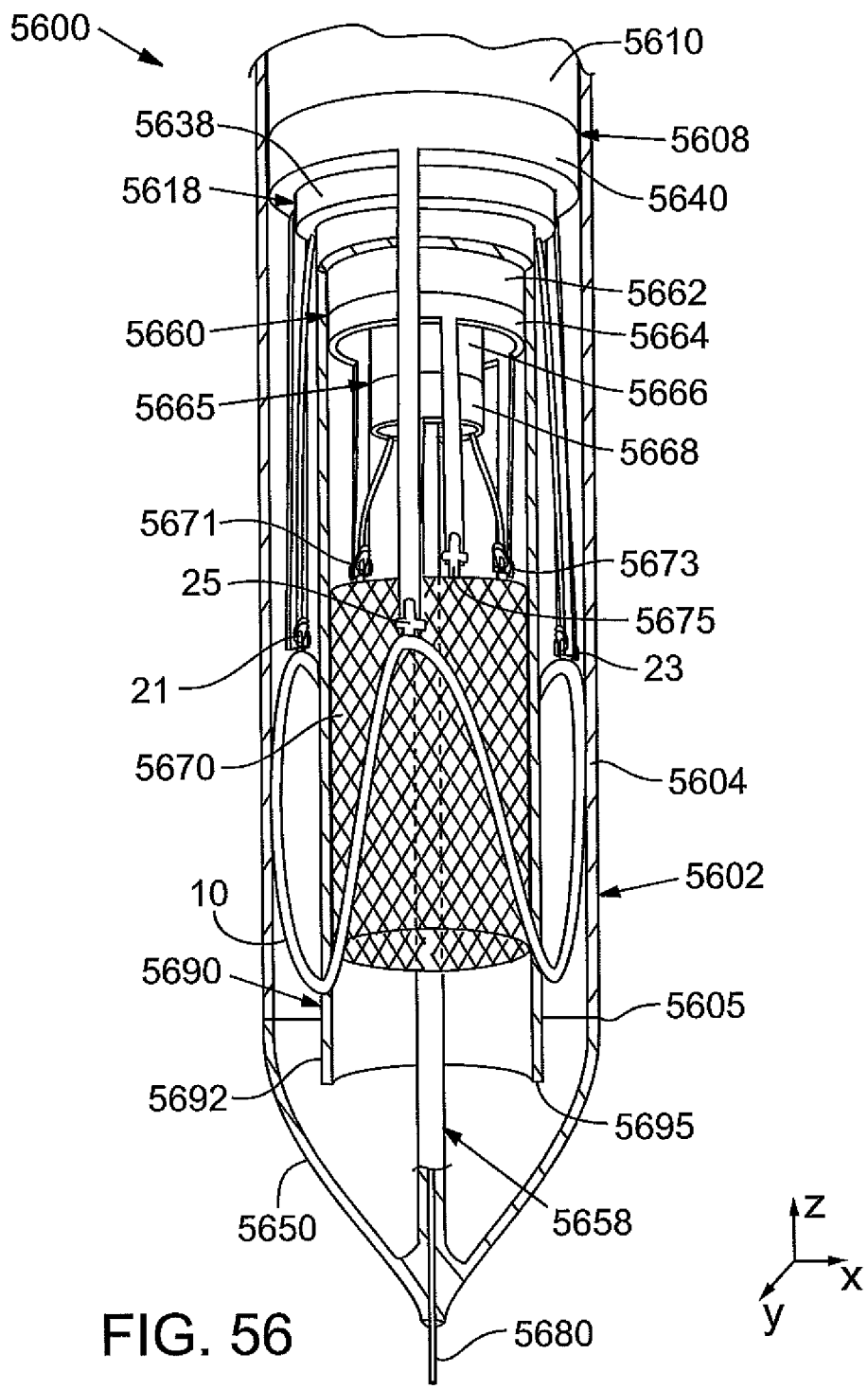
FIG. 56 is a front view of an exemplary integrated delivery system for delivering embodiments of the disclosed support structures. In particular.

FIG. 56 is a front view of the distal end portion of an exemplary delivery system 5600 for delivering the support stent 10 to its location adjacent the native aortic valve through a patient's vasculature (e.g., transfemorally). In contrast to the embodiment illustrated in FIGS. 40 and 41, the prosthetic valve used with the delivery system 5600 is a self-expanding prosthetic valve 5670. FIG. 56 shows the delivery system 5600 when the support stent 10 is in a compressed, predeployed state. The delivery system 5600 comprises a main catheter 5602 having an elongated shaft 5604, whose distal end 5605 is open and is configured to have a diameter that is the same as or approximately the same as nose cone 5650. In other embodiments, the distal end 5605 of the main catheter 5602 can be tapered (e.g., tapered into a conical shape comprising multiple "flaps" forming a protective nose cone that can be urged apart when the support stent 10 and any interior catheters are advanced therethrough or into any other tapered profile, such as those identified above with respect to the embodiment shown in FIGS. 40 and 41). Furthermore, for illustrative purposes, the main catheter 5602 is shown as being partially cut away, thus revealing the catheters in its interior.

A proximal end (not shown) of the main catheter 5602 is connected to a handle of the delivery system 5600. During delivery of a support stent, the handle can be used by a clinician to advance and retract the delivery system through the patient's vasculature. In a particular use, the delivery system 5600 is advanced through the aortic arch of a patient's heart in the retrograde direction after having been percutaneously inserted through the femoral artery. The main catheter can be configured to be selectively steerable or bendable to facilitate advancement of the delivery system 5600 through the patient's vasculature. An exemplary steerable catheter as can be used in embodiments of the disclosed technology is described in detail in U.S. Patent Application Publication No. 2007/0005131 (U.S. patent application Ser. No. 11/152,288), which is hereby expressly incorporated herein by reference.

The delivery system 5600 also includes a stent delivery outer catheter 5608 positioned in the interior of the main catheter 5602. The stent delivery outer catheter 5608 has an elongated shaft 5610 and an outer fork 5640 connected to a distal end portion of the shaft 5610. The shaft 5610 of the stent delivery outer catheter 5608 can be configured to be moveable axially relative to the other shafts of the delivery system 5600 (e.g., using a handle or lever (such as a lockable handle or lever) located at or near a proximal end of the delivery system 5600 as is known in the art). Furthermore, the shaft 5610 of the stent delivery outer catheter 5608 can be sized so that its exterior wall is adjacent to or in contact with the inner wall of the shaft 5604 of the main catheter 5602.

The delivery system 5600 also includes a stent delivery inner catheter 5618 positioned in the interior of the stent deliver outer catheter 5608. The stent delivery inner catheter 5618 can have an elongated shaft (not shown) and an inner fork 5638 secured to the distal end portion of the shaft. The shaft of the inner catheter 5618 can be configured to be moveable axially relative to the other shafts of the delivery system 5600 (e.g., using a handle or lever (such as a lockable handle or lever) located at or near a proximal end of the delivery system 5600 as is known in the art). Furthermore, the shaft of the inner catheter 5618 can be sized so that its exterior wall is adjacent to or in contact with the inner wall of the shaft 5610 of the stent delivery outer catheter 5608.

The delivery system 5600 further includes a prosthetic valve sheath 5690 positioned in the interior of the stent delivery inner catheter 5618. The prosthetic valve sheath 5690 encloses a prosthetic valve delivery outer catheter 5660, a prosthetic valve delivery inner catheter 5665, and a compressed prosthetic valve 5670. The prosthetic valve sheath 5690 comprises an elongated shaft 5692 that terminates in an open distal end. The shaft 5692 of the prosthetic valve sheath 5690 can be configured to be moveable axially relative to the other shafts in the delivery system 5600 (e.g., using a handle or lever (such as a lockable handle or lever) located at or near a proximal end of the delivery system 5600 as is known in the art). Furthermore, the shaft 5692 can be sized so that its exterior wall is adjacent to or in contact with the inner wall of the shaft 5620 of the stent delivery inner catheter 5618.

The prosthetic valve delivery outer catheter 5660 has an elongated shaft 5662 and an outer fork 5664 connected to a distal end portion of the shaft 5662. The shaft 5662 of the prosthetic valve delivery outer catheter 5660 can be configured to be moveable axially relative to the other shafts of the delivery system 5600 (e.g., using a handle or lever (such as a lockable handle or lever) located at or near a proximal end of the delivery system 5600 as is known in the art). Furthermore, the shaft 5662 of the prosthetic valve delivery outer catheter 5660 can be sized so that its exterior wall is adjacent to or in contact with the inner wall of the shaft 5692 of the prosthetic valve sheath 5690.

The prosthetic valve delivery inner catheter 5665 can have an elongated shaft 5666 and an inner fork 5668 secured to the distal end portion of the shaft 5666. The shaft 5666 of the inner catheter 5665 can be configured to be moveable axially relative to the other shafts of the delivery system 5600 (e.g., using a handle or lever (such as a lockable handle or lever) located at or near a proximal end of the delivery system 5600 as is known in the art).

In the illustrated embodiment, a nose cone catheter 5658 is located within the prosthetic valve delivery inner catheter 5665 and has a distal end that is attached to a nose cone 5650. In other embodiments, the nose cone 5650 is absent. The nose cone catheter 5658 can define a guide wire lumen through which a guide wire 5680 can be inserted. The guide wire 5680 can extend through a distal end of the nose cone 5650 and can be used, for example, to help ensure proper advancement of the main catheter 5602 and its interior catheters through the vasculature of a patient.

A prosthetic valve 5670 (e.g., a THV) is in a compressed or unexpanded state and is contained within the prosthetic valve sheath 5690. The prosthetic valve 5670 can be any suitable expandable prosthetic heart valve, such as those described in U.S. Patent Application Publication Nos. 2007/0112422 (U.S. application Ser. No. 11/280,063) and 2010/0049313 (U.S. application Ser. No. 12/429,040), which are expressly incorporated herein by reference. Furthermore, in the embodiment illustrated in FIG. 56, the prosthetic valve includes retaining arms 5671, 5673, and 5675, which are engaged with the prongs of the outer fork 5664 and the inner fork 5668 of the prosthetic valve delivery outer catheter 5660 and the prosthetic valve delivery inner catheter 5665 in the manner described above with respect to FIGS. 5 and 6 and as described in U.S. Patent Application Publication No. 2010/0049313 (U.S. application Ser. No. 12/429,040), which is expressly incorporated herein by reference. To deploy the prosthetic valve 5670 in the illustrated embodiment (advance the valve from the delivery system), the prosthetic valve sheath 5690 together with the prosthetic valve delivery outer catheter 5660 and the prosthetic valve inner catheter 5665 are advanced through the distal end 5605 of the main catheter 5602, and then the prosthetic valve sheath 5690 is withdrawn to reveal the valve 5670. These actions can be performed, for example, using one or more control handles or mechanisms (not shown) located at the proximal end of the main catheter 5602. These actions cause the prosthetic valve 5670 to be advanced outwardly through the distal end 5695 of the prosthetic valve sheath 5690 and to expand into its relaxed, uncompressed state. In the illustrated embodiment, the prosthetic valve 5670 is shown as being positioned concentrically with the support stent 10. In other embodiments, however, the support stent 10 can be positioned distally of the prosthetic valve 5670.

In FIG. 56, the support stent 10 is shown in a radially compressed state in the interior of the elongated shaft 5604 of the main catheter 5602. In the radially compressed state, the distance along the z axis between a peak and an adjacent valley of the support stent is greater than the distance along the z axis between the peak and the adjacent valley when the support stent is in it uncompressed state. The distal end portion of the shaft 5604 can also be referred to as a delivery sheath for the stent 10. In this undeployed and compressed state, the prongs of the outer fork 5640 and the inner fork 5638 of the stent delivery outer catheter 5608 and the stent delivery inner catheter 5618 engage the retaining arms 21, 23, 25 of the support stent 10 in the manner described above with respect to FIGS. 5 and 6. To deploy the support stent 10 in the illustrated embodiment, the main catheter 5602 is withdrawn over the stent delivery outer catheter 5608 and the stent delivery inner catheter 5618, thereby advancing the stent delivery outer catheter 5608 and the stent delivery inner catheter 5618 through the distal end 5605 of the main catheter 5602. This action can be performed, for example, using one or more control handles or mechanisms (not shown) located at the proximal end of the main catheter 5602. Once advanced through the main catheter 5602, the support stent 10 can expand into its relaxed, uncompressed state (shown, for example, in FIGS. 1 and 2).

As more fully illustrated below in FIGS. 57-61, a prosthetic valve (e.g., a THV) can be delivered to the aortic valve entirely through a tranfemoral approach (e.g., through the aortic arch of the heart) using the deployment system 5600. The prosthetic valve 5670 can be deployed transfemorally within the native valve such that the prosthetic valve is secured in place by frictional engagement between the support stent, the native leaflets, and the prosthetic valve. As explained above with reference to FIGS. 4 and 5, the support stent 10 can be shaped so that the native leaflets of the aortic valve become trapped or pinched between the support stent 10 and the exterior of the prosthetic valve 5670 when the prosthetic valve is expanded and deployed within the native valve. The deployment system 5600 can be used, for example, to deliver a support stent 10 to treat aortic insufficiency, as well as any other condition in which the aorta or aortic valve may not be in condition to help support the prosthetic valve (e.g., when the aortic annulus is too dilated or in which the leaflets of the aorta are too weak or soft to support the prosthetic valve).

FIGS. 57-61 illustrate one exemplary procedure for deploying the support stent and securing a prosthetic valve (e.g., a THV) to the support stent. In particular, FIGS. 57-61 are cross-sectional views through the left side of a patient's heart showing the acts performed in delivering the support stent 10 through the aortic arch to the aortic valve. In order to better illustrate the components of the delivery system 5600, the main catheter 5602 is shown partially cut away in FIGS. 57-61.

Figure 57:
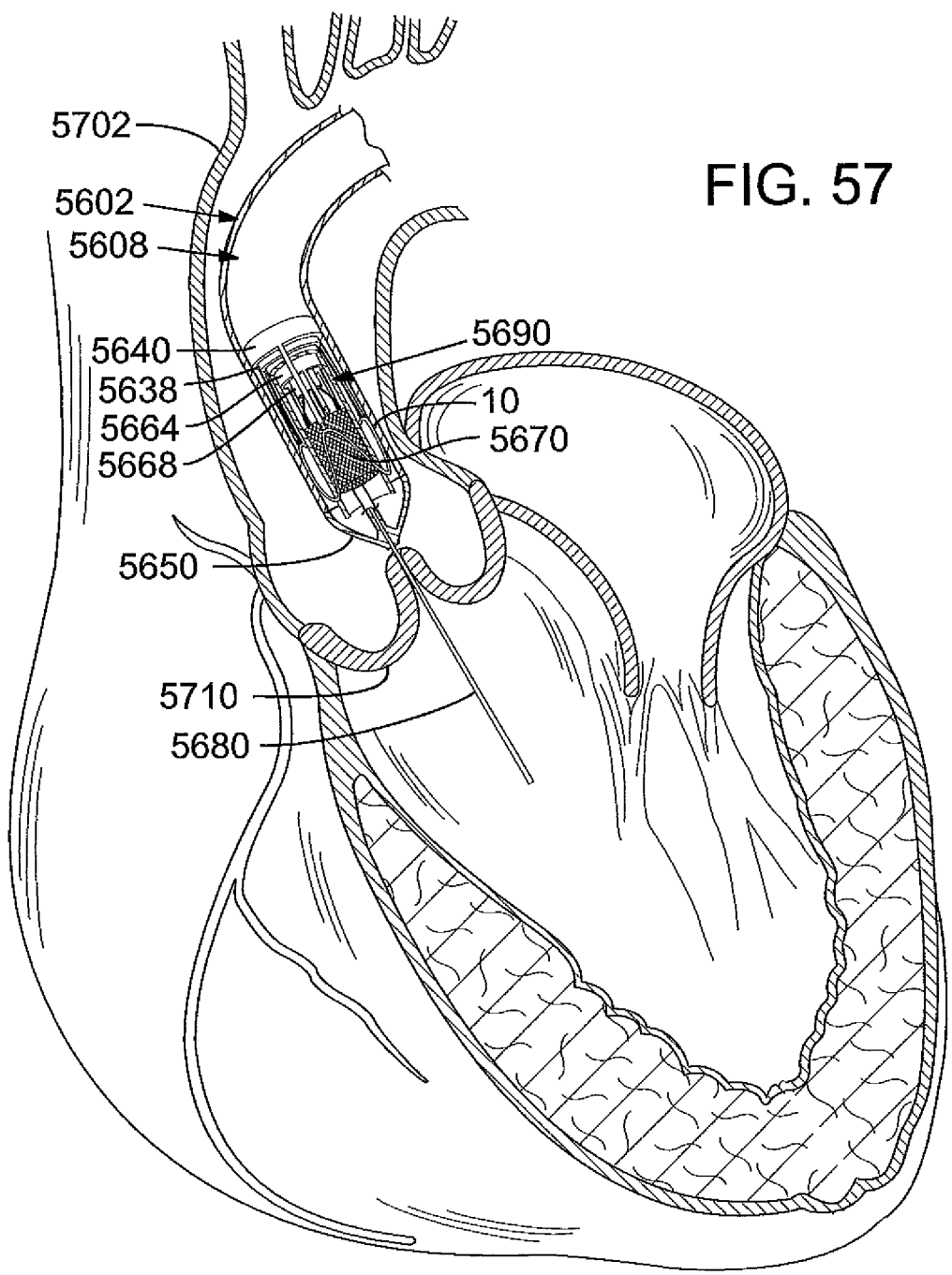
FIGS. 57-61 are cross-sectional views of a patient's heart illustrating how the delivery system of FIG. 56 can operate to deploy the support structure of FIG. 1 to a desired position on the patient's aortic valve.

FIG. 57 shows the main catheter 5602 of the delivery system 5600 as it is advanced through the aortic arch 5702 into a position near the surface of the outflow side of the aortic valve 5710. The delivery system 5600 can be inserted through the femoral artery of the patient and advanced into the aorta in the retrograde direction. In FIG. 57, the main catheter 5602 is advanced in the direction of guidewire 5680, which is shown as being extended through the aortic valve 5710. The delivery system 5600 is advanced to the point where the nose cone 5650 is located adjacent to the native leaflets of the aortic valve when the valve is closed. In FIG. 57, the support stent 10 is in its radially compressed, predeployment state. Also seen in FIG. 57 are the outer fork 5640 of the stent delivery out catheter 5608 and the inner fork 5638 of the stent delivery inner catheter 5618, which respectively couple the radially compressed support stent 10 to the distal ends of the stent delivery outer catheter 5608 and the stent delivery inner catheter 5618 (not visible in FIG. 57). FIG. 57 also shows the outer fork 5664 of the prosthetic valve delivery outer catheter 5660 and the inner fork 5668 of the prosthetic valve delivery inner catheter 5665, which respectively couple the radially compressed prosthetic valve 5670 to the distal ends of the prosthetic valve delivery outer catheter 5660 and the prosthetic valve delivery inner catheter 5665 (not visible in FIG. 56).

Figure 58:
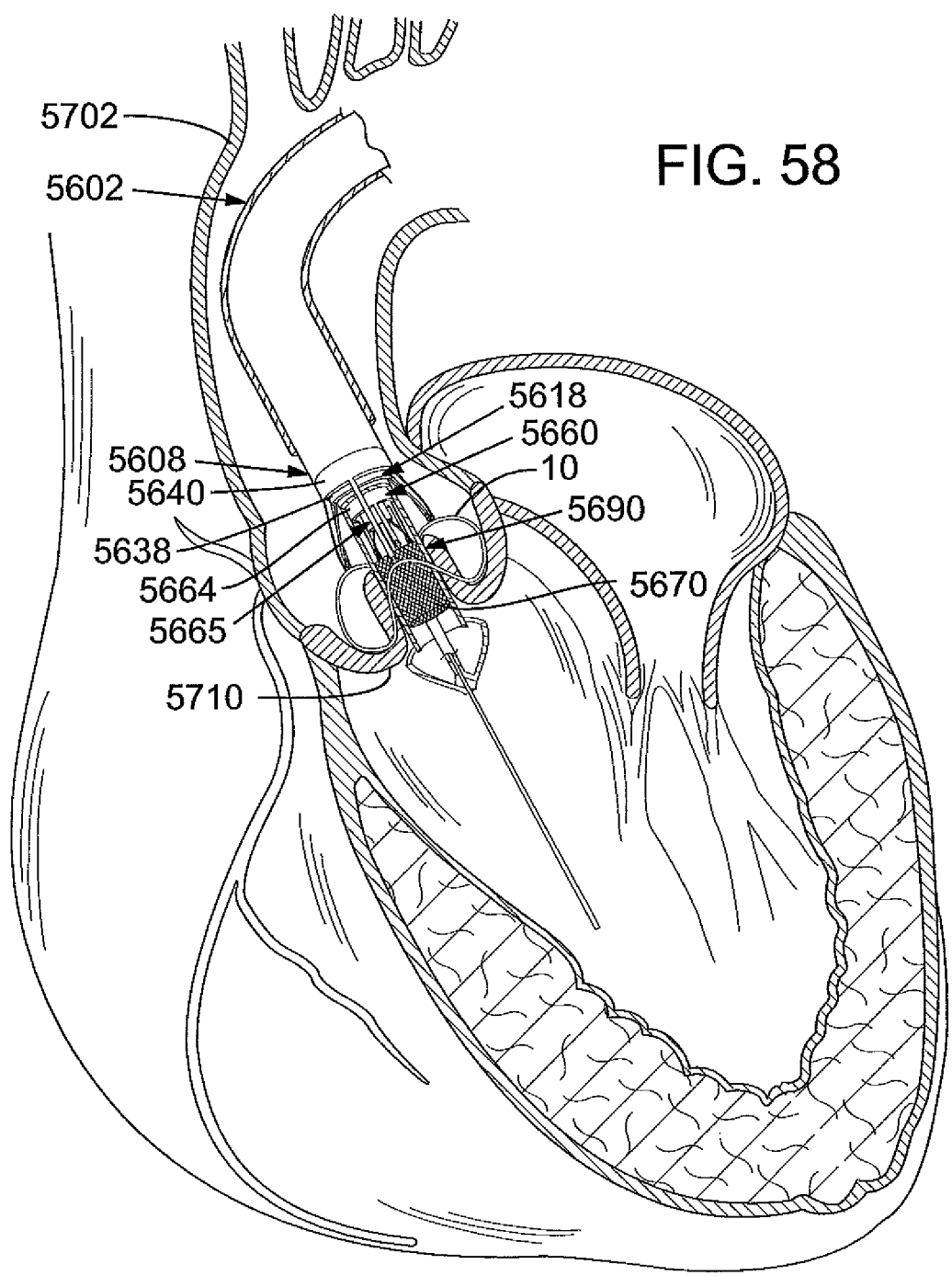

In FIG. 58, the main catheter 5602 is withdrawn from the stent delivery outer catheter 5608, the stent delivery inner catheter 5618, and the support stent 10. When the main catheter 5602 is withdrawn, the support stent 10 is no longer held within the inner walls of the main catheter and expands into its uncompressed, natural shape in a position above the aortic valve 5710. In FIG. 58, the support stent 10 is self-expanding. In other embodiments, however, the support stent may not be self-expanding. In such embodiments, the support stent can be made of a suitable ductile material, such as stainless steel. In addition, a mechanism for expanding the support stent can be included as part of the delivery system 5700. For example, and as explained above with respect to FIG. 8, the support stent can be disposed around a balloon of a balloon catheter in a compressed state.

In FIG. 58, the stent delivery outer catheter 5608 and the stent delivery inner catheter 5618 are also advanced toward the aortic valve 5710 but remain on the outflow side of the aortic valve 5710. In particular, the stent delivery outer catheter 5608 and the stent delivery inner catheter 5618 are positioned so that the support stent 10 is placed adjacent to or directly on the surface of the outflow side of the aortic valve. The support stent 10 is rotated and positioned as necessary so that the support stent 10 generally circumscribes the aortic valve and so that the peaks of the support stent are aligned with the tips of the natural leaflets of the aortic valve 5710. Therefore, when the prosthetic valve 5670 is expanded within the aortic valve 5710, the leaflets of the aortic valve will engage at least the majority of the surface in the interior of the support stent 10. This alignment will create an overall tighter fit between the support stent 10 and the prosthetic valve. In other embodiments, the support stent 10 is rotated and positioned as necessary so that the peaks of the support stent 10 are aligned with the commissures or other portions of the aortic valve. The position of the main catheter 5602 and the support stent 10 relative to the aortic valve 5710, as well as the position of other elements of the system, can be monitored using radiopaque markers and fluoroscopy, or using other imaging systems such as transesophageal echo, transthoracic echo, intravascular ultrasound imaging ("IVUS"), or an injectable dye that is radiopaque.

Also seen in FIG. 58 are the prongs of the outer fork 5640 and the prongs of the inner fork 5638. In the exemplary procedure, the prongs of the outer fork 5640 and the inner fork 5638 remain secured to the support stent 10 until the prosthetic valve 5670 is deployed and frictionally engaged to the support stent 10. The inner and outer forks desirably form a connection between the stent 10 and the delivery system 5600 that is secure and rigid enough to allow the clinician to hold the stent 10 at the desired implanted position against the flow of blood while the prosthetic valve 5670 is being implanted.

In FIG. 58, the prosthetic valve sheath 5690 (along with its interior catheters) is advanced through the aortic valve 5710 led by the nose cone 5650. In the illustrated position, the prosthetic valve sheath 5690 is advanced to a point where the compressed prosthetic valve 5670 is located in the aortic annulus and between the native aortic leaflets. In particular, the compressed prosthetic valve 5670 is located concentrically within the aortic valve 5710 and within the interior of the support stent 10. Radiopaque markers may be provided on the prosthetic valve sheath 5690, the prosthetic valve delivery outer catheter 5660, and/or the prosthetic valve delivery inner catheter 5665 to more accurately determine the position of the valve 5670 relative to the support stent 10 and the aortic valve 5710. In some embodiments, the clinician can adjust the position of the valve 5670 by actuating a steering or deflecting mechanism within the prosthetic valve sheath 5660, the prosthetic valve delivery outer catheter 5660, and/or the prosthetic valve delivery inner catheter 5665. Furthermore, the rotational orientation of the valve 5670 can be adjusted relative to the cusps and commissures of the native aortic valve by twisting the prosthetic valve sheath 5690, the prosthetic valve delivery outer catheter 5660, and/or the prosthetic valve delivery inner catheter 5665 from their proximal end and observing specific markers on the valve (or any of the catheters) under fluoroscopy. In order to better illustrate the components of the delivery system for the prosthetic valve, FIGS. 58-61 show the front third of the support stent 10 and the front of the prosthetic valve 5670, but do not show the portions of the native heart valve that would be secured by the front of the support stent 10. It is to be understood, however, that a corresponding leaflet of the native heart valve would be secured between the support stent 10 and the prosthetic valve 5670.

Figure 59:
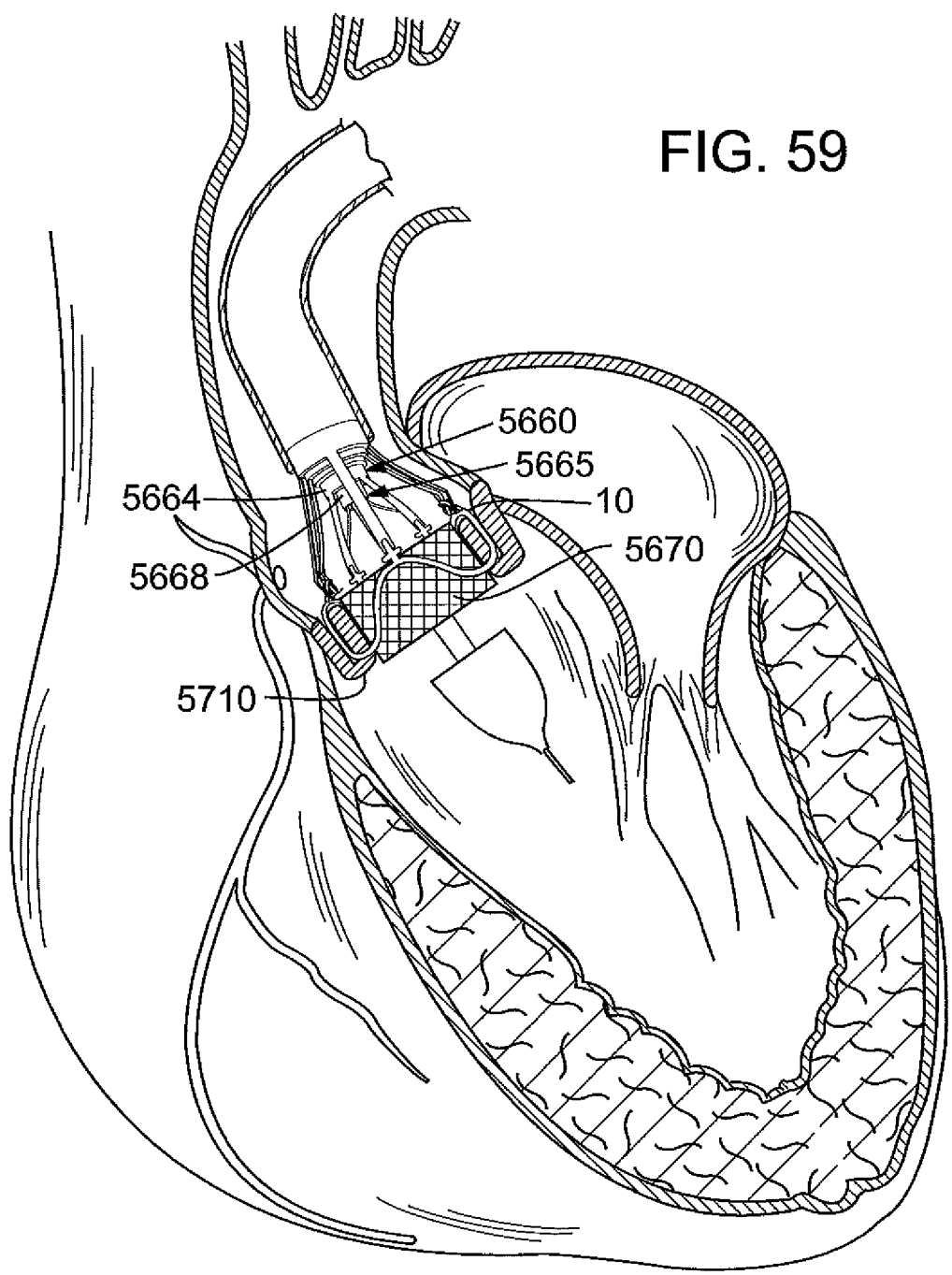

In FIG. 59, the prosthetic valve sheath 5690 is retracted such that the self-expandable prosthetic valve expands to engage the leaflets of the aortic valve 5710. Consequently, the leaflets of the aortic valve are urged against the inner wall of the support stent 10. In other words, the expansion of the prosthetic valve 5670 pinches the leaflets of the aortic valve 5710 between the support stent 10 and the prosthetic valve 5670, thereby securing the prosthetic valve 5670 within the annulus of the aortic valve.

Also seen in FIG. 59 are the prongs of the outer fork 5664 of the prosthetic valve delivery outer catheter 5660 and the prongs of the inner fork 5668 of the prosthetic valve delivery inner catheter 5665. The inner and outer forks desirably form a connection between the prosthetic valve 5670 and the delivery system 5600 that is secure and rigid enough to allow the clinician to properly orient the valve 5670 into its desired implanted position against the flow of blood through the aortic valve 5710.

Figure 60:
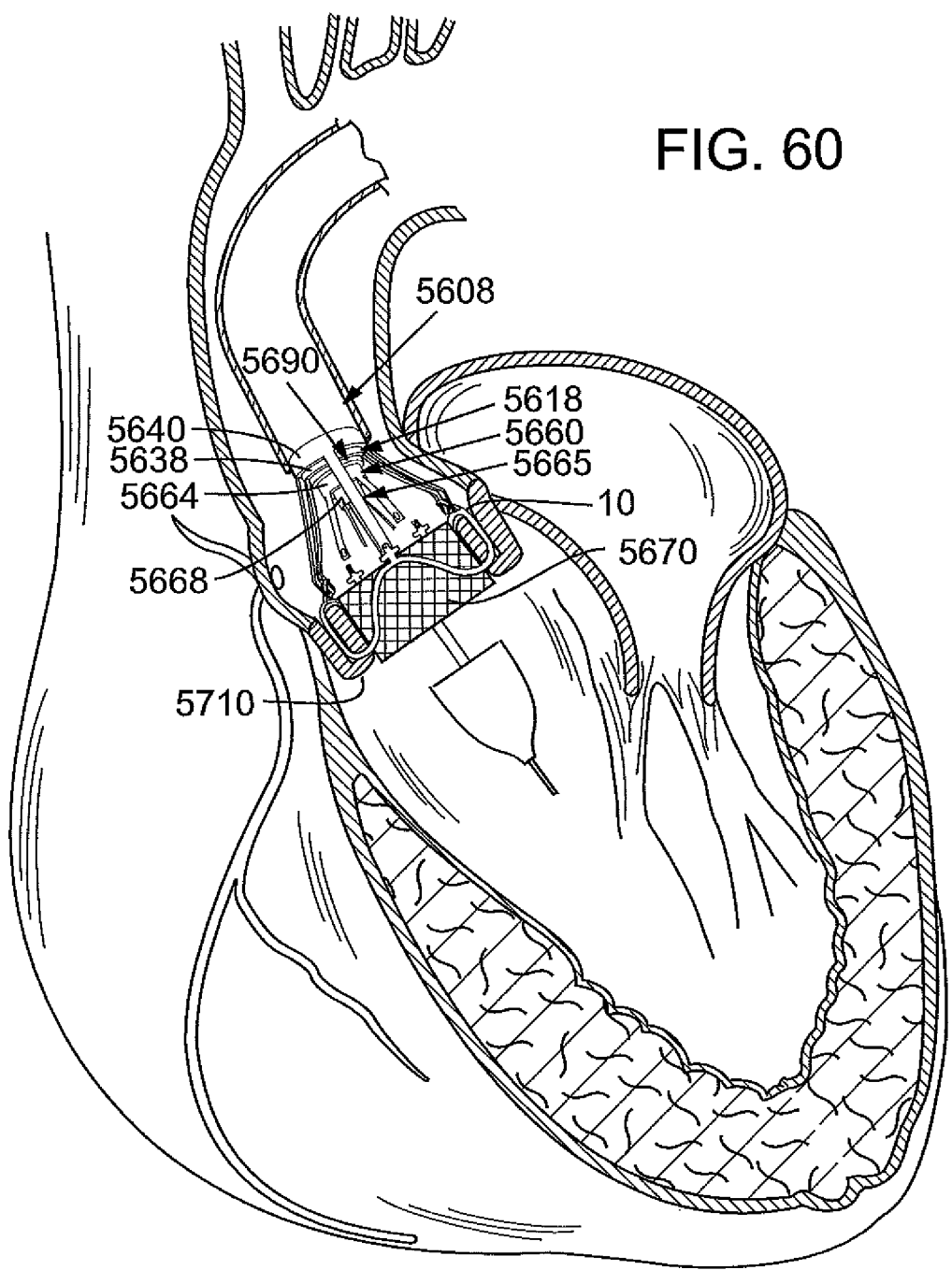

As shown in FIG. 60, once the prosthetic valve 5670 is secured into its desired position, the prosthetic valve delivery inner catheter 5665 of the delivery system 5600 can be retracted, thereby causing the prongs of the inner fork 5668 to become disengaged from the retaining arms of the prosthetic valve 5670. Once the prongs of the inner fork 5668 are disengaged, the prongs of the outer fork 5664 become disengaged from the retaining arms, and the prosthetic valve delivery outer catheter 5660 can be retracted.

With the prosthetic valve 5670 now disengaged, the stent delivery inner catheter 5618 of the delivery system 5600 can be retracted, thereby causing the prongs of the inner fork 5638 to become disengaged from the retaining arms of the support stent 10. Once the prongs of the inner fork 5638 are disengaged, the prongs of the outer fork 5640 become disengaged from the retaining arms, and the stent delivery outer catheter 5608 can be disengaged. In other embodiments, the support stent 10 is disengaged from the delivery system 5600 first, or the support stent 10 and the prosthetic valve 5670 are disengaged at least partially simultaneously.

Figure 61:
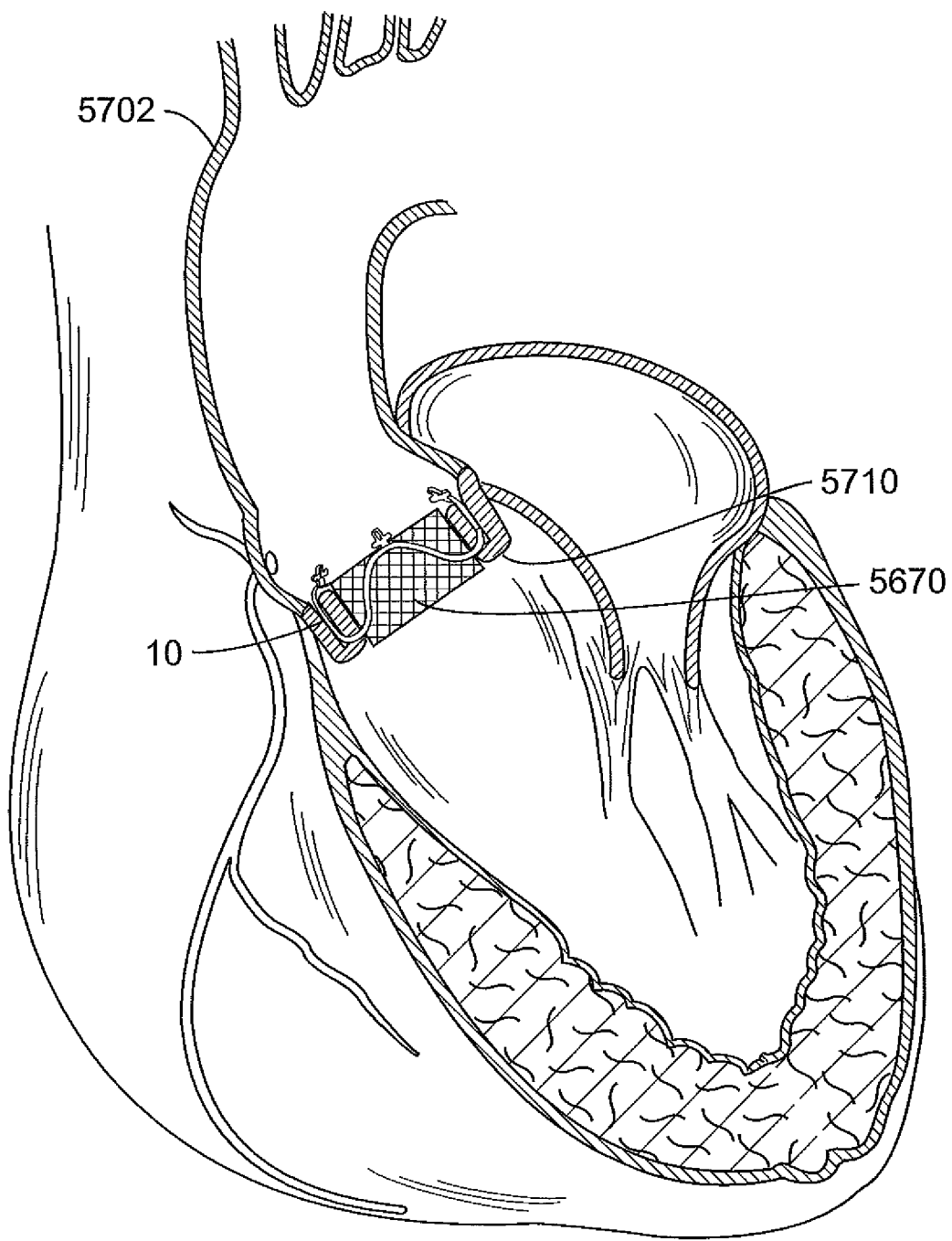

Once the support stent 10 and the prosthetic valve 5670 are disengaged from the delivery system 5600, the stent delivery outer catheter 5608, the stent delivery inner catheter 5618, the prosthetic valve sheath 5690, the prosthetic valve outer catheter 5660, and the prosthetic valve inner catheter 5665 can all be retracted into the main catheter 5602. The nose cone 5650 can also be retracted through the prosthetic valve 5670, and the delivery system 5600 can be retracted from the aortic arch 5702 over the guide wire 5680 and removed from the patient. The guide wire 5680 can then be withdrawn from the patient as well, leaving the prosthetic valve 5670 securely positioned within the aortic valve 5710 by the support stent 10 as shown by FIG. 61.

Figure 62:
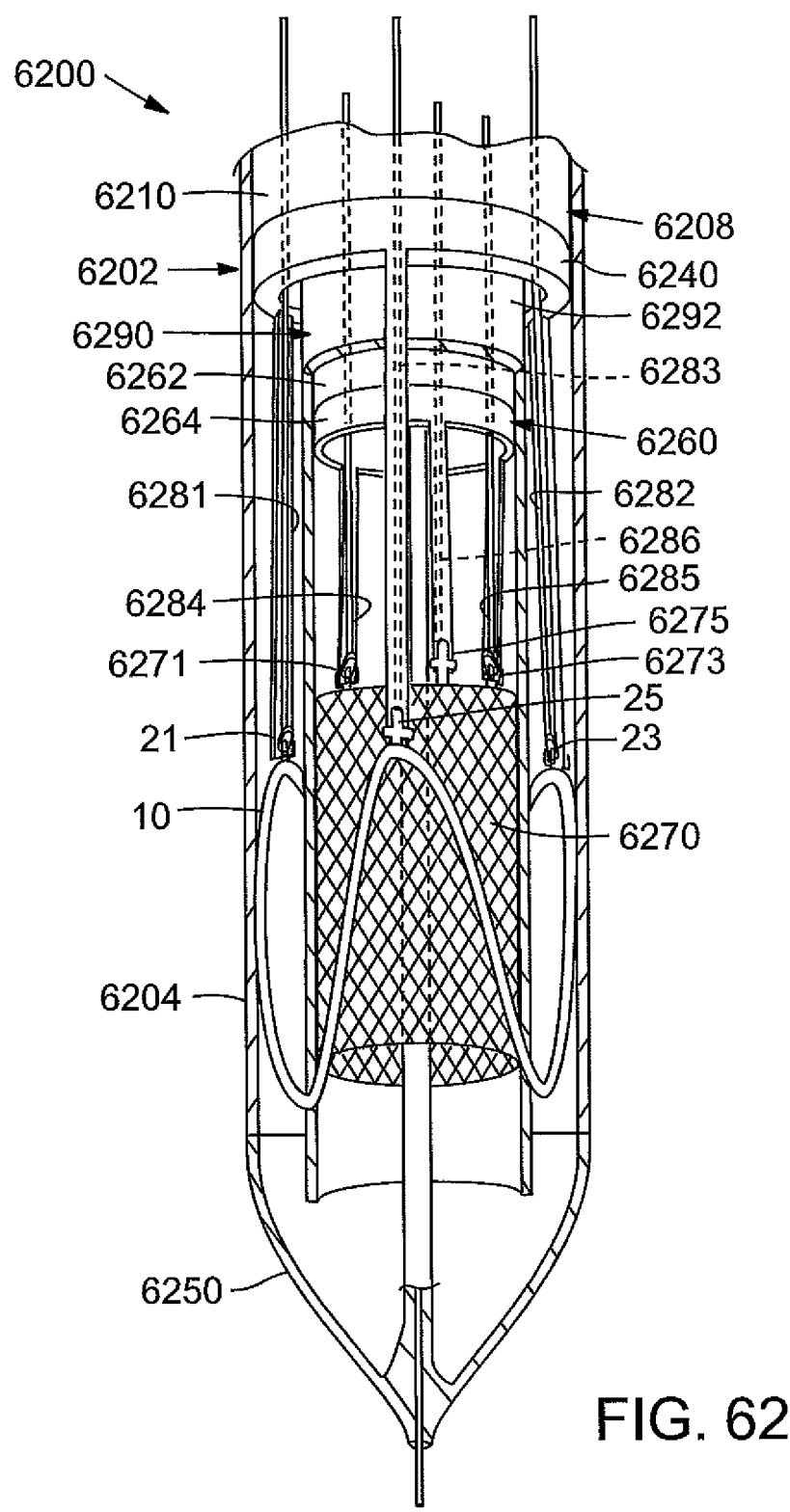
FIG. 62 is a front view of another exemplary integrated delivery system for embodiments of the disclosed support structures.

FIG. 62 is a front view of an embodiment of a delivery system 6200 that is similar to the embodiment shown in FIG. 56 but in which one or more of the stent delivery inner fork catheter and the prosthetic valve delivery inner catheter are replaced by one or more cables or wires. In particular, FIG. 62 shows the delivery system 6200 when the support stent 10 is in a compressed, predeployed state. The delivery system 6200 comprises a main catheter 6202 (which can be a steerable guide catheter) having an elongated shaft 6204 that is axially and rotatably movable relative to the other shafts of the delivery system 6200 (e.g., using a handle or lever (such as a lockable handle or lever) located at or near a proximal end of the delivery system 6200 as is known in the art). The delivery system 6200 further includes a nose cone 6250.

The delivery system 6200 also includes a stent delivery outer catheter 6208 positioned in the interior of the main catheter 6202. The stent delivery outer catheter 6208 has an elongated shaft 6210 and an outer fork 6240 connected to a distal end portion of the shaft 6210. The shaft 6210 of the stent delivery outer catheter 6208 can be configured to be moveable axially relative to the other shafts of the delivery system 6200 (e.g., using a handle or lever (such as a lockable handle or lever) located at or near a proximal end of the delivery system 6200 as is known in the art). Furthermore, the shaft 6210 of the stent delivery outer catheter 6208 can be sized so that its exterior wall is adjacent to or in contact with the inner wall of the shaft 6204 of the main catheter 6202.

Instead of a stent delivery inner catheter, the delivery system 6200 includes threads or wires 6281, 6282, 6283 having distal ends that form a hook, slip knot, suture loop, or other shape that allows the threads or wires to be releasably engage the retaining arms 21, 23, 25 of the support stent. The wires 6281, 6282, 6283 can alternatively include a fastening mechanism at their distal end that allows the wires to be releasably coupled to the retaining arms 21, 23, 25. In general, the wires 6281, 6282, 6283 operate in substantially the same fashion as the prongs of the inner fork 5668 of the stent delivery inner catheter 5665 shown in FIG. 56. For example, each of the wires 6281, 6282, 6283 can include a suture loop at its distal end that is configured to be threaded through the eyelets (not shown) of the retaining arms 21, 23, 25, thereby securing the prongs of the outer fork 6240 of the stent delivery outer catheter 6208 to the retaining arms in the fashion shown in FIG. 6. The wires 6281, 6282, 6283 can extend through the interior of the stent delivery outer catheter 6208 (e.g., through an annular lumen or one or more interior lumens of the stent delivery outer catheter 6208) to proximal ends at or near the proximal end of the main catheter 6202. The proximal ends of the wires 6281, 6282, 6283 can be coupled to a handle or other control mechanism configured to allow for the wires to be retracted relative to the stent delivery outer catheter 6208. When retracted, the distal ends of the wires 6281, 6282, 6283 become disengaged from the retaining arms 21, 23, 25 (e.g., by releasing a slip-knot or suture loop, by causing a hooked portion of the wires to be straightened and pulled through the eyelet of a retaining arm, or by another such releasing mechanism). Once the wires 6281, 6282, 6283 are disengaged, the prongs of the outer fork 6240 of the stent delivery outer catheter 6208 become disengaged, thereby releasing the support stent in its desired position.

The delivery system 6200 further includes a prosthetic valve sheath 6290 (which can alternatively be a steerable guide catheter) positioned in the interior of the stent delivery outer catheter 6208. The prosthetic valve sheath 6290 encloses a prosthetic valve delivery outer catheter 6260 and a compressed prosthetic valve 6270. The prosthetic valve sheath 6290 comprises an elongated shaft 6292 that terminates in an open distal end. The shaft 6292 of the prosthetic valve sheath 6290 can be configured to be moveable axially relative to the other shafts in the delivery system 6200 (e.g., using a handle or lever (such as a lockable handle or lever) located at or near a proximal end of the delivery system 6200 as is known in the art).

The prosthetic valve delivery outer catheter 6260 has an elongated shaft 6262 and an outer fork 6264 connected to a distal end portion of the shaft 6262. The shaft 6262 of the prosthetic valve delivery outer catheter 6260 can be configured to be moveable axially relative to the other shafts of the delivery system 6200 (e.g., using a handle or lever (such as a lockable handle or lever) located at or near a proximal end of the delivery system 6200 as is known in the art). Furthermore, the shaft 6262 of the prosthetic valve delivery outer catheter 6260 can be sized so that its exterior wall is adjacent to or in contact with the inner wall of the shaft 6292 of the prosthetic valve sheath 6290.

Instead of a prosthetic valve delivery inner catheter, the delivery system 6200 includes threads or wires 6284, 6285, 6286 having distal ends that form a hook, slip knot, suture loop, or other shape that allows the threads or wires to be releasably engage the retaining arms 6271, 6273, 6275 of the prosthetic valve 6270. The wires 6284, 6285, 6286 can alternatively include a fastening mechanism at their distal end that allows the wires to be releasably coupled to the retaining arms 21, 23, 25. In general, the wires 6284, 6285, 6286 operate in substantially the same fashion as the prongs of the inner fork 5668 of the prosthetic valve delivery inner catheter 5665 shown in FIG. 56. For example, each of the wires 6284, 6285, 6286 can include a suture loop at its distal end that is configured to be threaded through the eyelets (not shown) of the retaining arms 6271, 6273, 6275, thereby securing the prongs of the outer fork 6264 of the prosthetic valve delivery outer catheter 6260 to the retaining arms in the fashion shown in FIG. 6. The wires 6284, 6285, 6286 can extend through the interior of the prosthetic valve delivery outer catheter 6260 (e.g., through an annular lumen or one or more interior lumens of the prosthetic valve delivery outer catheter 6260) to proximal ends at or near the proximal end of the main catheter 6202. The proximal ends of the wires 6284, 6285, 6286 can be coupled to a handle or other control mechanism configured to allow for the wires to be retracted relative to the prosthetic valve delivery outer catheter 6260. When retracted, the distal ends of the wires 6284, 6285, 6286 become disengaged from the retaining arms 6271, 6273, 6275. Once the wires 6284, 6285, 6286 are disengaged, the prongs of the outer fork 6264 of the prosthetic valve delivery outer catheter 6260 become disengaged, thereby releasing the prosthetic valve in its desired position.

As with the delivery system 5600, a prosthetic valve 6270 (e.g., a THV) is in a compressed or unexpanded state and is contained within the prosthetic valve sheath 6290. The delivery system 6200 can be used to deliver the prosthetic valve 6270 to its desired location adjacent to or on the outflow side of the aortic valve in the manner described above with respect to FIGS. 57-61.

Figure 63:
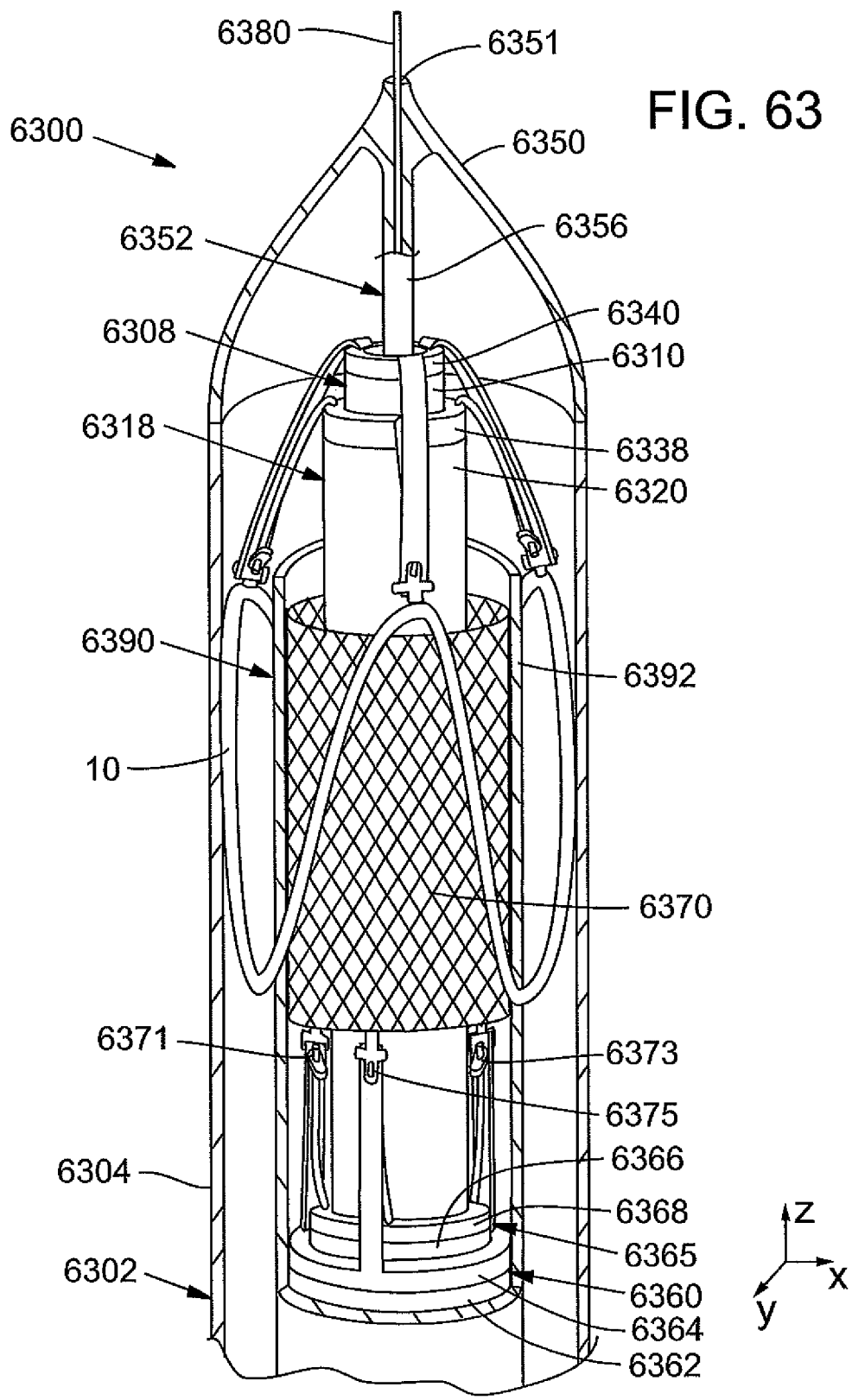
FIG. 63 is a front view of an exemplary integrated delivery system for delivering embodiments of the disclosed support structures. In particular.

FIG. 63 is a front view of the distal end portion of an exemplary delivery system 6300 for delivering the support stent 10 to its location adjacent the native aortic valve through a patient's left ventrical (e.g., transapically). In contrast to the embodiment illustrated in FIGS. 48 and 49, the prosthetic valve used with the delivery system 6300 is a self-expanding prosthetic valve 6370. FIG. 63 shows the delivery system 6300 when the support stent 10 is in a compressed, predeployed state. The delivery system 6300 comprises an introducer sheath 6302 having an elongated shaft 6304. The introducer sheath 6302 of the illustrated embodiment is configured to have the same or approximately the same circumference as a nose cone 6350. The nose cone 6350 can also be an elongated nose cone as in the embodiments illustrated in FIGS. 48-55. For illustrative purposes, the nose cone 6350 and the introducer sheath 6302 are shown as being partially cut away, thus revealing the catheters in its interior.

A proximal end (not shown) of the introducer sheath 6302 is connected to a handle of the delivery system 6300. During delivery of a support stent, the handle can be used by a clinician to advance and retract the delivery system 6300 through the patient's heart. In a particular use, the delivery system 6300 is advanced transapically over a guide wire through the left ventricle of a patient's heart after having been inserted through a puncture in the left ventricle.

The delivery system 6300 includes a prosthetic valve sheath 6390 positioned in the interior of the introducer sheath 6302. The prosthetic valve sheath 6390 comprises an elongated shaft 6392 that encloses a prosthetic valve delivery outer catheter 6360, a prosthetic valve delivery inner catheter 6365, and a compressed prosthetic valve 6370. The shaft 6392 of the prosthetic valve sheath 6390 terminates at an open distal end and can be configured to be moveable axially relative to the other shafts of the delivery system 6300 (e.g., using a handle or lever (such as a lockable handle or lever) located at or near a proximal end of the delivery system 6300 as is known in the art). Furthermore, in the illustrated embodiment, the shaft 6392 is the outermost catheter within the introducer sheath 6302.

The prosthetic valve delivery outer catheter 6360 has an elongated shaft 6362 and an outer fork 6364 connected to a distal end portion of the shaft 6362. The shaft 6362 of the prosthetic valve delivery outer catheter 6360 can be configured to be moveable axially relative to the other shafts of the delivery system 6300 (e.g., using a handle or lever (such as a lockable handle or lever) located at or near a proximal end of the delivery system 6300 as is known in the art). Furthermore, the shaft 6362 of the prosthetic valve delivery outer catheter 6360 can be sized so that its exterior wall is adjacent to or in contact with the inner wall of the shaft 6392 of the prosthetic valve sheath 6390.

The prosthetic valve delivery inner catheter 6365 can have an elongated shaft 6366 and an inner fork 6368 secured to the distal end portion of the shaft 6366. The shaft 6366 of the inner catheter 6365 can be configured to be moveable axially relative to the other shafts of the delivery system 6300 (e.g., using a handle or lever (such as a lockable handle or lever) located at or near a proximal end of the delivery system 6300 as is known in the art).

A self-expanding prosthetic valve 6370 (e.g., a THV) is in a compressed or unexpanded state and is contained within the prosthetic valve sheath 6390. The prosthetic valve 6370 can be any suitable self-expandable prosthetic heart valve, such as those described in U.S. Patent Application Publication Nos. 2007/0112422 (U.S. application Ser. No. 11/280, 063) and 2010/0049313 (U.S. application Ser. No. 12/429, 040), which are expressly incorporated herein by reference. Furthermore, in the embodiment illustrated in FIG. 63, the prosthetic valve includes retaining arms 6371, 6373, and 6375, which are engaged with the prongs of the outer fork 6364 of the prosthetic valve delivery outer catheter 6360 and the inner fork 6368 of the prosthetic valve delivery inner catheter 6365 in the manner described above with respect to FIGS. 5 and 6 and as described in U.S. Patent Application Publication No. 2010/0049313 (U.S. application Ser. No. 12/429,040), which is expressly incorporated herein by reference. To deploy the prosthetic valve 6370 in the illustrated embodiment, the introducer sheath 6302 is withdrawn so that the stent 10 can be positioned in the proper location adjacent to the outflow side of an aortic valve, and the prosthetic valve sheath 6390 is withdrawn to reveal the valve 6370. These actions can be performed, for example, using one or more control handles or mechanisms (not shown) located at the proximal end of the delivery system 6300. These actions cause the prosthetic valve 6370 to be advanced outwardly through the distal end 6395 of the prosthetic valve sheath 6390 and to expand into its relaxed, uncompressed state. In the illustrated embodiment, the prosthetic valve 6370 is shown as being positioned concentrically with the support stent 10. In other embodiments, however, the support stent 10 can be positioned distally of the prosthetic valve 6370.

In the illustrated embodiment, the delivery system 6300 further includes a stent delivery outer fork catheter 6308 and a stent delivery inner fork catheter 6318. In the illustrated embodiment, the stent delivery inner fork catheter 6318 comprises a stent delivery inner fork 6338 secured to a distal end of an elongated shaft 6320. The shaft 6320 can be sized to fit within the prosthetic valve delivery inner catheter 6365. The shaft 6320 can be configured to be moveable axially relative to the other shafts in the delivery system 6300 (e.g., using a handle or lever (such as a lockable handle or lever) located at or near a proximal end of the delivery system 6300 as is known in the art). Furthermore, the shaft 6320 can be sized so that its exterior wall is adjacent to or in contact with the inner wall of the shaft 6366 of the prosthetic valve delivery inner catheter 6360.

The stent delivery outer fork catheter 6308 comprises a stent delivery outer fork 6340 secured to a distal end of an elongated shaft 6310. In this embodiment, the shaft 6310 of the stent delivery outer fork catheter 6308 is sized to fit within the stent delivery inner fork catheter 6318. The shaft 6310 of the stent delivery outer fork catheter 6308 can be configured to be moveable axially relative to the other shafts of the delivery system 6300 (e.g., using a handle or lever (such as a lockable handle or lever) located at or near a proximal end of the delivery system 6300 as is known in the art). Furthermore, the shaft 6310 of the stent delivery outer fork catheter 6308 can be sized so that its exterior wall is adjacent to or in contact with the inner wall of the shaft 6320 of the stent delivery inner fork catheter 6318. (Note that this is in contrast to the delivery system 5600 described above in which the stent delivery outer catheter 5608 has a larger circumference than the stent delivery inner catheter 5618 and at least partially encloses the stent delivery inner catheter 5618.)

The stent delivery system 6300 further includes a nose cone catheter 6352 having a distal end to which the nose cone 6350 is secured. For example, a distal portion of the nose cone 6350 can be attached to the distal end of the nose cone catheter 6352. The nose cone 6350 can be attached to the nose cone catheter 6352, for instance, using a suitable adhesive, a frictional engagement mechanism (e.g., a snap-fit or threaded collar attachment), by forming the nose cone 6350 and the nose cone catheter 6352 as part of a single unibody element (e.g., using suitable molding techniques), or other such attachment mechanism. In the illustrated embodiment, shaft 6356 of the nose cone catheter 6352 can be sized so that its exterior wall is adjacent to or in contact with the inner wall of the shaft 6310 of the stent delivery outer fork catheter 6308. Furthermore, the shaft 6356 of the nose cone catheter 6352 can be configured to be moveable axially relative to the other shafts of the delivery system 6300 (e.g., using a handle or lever (such as a lockable handle or lever) located at or near a proximal end of the delivery system 6300 as is known in the art). Additionally, the nose cone catheter 6352 can define an interior lumen through a guide wire 6380 can extend. For instance, a guide wire 6380 can be inserted through the nose cone catheter 6352 such that it extends through a distal end 6351 of the nose cone 6350.

In FIG. 63, the support stent 10 is shown in a radially compressed state in the interior of the elongated shaft 6304 of the introducer sheath 6302. In this undeployed and compressed state, the prongs of the outer fork 6340 and the inner fork 6338 of the stent delivery outer fork catheter 6308 and the stent delivery inner fork catheter 6318 engage the retaining arms 21, 23, 25 of the support stent 10 in the manner described above with respect to FIGS. 5 and 6. To deploy the support stent 10 in the illustrated embodiment, the introducer sheath 6302 is withdrawn over the support stent 10 using one or more control handles or mechanisms (not shown) located at the proximal end of the introducer sheath 6302. When the introducer sheath 6304 is withdrawn over the support stent 10, the support stent can expand into its relaxed, uncompressed state (shown, for example, in FIGS. 1 and 2).

As more fully illustrated below in FIGS. 64-70, a prosthetic valve (e.g., a THV) can be delivered to the aortic valve entirely through a transapical approach (e.g., through the apex of the heart and through the left ventricle) using the deployment system 6300. The prosthetic valve 6370 can be deployed transapically within the native valve such that the prosthetic valve is secured in place by frictional engagement between the support stent, the native leaflets, and the prosthetic valve. As explained above with reference to FIGS. 4 and 5, the support stent 10 can be shaped so that the native leaflets of the aortic valve become trapped or pinched between the support stent 10 and the exterior of the prosthetic valve 6370 when the prosthetic valve is expanded and deployed within the native valve. The deployment system 6300 can be used, for example, to deliver a support stent 10 to treat aortic insufficiency, as well as any other condition in which the aorta or aortic valve may not be in condition to help support the prosthetic valve (e.g., when the aortic annulus is too dilated or in which the leaflets of the aorta are too weak or soft to support the prosthetic valve).

FIGS. 64-70 illustrate one exemplary procedure for deploying the support stent and securing a prosthetic valve (e.g., a THV) to the support stent using the delivery system 6300 or other such transapical delivery system. In particular, FIGS. 64-70 are cross-sectional views through the left side of a patient's heart showing the acts performed in delivering the support stent 10 through the left ventricle and into the annulus of the aortic valve. In order to better illustrate the components of the delivery system 6300, the introducer sheath 6302 and the nose cone 6350 are shown partially cut away in FIGS. 64-70.

Figure 64:
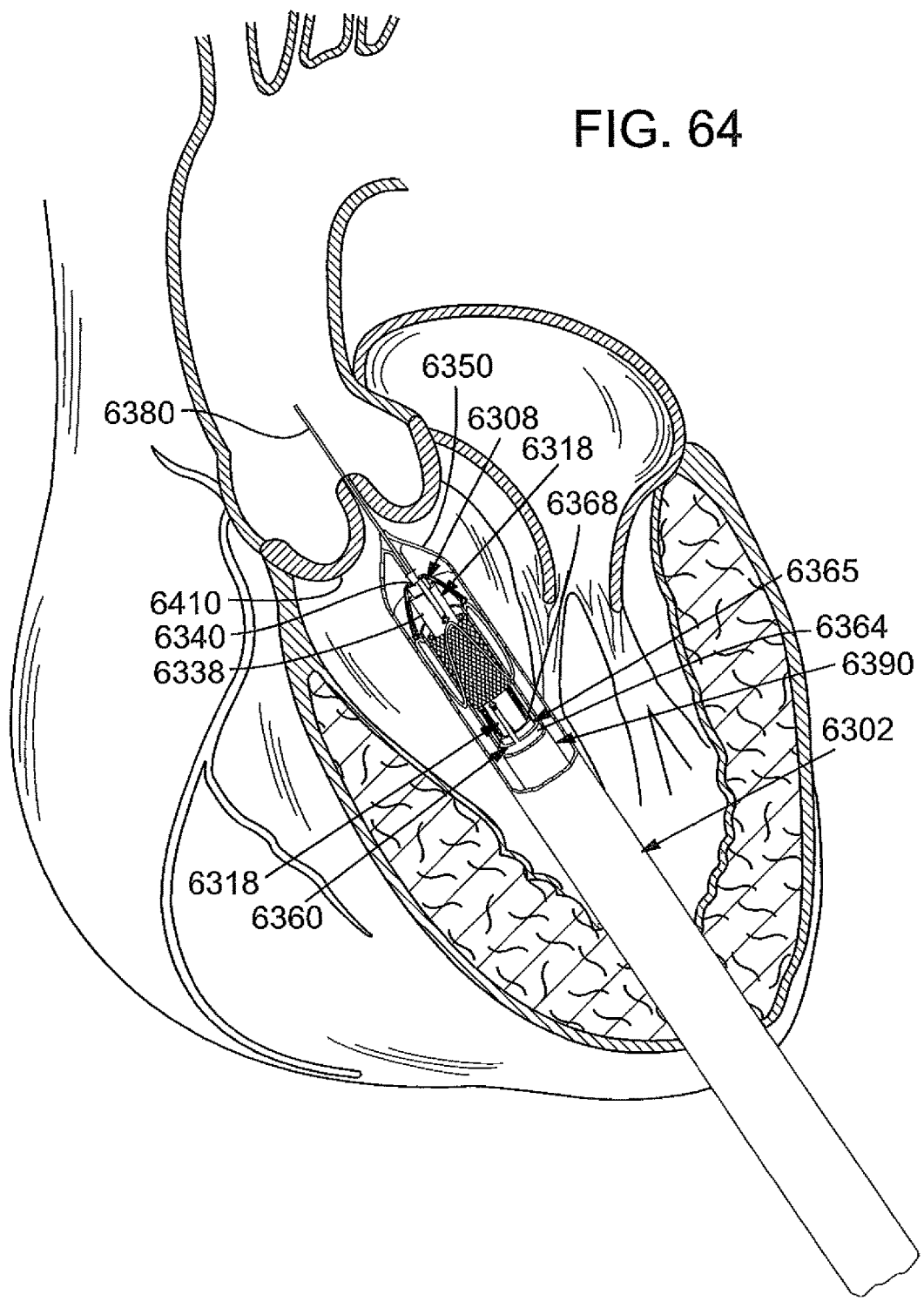
FIGS. 64-70 are cross-sectional views of a patient's heart illustrating how the delivery system of FIG. 63 can operate to deploy the support structure of FIG. 1 to a desired position on the patient's aortic valve.

FIG. 64 shows the introducer sheath 6302 and the nose cone 6350 of the delivery system 6300 as they are advanced toward the aortic valve 6410. FIG. 64 also shows the outer fork 6340 of the stent delivery outer fork catheter 6308, the inner fork 6338 of the stent delivery inner fork catheter 6318, the prosthetic valve sheath 6390, the outer fork 6364 of the prosthetic valve delivery outer catheter 6360, the inner fork 6368 of the prosthetic valve delivery inner catheter 6365, and the support stent 10. In FIG. 64, the introducer sheath 6302 is advanced in the direction of guidewire 6380, which is shown as being extended through the aortic valve 6410.

The introducer sheath 6302 and the nose cone 6350 are advanced over the guidewire 6380 through the annulus of the aortic valve 6410. In particular, the nose cone 6350 is advanced so that the support stent 10 is located in a position that is above the native leaflets of the aortic valve when the valve is open.

Figure 65:
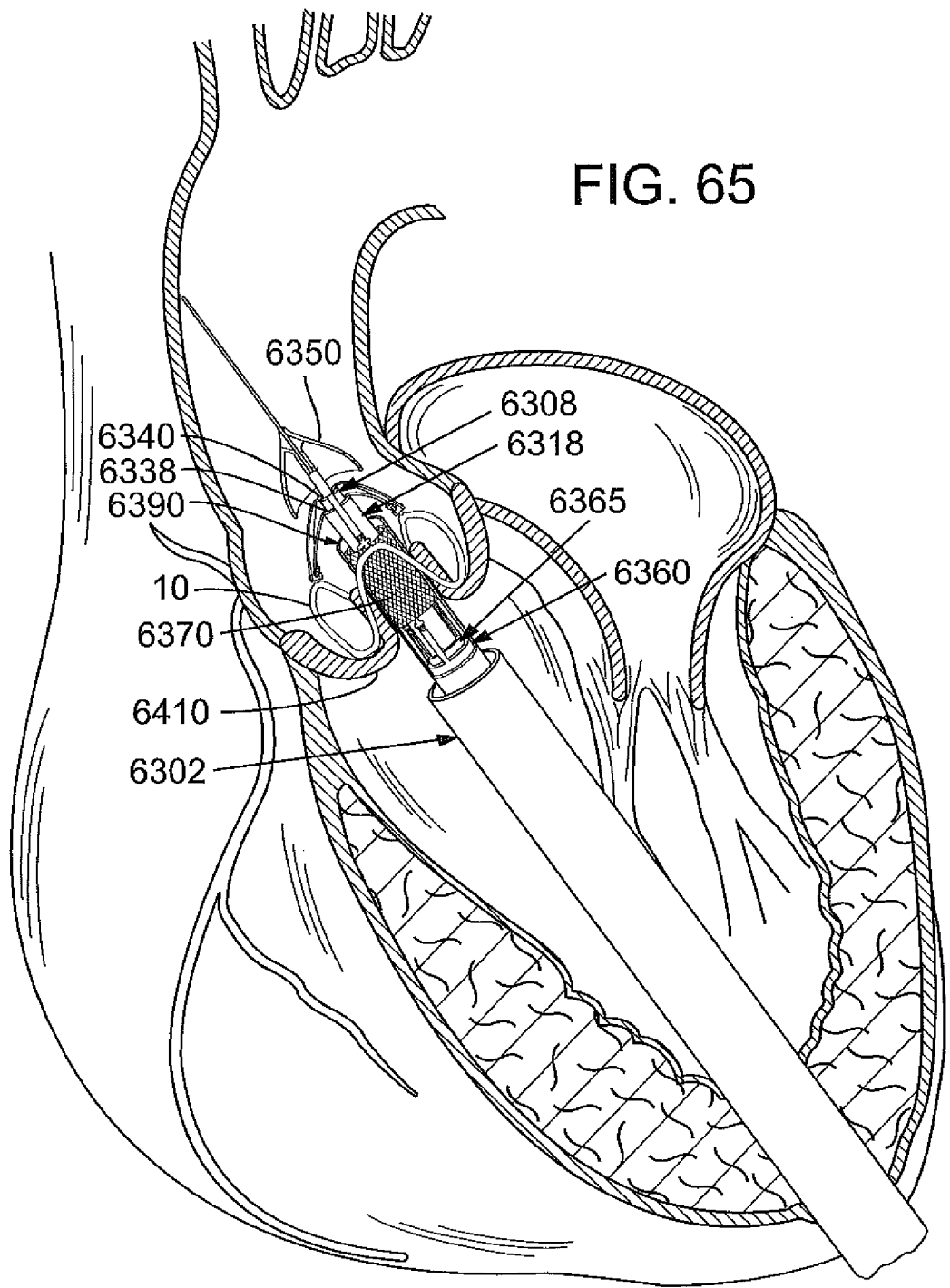

As shown in FIG. 65, the introducer sheath 6302 can be withdrawn proximally so that the introducer sheath no longer surrounds the stent delivery inner fork catheter 6318, the stent delivery outer fork catheter 6308, and the support stent 10. However, as shown in FIG. 65, the prosthetic valve sheath 6390 can continue to enclose the compressed prosthetic valve 6370. With the introducer sheath 6302 withdrawn, the support stent 10 is no longer held within the inner walls of the introducer sheath 6302 and expands into its uncompressed, natural shape in a position on the outflow side of the aortic valve 6410. In FIG. 65, the support stent 10 is self-expanding. In other embodiments, however, the support stent 10 may not be self-expanding. In such embodiments, the support stent 10 can be made of a suitable ductile material, such as stainless steel. In addition, a mechanism for expanding the support stent can be included as part of the delivery system 6300. For example, and as explained above with respect to FIG. 8, the support stent can be disposed around a balloon of a balloon catheter in a compressed state In FIG. 65, the stent delivery outer fork catheter 6308 and the stent delivery inner fork catheter 6318 are positioned so that the support stent 10 is placed adjacent to or directly on the surface of the outflow side of the aortic valve. The support stent 10 is rotated and positioned as necessary so that the support stent generally circumscribes the aortic valve and so that the peaks of the support stent are aligned with the tips of the natural leaflets of the aortic valve 6410. Therefore, when the prosthetic valve 6370 is expanded within the aortic valve 6410, the leaflets of the aortic valve will engage at least the majority of the surface in the interior of the support stent 10. In other embodiments, the support stent 10 is rotated and positioned as necessary so that the peaks of the support stent 10 are aligned with the commissures or other portions of the aortic valve. The position of the introducer sheath 6302, the nose cone 6350, the prosthetic valve 6370, and the support stent 10 relative to the aortic valve 6410, as well as the position of other elements of the system, can be monitored using radiopaque markers and fluoroscopy, or using other imaging systems such as transesophageal echo, transthoracic echo, intravascular ultrasound imaging ("IVUS"), or an injectable dye that is radiopaque.

Also seen in FIG. 65 are the prongs of the outer fork 6340 and the prongs of the inner fork 6338. In the exemplary procedure, the prongs of the outer fork 6340 and the inner fork 6338 remain secured to the support stent 10 until the prosthetic valve is deployed and frictionally engaged to the support stent. The inner and outer forks desirably form a connection between the stent 10 and the delivery system that is secure and rigid enough to allow the clinician to hold the stent 10 at the desired implanted position against the flow of blood while the prosthetic valve is being implanted.

Also seen in FIG. 65 is the valve delivery sheath 6390, which is advanced into the aortic valve 6410 so that the prosthetic valve 6370 is located within the interior of the annulus of the aortic valve and within the interior of the expanded support stent 10 (e.g., concentrically with the annulus of the aortic valve and the expanded support stent 10). Radiopaque markers may be provided on the prosthetic valve sheath 6390, the prosthetic valve delivery outer catheter 6360, and/or the prosthetic valve delivery inner catheter 6365 to more accurately determine the position of the valve 6370 relative to the support stent 10 and the aortic valve 6410. In some embodiments, the clinician can adjust the position of the valve 6370 by actuating a steering or deflecting mechanism within the prosthetic valve sheath 6360, the prosthetic valve delivery outer catheter 6360, and/or the prosthetic valve delivery inner catheter 6365. Furthermore, the rotational orientation of the valve 6370 can be adjusted relative to the cusps and commissures of the native aortic valve by twisting the prosthetic valve sheath 6390, the prosthetic valve delivery outer catheter 6360, and/or the prosthetic valve delivery inner catheter 6365 from their proximal end and observing specific markers on the valve (or any of the catheters) under fluoroscopy. At the point in the exemplary procedure illustrated in FIG. 65, the compressed support stent 6370 is ready to be expanded into the aortic valve 6410. In order to better illustrate the components of the delivery system for the prosthetic valve, FIGS. 65-70 show the front third of the support stent 10 and the front of the prosthetic valve 6370, but do not show the portions of the native heart valve that would be secured by the front of the support stent 10. It is to be understood, however, that a corresponding leaflet of the native heart valve would be secured between the support stent 10 and the prosthetic valve 6370.

Figure 66:
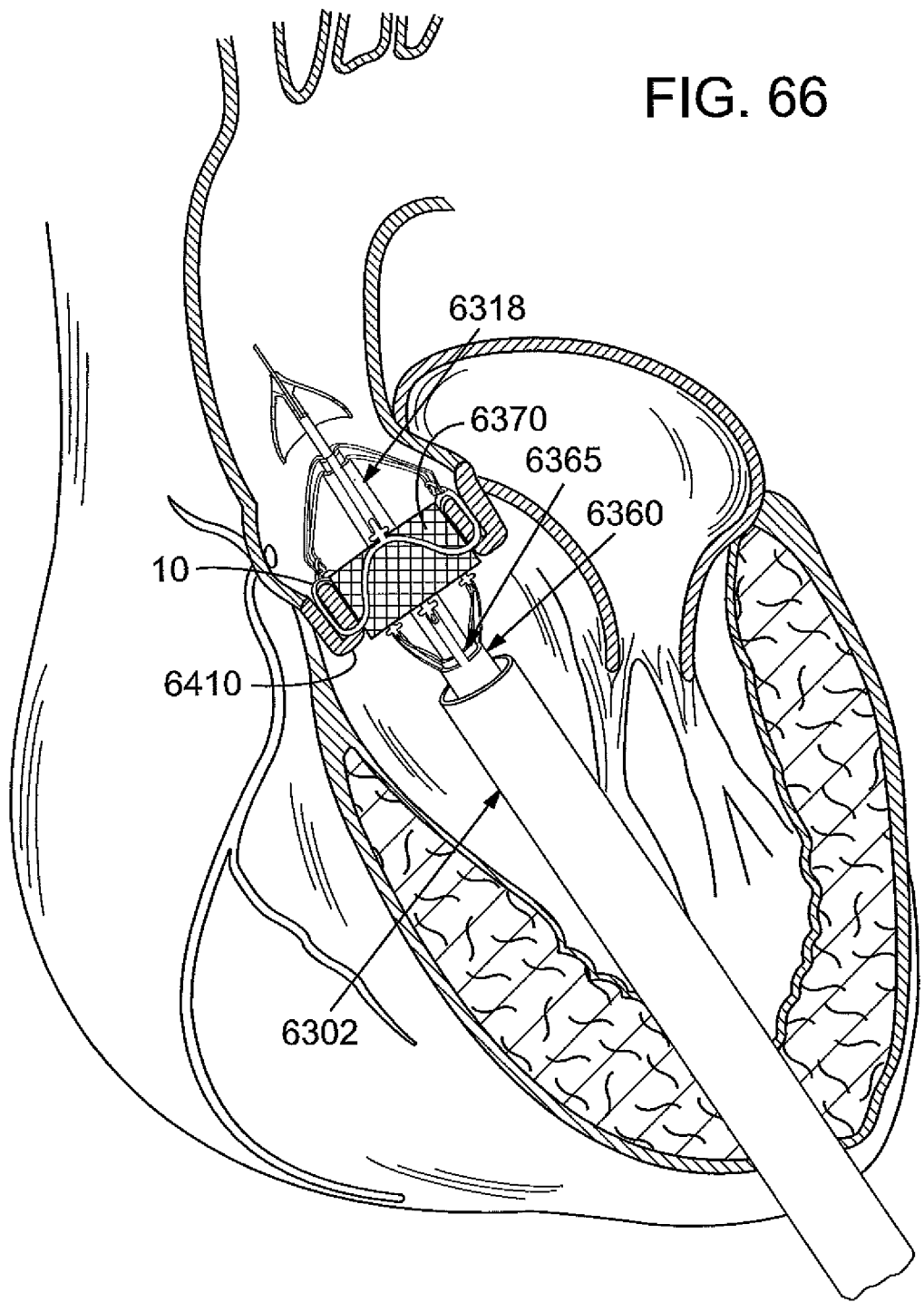

In FIG. 66, the prosthetic valve sheath 6390 (not visible in FIG. 66) is retracted such that the self-expandable prosthetic valve expands to engage the leaflets of the aortic valve 6410. Consequently, the leaflets of the aortic valve are urged against the inner wall of the support stent 10. In other words, the expansion of the prosthetic valve 6370 pinches the leaflets of the aortic valve 6410 between the support stent 10 and the prosthetic valve 6370, thereby securing the prosthetic valve within the annulus of the aortic valve.

Figure 67:
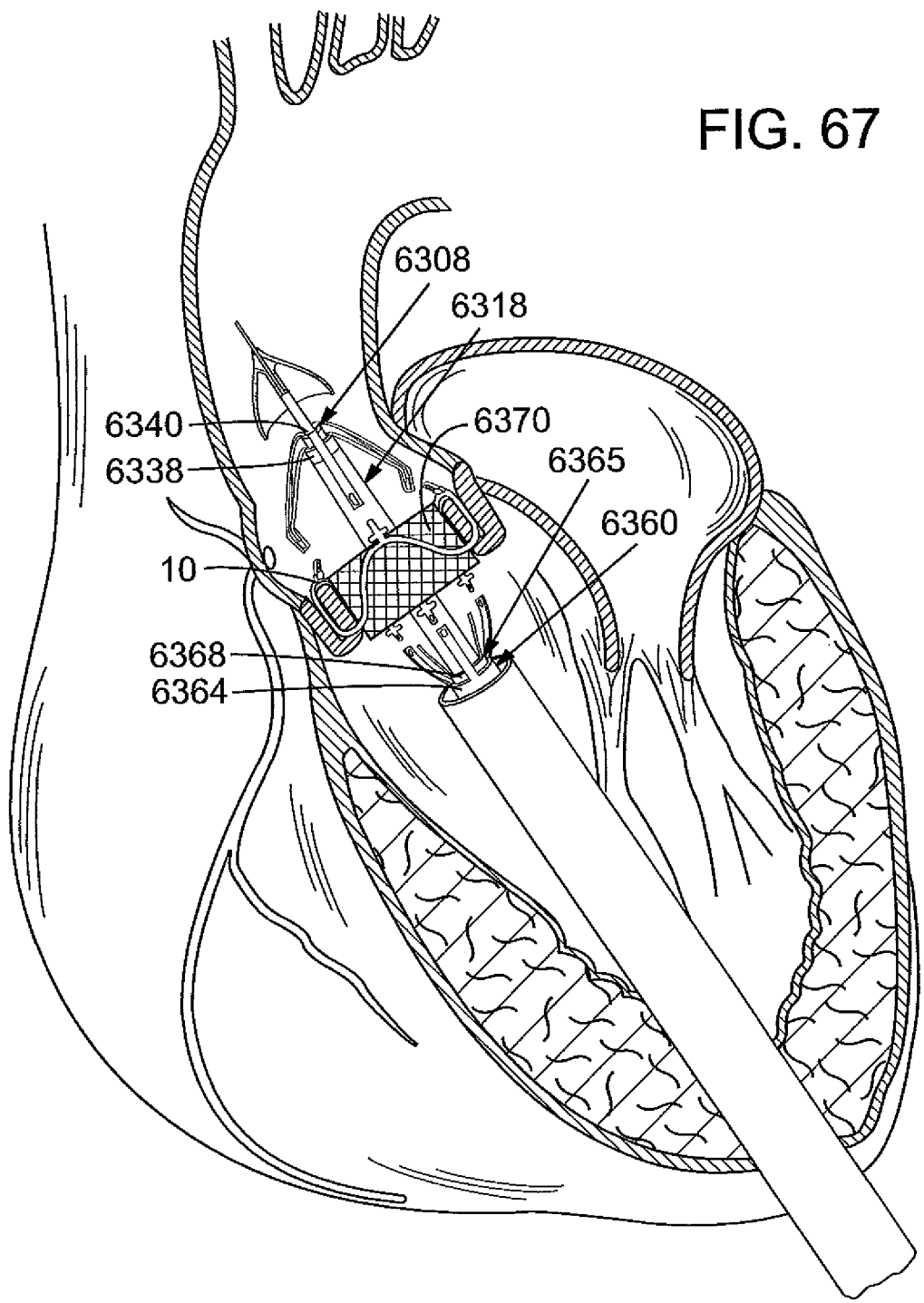

As shown in FIG. 67, once the prosthetic valve 6370 is secured into its desired position, the prosthetic valve delivery inner catheter 6365 of the delivery system 6300 can be retracted, thereby causing the prongs of the inner fork 6368 to become disengaged from the retaining arms of the prosthetic valve 6370. Once the prongs of the inner fork 6368 are disengaged, the prongs of the outer fork 6364 become disengaged from the retaining arms, and the prosthetic valve delivery outer catheter 6360 can be retracted.

With the prosthetic valve 6370 now disengaged, the stent delivery inner fork catheter 6318 of the delivery system 6300 can be advanced distally, thereby causing the prongs of the inner fork 6338 to become disengaged from the retaining arms of the support stent 10. Once the prongs of the inner fork 6338 are disengaged, the prongs of the outer fork 6340 become disengaged from the retaining arms, and the stent delivery outer fork catheter 6308 can be advanced distally. In other embodiments, the support stent 10 is disengaged from the delivery system 6300 first, or the support stent 10 and the prosthetic valve 6370 are disengaged at least partially simultaneously.

Figure 68:
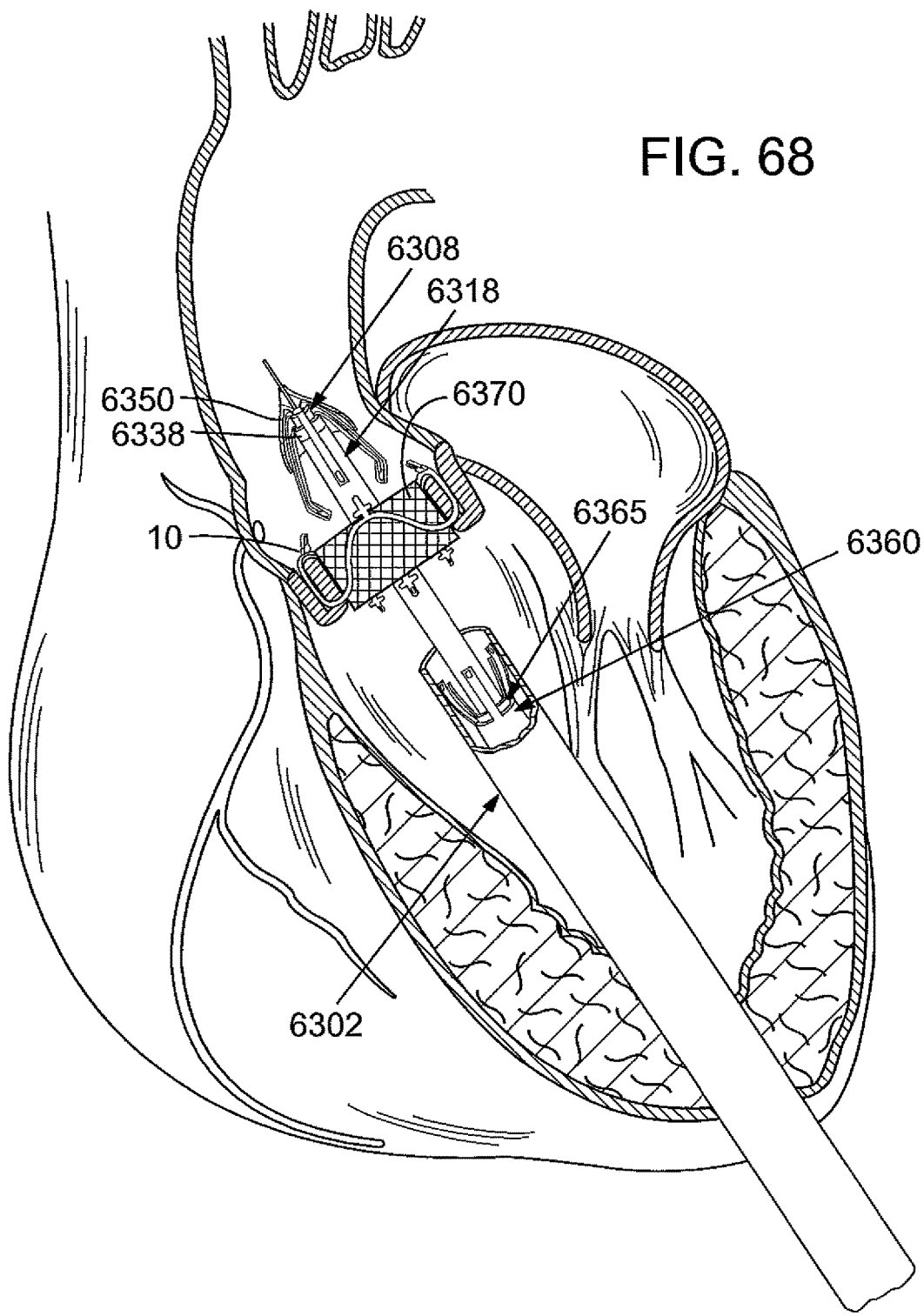

As shown in FIG. 68, once the support stent 10 and the prosthetic valve 6370 are disengaged from the delivery system 6300, the introducer sheath 6302 can be advanced over the prosthetic valve outer catheter 6360 and the prosthetic valve inner catheter 6365. The nose cone 6350 can also be retracted so as to partially enclose the stent delivery outer fork catheter 6318 and the stent delivery inner fork catheter 6318.

Figure 69:
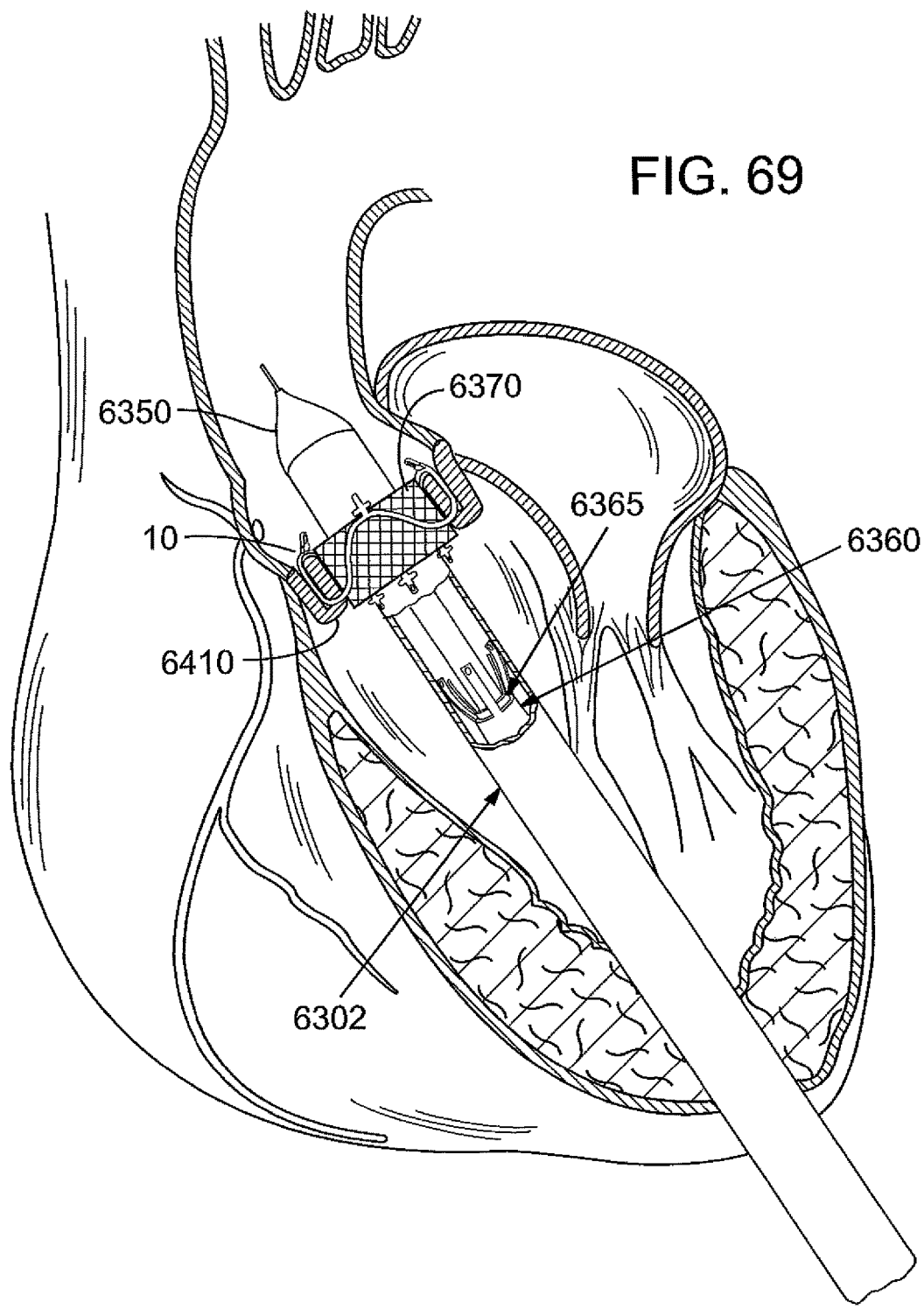
Figure 70:
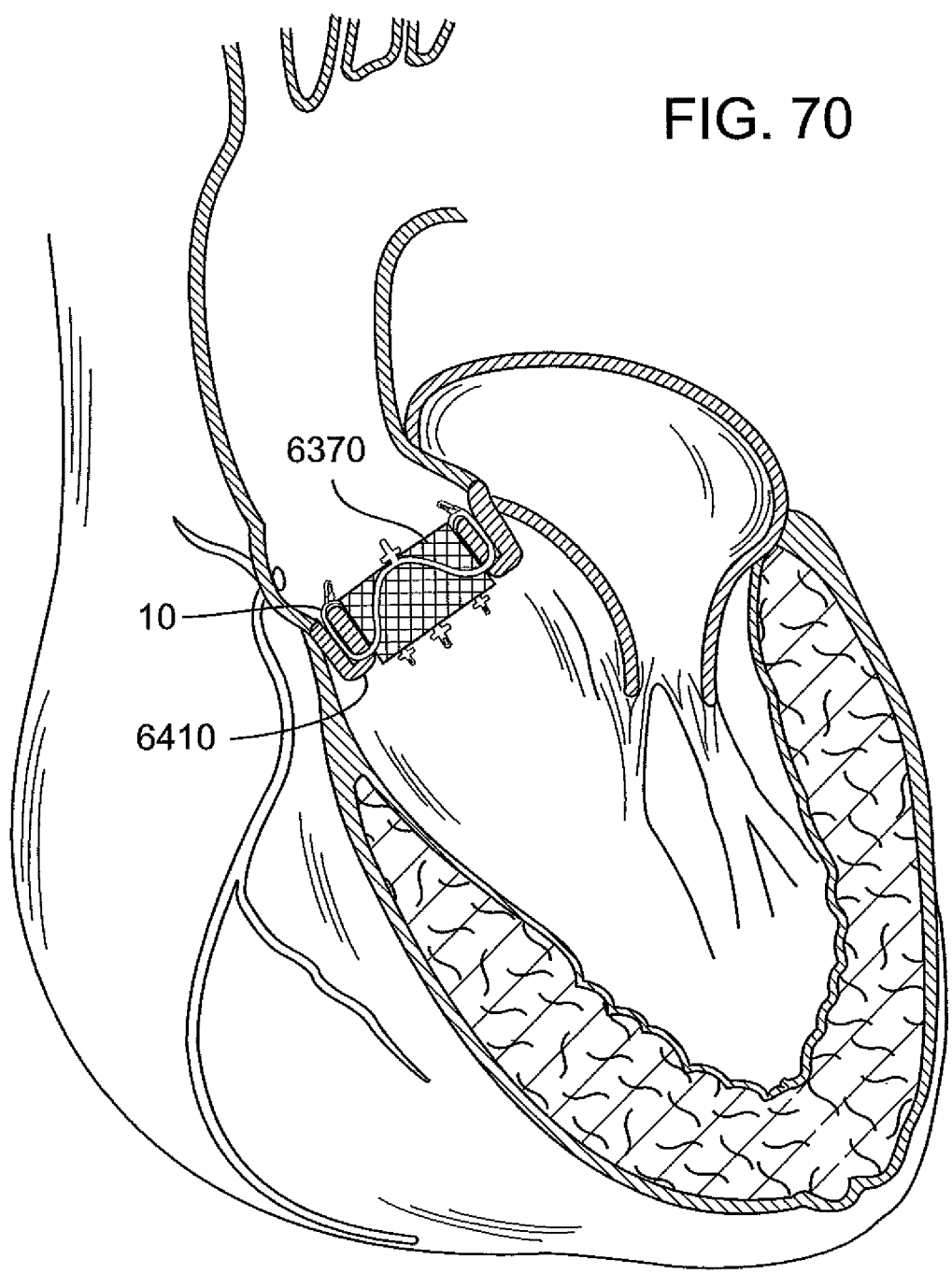

As shown in the FIG. 69, the introducer sheath 6302 can then be advanced to entirely enclose the prosthetic valve outer catheter 6360 and the prosthetic valve inner catheter 6365, and thereby aid the removal of the catheters from the aortic valve 6410. The introducer sheath 6302 (along with all of the interior catheters) and the nose cone 6350 can then retracted through the prosthetic valve 6370. The delivery system 6300 can then be removed from the ventricle of the patient. The guide wire 6380 can also be withdrawn from the patient as well, leaving the prosthetic valve 6370 securely positioned within the aortic valve 6310 by the support stent 10 as shown by FIG. 70.

Embodiments of a Collapsible Nose Cone

The nose cones that are used with any of the embodiments described herein can have a variety of shapes, sizes, and properties. In certain embodiments, for example, the nose cone can be configured to be collapsible. For instance, the nose cone can be adapted to be self-expanding in its natural state, but be collapsible into a compressed configuration when the nose cone is retracted within a surrounding catheter.

Figure 71A:
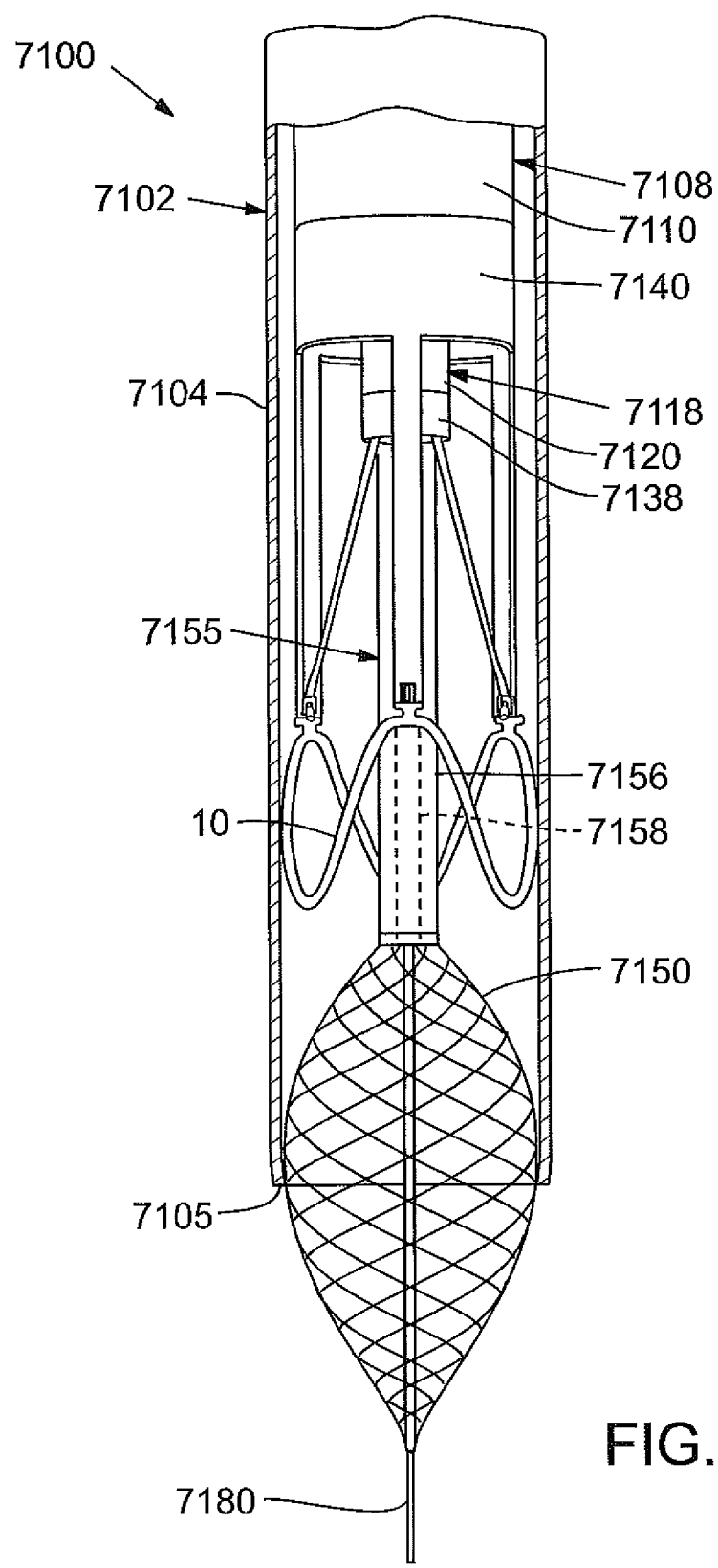
FIGS. 71A and 71B are front views of an exemplary delivery system having a collapsible nose cone. In particular.

FIG. 71A is a front view of the distal end portion of an exemplary stent delivery system 7100 comprising a collapsible nose cone. The stent delivery system 7100 is similar to the apparatus 100 shown in FIGS. 3 and 4 and shows the support stent 10 in a compressed, predeployed state. The delivery system 7100 comprises a main catheter 7102 having an elongated shaft 7104, whose distal end 7105 is open in the illustrated embodiment. The delivery system 7100 also includes a stent delivery catheter 7108 positioned in the interior of the main catheter 7102. The stent delivery catheter 7108 has an elongated shaft 7110 and an outer fork 7140 connected to a distal end portion of the shaft 7110. The delivery system 7100 also includes an inner catheter 7118 positioned in the interior of the stent deliver catheter 7108 and configured to be axially and rotatably movable relative to the other shafts of the delivery system 7100 (e.g., using a handle or lever (such as a lockable handle or lever) located at or near a proximal end of the delivery system 7100 as is known in the art). The inner catheter 7118 can have an elongated shaft 7120 and an inner fork 7138 secured to the distal end portion of the shaft 7120. The delivery system 7100 further includes a nose cone catheter 7155 positioned in the interior of the inner catheter 7118 and configured to be axially and rotatably movable relative to the other shafts of the delivery system 7100 (e.g., using a handle or lever (such as a lockable handle or lever) located at or near a proximal end of the delivery system 7100 as is known in the art). The nose cone catheter 7155 has an elongated shaft 7156 and a nose cone 7150 connected to a distal end portion of the shaft 7156. The nose cone 7150 can be connected to the shaft 7156 using a suitable adhesive (e.g., a bonding adhesive), a frictional engagement mechanism (e.g., a snap-fit or threaded collar attachment), by forming the nose cone 7150 and the nose cone catheter 7155 as part of a single unibody element (e.g., using suitable molding techniques), or other such attachment mechanism. The nose cone catheter can further include a guide wire lumen 7158 through which a guide wire, such as guide wire 7180, can be advanced. The guide wire 7180 can be used, for example, to help ensure proper advancement of the main catheter 7102 and its interior catheters through the vasculature of a patient.

In the illustrated embodiment, the collapsible nose cone 7150 is generally football-shaped. More generally, the illustrated nose cone 7150 can be said to form an ellipsoid whose polar radius (in the y-direction) is greater than the equatorial radius (in the x-direction). Such a shape can also be referred to as a spindle-shaped ellipsoid or a prolate spheroid. In the illustrated embodiment, the collapsible nose cone 7150 is formed from a wire mesh (or stented mesh) of a suitable shape-memory metal or alloy, such as spring steel, Elgiloy®, or Nitinol. During manufacture, the nose cone 7150 can be cut and heat treated so that it takes the desired nose cone shape but also has some flexibility to reduce trauma to the patient's vasculature. Furthermore, when the nose cone 7150 is made from a shape-memory metal or alloy, a protective covering can be used to cover the nose cone 7150 and further reduce any trauma to the patient's vasculature when the nose cone 7150 is advanced through it. For instance, the nose cone 7150 can be covered in a thin polymer or cloth cover (not shown). In other embodiments, the nose cone 7150 can be formed from a suitable foam that can compressed to a smaller state. In general, the nose cone 7150 can be fabricated from any material that allows the nose cone to automatically expand to its functional size and shape when deployed but also allows the nose cone to be radially compressed to a smaller profile.

Figure 71B:
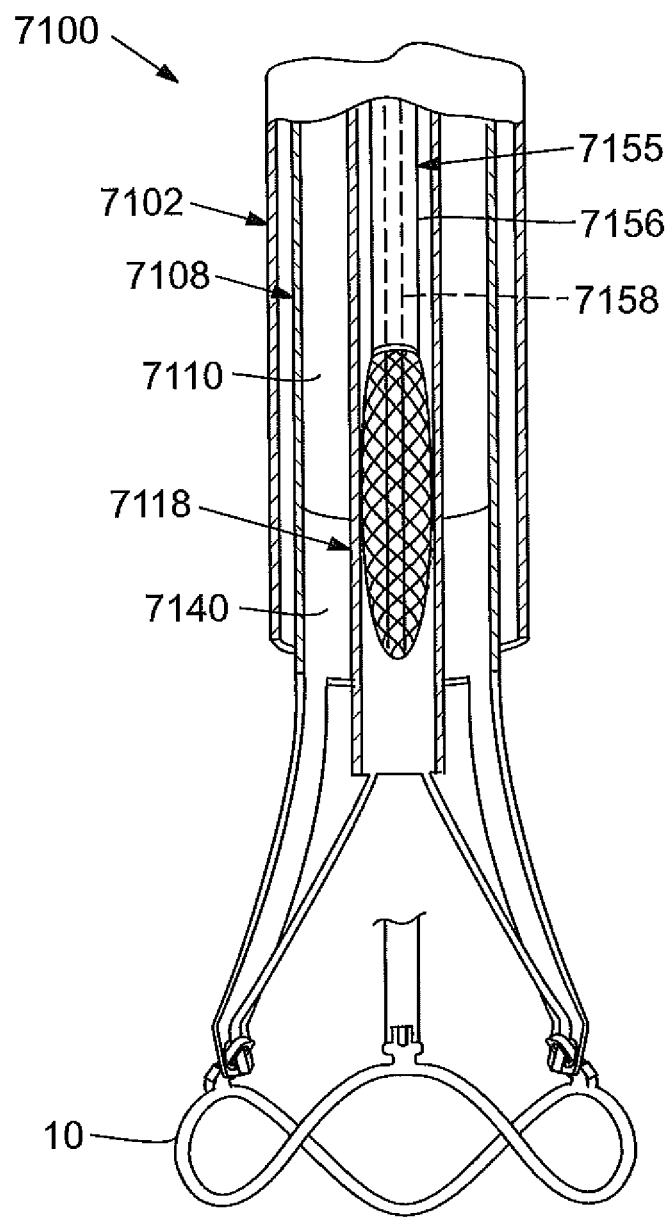

FIG. 71B is a front view showing the support stent 10 after it has been advanced from the distal end of the main catheter 7102. As seen in FIG. 71B, the support stent 10 now assumes its relaxed, uncompressed shape but remains connected to the outer fork 7140 and the inner fork 7138 at its retaining arms 21, 23, 25. FIG. 71B also shows the nose cone catheter 7155 withdrawn into the interior lumen of the inner catheter 7118. When the nose cone catheter 7155 is withdrawn into the inner catheter 7118, the collapsible nose cone 7150 is urged into its compressed state by the inner walls of the inner catheter 7118. In this withdrawn state, the nose cone 7150 is no longer located distally of the support stent 10, the outer fork 7140, or the inner fork 7138. Consequently, the support stent 10 can be positioned into the proper location adjacent to the aortic valve without any interference caused by the nose cone 7150. Furthermore, when a prosthetic valve is delivered to the aortic valve, the nose cone 7150 does not block or otherwise interfere with the placement of the prosthetic valve.

Although the compressible nose cone 7150 is shown as being used with a stent delivery system 7100 similar to that shown in FIGS. 3-4, it can be used with any of the delivery systems disclosed herein. A compressible nose cone can be used in such a system to aid guidance through the patient's vasculature, but can then be retracted into an interior lumen of the system so that the distal end of the system can be free from any interference the nose cone might otherwise cause.

Alternative Support Stent Designs

FIGS. 72-107 illustrate various alternative embodiments for the support stent that can be used together with any of the delivery systems described herein. The features shown in support stents illustrated in FIGS. 72-107 can be used alone or in various combination and subcombinations with one another as appropriate. The support stents in FIGS. 72-107 can have a generally annular or toroidal body formed from a suitable shape-memory metal or alloy, such as spring steel, Elgiloy®, or Nitinol. Desirably, the material from which the support stents are fabricated allows the support stent to automatically expand to its functional size and shape when deployed but also allows the support stent to be radially compressed to a smaller profile for delivery through the patient's vasculature. In other embodiments, however, the stent is not self expanding.

Figure 72:
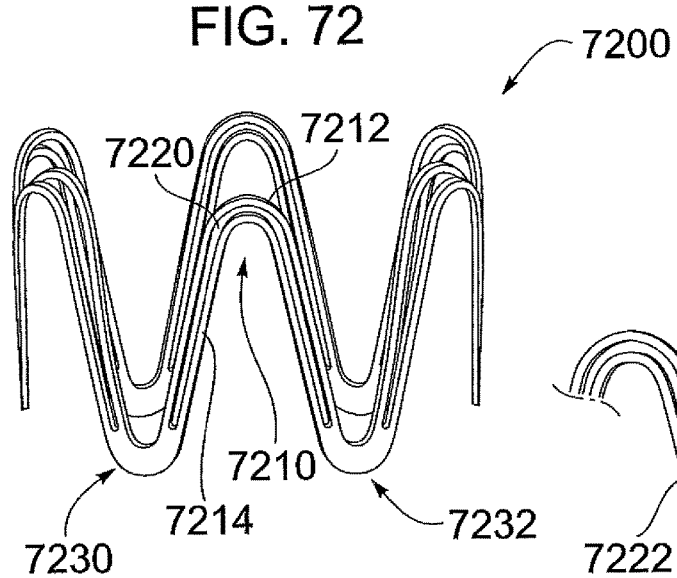
FIG. 72 is a perspective view of an alternative support stent design having spaced-apart support stent strut members.
Figure 74:
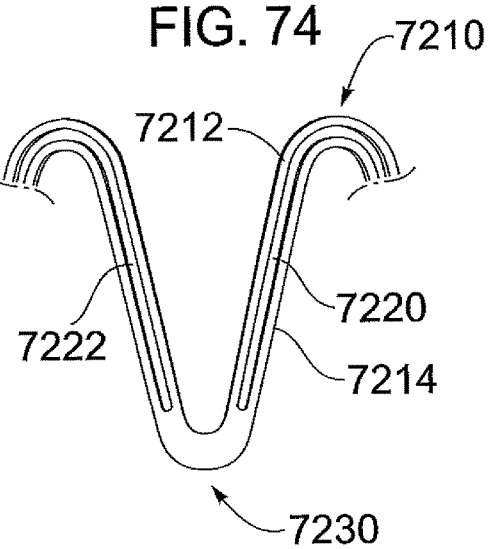
FIG. 74 is a front view of a portion of the support stent shown in FIG. 72.
Figure 73:
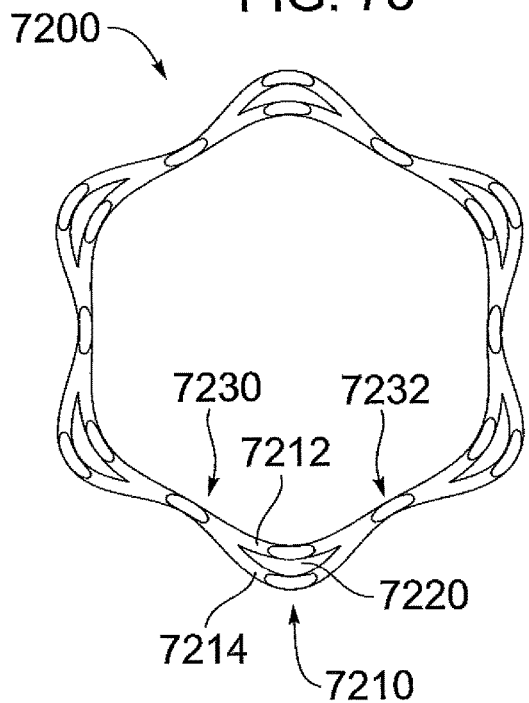
FIG. 73 is a top view of the support stent shown in FIG. 72

FIGS. 72-74 illustrate a support stent 7200 in which each peak includes two spaced-apart strut members. In particular, FIG. 72 is a perspective view of the support stent 7200, FIG. 73 is a top view of the support stent 7200. In the illustrated embodiment, the support stent 7200 includes six peaks and six valleys, although it should be noted that more or fewer peaks and valleys can be included in the support stent depending on the design. Furthermore, for ease of illustration, retaining arms (such as retaining arms 21, 23, 25 in FIG. 1) are omitted from the support stent 7200. It should be understood that retaining arms can be included on any one or more of the peaks of the support stent 7200 and be configured for use with a release mechanism associated with a corresponding support stent delivery system (e.g., using the mechanism described above with respect to FIGS. 5 and 6).

As seen in FIGS. 72 and 73, a respective peak 7210 includes an upper strut member 7212 and a lower strut member 7214. The upper strut member 7212 and the lower strut member 7214 can be separated by an aperture 7220 in the respective peak 7210 of the support stent 7200. For example, the aperture 7220 can extend along a majority of the respective peak 7210. The aperture 7220 can begin at a point of the support stent 7200 near a first adjacent valley 7230 and extend centrally through the respective peak 7210 to a point near a second adjacent valley 7232. The aperture 7220 can be manufactured into the support stent using a suitable milling or molding technique.

FIG. 74 is a partial front view of the valley 7230 further illustrating the construction of the aperture 7220 as well as an adjacent aperture 7222. FIG. 74 illustrates that the upper and lower strut members 7212, 7214 can be said to be connected at the valley 7230.

As best seen in FIGS. 72 and 73, the lower strut members (such as lower strut member 7214) are angled outwardly relative to the upper strut members (such as upper strut member 7212). Thus, the lower strut members form outer strut members and the upper strut members form inner strut members. Thus, the peaks of the lower strut members collectively define a diameter that is larger than the diameter collectively defined by the peaks of the upper strut members. In other embodiments, the upper strut members are angled outwardly relative to the lower strut members. In still other embodiments, only some of the upper strut members are angled outwardly relative to the lower strut members, or vice versa. In particular embodiments, the upper strut members can be configured so that they collectively define an annular interior having a diameter that approximately matches (or is slightly smaller than) the diameter of the prosthetic valve with which the support stent 7200 is to be used. For example, the interior defined by the upper strut members can be configured to be slightly smaller than the diameter of the prosthetic valve in its expanded state, thus helping to create a tighter fit with the prosthetic valve when the support stent 7200 is deployed. The lower strut members can be angled and configured so that their peaks collectively define a diameter that is substantially the same as the diameter of the aortic annulus. In particular embodiments, the angle and length of the lower strut members can be selected so that the lower strut members engage the leaflets of the aortic valve along substantially the entire length of each leaflet or at another point along each leaflet (e.g., at points in the aortic annulus where the commisure between two adjacent leaflets ends). In general, the outer strut members (e.g., the lower strut members in support stent 7200) can engage and urge together portions of the valve leaflets that are not otherwise engaged by the inner strut members (e.g, the upper strut members in support stent 7200). This helps reduce paravalvular leakage by reducing gaps between the valve leaflets.

Figure 75:
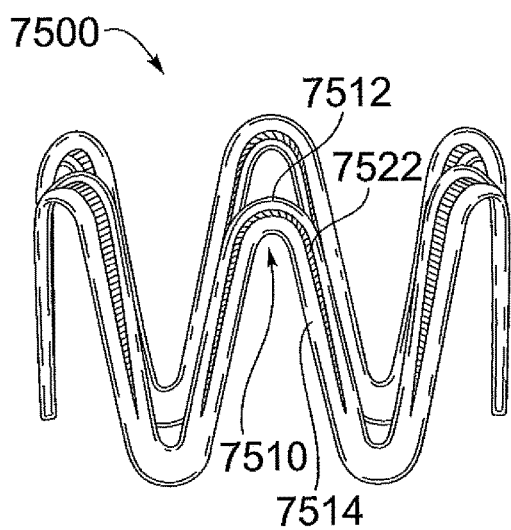
FIG. 75 is a perspective view of another alternative support stent design.

FIG. 75 shows an embodiment of a support stent 7500 similar to that of support stent 7200 except that the space between the upper strut members (such as respective upper strut member 7512) and the lower strut members (such as respective lower strut member 7514) of the peaks (such as respective peak 7510) are covered by a cloth or other impermeable material 7522. The impermeable material 7522 creates an additional barrier to help prevent valve leakage.

FIG. 76 shows an embodiment of a support stent 7600 similar to that of support stent 7200 except that the upper (and, in this embodiment, outer) strut members include projections that define interior spaces configured to enclose portions of adjacent valve leaflets. In the illustrated embodiment, the interior spaces defined by the projections extend into the apertures between the upper strut members and the lower (and inner) strut members of the support stent 7600. In certain embodiments, the interior spaces defined by the projections can have a different width (e.g., a smaller width) than the apertures. For example, in FIG. 76, a respective peak 7610 includes an upper strut member 7612 and a lower strut member 7614. The upper strut member 7612 further forms a projection 7640 that includes an interior space 7642 between respective sides of the projection. In the illustrated embodiment, the projection is U-shaped but can have other shapes as well (e.g., 0-shape, half-mooned-shape, semicircular, hook-shape or other such shapes).

When positioned adjacent to the outflow side of a patient's aortic valve and frictionally engaged to the leaflets of the aortic valve via the expansion of a prosthetic valve in the central interior of the support stent 7600, the upper strut member 7612 and the lower strut member 7614 can engage adjacent valve leaflets as shown in FIG. 77. In particular, FIG. 77 is a perspective view showing a first aortic valve leaflet 7750 and a second aortic valve leaflet 7752 captured in the interior of the projection 7640. As a result, the aortic valve leaflets 7750, 7752 are caused to coapt with each other along commissure 7760, thus helping to reduce or substantially eliminate paravalvular leaking through the leaflets. Also shown in FIG. 77 is expanded prosthetic valve 7770, which has an exterior surface that captures (or pinches) a portion of the first aortic valve leaflet 7750 and the second aortic valve leaflet 7752 against the upper strut member 7612 of the support stent 7600.

Figure 154:
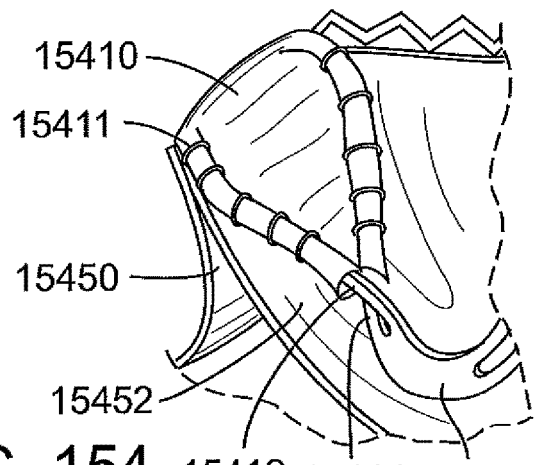
FIG. 154 is a perspective view of a modified version of the support stent of FIG. 76 engaging leaflets of a native heart valve.

FIG. 154 shows an embodiment of a support stent 15400 similar to that of support stent 7600 but includes a cover 15410 that extends between upper strut member 15412 and lower strut member 15414. The cover 15410 can be cloth, silicone, foam, or some other biocompatible material. In certain embodiments, the cover is secured to the frame by stitching 15411 or some other fastening mechanism (e.g., one or more sutures). The cover 15410 can operate to further reduce the paravalvular leaking through leaflets of the aortic valve, such as through first aortic leaflet 15450 and second aortic leaflet 15452.

FIG. 78 shows an embodiment of a support stent 7800 similar to that of support stent 7200 except that the aperture between the upper strut members and the lower strut members extends through the valleys of the support stent 7800. For example, an upper strut member 7812 is separated from a lower strut member 7814 by an aperture 7820 that extends through a majority of valley 7830. Furthermore, the upper strut member 7812 and the lower strut member 7814 are connected at a location in peak 7810.

FIG. 79 shows an embodiment of a support stent 7900 similar to that of support stent 7800 except that an interior 7942 formed between adjacent sides of a lower strut member 7914 in a peak 7910 has a smaller width than an interior 7944 formed between adjacent sides of an upper strut member 7912 in a valley 7930 of the support stent 7900. The peak 7910 of the support stent 7900 can be said to be generally cusp-shaped. The reduced width in the interior 7942 of the peak 7910 allows the support stent 7900 to pinch adjacent leaflets of the patient's aortic valve more closely, thereby reducing any potential leakage between the two leaflets.

When positioned adjacent to the outflow side of a patient's aortic valve and frictionally engaged to the leaflets of the aortic valve via the expansion of a prosthetic valve in the central interior of the support stent 7900, the upper (and, in this embodiment, inner) strut member 7912 and the lower (and, in this embodiment, outer) strut member 7914 can engage adjacent valve leaflets as shown in FIG. 80. In particular, FIG. 80 is a perspective view showing a first aortic valve leaflet 8050 and a second aortic valve leaflet 8052 captured in the interior 7942 formed between adjacent sides of the lower strut member 7914. As a result, the aortic valve leaflets 8050, 8052 are caused to coapt with each other along commissure 8060, thus helping to reduce or substantially eliminate paravalvular leaking through the leaflets. Also shown in FIG. 80 is expanded prosthetic valve 8070, which has an exterior surface that captures (or pinches) a portion of the first aortic valve leaflet 8050 and the second aortic valve leaflet 8052 against the upper strut member 7912 of the support stent 7900 as the upper strut member 7912 extends through valley 7930 of the support stent 7900.

FIGS. 81-82 show another embodiment of a support stent 8100. In FIGS. 81 and 82, the upper strut members for a given peak are disconnected from one another at the ends of the members closest to the peak. For example, for peak 8110, the upper strut members comprise a first upper strut arm 8112 and an adjacent second upper strut arm 8113. Each of the upper strut arms 8112, 8113 are connected to the support stent 8100 at locations 8132, 8133 located at or near valleys 8130, 8131. The upper strut arms 8112, 8113 can further comprise head portions 8116, 8117 having a generally circular shape at the ends of the upper strut arms 8112, 8113, respectively. The upper strut arms 8112, 8113 can have a variety of lengths, but in certain embodiments the upper strut arms 8112, 8113 extend higher along the support stent 8100 than the other components of the support stent. The support stent 8100 further includes lower strut members that are continuous and not divided into separate arms. For example, for respective peak 8110, the support stent 8100 includes a lower strut member 8114 that has a generally sinusoidal shape.

FIG. 81 shows the support stent 8100 before the support stent is set into its final shape (e.g., using a suitable shape set technique for shape memory alloys). FIG. 82 shows the support stent 8100 after it has been shape set into one exemplary configuration. In the configuration shown in FIG. 82, the first upper strut arm 8112 is configured to be crossed with the second upper strut arm 8113, thereby forming an interior 8144 having an apex 8145. Furthermore, the crossed upper strut arms 8112, 8113 can be configured to be angled outwardly relative to the lower strut member 8114. Thus, the crossed upper strut arms 8112, 8113 can form outer strut arms, where as the lower strut member 8114 can form an inner strut member.

When positioned adjacent to the outflow side of a patient's aortic valve and frictionally engaged to the leaflets of the aortic valve via the expansion of a prosthetic valve in the central interior of the support stent 8100, the first upper strut arm 8112, the second upper strut arm 8113, and the lower strut member 8114 can engage adjacent valve leaflets as shown in FIG. 83. In particular, FIG. 83 is a perspective view showing a first aortic valve leaflet 8350 and a second aortic valve leaflet 8352 captured in an interior 8144 formed between the first upper strut arm 8112 and the second upper strut arm 8113. In particular, the first upper strut arm 8112 and the second upper strut art 8113 can cause the aortic valve leaflets 8350, 8352 to be urged together at or near the apex 8145 of the interior 8144 formed between the upper strut arms along commissure 8360, thus helping to reduce or substantially eliminate paravalvular leaking through the leaflets. Also shown in FIG. 83 is expanded prosthetic valve 8370, which has an exterior surface that captures (or pinches) a portion of the first aortic valve leaflet 8350 and the second aortic valve leaflet 8352 against the lower strut member 8114 of the support stent 8100.

FIGS. 84-85 show another embodiment of a support stent 8400. In FIGS. 84 and 85, the upper strut members for a given peak are comprised of upper strut arms that are connected by a connecting member at the distal end of the upper strut arms. For example, for peak 8410, the upper strut members comprise a first upper strut arm 8412 and an adjacent second upper strut arm 8413. Each of the upper strut arms 8412, 8413 are connected to the support stent 8400 at locations 8432, 8433 located at or near valleys 8430, 8431. In this embodiment, the upper strut arms 8412, 8413 are connected to one another by a connecting member 8416. The upper strut arms 8412, 8413 can have a variety of lengths, but in certain embodiments the upper strut arms

8412, 8413 extend higher along the support stent than the other components of the support stent 8400. In certain embodiments, the upper strut arms 8412, 8413 and the connecting member 8416 shape the upper strut member of the support stent 8400 into a top-hat (or mesa) shape. The support stent 8100 further includes lower strut members that are continuous and not divided into separate arms. For example, for respective peak 8410, the support stent 8400 includes a lower strut member 8414 that has a generally sinusoidal shape.

FIG. 85 shows the support stent 8400 before the support stent is set into its final shape (e.g., using a suitable shape set technique for shape memory alloys). FIG. 85 shows the support stent 8500 after it has been shape set into one exemplary configuration. In the configuration shown in FIG. 85, the first upper strut arm 8412 is configured to be crossed with the second upper strut arm 8413, thereby forming a diamond-shaped interior 8444. Furthermore, the crossed upper strut arms 8412, 8413 can be configured to be angled outwardly relative to the lower strut member 8414. Thus, the crossed upper strut arms 8412, 8413 can form outer strut arms, where as the lower strut member 8414 can form an inner strut member.

Figure 86:
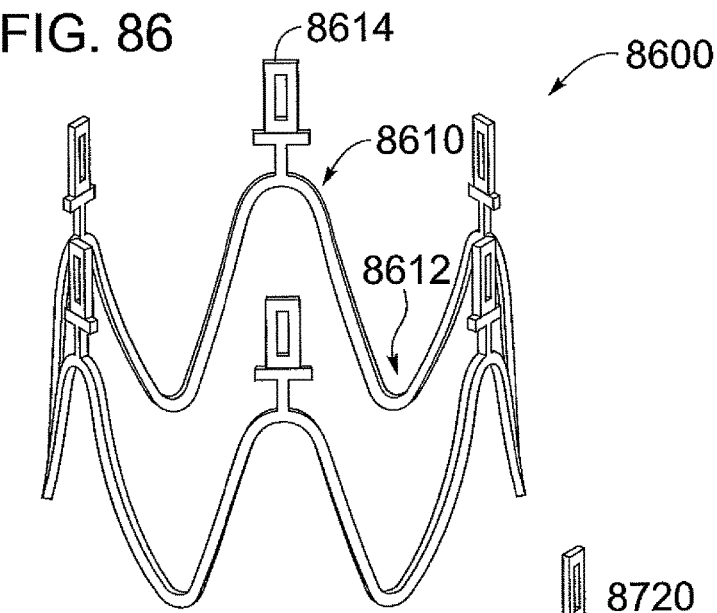
FIG. 86 is a perspective view of a support stent having six peaks and six valleys.

FIG. 86 shows an embodiment of a support stent 8600 having six peaks and six valleys. In particular, support stent 8600 has a generally sinusoidal shape forming six peaks (e.g., peak 8610) and six valleys (e.g., valley 8612). Furthermore, each of the peaks of the support stent 8600 includes a retaining arm (e.g., retaining arm 8614). In other embodiments, however, fewer than all of the peaks can comprise a retaining arm. For instance, every other peak can include a retaining arm. Additionally, the support stent can alternatively include any number of peaks or valleys.

Figure 87:
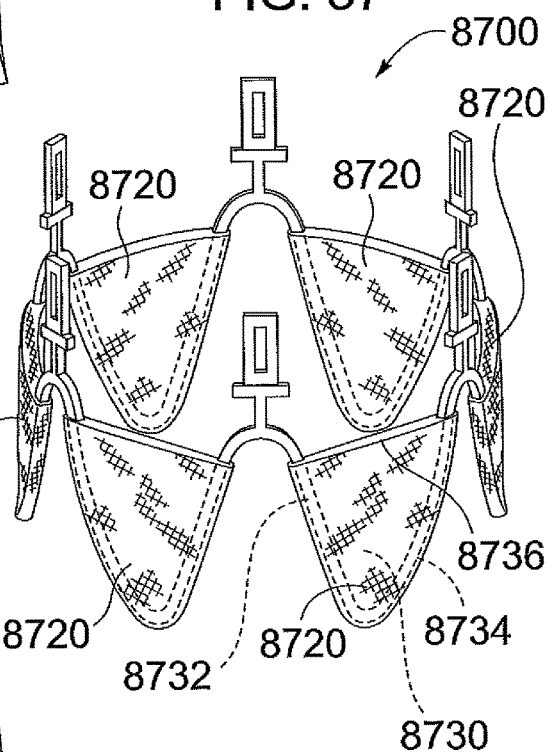
FIG. 87 is a perspective view of a support stent that includes covers configured to at least partially cover the valleys of the support stent.

FIG. 87 shows an embodiment of a support stent 8700 that is similar to support stent 8600 but includes covers 8720 that enclose at least a portion of one or more valleys of the support stent 8700. In the illustrated embodiment, a plurality of covers 8720 encloses substantially all of each valley in the support stent 8700, including the interior space of the valley defined between adjacent strut members of the support stent (e.g., interior space 8730 between first strut member 8732 and adjacent second strut member 8734). In other embodiments, the covers 8720 enclose only some of the valleys in the support stent 8700. Furthermore, the covers 8720 can form a complete enclosure or can be open at a top end, thus forming a basket-type cover. The covers 8720 can comprise cloth coverings and may define a hollow interior into which additional padding or other material can be inserted. The covers 8720 can also be formed from silicone, foam, or some other biocompatible material. In certain embodiments, wires or other support bands (e.g., wire 8736) are positioned between adjacent strut members of a valley at or near the adjacent peaks of the valley. For instances, the wires or support bands can be threaded through eyelets (not shown) formed in the support stent 8700. The upper ends of the covers 8720 can be attached to the wires or support bands (e.g., using a suitable stitch or other attachment mechanism). Consequently, the covers 8720 can be held in place when the support stent is in a compressed state. Desirably, the covers 8720 are adapted to create a larger surface area of the support stent 8700 that engages the native leaflets of the heart valve when the support stent 8700 is inserted. This larger surface area reduces the overall force experienced between the native valve leaflets and the support stent 8700, making the fit between the native valve leaflets and the support stent 8700 less traumatic to the native valve leaflets. In certain embodiments, additional padding (e.g., additional or thicker cloth, silicone, or foam) can be placed at or near the nadir (or base) of the valleys of the support stent 8700 (e.g., additional padding within each of the covers 8720 at a location adjacent to the nadir of a valley).

Figure 88:
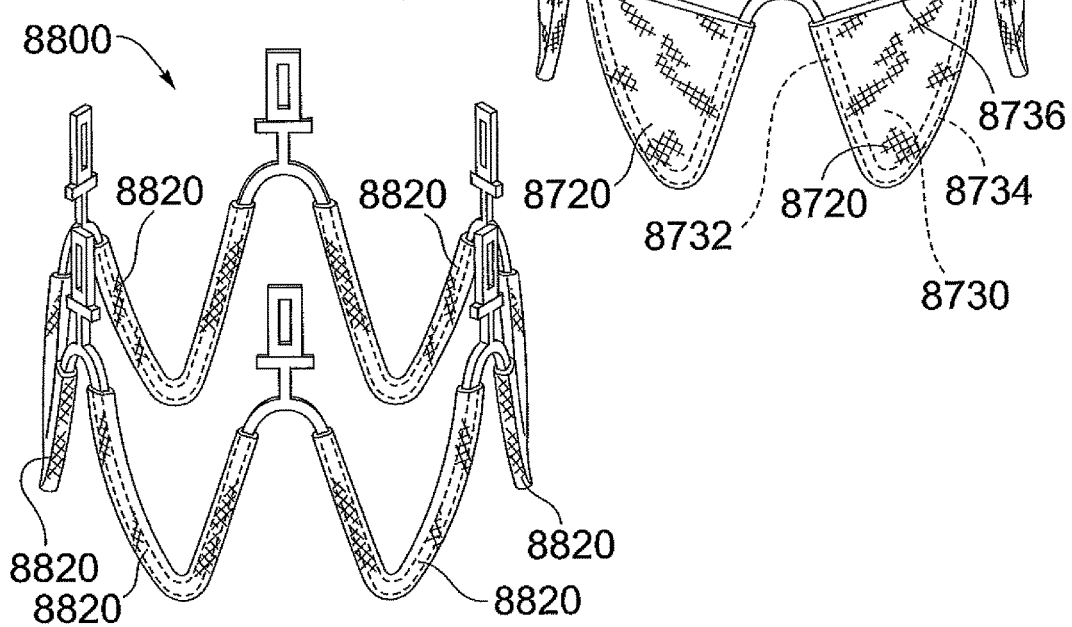
FIG. 88 is a perspective view of a support stent that includes tubular covers configured to at least partially cover the body of the support stent.

FIG. 88 shows an embodiment of a support stent 8800 that is similar to support stent 8600 but includes tubular covers 8820 that enclose at least some of the support stent. In the illustrated embodiment, a plurality of tubular covers 8820 encloses substantially all of each valley in the support stent 8800. In other embodiments, the tubular covers 8820 enclose only some of the valleys in the support stent 8800. Furthermore, the tubular covers 8820 can form a complete enclosure over the body of the support stent 8800 in the desired locations. In other embodiments, however, the tubular covers 8820 can have an open side or portion (e.g., the covers 8820 can be C-shaped or cover just one side of the support stent) The tubular covers 8820 can comprise tubular cloth coverings and may define a hollow interior into which additional padding or other material can be inserted. The tubular covers 8820 can alternatively be formed from silicone, foam, or some other biocompatible material. Desirably, the tubular covers 8820 are adapted to provide a softer surface that engages the native leaflets of the heart valve when the support stent is inserted. The tubular covers 8820 also create a larger surface area of the support stent 8800, thereby reducing the overall force that is experienced between the native valve leaflets and the support stent 8800. In certain embodiments, additional padding (e.g., additional or thicker cloth, silicone, or foam) can be placed at or near the nadir (or base) of the valleys of the support stent 8800 (e.g., additional padding within each of the tubular covers 8820 at a location adjacent to the nadir of a valley).

FIG. 89 shows an embodiment of a support stent 8900 that is similar to support stent 8600 but includes foot projections 8920 positioned at or adjacent to the nadir of the valleys of the support stent 8900. The foot projections 8920 can be formed to be an integral part of the body of the support stent 8900 or can comprise separate members that are attached to the support stent 8900 (e.g., using a suitable adhesive or bonding agent, mechanical fastener, or other attachment mechanism). In still other embodiments, the foot projections 8920 can be part of a covering that covers the body of the support stent 8900. For example, in particular implementations, the foot projections 8920 are part of an overmold that is molded over a body 8902 of the support stent 8900. The overmold can be formed of a suitable biocompatible material (e.g., silicone) that helps reduce the trauma between the support stent 8900 and the native valve leaflets. The shape of the foot projections 8920 can vary from implementation to implementation, but in the implementation illustrated in FIG. 89 comprises a tongue-shaped projection that is outwardly flanged. Furthermore, in the illustrated embodiment, six foot projections 8920 are shown. In other embodiments, more or fewer foot projections are present. In general, the foot projections 8920 create a larger surface area at the bottom of the support stent 8900 where the support stent 8900 engages the upper surface of the outflow side of a patient's aortic valve. The increased surface area created by the foot projections 8920 helps distribute the overall force that is experienced between the native valve leaflets and the support stent 8900, making the support stent 8900 less traumatic to the native heart valve. The foot projections 8920 can also be used to engage a side wall of the aortic valve, which is typically more durable and less sensitive to trauma as the tissue of the native leaflets of a patient's heart valve.

FIG. 90 shows an embodiment of a support stent 9000 having foot projections 9020 that are integrally formed as part of the body of the support stent 9000. The foot projections 9020 are generally tongue-shaped but curve outwardly and then upwardly so as to have a U-shaped (or hook-shaped) profile. Although the foot projections 9020 are integrally formed as part of the support stent 9000, the foot projections can alternatively be separate members that are attached to the body of the support stent. Furthermore, in the illustrated embodiment, six foot projections 9020 are shown. In other embodiments, more or fewer foot projections are present. Each of the foot projections 9020 optionally includes one or more apertures 9022 (only two representative ones of which are shown in FIG. 90). The apertures 9022 can also improve the compressibility of the support stent 9000 so that the foot projections do not substantially affect the diameter to which the support stent 9000 can be compressed during delivery. In use, the apertures 9022 can also help increase the friction between a respective foot projection and the surface of the native heart valve (e.g., the surface of the aortic annulus), and thereby help prevent the support stent 9000 from rotating out of its desired petition. In general, the foot projections 9020 create a larger surface area at the bottom of the support stent 9000 where the support stent 9000 engages the upper surface of the outflow side of a patient's aortic valve. The increased surface area created by the foot projections 9020 helps distribute the overall force that is experienced between the native valve leaflets and the support stent 9000, making the support stent 9000 less traumatic to the native heart valve. The foot projections 9020 can also be used to engage a side wall of the aortic valve, which is typically more durable and less sensitive to trauma as the tissue of the native leaflets of a patient's heart valve.

FIG. 91 shows an embodiment of a support stent 9100 having loop projections 9120 that are integrally formed as part body of the support stent 9100. The loop projections 9120 extend outwardly from the diameter of a main body portion 9102 of the support stent 9100. Furthermore, in the illustrated embodiment, each of the loop projections 9120 is connected to the support stent 9100 at locations at or near the nadirs of adjacent valleys of the support stent 9100. For example, a respective one of the loop projections 9120 has ends that merge with the main body portion 9102 of the support stent 9100 at a first location 9104 near a first nadir 9105 and at a second location 9106 near a second nadir 9107. Although the loop projections 9120 are integrally formed as part of the support stent 9100, the loop projections can alternatively be separate members that are attached to the body of the support stent. Furthermore, in the illustrated embodiment, three loop projections 9120 are shown. In other embodiments, more or fewer loop projections are present. In general, the loop projections 9120 create a larger surface area at the bottom of the support stent 9100 where the support stent 9100 engages the upper surface of the outflow side of a patient's aortic valve. The increased surface area created by the loop projections 9120 helps distribute the overall force that is experienced between the native valve leaflets and the support stent 9100, making the support stent 9100 less traumatic to the native heart valve. The loop projections 9120 can also be used to engage a side wall of the aortic valve, which is typically more durable and less sensitive to trauma as the tissue of the native leaflets of a patient's heart valve.

For any of the embodiments described above, the support stent can additionally include a cover or coating that helps lessen the trauma to a native heart valve and/or further increase the surface area of the support stent. For example, the cover or coating can be formed from cloth, silicone, foam, or some other biocompatible material. In particular embodiments, the support stents include an overmold of a suitable biocompatible material (e.g., silicone) or are dipped to have a coating of a suitable biocompatible material. Additionally, and as explained above with respect to FIG. 89, the foot projections or loop projections of any of the described embodiments can be formed as part of a mold or covering that surrounds the main body of the support stent.

Furthermore, for any embodiment that includes a covering or cover of any type, combinations of materials can be used to form the covering. For example, a multi-material cover or covering can be used that provides added padding or softness to certain desired portions of the support stent, whereas the remainder of the cover or covering may include a thinner material. For instance, a thicker (or softer) material can be used to form an inward-facing side of the cover (a side of the cover that faces the interior of the support stent and engages the native valve leaflets) whereas a thinner material can be used to form an outward-facing side of the cover (a side of the cover that faces toward the walls of the heart valve). Additionally, for any embodiment that includes a covering or cover of any type, multiple layers of a material can be used to form the cover. The multiple layers can comprise one or more different materials. For example, in certain embodiments, two or more materials are sewn together and used to create a fabric that is used to form the covers for the support stent. For instance, a thick cloth material can be sewn to a thin cloth material, resulting in a multi-layer, multi-material fabric. This fabric can then be used to form any of the covers described herein. By using such a multi-layered and multi-material fabric, the cover can have an interior fabric (the fabric that contacts the main body of the support stent) that is different than an exterior fabric (the fabric that is on the outside of the cover and faces the surrounding native heart valve or prosthetic valve). For instance, the interior fabric can be a thick fabric and the exterior fabric can be a thin fabric, or vice versa. The covering can also be designed to cover only certain desired surfaces of the support stent. For example, in certain embodiments, covering material is only located on the inner (or inward-facing) surface of the support stent. Such embodiments provide abrasion protection to the native leaflets but reduce the quantity of extra material added to the support stent, thus reducing the crimped profile of the support stent. In other embodiments, the covering material surrounds both the inward-facing and outward-facing surface of some portion of the support stent but only cover an inward-facing surface of other portions of the support stent. For example, the lower portion of the support stent body can be completed covered (including its inward- and outward-facing surface) whereas the remaining portion of the support stent body can be either uncovered or covered only on its inward-facing surface. Further, for any embodiment that includes a covering or cover of any type, pockets can be sewn into or otherwise formed in the interior of the covering or cover. The pockets can be sized to receive corresponding valleys and/or peaks of the support stent, thereby helping to secure the cover or covering to the support stent. Exemplary embodiments of support stents that have covers with at least some of the above features are described below with respect to FIGS. 92-103 and 108-109. It should be understood, however, than any of these features can be utilized with any of the covers or coverings described herein.

Figure 92:
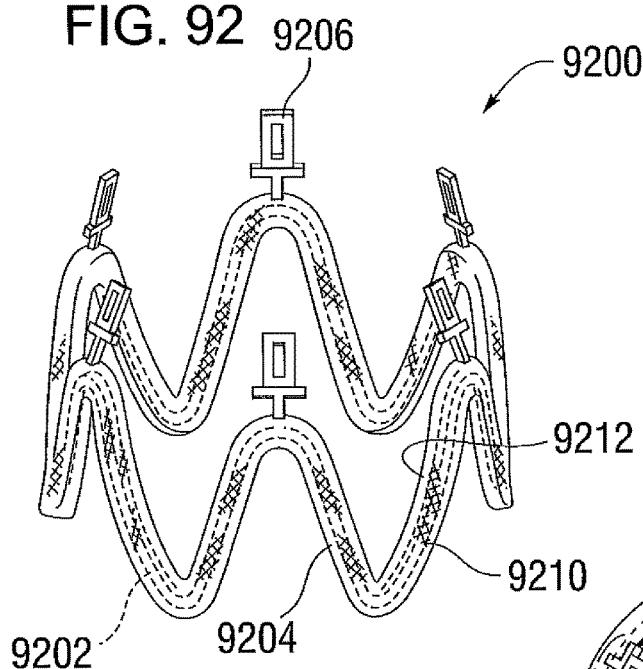
FIG. 92 is a perspective view of a support stent that is at least partially covered by a multi-material cover.
Figure 93:
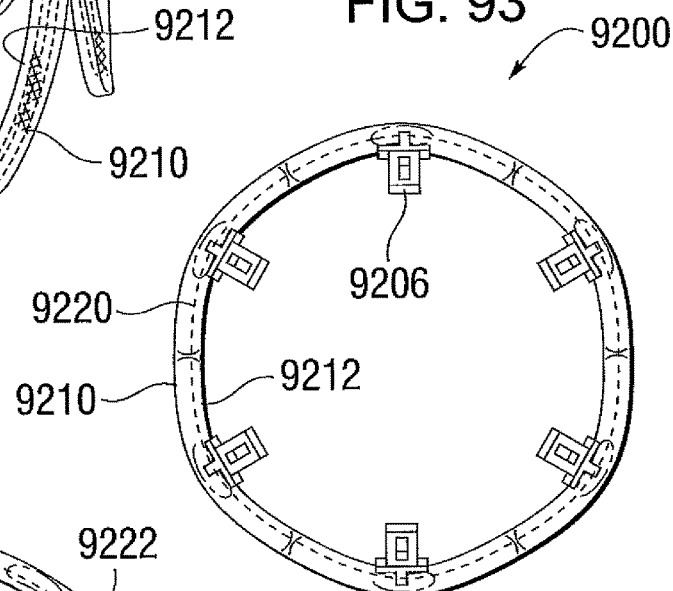
FIG. 93 is a top view of the support stent of FIG. 92.
Figure 94:
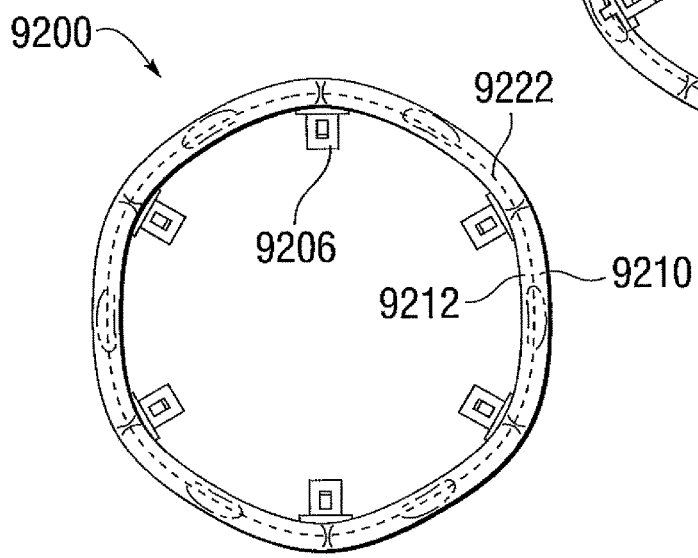
FIG. 94 is a bottom view of the support stent of FIG. 92.

FIGS. 92-94 show an embodiment of a support stent 9200 whose main body 9202 is covered by a multi-material cover

9204. In particular, FIG. 92 is a perspective view of the support stent 9200, FIG. 93 is a top view of the support stent 9200, and FIG. 94 is a bottom of the support stent 9200. The multi-material cover 9204 comprises an outward-facing portion 9210 formed of a first material that is cut and shaped to cover the main body 9202 along its outward-facing (or exterior) side and an inward-facing portion 9212 formed of a second material that is cut and shaped to cover the main body 9202 along its inward-facing (or interior) side. The first material can be a thinner material relative to the second material. For example, the first material can be a thin cloth fabric, whereas the second material can be a thick cloth fabric. The multi-material cover 8204 can be formed by sewing the outward-facing portion 9210 to the inward-facing portion 9212 at a top seam 9220 and a bottom seam 9222. Eyelets can be formed in the multi-material cover 9204 to allow the retaining mechanisms (such as retaining mechanism 9206) to be exposed through the multi-material cover. The added thickness in the inward-facing portion 9212 can reduce the trauma experienced by the leaflets of the native heart valve when a prosthetic valve is expanded in the interior of the support stent 9200, thereby pinching the leaflets of the native heart against the inward-facing portion 9212. Furthermore, the thin fabric used on the outward-facing portion 9210 helps maintain the compressibility of the support stent 9200. Consequently, the support stent 9200 can be delivered to the native heart using a delivery system having a desirably small diameter. In certain embodiments, additional padding can be inserted between the main body 9202 of the support stent 9200 and the interior of the multi-material cover 9204. Furthermore, any suitable biocompatible material can be used to form the portions of the multi-material cover (e.g., silicone, cloth, or other such biocompatible materials).

Figure 99:
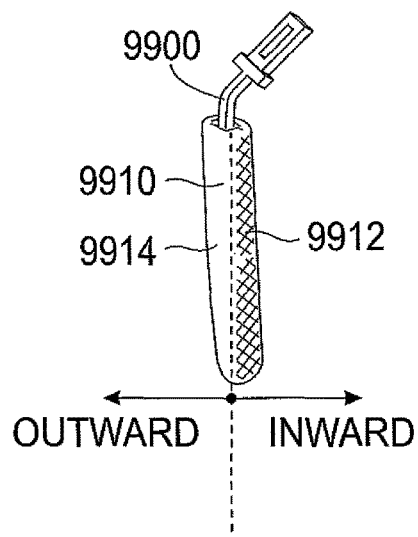
FIG. 99 is a side view of a support stent portion showing a portion of a multi-material cover that is used to cover the support stent.
Figure 100:
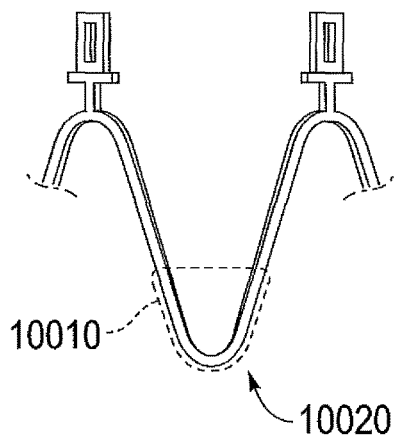
FIG. 100 is a front view showing a portion of a support stent and highlighting a location where thicker material for a cover can be used.

FIG. 99 is a side view of support stent member 9900 covered by an embodiment of a multi-material cover 9910. In particular, the multi-material cover 9910 comprises an inward-facing side 9912 and an outward-facing side 9914. The inward-facing side 9912 of the cover 9910 is the side that pinches a native valve leaflet to the exterior of an expanded prosthetic valve, whereas the outward-facing side 9914 is the side that faces outwardly from the support stent in the direction of the surrounding aortic valve walls. The inward-facing side 9912 can comprise a thicker, or more padded, material (e.g., a thick cloth), whereas the outward-facing side 9914 can comprise a thinner, less or less padded, material (e.g., a thinner cloth). In certain embodiments, the thicker, or more padded material, is more specifically positioned on a cover for the support stent. For example, and as illustrated schematically in FIG. 100, a cover can comprise thicker, more padded material, in locations of the support stent that are inward-facing and adjacent or near a nadir of a support stent valley. Location 10010 illustrates one such location in the nadir of the support stent valley 10020. By using a cover that only has the thicker material on its inward-facing side or in locations of the support stent where added padding is desirable (such as in the interior of the stent adjacent to the nadirs of the support stent valleys), the support stent can have padding to reduce the trauma experienced by the native valve leaflets but can also have a profile when the support stent is compressed that allows the support stent to be inserted into a suitable delivery system (e.g., any of the delivery systems described above).

FIG. 95 shows an embodiment of a support stent 9500 whose main body 9502 is covered by a cover 9504. As shown in FIG. 95, the cover 9504 encloses substantially all of the main body 9502 except for the retaining mechanisms (e.g., retaining mechanism 9506). Any suitable biocompatible material can be used to form cover 9504 (e.g., silicone, cloth, or other such biocompatible materials). In the illustrated embodiment, foam padding 9510 is inserted into the cover 9504. In particular, foam padding is added to the cover 9504 at or near each of the nadirs of the valleys of the support stent. For example, the cover 9504 is stuffed with a suitable foam stuffing or inserted at a location of the cover adjacent to nadir 9520. The added thickness at the nadirs of the valleys of the support stent 9500 can help reduce the trauma experienced by the leaflets of the native heart valve when a prosthetic valve is expanded in the interior of the support stent 9500, thereby bending the leaflets at the nadirs of the support stent 9500 and pinching the leaflets of the native heart against interior sides of the support stent.

FIG. 96 shows an embodiment of a support stent 9600 whose main body 9602 is covered by a cover 9604 except for the retaining mechanisms (e.g., retaining mechanism 9606). The cover 9604 encloses at least a portion of one or more valleys of the support stent 9600. In the illustrated embodiment, the cover 9604 encloses substantially all of each valley in the support stent 9600, including the interior space of the valley defined between adjacent strut members of the support stent (e.g., interior space 9630 between first strut member 9632 and adjacent second strut member 9634). The cover 9604 can form a complete enclosure or can be open at a top end, thus forming a basket-type cover. The cover 9604 can comprise a cloth covering and may defines a hollow interior into which additional padding or other material can be inserted. The cover 9604 can also be formed from silicone, foam, or some other biocompatible material. In the illustrated embodiment, the cover 9604 is formed by joining individual covers (e.g., covers 9610, 9612) together (e.g., be sewing the covers 9610, 9612 together). Furthermore, the cover 9604 includes pockets (e.g., pockets 9620, 9622) in the interior of the cover 9604 that are configured to receive and hold the cover 9604 to the main body 9602 of the support stent 9600. In one exemplary process, the cover 9604 can be fabricated by first cutting two V-shaped pieces that have an outline corresponding to the valleys of the support stent. Some additional material (e.g., about 1 mm) can be left around the edge of each piece. Two fractional-V-shaped pieces are also cut. The fractional-V-shaped pieces have the same shape as the V-shaped pieces but have less than the full height of the V-shaped pieces (e.g., only half of the height of the V-shaped pieces). The two fractional-V-shaped pieces are set on top of the V-shaped pieces, and all four pieces are sewn together on their lateral edges (the top of the pieces is left open). The resulting cover is then inverted so that the fractional-V-shaped pieces form an interior pocket into which a respective valley of the support stent 9600 can be inserted. Covers for the other valleys of the support stent 9600 can be formed in a similar fashion. The tops of the covers can then be sewn or otherwise connected together, thereby forming a complete cover 9604. As more fully explained above with respect to FIG. 87, wires or other support bands can be positioned between adjacent strut members of a valley at or near the adjacent peaks of the valley to provide a support for holding the cover 9604 in position. Desirably, the cover 9604 creates a larger surface area of the support stent 9600 that engages the native leaflets of the heart valve when the support stent is inserted. This larger surface area reduces the overall force experienced between the native valve leaflets and the support stent 9600, thus making the fit between the native valve leaflets and the support stent less traumatic to the native valve leaflets. In certain embodiments, additional padding (e.g., additional or thicker cloth, silicone, or foam) can be placed within the cover 9604 (e.g., at or near the nadir of the valleys of the support stent 9600).

FIG. 97 shows an embodiment of a support stent 9700 similar to support stent 9600 but with a cover 9704 that includes portions that extend below the bottom of the main body of the support stent 9700. In the illustrated embodiment, the cover 9704 has three portions that extend below the main body of the support stent, corresponding to the three native leaflets of an aortic valve. For example, the cover 9704 includes a portion 9720 formed over adjacent valleys of the support stent and also over the peak that is defined between the adjacent valleys. Furthermore, the portion 9720 is generally V-shaped and has a bottom end 9722 that extends below the bottom of the support stent 9700. In the illustrated embodiment, the portion 9720 further includes interior pockets 9710, 9712 into which adjacent valleys (e.g., valleys 9730, 9732) of the support stent can be inserted. The cover 9704 can be created in a manner similar to that described above for FIG. 96 but with pieces sized and shaped to form the portions that extend below the bottom of the main body of the support stent 9700. As with the embodiment of FIG. 96, the cover 9704 creates a larger surface area of the support stent 9700 that engages the native leaflets of the heart valve when the support stent is inserted. For example, the portions of the cover 9704 that extend below the main body help distribute the stress caused by the support stent more evenly, thus making the support stent less traumatic, and also help hold the support stent in its desired position. Additionally, the portions of the cover 9704 that are located near the native comissures of the native valve leaflets can provide a further barrier between the outflow and inflow side of the aortic valve, thereby helping to prevent paravalvular leakage. Additional padding (e.g., additional or thicker cloth, silicone, or foam) can be placed within the cover 9704 (e.g., at or near the nadir of the valleys of the support stent 9700 or at or near the bottom end 9722).

FIG. 98 shows an embodiment of a support stent 9800 similar to support stent 9700 but with a cover 9804 that includes portions that extend below the bottom of the main body of the support stent 9800. In the illustrated embodiment, the cover 9804 has three portions that extend below the main body of the support stent, corresponding to the three native leaflets of an aortic valve. For example, the cover 9804 includes a portion 9820 formed partially over adjacent valleys of the support stent 9800 and also partially over the peak that is defined between the adjacent valleys. As shown in FIG. 98, peaks of the support stent 9800 (such as peaks 9840, 9842) can be entirely enclosed by the cover except for the retaining mechanisms. The portion 9820 is generally V-shaped and has a bottom end 9822 that extends below the bottom of the support stent 9800. In the illustrated embodiment, the portion 9820 further includes interior pockets 9810, 9812 into which adjacent valleys (e.g., valleys 9830, 9833) of the support stent can be inserted. The cover 9804 can be created in a manner similar to that described above for FIG. 96 but with pieces sized and shaped to form the portions that extend below the bottom of the main body of the support stent 9800. As with the embodiment of FIG. 96, the cover 9804 creates a larger surface area of the support stent 9800 that engages the native leaflets of the heart valve when the support stent is inserted. For example, the portions of the cover 9804 that extend below the main body help distribute the stress caused by the support stent more evenly, thus making the support stent less traumatic, and also help hold the support stent in its desired position. Additionally, the portions of the cover 9804 that are located near the native comissures of the native valve leaflets can provide a further barrier between the outflow and inflow side of the aortic valve, thereby helping to prevent paravalvular leakage. Additional padding (e.g., additional or thicker cloth, silicone, or foam) can be placed within the cover 9804 (e.g., at or near the nadir of the valleys of the support stent 9800 or at or near the bottom end 9822).

Figure 108:
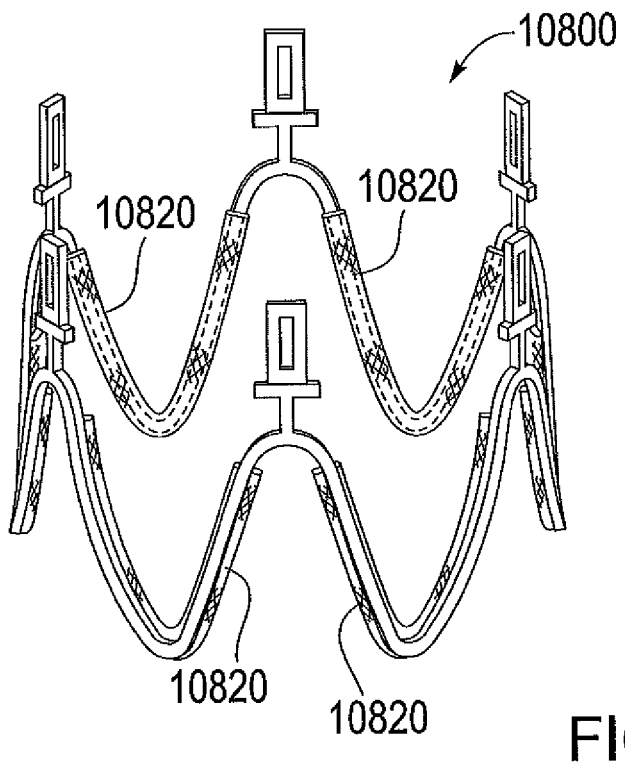
FIG. 108 is a perspective view of a support stent that includes covers configured to at least partially cover the inward-facing surface of the body of the support stent.

In other embodiments, one or more portions of the covering are positioned solely on the inward-facing surface of the support stent. For example, FIG. 108 shows an embodiment of a support stent 10800 that is similar to support stent 8800 shown in FIG. 88 but has covers (e.g., covers 10820) positioned only on the inward-facing surface of the support stent 8800. The covers can comprise cloth coverings and may define a hollow interior into which additional padding or other material can be inserted. The covers can alternatively comprise padding formed from silicone, foam, or some other biocompatible material. The covers 10820 can be attached to the support stent 10800 using a variety of mechanisms, including stitching around the support stent 10800, a biocompatible adhesive, or other attachment mechanism. Desirably, the covers 10820 are adapted to provide a softer surface that engages the native leaflets of the heart valve when the support stent is inserted. In certain embodiments, additional padding (e.g., additional or thicker cloth, silicone, or foam) can be placed at or near the nadir (or base) of the valleys of the support stent 10800.

Figure 155:
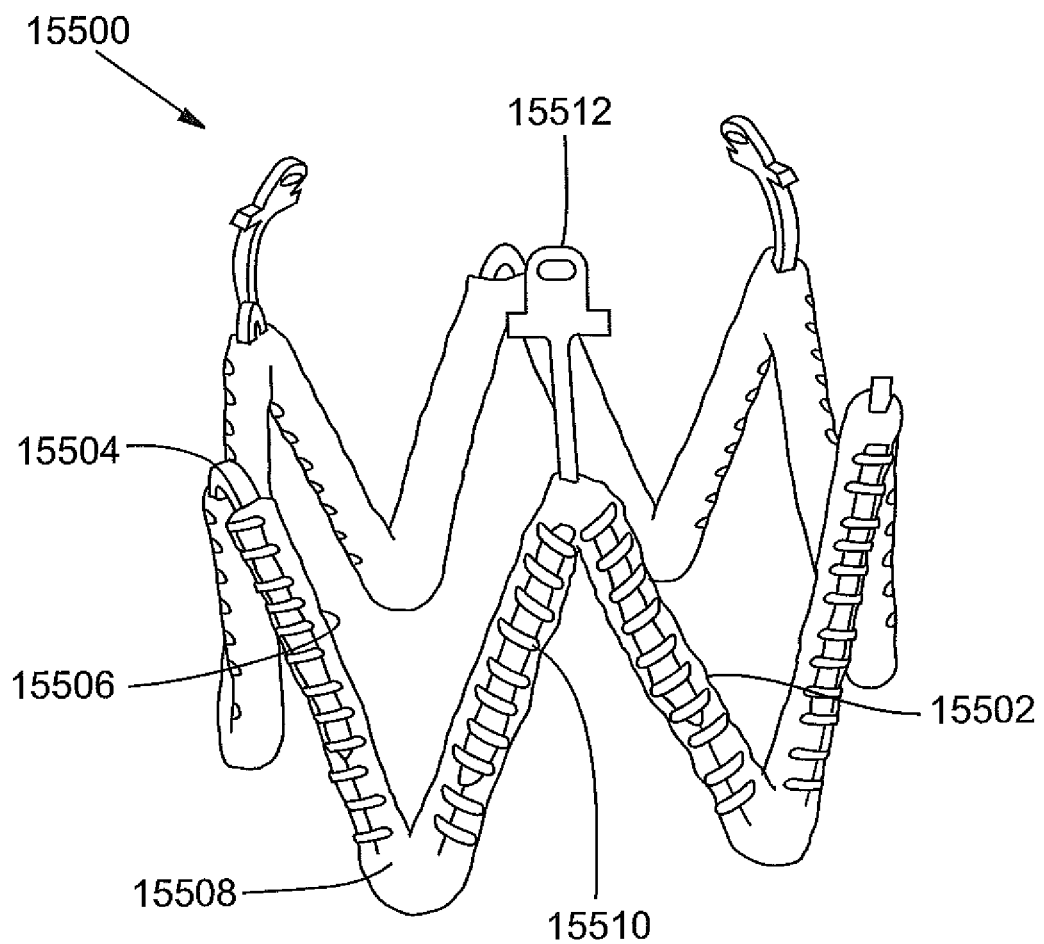
FIG. 155 is a perspective view of a support stent that is at least partially covered by a cover.

Furthermore, in certain embodiments, the covers can be configured to surround both the inward-facing and outward-facing surface of some portion of the support stent while other portions of the support stent have only their inward-facing surface covered. For example, the lower portion of the support stent body (e.g., the lower 2 mm of the support or approximately the lower 2 mm of the support stent) can be completely covered (including its inward- and outward-facing surface) whereas the remaining portion of the support stent body can be either uncovered or covered only on its inward-facing surface. For instance, FIG. 155 shows an embodiment of a support stent 15500 that has a cover 15502 that covers more of the inward-facing surface of the support stent body than the outward-facing surface. The cover 15502 can comprise a cloth covering. Further, the cover can define a hollow interior into which additional padding or other material can be inserted, or the cover can just cover a frame 15504 of the support stent 15500 as illustrated. The cover 15502 can alternatively comprise padding formed from silicone, foam, or some other biocompatible material. The cover 15502 can be attached to the support stent 15500 using a variety of mechanisms, including stitching around the frame 15504 of the support stent, a biocompatible adhesive, or other attachment mechanism. In the illustrated embodiment, and as seen at 15508, the cover 15502 covers both the inward-facing side and the outward-facing side of the frame 15504 at locations at or near the nadir (or base) of the valleys of the support stent 15500 (e.g., the cover 15502 can cover the lower 1-10 mm of the frame 15504). However, and as seen at 15506, the cover 15502 covers more of the inward-facing side of the frame 15504 than the outward-facing side. For example, the cover 15502 can cover substantially all of the inward-facing side of the frame 15504, as illustrated, or can cover any portion of the inward-facing side greater than the outward-facing side. Further, the cover 15502 can be formed so that is does not cover the eyelets of the frame 15504 (such as eyelet 15512). In the illustrated embodiment, the upper portion of the cover 15502 is held to the frame 15504 by stitching (e.g., stitching 15510). Desirably, the cover 15502 is adapted to provide a softer surface that engages the native leaflets of the heart valve when the support stent is inserted. In certain embodiments, additional padding (e.g., additional or thicker cloth, silicone, or foam) can be placed at or near the nadir (or base) of the valleys of the support stent 15500.

Figure 109:
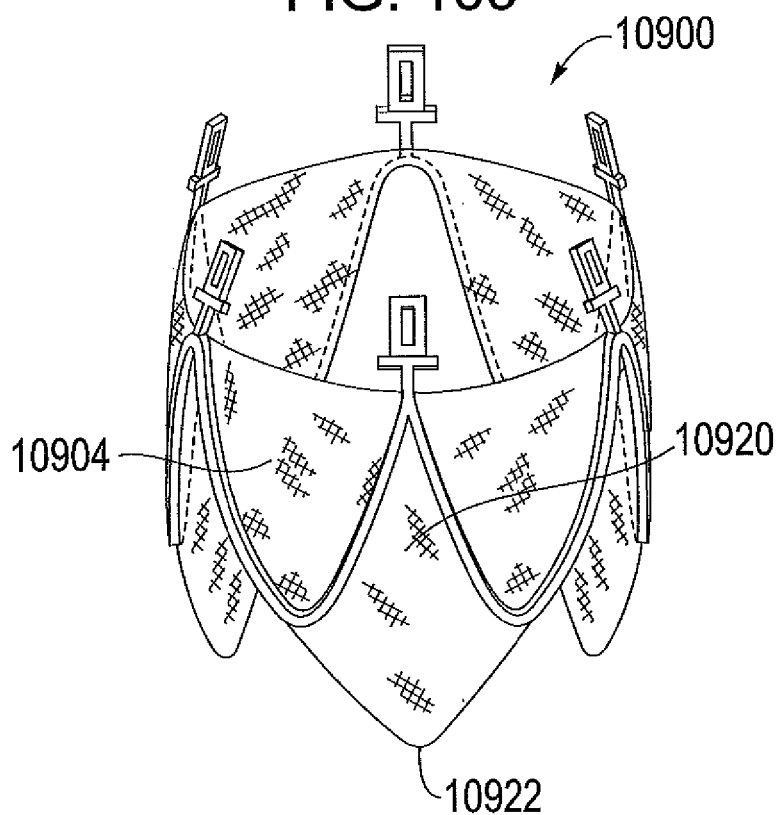
FIG. 109 is a perspective view of another support stent that includes covers configured to at least partially cover the inward-facing surface of the body of the support stent.

FIG. 109 shows another embodiment of a support stent 10900 similar to support stent 9700 shown in FIG. 97 but with a cover 10904 that is positioned only on the inward-facing surface of the support stent 10900. In the illustrated embodiment, the cover 10904 has three portions that extend below the main body of the support stent, corresponding to the three native leaflets of an aortic valve. For example, the cover 10904 includes a portion 10920 that spans across adjacent valleys of the support stent and also over the peak that is defined between the adjacent valleys. Furthermore, the portion 10920 is generally V-shaped and has a bottom end 10922 that extends below the bottom of the support stent 10900. The covers 10904 can be attached to the support stent 10900 using a variety of mechanisms, including stitching around the support stent 10900, a biocompatible adhesive, or other attachment mechanism. The cover 10904 creates a larger surface area of the support stent 10900 that engages the native leaflets of the heart valve when the support stent is inserted. Additional padding (e.g., additional or thicker cloth, silicone, or foam) can be at or near the nadir of the valleys of the support stent 10900 or at or near the bottom end 10922. Furthermore, in certain embodiments, the cover can be configured to surround both the inward-facing and outward-facing surface of some portion of the support stent while other portions of the support stent have only their inward-facing surface covered. For example, the lower portion of the support stent body (e.g., the lower 2 mm of the support stent or approximately the lower 2 mm of the support stent) can be completely covered (including its inward- and outward-facing surface) whereas the remaining portion of the support stent body can be either uncovered or covered only on its inward-facing surface.

Figure 101:
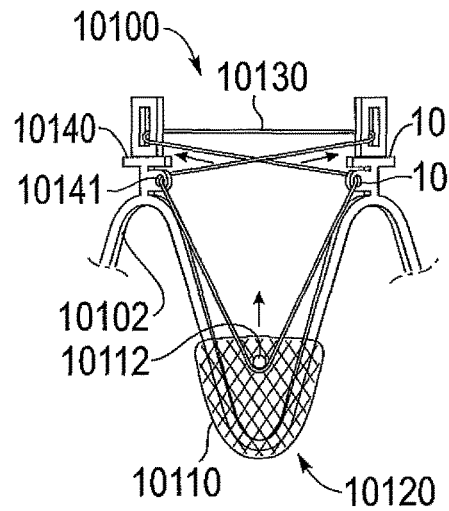
FIG. 101 is a front view of support stent portion that includes an embodiment of a mechanism for moving a cover into a final position on the support stent when the support stent is expanded.
Figure 102:
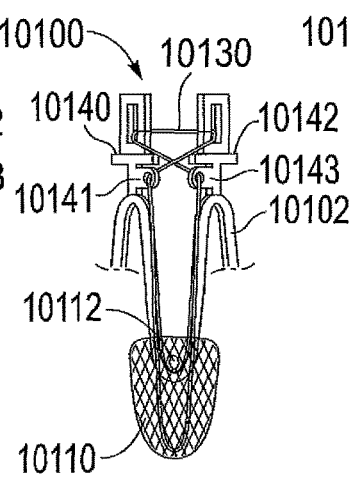
FIG. 102 is a side view of the support stent portion shown in FIG. 101 when the support stent is in a compressed state.
Figure 103:
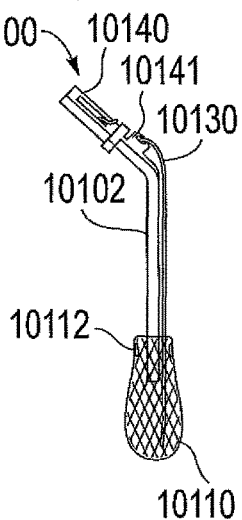
FIG. 103 is a side view of the support stent portion shown in FIG. 101 when the support stent is in a compressed state.

In certain embodiments, the cover for the support stent or for a portion of the support stent is configured to be moved into place upon expansion of the support stent. An exemplary mechanism 10100 for moving a cover for a valley of a support stent into place upon expansion of the support stent is illustrated in FIG. 101. The mechanism 10100 comprises a cover 10110 having a pin member 10112 that extends across the interior of the cover (e.g., from an inward-facing of the cover to an outward-facing side of the cover). The pin member 10112 is located above a respective valley 10120 of support stent 10102. The mechanism 10100 further includes a wire or thread 10130 that is strung between a first retaining mechanism head 10140 and a second adjacent retaining mechanism head 10142 in a criss-cross fashion. To enable the illustrated criss-cross threading, the first retaining mechanism head 10140 includes a first eyelet 10141 and the second retaining mechanism head 10142 includes a second eyelet 10143 through which the wire or thread 10130 is threaded. The wire or thread 10130 can alternatively be strung in a straight loop (without any criss-cross) between the retaining mechanisms heads 10140, 10142. The wire or thread 10130 is further configured so that it extends into the interior of the cover 10110 below the pin member 10112. FIG. 101 shows the mechanism 10100 as the support stent 10102 is expanding and the wire or thread 10130 engages the pin member 10112 and pulls the cover 10110 taut against the frame of the support stent. FIGS. 102 and 103 show the mechanism when the support stent 10102 is in a compressed state. In particular, FIG. 102 is a front view of the mechanism 10100 and FIG. 103 is a side view of the mechanism.

As seen in FIG. 102, portions of the cover 10110 can be disposed below the support stent 10102 when the support stent is in its compressed state. This allows the compressed support stent 10102 to be compressed more tightly in its compressed state. Furthermore, when the support stent 10102 is loaded into the interior of a catheter in a suitable delivery system (such as any of the delivery systems described above), the support stent 10102 can be loaded first followed by one or more covers (such as cover 10110). In other words, the support stent 10102 and its associated covers can be loaded serially.

FIGS. 104-107 show a variety of different designs that can be used to form any of the support stents described above. In general, the designs shown in FIGS. 104-107 can help increase the compressibility of the support stent, thereby allowing the support stent to be delivered in a delivery system having a desirably small diameter. The designs can also help increase the strength of the support stents. It should be noted that the designs FIGS. 104-107 show the stent designs as if they were unrolled and flattened. It should be understand, however, that in practice the stent designs would be annular in shape as described above with respect to FIGS. 1 and 2. Furthermore, for ease of illustration, the stent designs in FIGS. 104-107 omit the one or more retaining arms that may be formed at one or more of the peaks of the support stent and that allow for the support stent to be released coupled to one or more catheters of the delivery system.

Figure 104:
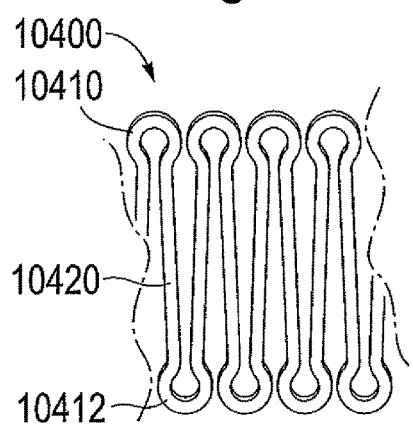
FIGS. 104-107 show a variety of different designs that can be used to form any of the disclosed support stents.

FIG. 104 shows a stent design 10400 in which one or more struts of the stent include ends having enlarged circular heads. For example, strut 10420 is integrally connected to a first enlarged circular head 10410 and an opposite second enlarged circular head 10412. The circular heads (e.g., circular heads 10410, 10412) allow for the struts of the stent to be more easily compressed without causing undue stress or fatigue at the peaks and valleys of the support stent. In the stent design 10400 illustrated in FIG. 104, each of the peaks and valleys has a uniform (or approximately uniform) height.

Figure 105:
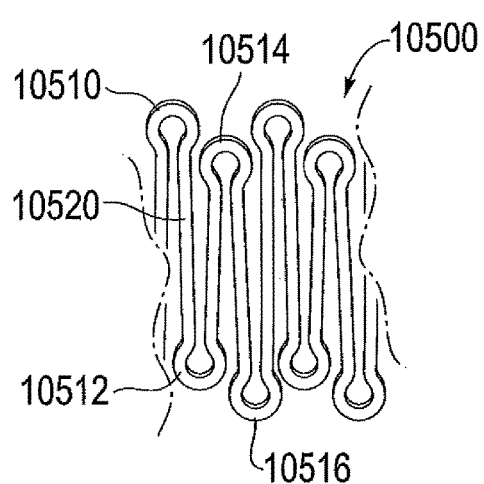

FIG. 105 shows a stent design 10500 similar to that shown in FIG. 104 except that adjacent circular heads of the support stent have different heights. For example, enlarged circular head 10510 at a first peak of the stent design 10500 has a different height than adjacent enlarged circular head 10514 at an adjacent second peak. Similarly, enlarged circular head 10512 at a first valley of the stent design 10500 has a different height than adjacent enlarged circular head 10516 at an adjacent valley. The heads can be said to have staggered heights. This design allows the struts of the design (e.g., strut 10520) to be further compressed because adjacent circular heads in the stent design 10500 do not contact each other at their widest points when the support stent is compressed.

Figure 106:
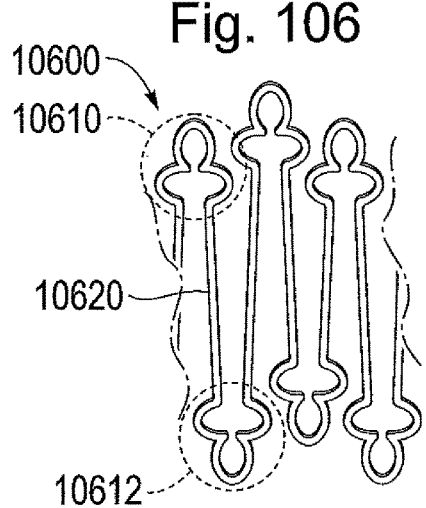

FIG. 106 shows a stent design 10600 that is similar to that shown in FIG. 105 except that the stent design includes clover-shaped heads at the ends of the respective struts. For example, strut 10620 is integrally connected to a first enlarged clover-shaped head 10610 and an opposite second enlarged clover-shaped head 10612. The clover-shaped heads (e.g., clover-shaped heads 10610, 10612) also allow for the struts of the stent to be more easily compressed without causing undue stress or fatigue at the peaks and valleys of the support stent. In the stent design 10600 illustrated in FIG. 106, the peaks and valleys have staggered heights as with stent design 10500 shown in FIG. 105.

Figure 107:
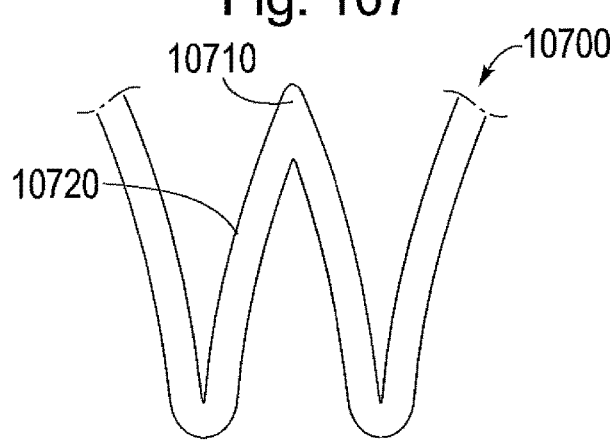

FIG. 107 shows a stent design 10700 in which one or more of the peaks or valleys has an arch-shape. For example, the stent design 10700 includes an arch-shaped peak 10710 (a gothic-arch-shaped peak in the illustrated design). The arch shapes of the one or more peaks allow for the struts of the stent (e.g., strut 10720) to be more easily compressed without causing undue stress or fatigue at the peaks and valleys of the support stent. In the stent design 10700 illustrated in FIG. 107, each of the peaks and valleys has a uniform (or approximately uniform) height. In other designs, the peaks and valleys have staggered heights as with stent design 10500 shown in FIG. 105.

Exemplary Embodiments of Support Stent Delivery Aids

Accurate delivery of a support stent to a patient's heart valve can sometimes be challenging. For example, in certain circumstances, the support stent may be positioned such that it surrounds some, but not all, of the native heart valve leaflets. Furthermore, the support stent may not be oriented correctly relative to the native heart valve leaflets. In such situations, the support stent may not properly secure the prosthetic heart valve to the native valve leaflets, resulting in an unstable prosthetic heart valve and undesirable paravalvular leakage. Accordingly, for certain embodiments of the disclosed technology, support stent delivery aids are desirable. The embodiments described in this section include systems and mechanisms that aid in the delivery of a support stent by stabilizing the native heart valve leaflets during the delivery process and/or increasing the visibility of the locations of the native leaflets. Furthermore, it should be understood that although the exemplary systems described in this section are described and illustrated as being transapically deployed, any of the systems can be transfemorally deployed. For example, any of the systems can be incorporated into any of the transfemoral support stent delivery systems described above (e.g., by incorporating one or more additional catheters into any of the systems) or as an independent delivery system that is deployed at least partially simultaneously with any of the support stent delivery systems.

Figure 110:
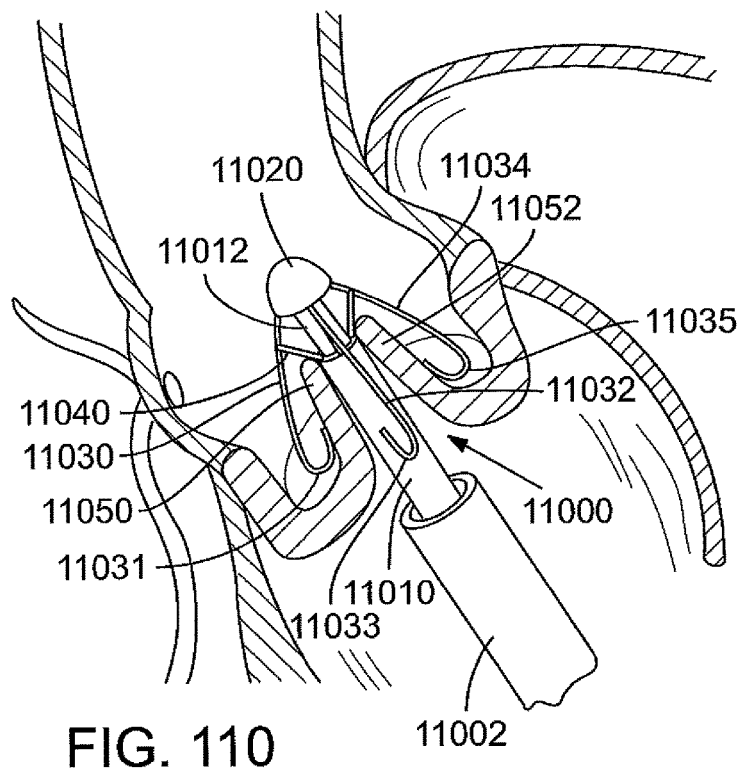
FIG. 110 is a cross-sectional view of a patient's heart illustrating a first exemplary embodiment of a leaflet stabilizing system.

FIG. 110 is a cross-sectional view through the left side of a patient's heart illustrating operation of an embodiment of a leaflet stabilizing system 11000. In particular, the leaflet stabilizing system 11000 comprises a main catheter 11002 having an elongated shaft whose distal end is open in the illustrated embodiment. The leaflet stabilizing system 11000 includes a leaflet stabilizer outer catheter 11010 positioned in the interior of the main catheter 11002 and a leaflet stabilizer inner catheter 11012 positioned in the interior of the leaflet stabilizer outer catheter 1110. The leaflet stabilizer outer catheter 11010 and the leaflet stabilizer inner catheter 11012 are configured to be axially and rotatably movable relative to one another as well as relative to the main catheter 11002 (via two or more lockable handles or levers located at or near the proximal end of the leaflet stabilizing system 11000 (not shown)). In the illustrated embodiment, an end cap 11020 is located at a distal end of the leaflet stabilizer inner catheter 11012. Stabilizer arms 11030, 11032, 11034 extend from a lower portion or edge of the end cap 11020 toward the proximal end of the system 11000. In other embodiments, the stabilizer arms 11030, 11032, 11034 are not coupled to the end cap 11020, but are coupled to the distal end of the leaflet stabilizer inner catheter 11012 or to another piece or component coupled to the distal end of the leaflet stabilizer inner catheter 11012. The stabilizer arms 11030, 11032, 11034 can be formed from a shape-memory alloy (e.g., Nitinol) and be shape set to extend outwardly from the shaft of the leaflet stabilizer inner catheter 11012 at an angle (e.g., an approximately 20-, 33-, or 45-degree angle, or any other angle relative to the shaft of the leaflet stabilizer inner catheter 1112). The stabilizer arms 11030, 11032, 11034 can further be coated or covered with a radiopaque substance in order to improve the visualization of the stabilizer arms during deployment. The stabilizer arms 11030, 11032, 11034 can further include respective loop portions (or hook portions) 11031, 11033, 11035 at their free ends (referred to as their distal ends). The stabilizer arms 11030, 11032, 11034 can further be pivotally coupled to the distal end of the leaflet stabilizer outer catheter 11010 via one or more pivot arms. A representative pivot arm 11040 is referenced in FIG. 110. The one or more pivot arms can be configured to pivot at one of or both of the distal end of the leaflet stabilizer outer catheter 11010 or a region of the respective stabilizer arm near the end cap. The pivot arms (such as pivot arm 11040) are positioned and configured to create an umbrella-arm mechanism that draws the stabilizer arms radially inward when the leaflet stabilizer outer catheter 11010 is moved axially toward the proximal end of the system 11000 relative to the leaflet stabilizer inner catheter 11012, and that extends the stabilizer arms radially outward when the leaflet stabilizer outer catheter 11010 is moved axially toward the distal end of the system (toward the end cap 11020) relative to the leaflet stabilizer inner catheter 11012.

In use, the main catheter 11002 of the leaflet stabilizer system 11000 is extended transapically through a puncture in the patient's left ventricle. During this time, the stabilizer arms 11030, 11032, 11034 can be pulled against the shaft of the leaflet stabilizer outer catheter 11010 and retracted inside the interior of the main catheter 11002. The distal end of the system 11000 can be positioned adjacent to the inflow side of the aortic valve. The leaflet stabilizer outer catheter 11010 and the leaflet stabilizer inner catheter 11012 can then be extended distally through the leaflets of the aortic valve (two of which are shown as leaflets 11050, 11052) until the stabilizer arms are advanced completely through the aortic valve. During this process, the stabilizer arms 11030, 11032, 11034 can remain pulled against the shaft of the leaflet stabilizer outer catheter 11014 (via the pivot arms and the relative retraction of the leaflet stabilizer outer catheter 11010). The stabilizer arms can then be urged radially outwardly by moving the leaflet stabilizer outer catheter 11010 distally relative to the leaflet stabilizer inner catheter 11012, thereby causing the pivot arms to push the stabilizer arms 11030, 11032, 11034 radially outward. The leaflet stabilizer outer catheter 11010 and the leaflet stabilizer inner catheter 11012 can then be retracted together until the loop portions 11031, 11033, 11035 engage the surface of the valve leaflets (including leaflets 11050, 11052).

To stabilize the leaflets into a position that allows for easier transfemoral placement of the support stent (using, for example, any of the transfemoral support stent delivery systems described above), the stabilizer arms 11030, 11032, 11034 can then be drawn radially inward by retracting the leaflet stabilizer outer catheter 11010 relative to the leaflet stabilizer inner catheter 11012. This causes the leaflets to be pulled together and urged toward the center of the leaflet stabilizer system, thereby suppressing the movement of the leaflets during the systolic and diastolic phase of the patient's heartbeat. In this stabilized position, a support stent can be more easily deployed so that the native valve leaflets are properly positioned in the interior of the support stent and aligned as desired. Furthermore, the stabilizer arms 11030, 11032, 11034 can function as guide rails that further aid in the deployment of a support stent. For example, the stabilizer arms 11030, 11032, 11034 can act as guide rails that engage the peaks of the support stent and cause the support stent to rotate into the correct position as the support stent is advanced through the aortic arch onto the surface of the outflow side of the aortic valve. In particular, as the support stent is advanced into position, the frame of the support stent will engage the stabilizer arms 11030, 11032, 11034 and rotate the support stent due to its sinusoidal shape until the stabilizer arms engage the support stent at the apices of respective peaks of the support stent. This action causes the support stent to rotate to a position that is aligned with the stabilizer arms 11030, 11032, 11034.

To further aid in the positioning of the support stent, the stabilizer arms 11030, 11032, 11034 can be rotated into a proper position within the aortic valve by rotating the system 11000 or by rotating the leaflet stabilizer outer catheter 11010 and the leaflet stabilizer inner catheter 11012. This rotation can occur when the support stent is deployed from a support stent delivery catheter (such as any of the support stent delivery catheters introduced above) and when the support stent is engaged with the stabilizer arms 11030, 11032, 11034. To allow for easier rotation, the prongs of the support stent delivery system that are used to retain and disengage the support stent can be manufactured to be flexible. By using the stabilizer system 11000 to aid in the rotation of the support stent on the outflow side of the aortic valve, rotation of the support stent is made easier. For example, when deployed, a transfemoral support stent delivery system (such as any of the transfemoral delivery systems described above) will include a number of arches and bends in its overall shape. The numerous arches and bends that are present when the transfemoral support stent delivery system is deployed can increase the frictional force within the system that must be overcome before rotation of the support stent can be achieved. By using the stabilizer system 11000 to affect rotation of the support stent, the support stent can be more easily rotated because the leaflet stabilizer system 11000 is typically a straight catheter that is much shorter in length than the transfemoral support stent delivery system.

Figure 111:
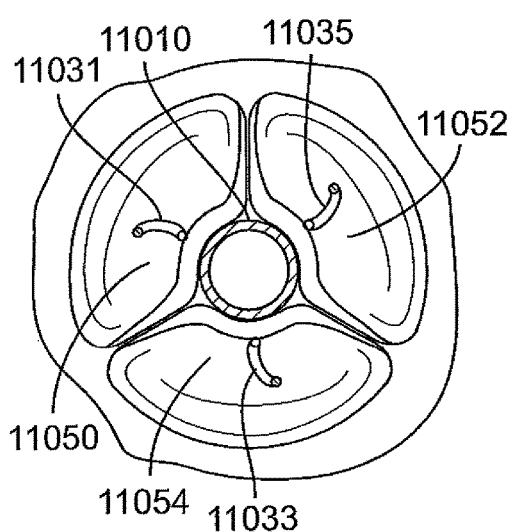
FIG. 111 is a cross-sectional top view of the leaflet stabilizing system of FIG. 110 showing a first orientation of leaflet stabilizer arms.

FIG. 111 is a cross-sectional top view of the patient's aortic valve in FIG. 110 with the stabilizer arms engaging the leaflets. In particular, FIG. 111 shows loop portions 11031, 11033, 11035 engaging leaflets 11050, 11052, 11054 near their ends. FIG. 111 further shows that the leaflets 11050, 11052, 11054 can be drawn together and held in a stabilized position that creates a large target area where the support stent can be deployed and surround the leaflets. Although the leaflets are shown in FIG. 111 as being held against the shaft of the leaflet stabilizer outer catheter 11014, the stabilizer arms 11030, 11032, 11034 can be operated so that the leaflets are opened wider, thereby allowing blood to more easily flow through the valve during support stent deployment while still stabilizing the leaflets.

Figure 112:
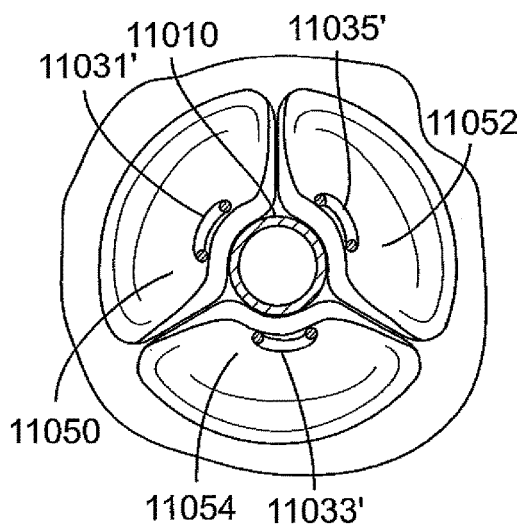
FIG. 112 is a cross-sectional top view of the leaflet stabilizing system of FIG. 110 showing a second orientation of leaflet stabilizer arms.

FIG. 112 is also cross-sectional top view of a patient's aortic valve similar to FIG. 111. In FIG. 112, however, the loop portions 11031', 11033', 11035' have an alternative orientation. In particular, the loop portions 11031', 11033', 11035' are configured to lie flat against the leaflets 11050, 11052, 11054, thereby creating a larger contact area with the leaflets. As in FIG. 111, FIG. 112 shows that the leaflets 11050, 11052, 11054 can be drawn together and held at a stabilized position that creates a large target area for the support stent.

Figure 113:
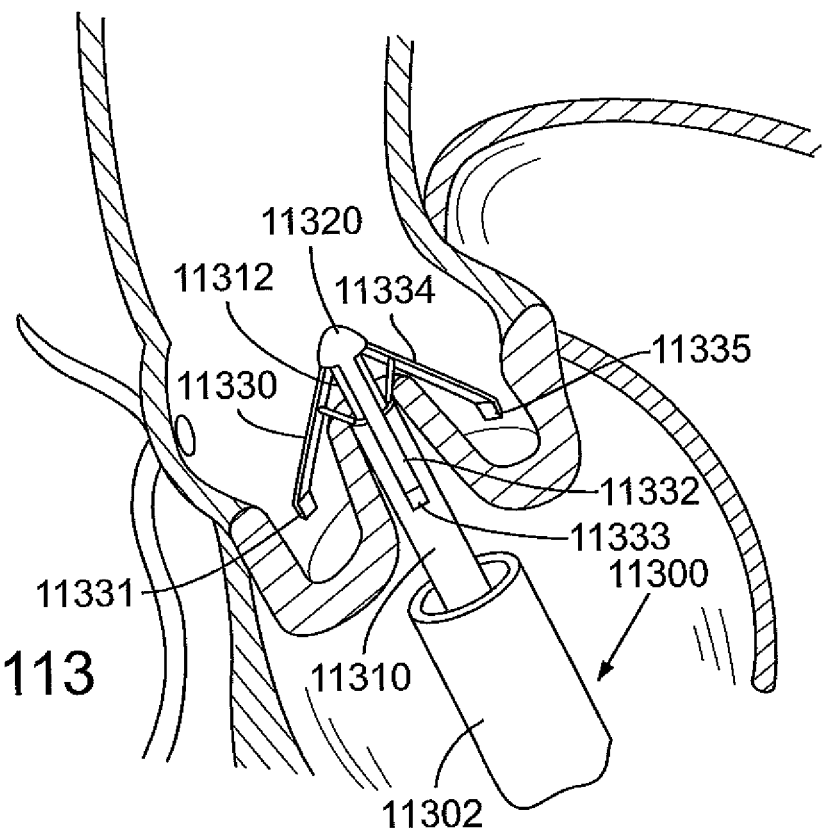
FIG. 113 is a cross-sectional view of a patient's heart illustrating a second exemplary embodiment of a leaflet stabilizing system.

FIG. 113 is a cross-sectional view through the left side of a patient's heart illustrating operation of another embodiment of a leaflet stabilizing system 11300. Leaflet stabilizing system 11300 is similar to leaflet stabilizing system 11000 and comprises a similar main catheter 11302, leaflet stabilizer outer catheter 11310, leaflet stabilizer inner catheter 11312, and end cap 11320. In FIG. 113, stabilizer arms 11330, 11332, 11334 are not formed from a wire, but instead include an upper surface and a lower surface. In the illustrated embodiment, the upper surface is flat or generally flat, though it can be curved or have some other surface contour. The stabilizer arms 11330, 11332, 11334 additionally include inwardly-angled lip portions 11331, 11333, 11335 at their distal ends that help the stabilizer arms securely engage the native leaflets of the heart and also helps the stabilizer arms 11330, 11332, 11334 be retracted into the main catheter 11302. In use, the leaflet stabilizing system 11300 operates in a fashion similar to the leaflet stabilizing system 11000. For example, the stabilizer arms 11330, 11332, 11334 can function as guide rails that further aid in the deployment of a support stent and can also be used to help rotate the support stent into its proper orientation when the support stent is deployed transfemorally. The shape of the stabilizer arms in FIGS. 110-113 should not be construed as limiting, however, as the stabilizer arms can have a wide variety of configurations. Furthermore, in certain embodiments, a ring or ring-shaped member is coupled to the distal ends of the stabilizer arms and can be configured so that the diameter of the ring decreases as the stabilizer arms are retracted toward the leaflet stabilizer outer catheter (e.g., using a telescoping configuration for the ring).

Figure 114:
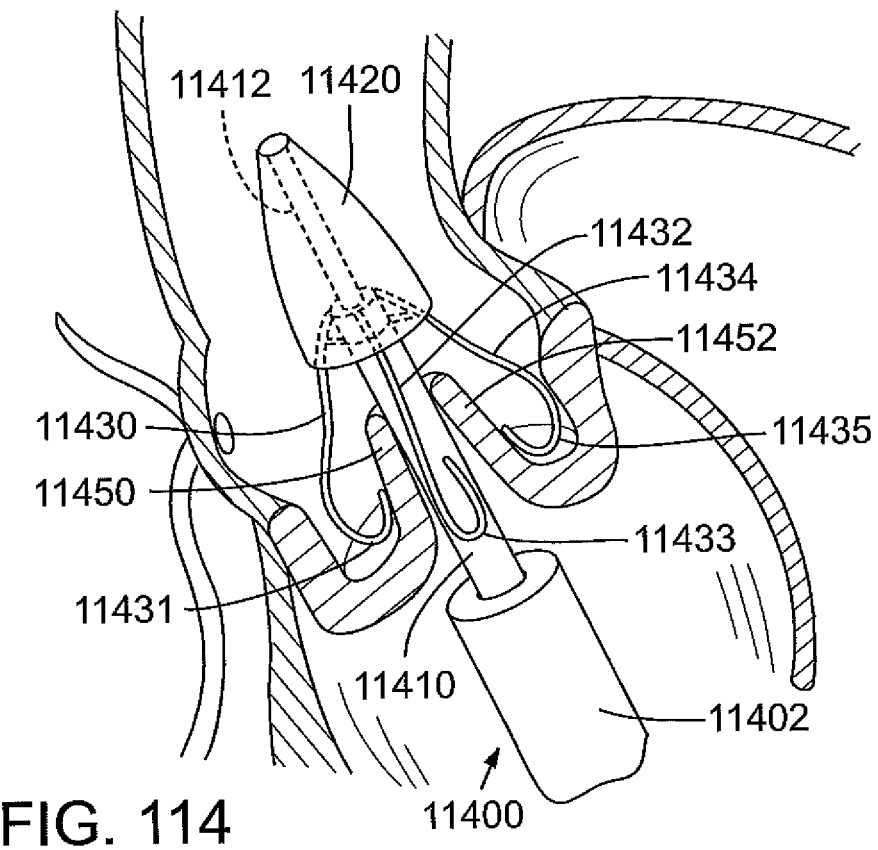
FIG. 114 is a cross-sectional view of a patient's heart illustrating a third exemplary embodiment of a leaflet stabilizing system.

FIG. 114 is a cross-sectional view through the left side of a patient's heart illustrating operation of another embodiment of a leaflet stabilizing system 11400 in which the stabilizing arms are retractable into a nose cone. The leaflet stabilizing system 11400 comprises a main catheter 11402 having an elongated shaft. The leaflet stabilizing system 11400 further includes a leaflet stabilizer outer catheter 11410 positioned in the interior of the main catheter 11402 and a leaflet stabilizer inner catheter 11412 positioned in the interior of the leaflet stabilizer outer catheter 11410. The leaflet stabilizer outer catheter 11410 and the leaflet stabilizer inner catheter 11412 are configured to be axially and rotatably movable relative to one another as well as relative to the main catheter 11402 (via two or more lockable handles or levers located at or near the proximal end of the leaflet stabilizing system 11400 (not shown)). In the illustrated embodiment, a nose cone 11420 is located at and coupled to a distal end of the leaflet stabilizer inner catheter 11412. In the illustrated embodiment, and as more fully shown in FIGS. 115-118, the nose cone 11420 is at least partially hollow. Stabilizer arms 11430, 11432, 11434 can be coupled to a distal end of the leaflet stabilizer outer catheter 11412 (or to an attachment or other component coupled to the leaflet stabilizer outer catheter 11412) and extend toward the proximal end of the system 11400. The stabilizer arms 11430, 11432, 11434 can be formed from a shape-memory alloy (e.g., Nitinol) and be shape set to extend outwardly from the shaft of the leaflet stabilizer outer catheter 11410 at a desired angle. The stabilizer arms 11430, 11432, 11434 can further include respective loop portions (or hook portions) 11431, 11433, 11435 at their distal ends, which can be oriented radially, circumferentially, or in any other orientation around the shaft of the leaflet stabilizer outer catheter 11410.

Figure 115:
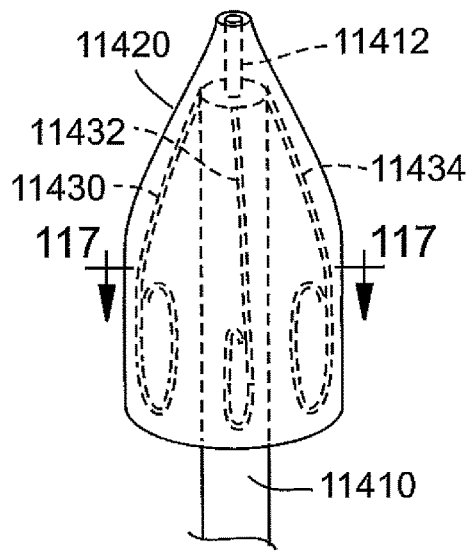
FIG. 115 is a perspective front view of the nose cone of the leaflet stabilizing system of FIG. 114 with the stabilizer arms in an undeployed state.
Figure 117:
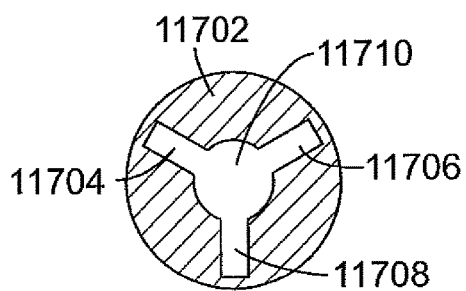
FIG. 117 is a cross-sectional top view of an exemplary embodiment of the nose cone of FIG. 115.

FIG. 115 is a front perspective view of the distal end of the leaflet stabilizing system 11400 with the stabilizer arms 11430, 11432, 11434 in an un-deployed, retracted state within the nose cone 11420. The nose cone 11420 can be hollow or can include shaped sleeves configured to receive the stabilizer arms 11430, 11432, 11434. FIG. 117, for example, is a cross-section view of a nose cone 11702 having shaped sleeves 11704, 11706, 11708 sized to receive stabilizer arms and a lumen 11710 sized to receive the leaflet stabilizer outer catheter 11410.

Figure 116:
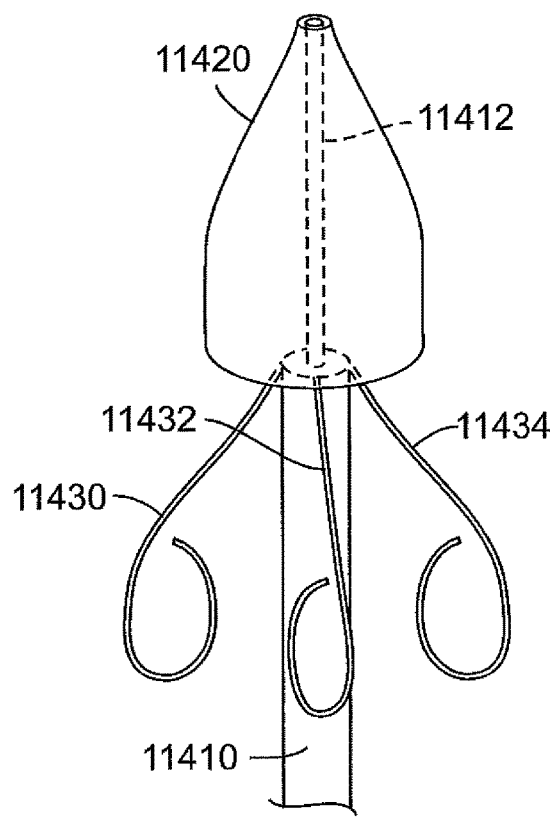
FIG. 116 is a perspective front view of the nose cone of the leaflet stabilizing system of FIG. 114 with the stabilizer arms in a deployed state.

FIG. 116 is a front perspective view of the distal end of the leaflet stabilizing system 11400 with the stabilizer arms 11430, 11432, 11434 in a deployed state. In FIG. 116, the leaflet stabilizer outer catheter 11410 is retracted proximally relative to the leaflet stabilizer inner catheter 11412, thereby releasing the stabilizer arms 11430, 11432, 11434 from the nose cone. In the illustrated embodiment, the stabilizer arms 11430, 11432, 11434 are shape set to extend radially outwardly from the leaflet stabilizer outer catheter 11412 at a desired angle.

Figure 118:
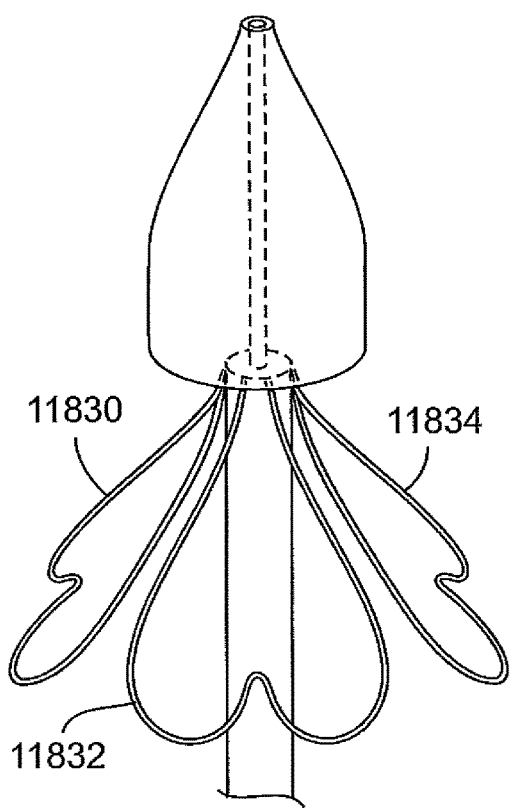
FIG. 118 is a perspective front view of the nose cone of the leaflet stabilizing system of FIG. 114 where the stabilizer arms have a leaf-shaped profile.

The shape of the stabilizer arms 11430, 11432, 11434 shown in FIGS. 114-116 should not be construed as limiting, as the stabilizer arms can have a variety of shapes and orientations. For example, the stabilizer arms could be oriented so that the loop portions are oriented circumferentially around the leaflet stabilizer outer catheter 11412 (similar to the stabilizer arms shown in FIG. 112). Alternatively, the distal ends of the stabilizer arms can form multiple loops, a clover-shape, or any other closed loop or open loop shape. For example, FIG. 118 is a front perspective view of the distal end of a leaflet stabilizing system 11800 with stabilizer arms 11830, 11832, 11834 in a deployed state. In the illustrated embodiment, the stabilizer arms 11830, 11832, 11834 have a generally leaf-shaped profile. Such wide, closed-loop shapes can allow the stabilizer arms 11830, 11832, 11834 to engage the native leaflets across a wider area, thereby creating greater control over the native leaflets.

In use, and as best shown in FIG. 114, the main catheter 11402 of the leaflet stabilizer system 11400 is extended transapically through a puncture in the patient's left ventricle. The stabilizer arms 11430, 11432, 11434 can be in their un-deployed state within the nose cone 11420. For example, the leaflet stabilizer outer catheter 11410 can be extended distally relative to the leaflet stabilizer inner catheter 11412 so that the stabilizer arms 11430, 11432, 11434 are enclosed within the nose cone 11420. The distal end of the system 11400 is then positioned adjacent to the inflow side of the aortic. The leaflet stabilizer outer catheter 11410, the leaflet stabilizer inner catheter 11412, and the nose cone 11420 can then be extended distally through the leaflets of the aortic valve (two of which are shown as leaflets 11450, 11452) until the nose cone 11420 is advanced completely through the aortic valve. The nose cone 11420 can then be extended distally relative to the leaflet stabilizer inner catheter 11412, thereby revealing the stabilizer arms and allowing them to extend radially outwardly. The leaflet stabilizer outer catheter 11410 and the leaflet stabilizer inner catheter 11412 can then be retracted together until the loop portions 11431, 11433, 11435 engage the outflow surface of the valve leaflets (including leaflets 11450, 11452). This causes the leaflets to be pulled together and urged toward the center of the leaflet stabilizing system, thereby suppressing the movement of the leaflets during the systolic and diastolic phase of the patient's heartbeat. As with the embodiment shown in FIG. 111, the illustrated leaflet stabilizer system 11400 creates a large target area where the support stent can be deployed and aligned with the leaflets. Furthermore, and as with the embodiment illustrated in FIG. 111, the stabilizer arms 11430, 11432, 11434 can function as guide rails that further aid in the deployment of a support stent and can also be used to help rotate the support stent into its proper orientation when the support stent is deployed transfemorally.

FIG. 119 is a front view of a further exemplary leaflet stabilizing system 11900. In particular, FIG. 119 shows the leaflet stabilizing system 11900 when stabilizing arms 11930, 11932, 11934 are in a un-deployed state. The delivery system 11900 comprises a main catheter 11902 (which can be a steerable guide catheter) having an elongated shaft. In the illustrated embodiment, the main catheter 11902 comprises three stabilizer arm lumens 11910, 11912, 11914 that extend longitudinally through the main catheter 11902 and to a distal end 11904. FIG. 120 is a top view of the leaflet stabilizing system 11900 and shows the relative arrangement of the stabilizer arm lumens 11910, 11912, 11914 on the distal end 11904 of the main catheter 11902 according to one embodiment. It should be understood that other arrangements are also possible. Furthermore, although the illustrated embodiment shows three stabilizer arm lumens 11910, 11912, 11914, more or fewer lumens can be included in other embodiments of the system 11900. Furthermore, although the distal end 11904 of the illustrated embodiment is not tapered, the distal end can be tapered. Furthermore, embodiments of the system 11900 can also include a tapered nose cone portion (e.g., the distal end can include multiple "flaps" forming a protective nose cone that can be urged apart when the stabilizer arms 11930, 11932, 11934 are deployed.

The stabilizer arms 11930, 11932, 11934 extend through the stabilizer arm lumens 11910, 11912, 11914 and through a proximal end 11906 of the system 11900. In the illustrated embodiment, the stabilizer arms 11930, 11932, 11934 are formed from a shape-memory alloy (e.g., Nitinol) and include a lumen. For example, the stabilizer arms 11930, 11932, 11934 can be formed from thin-bore shape-memory alloy tubing that can act as an inflation lumen.

As more fully discussed below with respect to FIGS. 120 and 121, the stabilizer arms 11930, 11932, 11934 can be shape set so that the stabilizer arms extend radially outwardly and loop backward in the proximal direction of the system 11900 when the stabilizer arms are deployed. In the illustrated embodiment, inflatable balloons 11931, 11933, 11935 are affixed to the distal ends of the stabilizing arms 11930, 11932, 11934. The inflatable balloons 11931, 11933, 11935 can be formed from a latex or other suitable biocompatible material. Additionally, the inflatable balloons 11931, 11933, 11935 can be at least partially coated with radiopaque markings that allow the balloons to be more easily viewed using suitable imaging techniques (e.g., fluoroscopy). In some embodiments, a radiopaque agent is used to inflate the balloons 11931, 11933, 11935, thereby making the balloons visible using suitable imaging techniques.

A proximal end of the main catheter 11902 includes a handle 11940 that is coupled to the stabilizer arms 11931, 11933, 11935 and allows for the stabilizer arms to be uniformly deployed from or retracted into the main catheter 11902. In other embodiments, the stabilizer arms can be individually controlled. In the illustrated embodiment, the handle 11940 further includes an inflation lumen 11942 which is fluidly coupled to the lumens of the stabilizing arms 11930, 11932, 11934. Thus, the balloons 11931, 11933, 11935 can be inflated and deflated through the use of the inflation lumen 11942. In other embodiments, the inflation lumen is located elsewhere on the system 11900. For example, the main catheter 11902 can include an inflation lumen that is fluidly coupled to the lumens of the stabilizing arms 11930, 11932, 11934. In one particular implementation, an inflation lumen located on the main catheter 11902 can be fluidly coupled to a chamber in the main catheter 11902 through which the stabilizing arms 11930, 11932, 11934 pass. The stabilizing arms 11930, 11932, 11934 can include inflation apertures bored into the sides of their bodies, thereby fluidly coupling the lumens of the stabilizing arms with the chamber and the inflation lumen.

Figure 121:
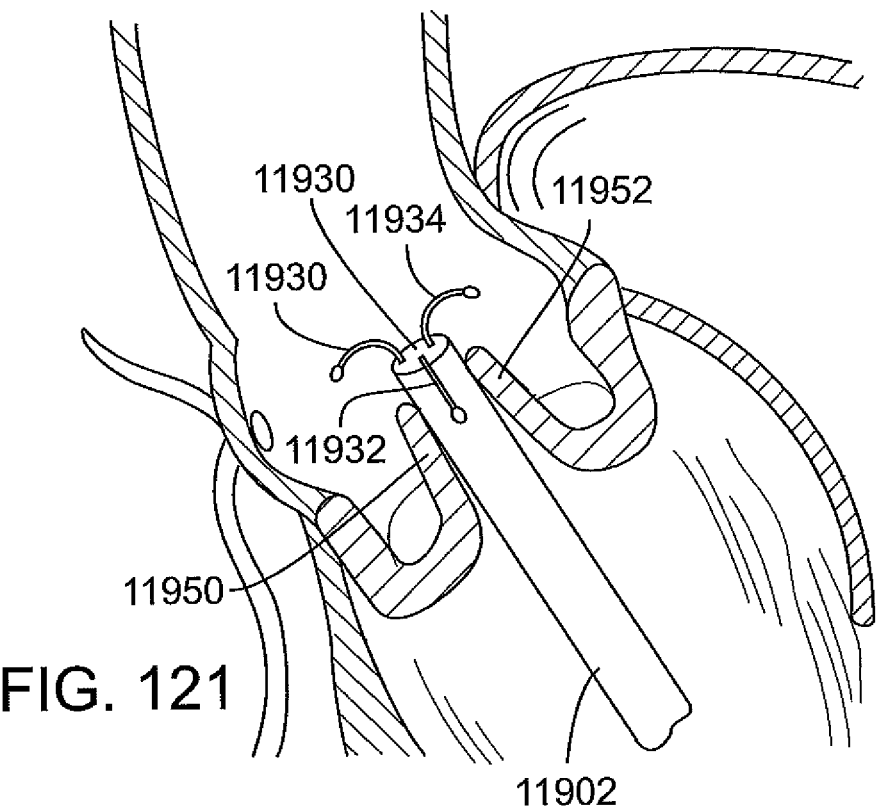
FIGS. 121-122 are cross-sectional views of a patient's heart illustrating how the leaflet stabilizing system of FIG. 119 can operate to stabilize the native valve leaflets.
Figure 122:
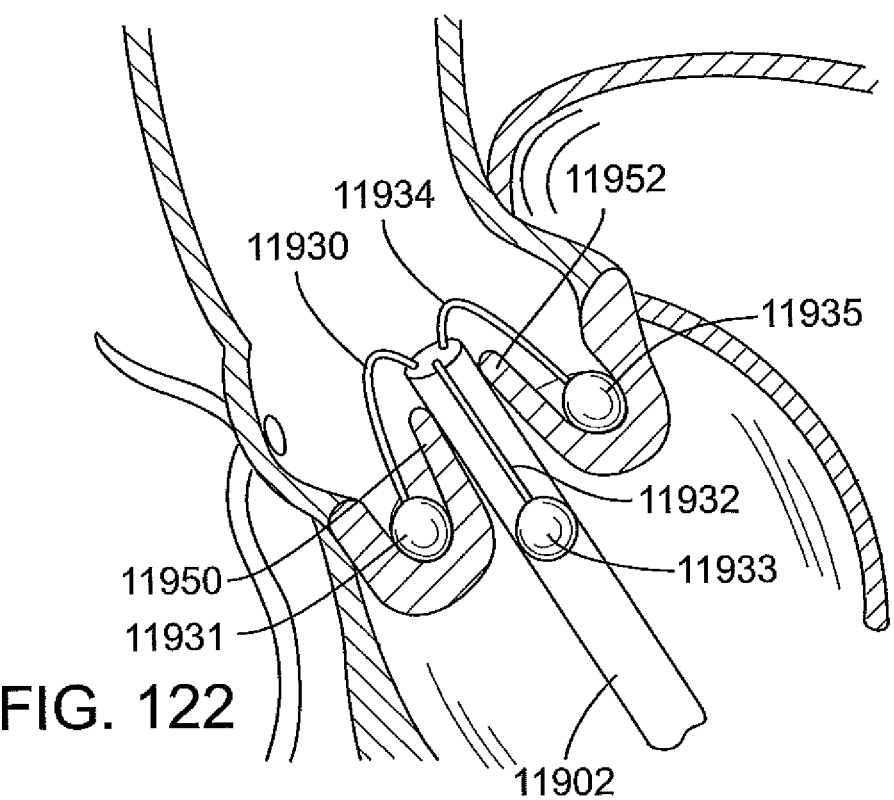

In use, and as best shown in FIGS. 121 and 122, the main catheter 11902 of the leaflet stabilizer system 11900 is extended transapically through a puncture in the patient's left ventricle. During this stage, the stabilizer arms 11930, 11932, 11934 can be in their un-deployed state within the main catheter 11902. The distal end 11904 of the main catheter can be advanced through the native leaflets of the aortic valve (two of which are shown as leaflets 11950, 11952) until the distal end is positioned on the outflow side of the aortic valve. The stabilizer arms 11930, 11932, 11934 can then be advanced out of the main catheter 11902 (e.g., by advancing the handle 11940 relative to the main catheter 11902). In the illustrated embodiment, the stabilizer arms are formed of a shape-memory allows that is shape set so that the stabilizer arms 11930, 11932, 11934 extend radially outward from the main catheter 11902 and loop back toward the surface of the outflow side of the aortic valve. The stabilizer arms 11930, 11932, 11934 can be advanced until the balloons 11931, 11933, 11935 engage the outflow surface of the valve leaflets (including leaflets 11950, 11952).

As shown in FIG. 122, the balloons 11931, 11933, 11935 are inflated by pumping a suitable fluid into the lumens of the stabilizer arms 11930, 11932, 11934 via the inflation lumen 11942. This causes the balloons 11931, 11933, 11935 to expand and push the leaflets together. As explained above, the fluid used to inflate the balloons 11931, 11933, 11935 can comprise a radiopaque agent, thereby increasing the visibility of the balloons through suitable imaging techniques and allowing the balloons to be more precisely positioned relative to the leaflets of the aortic valve. The balloons 11931, 11933, 11935 further operate to suppress the movement of the leaflets during the systolic and diastolic phase of the patient's heartbeat. As with the embodiment shown in FIG. 111, the illustrated leaflet stabilizer system 11900 creates a large target area where the support stent can be deployed and aligned with the leaflets. Furthermore, and as in FIG. 111, the stabilizer arms 11930, 11932, 11934 can function as guide rails that further aid in the deployment of a support stent and can also be used to help rotate the support stent into its proper orientation when the support stent is deployed transfemorally.

Figure 123:
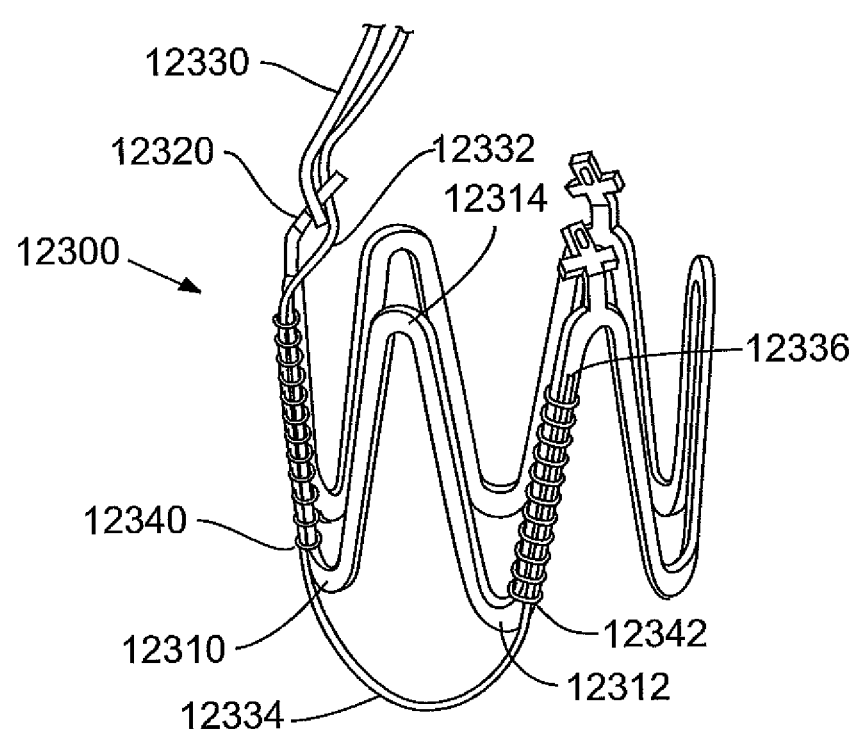
FIG. 123 is a perspective front view of a fifth exemplary embodiment of a leaflet stabilizing system.

FIG. 123 is a perspective view of a further embodiment of a support stent 12300 comprising a leaflet stabilizing mechanism. In the illustrated embodiment, the leaflet stabilizing mechanism is formed from a wire that extends between adjacent valleys of the support stent. In particular, the support stent 12300 shown in FIG. 123 includes a peak having a retaining arm 12320. As explained above, the retaining arm 12320 can be releasably coupled to a support stent delivery system that includes an outer prong 12330 and a release wire 12332, which is threaded through an aperture of the retaining arm when the retaining arm is bent through an aperture of the outer prong. Thus, the release wire 12332 secures the retaining arm 12320 to the outer prong 12330 until it is withdrawn (e.g., by a user at the proximal end of the support stent delivery system). It should be understood that only a single outer prong and release are illustrated in FIG. 123 for illustrative purposes only. In actual implementations, additional outer prongs and release wires can be included as part of the overall support stent delivery system (e.g., the support stent delivery system can include three outer prongs and three release wires releasably coupled to the support stent). In the illustrated embodiment, the release wire 12332 extends through sutures (including representative suture 12340) along a first frame member of the support stent and to a first valley 12310 of the support stent, and further extends across to a second adjacent valley 12312 and through sutures (including representative suture 12342) along a second adjacent frame member of the support stent. In this way, the release wire forms a loop 12334 that extends below the bottom edge of the support stent 12300 and that is located opposite of a respective peak 12314 of the support stent. The release wire 12332 can be formed from a variety of different materials, but in one embodiment is formed from a biocompatible metal or alloy. The release wire 12332 is desirably flexible enough to achieve the illustrated loop shape, but is also rigid enough to act as a stabilizer arm that engages and resists the movement of a native heart valve leaflet when the support stent 12300 is advanced into a position adjacent to the outflow side of the heart valve.

In use, for example, when the support stent 12300 is deployed from a support stent delivery system (such as any of the delivery systems described above) and advanced toward the outflow side of the aortic valve, the loop 12334 can engage a native heart valve leaflet. As the support stent 12300 is advanced, the loop 12334 can press against the leaflet and suppress its movement during the patient's heart beat. The loop 12334 can further be configured so that it is angled slightly inwardly, so that when the loop deforms, it deforms inwardly into the interior of the support stent 12300. Therefore, as the support stent 12300 is advanced into position, the loop 12334 can operate to engage and urge the native leaflet inwardly, while also preventing the leaflet from flapping open to the exterior of the support stent. Furthermore, the loop 12334 creates a wider area of contact against the native leaflets than the valleys of the support stent, making it more likely that as the loop 12334 engages the leaflet and urges it inwardly, the corresponding peaks and valleys of the support stent will be located radially outward of the leaflets, rather than straddling the native leaflet or being located radially inward of the native leaflets. Once the support stent 12300 is located in its desired position on the native valve, the release wire 12332 can be removed from the support stent (e.g., by an operator withdrawing the release wire at a proximal end of the support stent delivery system). This action removes the loop 12334, freeing the native leaflet it engaged, and releases the support stent from the delivery system. In some embodiments, the release wire 12332 is withdrawn in at least two stages. In a first stage, for example, the release wire 12332 can be withdrawn partially so that the loop 12334 is removed but the support stent 12300 remains coupled to the prong 12330. A prosthetic valve can then be positioned into the interior of the support stent and expanded. In a second stage, the release wire 12332 can be fully withdrawn, thereby releasing the support stent from the prong 12330.

For any of the leaflet stabilizing systems introduced above, it should be understood that the leaflet stabilizing arms can be configured to be individually controllable or controllable in different groupings. Further, any of the leaflet stabilizing arms can include relief cuts or small springs that allow the arms to achieve a desired flexibility. Additionally, the systems introduced above should not be construed as limiting, as other leaflet stabilizing systems or mechanisms can be used to aid in the delivery of a support stent. For example, a leaflet stabilizing system that is configured to extend a wire lasso or other closed loop from its distal end can be used. The wire lasso or loop can be shaped so that its diameter is large enough to surround at least a portion of the native valve leaflets when deployed. Once the wire lasso surrounds the native valve leaflets, the lasso can be partially retracted into the delivery system, thereby shrinking the size of the loop formed by the lasso and capturing the native valve leaflets into the loop. The delivery system can then be retracted partially or moved as appropriate in order to hold the native leaflets in a stabilized position while the support stent is delivered. In another embodiment, the support stent delivery system (e.g., a transfemoral support stent delivery system) is modified to include an inner catheter having a distal end attached to a disc or disc plunger. During delivery of the support stent, the disc can be advanced to engage the leaflets and constrict the leaflets during stent delivery. In still another embodiment, the support stent delivery system (e.g., a transfemoral support stent delivery system) is modified to include an inner catheter from which three leaflet stabilizing arms can be deployed. The leaflet stabilizing arms can have shapes similar to those described herein and can initially extend outwardly to a large radius within the aorta. Once advanced to engage the native heart valve leaflets, the leaflet stabilizing arms can be urged together (radially inwardly). This action can be performed, for example, by advancing a washer around the leaflet stabilizing arms or advancing a sheath or catheter around the arms. As a result of the leaflet stabilizing arms being drawn together, the leaflets are held in a stabilized position and the support stent can be delivered more reliably to a position around the leaflets. Furthermore, for the systems described above with respect to FIGS. 110-122, the leaflet stabilizing arms can also operate to expand the pinch to a diameter larger than its natural diameter. This expansion further helps the support stent capture all of the leaflets of the native heart valve. Expansion of the support stent can also be performed using a balloon catheter (e.g., delivered transapically or integrated into the support stent delivery system) that can be expanded within the support stent before it is delivered onto the leaflets. Additionally, the leaflet stabilizing arms of any of the embodiments described above can be replaced with a wire basket formed from three wires. In certain implementations, the wires are oriented to correspond to the locations of the commissures of the aortic valve. In use, the wire basket can be urged through the aortic valve by aligning the wires with the commissures. The native heart valve leaflets are thus at least partially enclosed within the distal portion of the wire basket. The support stent can then be delivered and advanced onto the wire basket whereby the wires act as guide rails for the support stent.

Exemplary Embodiments of Support Stent Securing Mechanisms

FIGS. 124-139 illustrate various embodiments for the support stent that can be used together with any of the delivery systems described herein. In particular, the illustrated embodiments include mechanisms or means for further securing the support stent to a prosthetic heart valve (e.g., to the frame of a prosthetic heart valve). The disclosed securing mechanisms can be particularly useful securing the prosthetic heart valve to the support stent and the native aortic valve during the diastolic phase of a patient's heart beat, which creates a greater pressure differential than the systolic phase. The features shown in support stents illustrated in FIGS. 124-139 can be used alone or in various combination and subcombinations with one another as appropriate. Additionally, any of the features of the support stents illustrated in FIGS. 124-139 can be used in combination with any of the features described in the other support stent embodiments disclosed herein. For example, any portion of the support stents described in this section can be covered with a cloth or other biocompatible material as described above in order to reduce any sharp or hard edges in the design. The support stents in FIGS. 124-139 can have a generally annular or toroidal body formed from a suitable shape-memory metal or alloy, such as spring steel, Elgiloy®, or Nitinol. Desirably, the material from which the support stents are fabricated allows the support stent to automatically expand to its functional size and shape when deployed but also allows the support stent to be radially compressed to a smaller profile for delivery through the patient's vasculature. In other embodiments, however, the stent is not self expanding.

FIG. 124 illustrates a support stent in which one or more peaks include an inward-facing projection. In particular, FIG. 124 is a perspective view of support stent 12400, which includes six peaks and six valleys. It should be noted, however, that more or fewer peaks and valleys can be included in the support stent depending on the design. In the illustrated embodiment, projections 12410, 12412, 12414, 12416, 12418, 12420 protrude inwardly from the apices of respective peaks 12430, 12432, 12434. 12436, 12438, 12440. More of fewer projections can be included in the support stent design depending on the design. The projections 12410, 12412, 12414, 12416, 12418, 12420 are configured to extend slightly upwardly from their base. Furthermore, in certain embodiments, the projections 12410, 12412, 12414, 12416, 12418, 12420 are configured to be bendable upon application of a sufficient force. The projections 12410, 12412, 12414, 12416, 12418, 12420 can be used to secure the support stent 12400 to the frame of a prosthetic valve and to help prevent the undesired movement of the prosthetic valve. In particular, the projections 12410, 12412, 12414, 12416, 12418, 12420 are used to resist movement of the transcatheter heart valve into the patient's left ventricle as a result of the pressure differential created during the filling of the ventricle during the diastole phase.

FIG. 125 is a perspective view of the support stent 12400 engaged with the frame of a prosthetic valve 12450. In particular, the projections 12410, 12412, 12414, 12416, 12418, 12420 are positioned so that they extend through the upper portion of diamond-shaped frame elements 12460, 12462, 12464, 12466, 12468, 12470. The slightly upward trajectory of the projections 12410, 12412, 12414, 12416, 12418, 12420 helps prevent the prosthetic valve 12450 from moving downward, thereby better securing the prosthetic valve within the interior of support stent 12400.

FIG. 126 is a side view of the support stent 12400 engaged with the frame of the prosthetic valve 12450 when the prosthetic valve is located in a patient's aortic valve. As explained above, the prosthetic valve 12450 can be expanded within the aortic valve and the interior of the support stent 12400, thereby frictionally securing the prosthetic valve 12450 into the valve by "pinching" the native valve leaflets (including leaflets 12460, 12462) between the interior of the support stent 12400 and the exterior of the frame of the prosthetic valve 12450. Projections 12410, 12412, 12414, 12416 can extend through apertures in the upper portion of the frame of the prosthetic valve 12450 upon expansion of the prosthetic valve 12450, thereby creating a further mechanical engagement that prevents the prosthetic valve 12450 from moving, or slipping, into the left ventricle. In certain embodiments, the expanded prosthetic valve 12450 is moved upward (in the direction of the outflow side of the valve) into the aortic valve while the support stent 12400 is held in place by a support stent delivery system (e.g., any of the support stent delivery systems described above). This action causes the top edge of the frame of the prosthetic valve 12450 to first bend the projections 12410, 12412, 12414, 12416 and then cause the projections to "snap" back to their original position once the top edge of the frame passes the projections, thereby securing the prosthetic valve to the support stent in the configuration shown in FIG. 126. In other words, the projections act as a "snap-fit" mechanism for securing the prosthetic valve to the support stent. In FIG. 126, the support stent 12400 is shown partially cut away so that only the back half of the support stent 12400 is illustrated. It should be understood, however, that the front half of the support stent 12400 also surrounds the prosthetic valve 12450 and further includes projections for holding the support stent 12400 in place.

The projections shown in FIG. 124 can be located at a variety of different positions on the support stent, including at or near the apices of the peaks of the support stent, near the middle of the support stent, or at or near the bottom (or nadirs) of the valleys of the support stent. For example, FIG. 127 illustrates a support stent 12700 similar to support stent 12400 in which three inward-facing, projections 12710, 12712, 12714 are located at the apices of the peaks of the support stent. In particular, the projections 12710, 12712, 12714 are located at the apices of the peaks of the support stent that do not also include a retaining arm 12720, 12722, 12724. As with support stent 12400, the projections 12710, 12712, 12714 are configured to extend slightly upwardly from their base. Furthermore, in certain embodiments, the projections 12710, 12712, 12714 are configured to be bendable upon application of a sufficient force. When engaged with a prosthetic valve (e.g., in a fashion similar to that shown in FIG. 125 or 126), the projections 12710, 12712, 12714 resist movement of the transcatheter heart valve into the patient's left ventricle as a result of the pressure differential created during the filling of the ventricle during the diastole phase.

FIG. 128 illustrates another embodiment of a portion of a support stent 12800 in which an inward-facing projection is formed along an edge of the support stent such that it can be bent into the cylindrical plane of the support stent. For example, in the embodiment illustrated in FIG. 128, a projection 12810 is located at a bottom edge of an apex of a peak 12812 of the support stent 12800. Furthermore, the projection 12810 is located on a peak that additionally includes a retaining arm 12820. As shown in FIG. 128, the retaining arm 12820 can be secured to a prong 12830 of a support stent delivery system (e.g., any of the support stent delivery systems described above) via a release wire 12832. In the illustrated embodiment, the release wire 12832 passes through sutures 12840, 12842 secured on a first side of the peak 12812 and through sutures 12844, 12846, 12848 secured on a second side of the peak 12812. The release wire 12832 thereby holds the first side of the peak 12812 next to the second side of the peak, effectively compressing the two peaks together. A distal end 12833 of the release wire 12832 is illustrated in FIG. 128. The proximal end (not shown) of the release wire 12832 can run through a catheter of the support stent delivery system to a proximal end of the delivery system, where it can be retracted by an operator. As illustrated in FIG. 128, the release wire 12832 also engages the projection 12810 on the inward-facing side of the support stent 12800, thereby holding the projection 12810 in the cylindrical (z-directional) plane of the support stent. When the release wire 12832 is removed (e.g., by an operator of the support stent delivery system retracting the release wire), the two peaks move apart into their deployed configuration and the projection 12810 moves inward and upward into the interior of the support stent, thereby forming a projection similar to that illustrated in FIG. 127. By allowing the projection 12810 to protrude inwardly only when the release wire is retracted, a prosthetic valve can be more easily placed and appropriately oriented within the support stent 12800 before the support stent is secured to the prosthetic valve using projections such as projection 12810. Once released, the projection 12810 can engage the prosthetic valve in a manner similar to that illustrated in FIGS. 125 and 126, thereby helping to prevent the unwanted movement of the prosthetic valve into the ventricle. Furthermore, it is to be understood that the configuration illustrated in FIG. 128 (or a similar configuration) can be repeated along one or more other peaks of the support stent.

FIGS. 129 and 130 illustrate another mechanism for further securing a support stent to a prosthetic valve, especially in order to prevent the prosthetic valve from moving or slipping into the patient's ventricle during the diastolic phase of the patient's heartbeat. FIG. 129 is a side view of a portion of an exemplary support stent 12900 in a flattened state. In particular, FIG. 129 illustrates a peak 12910 and two adjacent valleys 12920, 12922 of a support stent 12900. As illustrated by arrow 12930, the support stent has a first diameter (or width) at the valleys 12920, 12922 and, as illustrated by arrow 12932, a second diameter (or width) at the peak 12910. In the illustrated embodiment, the first diameter is greater than the second diameter. The increased diameter or width can be just at the base of the valleys 12920, 12922 or can increase gradually as the support stent transitions from the peak 12910 and the valleys 12920, 12922. As a result of the increased diameter (or width), the support stent 12900 is more resilient to bending at or near the valleys (or base) of the frame of the support stent 12900. In other words, the support stent 12900 is more rigid, or inflexible, toward the lower half of the support stent, and is more flexible toward the upper half of the support stent.

FIG. 130 is a schematic cross-sectional side view of a patient's aortic valve in which the support stent 12900 surrounds a prosthetic heart valve 12950 (shown in its entirety for illustrative purposes) and frictionally secures native heart valve leaflets 12960, 12962 between the support stent 12900 and the prosthetic heart valve. As illustrated in FIG. 130, when the prosthetic heart valve 12950 is expanded in the aortic valve and in the interior of the support stent 12900, the upper portion of the support stent flexes outwardly more than the lower portion of the support stent. Thus, in certain embodiments, the support stent 12900 has a smaller diameter at its bottom edge than it has at it upper edge (e.g., the support stent 12900 has a generally frustoconical shape when deployed into an expanded state in the native valve). In the illustrated embodiment, the prosthetic heart valve 12950 also has a smaller diameter at its bottom edge than it has at its upper edge (e.g., the prosthetic heart valve 12950 also has a generally frustoconical shape). In particular implementations, the prosthetic heart valve 12950 is specifically designed to function with a smaller diameter at its lower edge, although prosthetic heart valves that typically expand into valves having a constant diameter can also be used. As a result of the cone-like shape of the support stent 12900 and the prosthetic heart valve 12950, movement of the prosthetic heart valve into the patient's left ventricle is resisted during the diastolic phase of the patient's heart beat, thus creating a more secure placement of the prosthetic heart valve in the patient's aortic valve.

FIG. 131 illustrates a further embodiment of a support stent 13100 in which all or a portion of the interior surface of the support stent 13100 includes a roughened, corrugated, or other surface comprising multiple ridges configured to engage and resist relative movement of an opposing surface.

In particular, the support stent 13100 shown in FIG. 131 includes multiple upwardly angled ridges (or teeth) 13110, 13112 that engage native heart valve leaflets 13160, 13162 and press the leaflets against the exterior surface of prosthetic heart valve 13150. The native heart valve leaflets 13160, 13162 are typically thin leaflets, such that the leaflets are pressed into one or more of the apertures of the frame (e.g., diamond-shaped apertures of the frame) of the prosthetic heart valve 13150, thereby creating a secure, frictional engagement of the support stent to the prosthetic heart valve 13150. This frictional engagement helps resist movement of the prosthetic heart valve 13150 into the patient's left ventricle, especially during the diastolic phase of the patient's heart beat.

FIG. 132 is a perspective view illustrating a support stent 13200 in which one or more valleys of the support stent include longitudinal arms that extend downward and include a protrusion, flange, or platform designed to engage a bottom edge of the frame of a prosthetic heart valve. In particular, FIG. 132 is a perspective view of the support stent 13200, which includes six peaks and six valleys. It should be noted, however, that more or fewer peaks and valleys can be included in the support stent depending on the design. In the illustrated embodiment, longitudinal arms 13210, 13212, 13214 extend from the bottom edges of the nadirs of respective valleys 13220, 13222, 13224. In other embodiments, however, the longitudinal arms extend downward from the top edges of the apices of respective peaks of the support stent (e.g., from the top edge of every other peak of a six-peak support stent) or from the bottom edges of the apices of the respective peaks (e.g., from the bottom edge of every other peak of a six-peak support stent). In such embodiments, the longitudinal arms extend downward along the length of the exterior of the support stent to distal ends below the support stent at positions similar to the longitudinal arms 13210, 1312, 13214 of FIG. 132.

The longitudinal arms 13210, 13212, 13214 of the illustrated embodiment include inward-facing protrusions 13230, 13232, 13234 configured to engage and support the frame of a prosthetic heart valve. The protrusions 13230, 13232, 13234 can have a variety of shapes and configurations, and in the illustrated embodiment have a general spoon shape. Furthermore, the protrusion 13230, 13232, 13234 can be fabricated from the same material as the support stent 13200 or can be fabricated using a more rigid, or stronger, material than the support stent. In practice, the protrusions 13230, 13232, 13234 are used to secure the support stent 13200 to the frame of a prosthetic valve and to help prevent the undesired movement of the prosthetic valve. In particular, the longitudinal arms 13210, 13212, 13214 and protrusions 13230, 13232, 13234 operate to resist movement of the transcatheter heart valve into the patient's left ventricle as a result of the pressure differential created during the filling of the ventricle during the diastole phase.

FIG. 133 is a perspective view of the support stent 13200 engaged with a prosthetic heart valve 13250. In particular, the lower edge of the frame of the prosthetic heart valve 13250 is engaged with the protrusions 13230, 13232, 13234. As a result of the protrusions 13230, 13232, 13234, the prosthetic heart valve cannot migrate or move downwardly beyond the protrusions.

FIG. 134 is a bottom view of the support stent 13200 positioned in a native heart valve 13260. As illustrated, the protrusions 13230, 13232, 13234 and portions of the longitudinal arms 13210, 13212, 13214 extend through the aortic valve and into the inflow side of the aortic valve. For example, the longitudinal arms 13210, 13212, 13214 can be oriented so that they extend through the aortic valve along the commissures of the native heart valve leaflets and generally at locations near or adjacent to the cusps of the native heart valve leaflets. As noted above, the support stent 13200 and the protrusions 13230, 13232, 13234 resist movement of the prosthetic heart valve into the left ventricle.

The longitudinal arms 13210, 13212, 13214 can provide additional advantages to the support stent 13200. For example, when delivering the support stent 13200, the support stent can be initially positioned in the aortic valve so that the longitudinal arms 13210, 13212, 13214 extend through the aortic valve (e.g., by pushing the longitudinal arms through the valve during the delivery process). When the protrusions 13230, 13232, 13234 are located on the inflow side of the native aortic valve, the protrusions help secure the support stent 13200 to the aortic valve by preventing movement of the support stent upward into the aorta during the systolic phase of the patient's heartbeat. Furthermore, because the support stent is delivered so that the support stent surrounds the native heart valve leaflets, the peaks of the support stent act to prevent movement of the support stent 13200 into the left ventricle. Consequently, the support stent 13200 is self secured into the aortic valve. This configuration allows the support stent delivery system for the support stent 13200 to be removed from the patient's vasculature after delivery of the support stent. Consequently, the support stent can be delivered using a first delivery system (a transfemoral or transapical delivery system), and the prosthetic heart valve can be delivered using a second delivery system (a transfemoral or transapical delivery system) after the first delivery system is removed from the patient's vasculature.

The shape of the protrusions 13230, 13232, 13234 shown in FIG. 132 should not be construed as limiting in any way, as a number of other shapes or configurations are possible that result in a support stent that at least partially extends through the native heart valve, and thereby acts to secure itself to the native heart valve. For example, FIG. 135 is a perspective view of a support stent 13500 that includes longitudinal arms 13510, 13512, 13514 coupled to a generally circular member 13520. The circular member 13520 can include a flange (or one or more flange members) that are configured to engage the lower edge of the frame of a prosthetic heart valve and resist movement of the prosthetic heart valve relative to the support stent 13500. FIG. 136 is a perspective view of another embodiment of a support stent 13600 that includes longitudinal arms 13610, 13612, 13614 that end with respective hook portions 13620, 13622, 13624. Each of the hook portions 13620, 13622, 13624 includes two inwardly angled members that are configured to engage a bottom edge of a frame of a prosthetic heart valve and resist movement into the patient's ventricle.

FIG. 137 is a side view of another embodiment of a support stent 13700 flattened out to better illustrate its shape. In support stent 13700, one or more of the valleys of the support stent are configured to be extended valleys and to include a curved portion that forms an inward-facing protrusion that operates to engage a prosthetic heart valve and resist movement of the heart valve. In the illustrated embodiment, for example, the support stent 13700 includes nine peaks (three of which include retaining arms 13740, 13742, 13744) and nine valleys (three of which form extended portions 13710, 13712, 13714). The extended portions 13710, 13712, 13714 are valleys of the support stent 13700 that extend longitudinally further than the adjacent valleys. The extended portions 13710, 13712, 13714 further include curved end portions 13720, 13722, 13724 that are configured to curve inwardly (e.g., toward the center of the support stent) when the support stent 13700 is in its normal annular or toroidal configuration. The curved end portions 13720, 13722, 13724 are configured to function similar to the protrusions 13230, 13232, 13234 described above and engage and resist downward movement of a prosthetic heart valve that is frictionally secured to the support stent 13700. Furthermore, the extended portions 13710, 13712, 13714 are configured so that they can extend through the aortic valve at the commissures of the native heart valve leaflets and into the inflow side of the aortic side. For example, the extended portions 13710, 13712, 13714 can be positioned at locations near or adjacent to the cusps of the native heart valve leaflets. A prosthetic heart valve can then be expanded into the interior of the support stent such that the prosthetic valve is adjacent to or engages the curved end portions 13720, 13722, 13724.

When delivering the support stent 13700, the extended portions 13710, 13712, 13714 can be held together in a central location until the main body of the support stent is properly oriented and positioned. The extended portions 13710, 13712, 13714 can then be released such that they extend downwardly into their desired positions. FIGS. 138 and 139 illustrate exemplary support stent delivery systems 13800, 13900 for delivering the support stent 13700 in this manner. For instance, support stent delivery system 13800 includes a support stent delivery outer catheter 13810 having outer prongs 13812, 13814, 13816 that are releaseably coupled to retaining arms 13740, 13742, 13744 via retaining wires 13813, 13815 (not visible), 13817, which can be withdrawn from the retaining arms in order to release the support stent. Also shown in FIG. 138 is an inner catheter 13820 having an at least partially hollow nose cone 13822 in which the ends of extended portions 13710, 13712 (not visible), 13714 are positioned. The nose cone 13822 is configured to hold the extended portions 13710, 13712, 13714 together within the nose cone. In use, the support stent delivery system 13800 can be used to deliver the support stent 13700 transfemorally. The nose cone 13822 can be advanced through the aortic valve so that the main body portion of the support stent 13700 can be positioned adjacent to the outflow side of the aortic valve and in an orientation that surrounds the native valve leaflets. Once the main body of the support stent 13700 is properly positioned, the inner catheter 13820 can be advanced distally relative to the support stent outer catheter 13810, thereby causing the extended portions 13710, 13712, 13714 to be released from the nose cone and to extend into their natural state (e.g., to extend downwardly from the support stent 13700). In their deployed configuration, the extended portions 13710, 13712, 13714 can extend through the aortic valve through the commissures between the native valve leaflets and at locations at or near the cusps of the native valve leaflets. A prosthetic heart valve can then be expanded into the native heart halve and can be frictionally secured to the support stent 13700 as described above.

FIG. 139 shows another embodiment of a support stent delivery system 13900 that is similar to the support stent delivery system 13800 but which uses a retaining wire or retaining catheter mechanism to release the extended portions 13710, 13712 (not visible), 13714 of the support stent 13700. In particular, the support stent delivery system 13900 includes an inner catheter 13920 through which a release wire or release rod 13922 extended. Sutures (such as suture 13930) are located at or near the distal end of the release wire or release rod 13922 and are used to connect the release wire or release rod 13922 to respective extended portions 13710, 13712, 13714. Consequently, the extended portions 13710, 13712, 13714 are held to the release wire or release rod 13922. To release the extended portions 13710, 13712, 13714, the release wire or release rod 13922 can be retracted into the inner catheter 13920, thereby removing the release wire or release rod 13922 from the sutures and allowing the extended portions to expand into their natural state.

Any of the embodiments shown in FIGS. 124-137 can also be implemented as a two-part design in which a support stent not having inward-facing projections, extension portions, a specialized interior surface, or a varied diameter or thickness is coupled to a secondary frame that includes such features. For example, a secondary frame comprising projections, such as any of the projections described above or illustrated in FIGS. 124-128, can be implemented. The secondary frame can be an expandable frame and can further include a mechanism for securing itself to the interior of the original support stent (e.g., using outward-facing projections, extension portions with outward-facing projections, retaining arms, or other such mechanisms). In use, the original support stent can be delivered to a position adjacent to or near the outflow side of a patient's aortic valve. The secondary frame can then be delivered and expanded into the interior of the support stent, thereby securing itself to the support stent and forming a modified two-part support stent that includes one or more of the features introduced above for further securing the support stent to the prosthetic heart valve. A prosthetic heart valve can then be delivered into the interior of the two-part support stent and expanded such that it frictionally engages the native heart valve leaflets against the interior of the secondary frame and is further secured via the one or more additional mechanisms (e.g., inward-facing projections, extension portions having inward-facing projections, a specialized interior surface, or a varied diameter or thickness).

Further Support Stent Embodiments for Other Valve Configurations

The above embodiments are shown as being used in conjunction with a prosthetic heart valve having a generally constant diameter. It should be understood, however, that any of the disclosed embodiments can be used in connection with prosthetic heart valves having other shapes. Furthermore, and as more fully discussed below, the shape of the prosthetic heart valve can affect the shape and configuration of the support stent.

Figure 140:
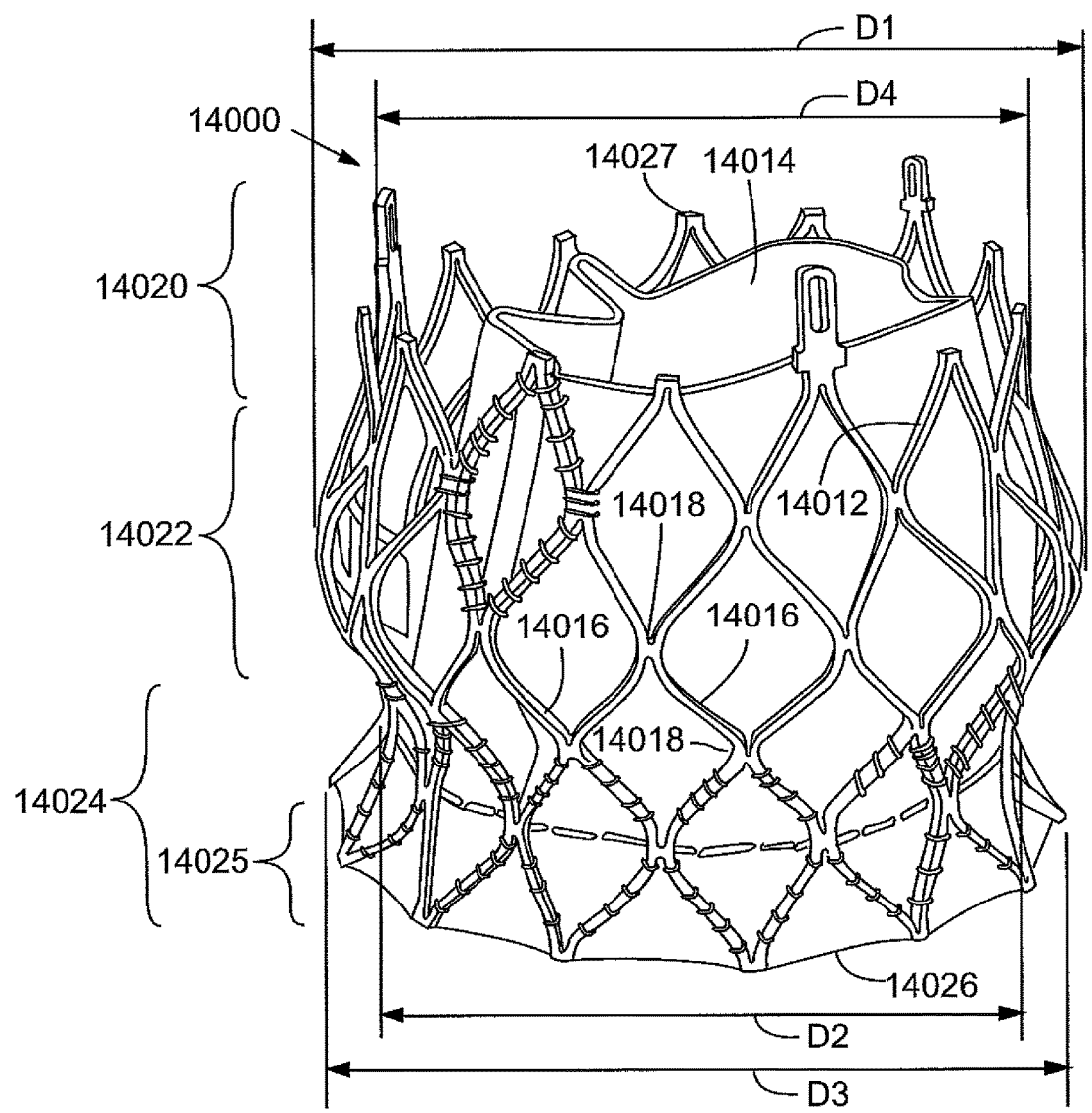
FIG. 140 is a perspective view of an exemplary prosthetic heart valve having an intermediate section with a greater diameter than other portions of the heart valve.

For example, FIG. 140 illustrates a prosthetic heart valve 14000 that can be used with any of the support stents described above. In particular, FIG. 140 is a perspective view of a prosthetic aortic heart valve 14010 that includes an expandable frame member, or stent, 14012 that supports a flexible prosthetic leaflet section 14014. The valve 14000 is radially compressible to a compressed state for delivery through the vasculature of a body to a deployment site and expandable to its functional size shown in FIG. 140 at the deployment site. In certain embodiments, the valve 14000 is self-expanding; that is, the valve can radially expand to its functional size when advanced from the distal end of a delivery system. In other embodiments, the valve can be a balloon-expandable valve that can be adapted to be mounted in a compressed state on the balloon of a delivery catheter. The illustrated valve 14000 is adapted to be deployed in the native aortic annulus, although it also can be used to replace the other native valves of the heart. Moreover, the valve 14000 can be adapted to replace other valves within the body, such a venous valve.

The frame 14012 can be formed from a plurality of longitudinally extending, generally sinusoidal shaped frame members, or struts, 14016. The struts 14016 are formed with alternating bends and are integrally joined (or otherwise secured to each other) at nodes 14018 formed from the vertices of adjacent bends so as to form a mesh structure. The struts 14016 can be made of a suitable shape memory material, such as the nickel titanium alloy known as Nitinol, that allows the valve to be compressed to a reduced diameter for delivery in a delivery system and then causes the valve to expand to its functional size inside the patient's body when deployed from the delivery system.

The frame 14012 has an inflow end 14026 and an outflow end 14027. The mesh structure formed by struts 14016 comprises a generally cylindrical "upper" or outflow end portion 14020, an outwardly bowed or distended intermediate section 14022, and an inwardly bowed "lower" or inflow end portion 14024. The intermediate section 14022 desirably is sized and shaped to extend into the Valsalva sinuses in the root of the aorta to assist in anchoring the valve in place once implanted. As shown, the mesh structure desirably has a curved shape along its entire length that gradually increases in diameter from the outflow end portion 14020 to the intermediate section 14022, then gradually decreases in diameter from the intermediate section 14022 to a location on the inflow end portion 14024, and then gradually increases in diameter to form a flared portion 14025 terminating at the inflow end 14026. The inflow end portion 14024 can therefore be said to have an hourglass shape below the outwardly bowed intermediate section 14022. When the valve is in its expanded state, the intermediate section 14022 has a diameter $D_1$, the inflow end portion 14024 has a minimum diameter $D_2$, the inflow end 14026 has a diameter $D_3$, and the outflow end portion 14020 has a diameter $D_4$, where $D_2$ is less than $D_1$ and $D_3$ and (optionally) $D_4$. In addition, $D_1$ and $D_3$ desirably are greater than the diameter than the native annulus in which the valve is to be implanted. In this manner, the overall shape of the stent 14012 assists in retaining the valve at the implantation site. Further embodiments and details of the support stent 14000 are described in U.S. Patent Application Publication No. 2010/0049313 (U.S. application Ser. No. 12/429,040), which is hereby incorporated herein by reference.

FIGS. 141-148 illustrate various embodiments for a support stent that can be used together with any of the delivery systems described herein and that can be used with the prosthetic heart valve 14000 or other similar prosthetic heart valves. In particular, the embodiments illustrated in FIGS. 141-144 illustrate embodiments in which the frame of the support stent has a particular configuration or shape designed to better function with and complement a corresponding prosthetic heart valve. Further, the embodiments illustrated in FIGS. 145-148 illustrate embodiments in which the frame of the support stent includes mechanisms for engaging and securing (or retaining) the support stent to the prosthetic heart valve. The securing mechanisms shown in FIGS. 145-148 can be particularly useful in securing the prosthetic heart valve to the support stent and the native aortic valve during the diastolic phase of a patient's heart beat, which creates a greater pressure differential than the systolic phase. It should be understood that any of the mechanisms introduced elsewhere in this disclosure for securing the support stent to the prosthetic valve (e.g., any of the mechanisms shown in FIGS. 124-139) can be used in various combinations and subcombinations with embodiments shown in FIGS. 141-148 and vice versa. Furthermore, any portion of the support stent can be covered with a cloth or other biocompatible material as described above in order to reduce any sharp or hard edges in the design. As with the other support stents described herein, the support stents in FIGS. 141-148 can have a generally annular or toroidal body formed from a suitable shape-memory metal or alloy, such as spring steel, Elgiloy®, or Nitinol. Desirably, the material from which the support stents are fabricated allows the support stent to automatically expand to its functional size and shape when deployed but also allows the support stent to be radially compressed to a smaller profile for delivery through the patient's vasculature. In other embodiments, however, the stent is not self expanding.

Figure 141:
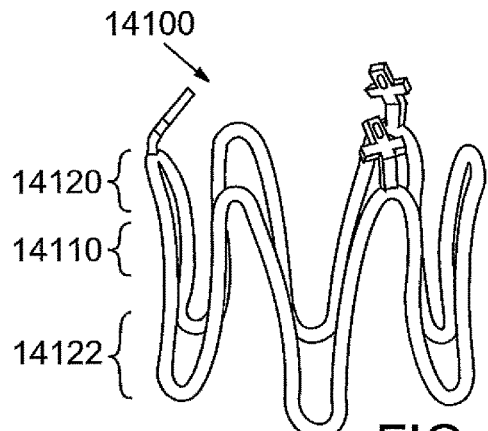
FIG. 141 is a perspective view of an embodiment of a support stent having a generally hourglass-shaped frame.

FIG. 141 illustrates a support stent 14100 in which the frame of the support stent is shape set into an hourglass shape. In particular, FIG. 141 is a perspective view of an hourglass-shaped support stent 14100 that includes six peaks and six valleys. It should be noted, however, that more or fewer peaks and valleys can be included in the support stent depending on the design. The hourglass shape of support stent 14100 means that the diameter of the support stent at a central or middle portion 14110 is less than the diameter of the support stent at a top portion 14120 or bottom portion 14122. When a prosthetic valve such as prosthetic valve 14000 is deployed within the support stent 14100 (or when a prosthetic valve having a constant or substantially constant diameter is deployed within the support stent), the support stent 14100 imparts more frictional force at the center or middle portion 14110 of the support stent than other portions, thereby creating an area of increased radial force. Because the prosthetic valve 14000 includes an intermediate portion 14022 with a large diameter, the frictional force can be relatively large at this portion of the prosthetic valve, creating a more secure fit between the support stent, the prosthetic valve, and the interposed native valve leaflets.

Figure 142:
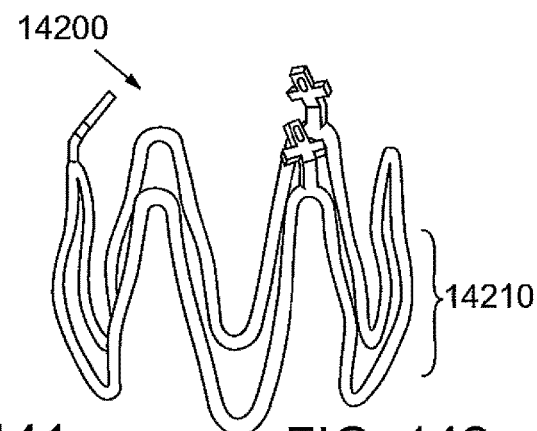
FIG. 142 is a perspective view of an embodiment of a support stent having a frame with an outwardly bowed portion.

FIG. 142 illustrates a support stent 14200 in which the frame of the support stent is shape set into an at least partially outwardly bowed (or inverted hourglass) shape. In particular, FIG. 142 is a perspective view of an at least partially outwardly bowed support stent 14200 that includes six peaks and six valleys. It should be noted, however, that more or fewer peaks and valleys can be included in the support stent depending on the design. In particular implementations, the shape is configured to at least partially complement the shape of the prosthetic heart valve. For instance, an outwardly bowed portion 14210 of the support stent 14200 can be configured to complement the intermediate section 14022 of the prosthetic heart valve 14000.

Figure 143:
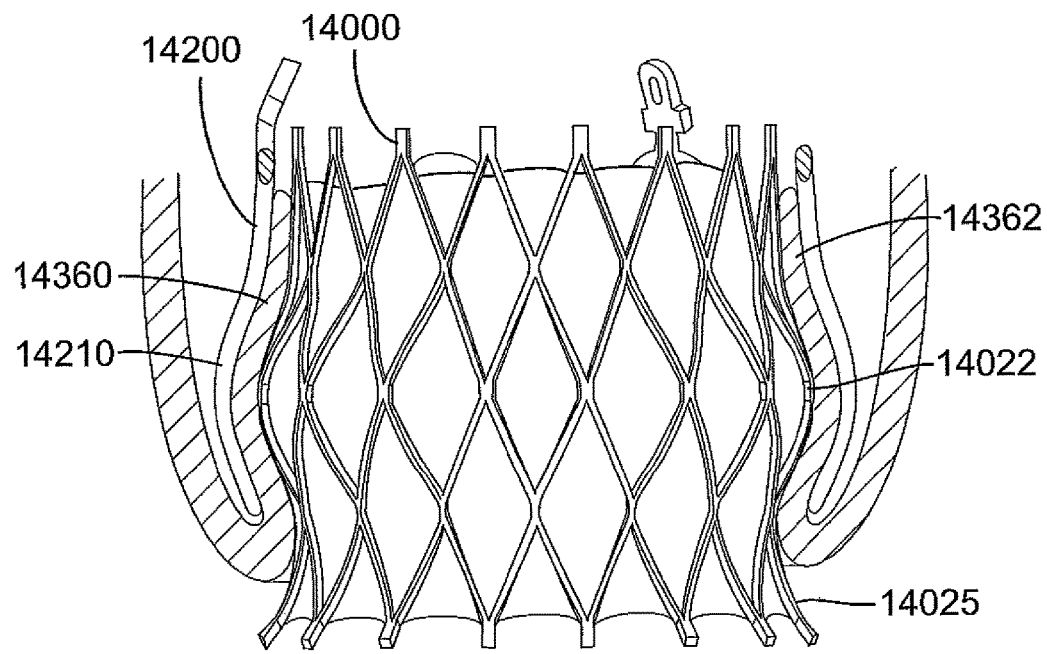
FIG. 143 is a cross-sectional side view of a patient's aortic valve in which the support stent of FIG. 142 frictionally secures the prosthetic heart valve of FIG. 140 into position within the aortic valve.

FIG. 143 is a schematic cross-sectional side view of a patient's aortic valve in which the support stent 14200 surrounds a prosthetic heart valve (illustrated as the prosthetic heart valve 14000, which is shown in its entirety for illustrative purposes) and frictionally secures native heart valve leaflets 14360, 14362 between the support stent 14200 and the prosthetic heart valve. As illustrated in FIG. 143, when the prosthetic heart valve 14000 is expanded in the aortic valve and in the interior of the support stent 14200, the outwardly bowed portion 14210 of the support stent complements at least a portion of the shape of the prosthetic heart valve, and in particular the intermediate portion 14022 of the prosthetic heart valve above the flared end portion 14025. With the shape of the support stent being configured to at least partially complement the prosthetic heart valve 14000, the frictional force between the support stent, the prosthetic heart valve, and the interposing native heart valves can be more evenly distributed.

Figure 144:
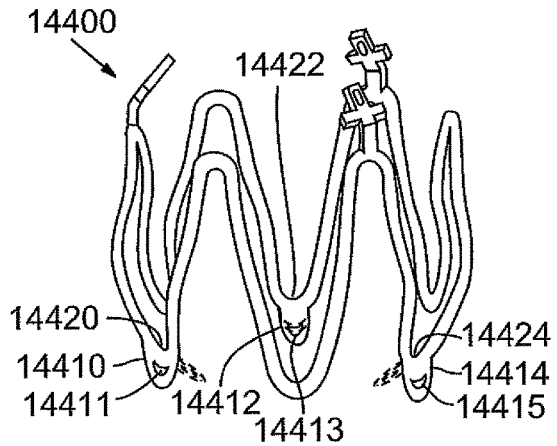
FIG. 144 is a perspective view of an embodiment of a support stent in which one or more respective valleys of the support stent are shape set to form inward-projecting protrusions.

FIG. 144 illustrates a perspective view illustrating a support stent 14400 in which one or more valleys of the support stent are formed to include inward-facing protrusions or flanges. In particular, FIG. 144 is a perspective view of the support stent 14400, which includes six peaks and six valleys. It should be noted, however, that more or fewer peaks and valleys can be included in the support stent depending on the design. In the illustrated embodiment, protrusions 14410, 14412, 14414 are formed from the tips of respective valleys 14420, 14422, 14424 being inwardly shape set. In other words, one or more valleys of the support stent are bent, or shaped (e.g., into a J-shape), so that they form protrusions at their tips that bend radially inward. In FIG. 144, dashed lines show the protrusions in their natural, inward-facing state. The inward-facing protrusions 14410, 14412, 14414 are configured to create increased frictional engagement between the support stent 14400 and the prosthetic heart valve 14400 (or other prosthetic heart valve having differing diameters) at a location of the prosthetic heart valve between the minimum diameter D2 and the maximum diameter D1. For example, when the prosthetic heart valve 14000 is deployed within the support stent 14400, the protrusions 14410, 14412, 14414 can create further radial force against the prosthetic heart valve at a lower portion of the intermediate section 14022, or an upper portion of the inflow end portion 14024 (e.g., at a location in the hourglass-shaped section of the prosthetic heart valve). By increasing the frictional force against the frame of the prosthetic heart valve, the protrusions 14410, 14412, 14414 can be used to help frictionally secure the support stent 14400 to the frame of the prosthetic valve and help prevent the undesired movement of the prosthetic valve. In particular, the protrusions 14410, 14412, 14414 operate to resist movement of the prosthetic heart valve (e.g., the prosthetic heart valve 14000) into the patient's left ventricle as a result of the pressure differential created during the filling of the ventricle during the diastole phase.

The illustrated protrusions 14410, 14412, 14414 include respective apertures 14411, 14413, 14415 that can be used to selectively release the protrusions from an undeployed state to a deployed state. For example, in certain embodiments of the disclosed technology, the protrusions 14410, 14412, 14414 can be held in an undeployed state during delivery of the support stent (e.g., in a state in which the protrusions are held in the vertical (or cylindrical) plane or slightly outward of the vertical (or cylindrical) plane of the support stent, as shown in FIG. 144) by virtue of respective release wires being inserted through each of the apertures 14411, 14413, 14415. The release wires can be positioned on the radially outward side of the support stent and can extend longitudinally into a delivery catheter of the support stent delivery system (e.g., any of the support stent delivery systems disclosed herein). The release wires can extend through the support stent delivery system to a proximal end of the system, where the wires can be retracted by an operator. For example, the release wires can be withdrawn from the apertures 14411, 14413, 14415 by an operator retracting the release wires. Such retraction of the release wires causes the wires to become disengaged from the apertures 14411, 14413, 14415 and allows the protrusions 14410, 14412, 14414 to move to their deployed, inward-facing state (represented in dashed lines in FIG. 144).

Figure 146:
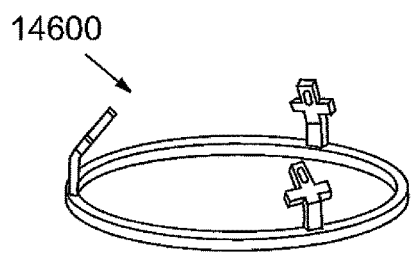
FIG. 146 is a perspective view of an embodiment of a support stent having a flat ring shape.

FIG. 146 is a further embodiment of a support stent that can be used to frictionally secure interposed native valve leaflets to a prosthetic heart valve. In particular, FIG. 146 is a perspective view of support stent 14600 that has a generally ring, or halo, shape. In contrast to the support stents described herein that have a sinusoidally shaped frame, the support stent 14600 does not take the shape or profile of the commisures or native valve leaflets into consideration. Nonetheless, the support stent 14600 can be used to engage and secure the native leaflets between the support stent and the exterior of the prosthetic heart valve (e.g., the prosthetic heart valve 14000). For example, the support stent 14600 can be deployed to circumferentially surround a portion of the prosthetic heart valve 14000 (e.g., using any of the support stent delivery systems disclosed herein). In particular, the support stent 14600 can be deployed such that it engages any part of the outflow end portion 14020 of the prosthetic heart valve 14000. In other embodiments, the support stent 14600 can be deployed such that it engages the lower part of the intermediate portion 14022 or any part of the inflow end portion 14024 located on the outflow side of the aortic valve. In such a location, the support stent 14600 is located beneath the largest diameter D1 of the prosthetic heart valve 14000, and thus further prevents the prosthetic valve 14000 from moving into the patient's left ventricle during the high-pressure diastolic phase of the patient's heart beat. In particular embodiments, the ring-shaped support stent 14600 can be at least partially covered by a cloth or other biocompatible material. When the support stent 14600 is pushed onto the outflow side of the native valve leaflets, the cloth or other material can help reduce or prevent any paravalvular leakage through the native valve leaflets.

Figure 147:
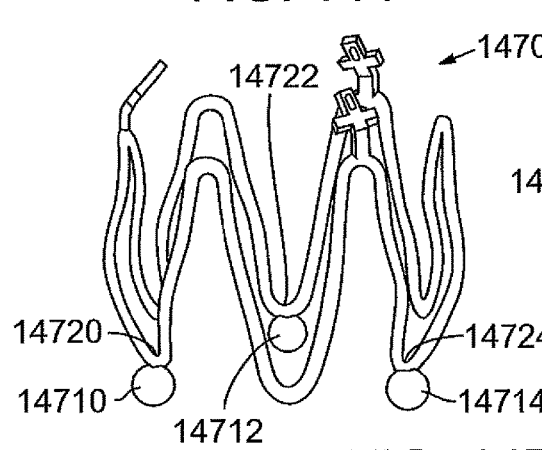
FIG. 147 is a perspective view of an embodiment of a support stent in which one or more spherical members extend from a bottom edge of the support stent.

FIG. 147 is a perspective view illustrating a support stent 14700 in which one or more valleys of the support stent are attached to spherical members (or spherical protrusions) 14710, 14712, 14714. In particular, FIG. 147 is a perspective view of the support stent 14700, which includes six peaks and six valleys, but more or fewer peaks and valleys can be included in the support stent depending on the design. In the illustrated embodiment, spherical members 14710, 14712, 14714 are attached to the bottom edge of respective valleys 14720, 14722, 14724 (e.g., via a weld, adhesive, or other fastening mechanism). In other embodiments, the spherical members 14710, 14712, 14714 are integrally formed into the valleys 14720, 14722, 14724 during the support stent manufacturing process. The spherical members 14710, 14712, 14714 are configured to create increased frictional engagement between the support stent 14700 and the prosthetic heart valve 14000 (or other prosthetic heart valve having differing diameters) at a location of the prosthetic heart valve between the minimum diameter D2 and the maximum diameter D1. For example, when the prosthetic heart valve 14000 is deployed within the support stent 14700, the spherical members 14710, 14712, 14714 can create further radial force against the prosthetic heart valve at a lower portion of the intermediate section 14022, or an upper portion of the inflow end portion 14024 (e.g., at a location in the hourglass-shaped section of the prosthetic heart valve where the diameter of the prosthetic heart valve increases in the direction toward the outflow side of the valve). By increasing the frictional force against the frame of the prosthetic heart valve, the spherical members 14710, 14712, 14714 can be used to help frictionally secure the support stent 14400 to the frame of the prosthetic valve and help prevent the undesired movement of the prosthetic valve. In particular, the spherical members 14710, 14712, 14714 operate to resist movement of the prosthetic heart valve (e.g., the prosthetic heart valve 14000) into the patient's left ventricle as a result of the pressure differential created during the filling of the ventricle during the diastole phase. The shape of the spherical members 14710, 14712, 14714 should not construed as limited, as differently shaped protrusions can extend from or be attached to a bottom edge of one or more valleys of the support stent (e.g., ellipsoidal protrusions, prong-shaped protrusions, hook-shaped protrusions, and the like). The spherical members 14710, 14712, 14714 (or other protrusions) can also be angled inwardly in order to create even greater frictional force when engaged with a prosthetic heart valve.

Figure 145:
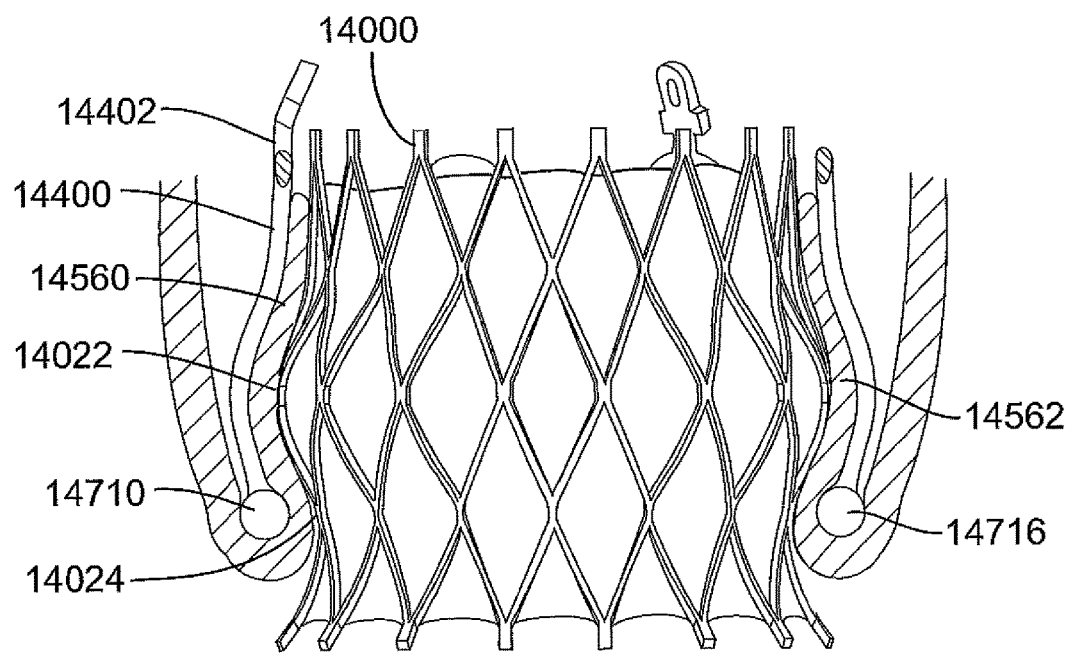
FIG. 145 is a cross-sectional side view of a patient's aortic valve in which the support stent of FIG. 147 frictionally secures the prosthetic heart valve of FIG. 140 into position within the aortic valve.

FIG. 145 is a schematic cross-sectional side view of a patient's aortic valve in which the support stent 14700 surrounds a prosthetic heart valve (illustrated as the prosthetic heart valve 14000, which is shown in its entirety for illustrative purposes) and frictionally secures native heart valve leaflets 14560, 14562 between the support stent 14700 and the prosthetic heart valve. In FIG. 145, the support stent 14700 includes spherical member 14710 and a spherical member 14716 located at an opposite valley of the support stent. As can be seen in FIG. 145, the spherical members 14710, 14716 create a smaller diameter of the support stent 14700 at a location of the prosthetic heart valve 14000 where the diameter of the prosthetic heart valve increases in the direction of the outflow end of the prosthetic heart valve (e.g., between the maximum diameter of the intermediate section 14022 and the minimum diameter of the inflow end portion 14024). Thus, the spherical members 14710, 14716 create a larger radially inward force at their location, and further secure the prosthetic heart valve 14000 against undesired movement (e.g., movement into the left ventricle).

Figure 148:
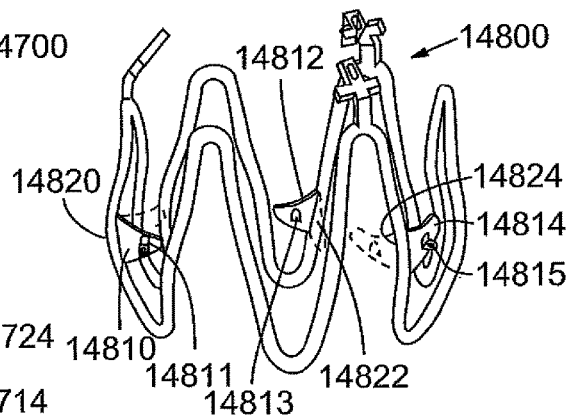
FIG. 148 is a perspective view of an embodiment of a support stent in which one or more inward-facing protrusions extend from portion of the frame support stent between a respective peak or valley of the frame.

FIG. 148 is a perspective view illustrating a support stent 14800 in which the frame of the support stent includes one or more inward-facing protrusions or prongs at locations between the peaks and valleys of the frame. In particular, FIG. 148 is a perspective view of the support stent 14800, which includes six peaks and six valleys, but more or fewer peaks and valleys can be included in the support stent depending on the design. In the illustrated embodiment, protrusions 14810, 14812, 14814 extend from locations 14820, 14822, 14824 of the support stent frame that are between respective peaks and valleys of the support stent. Further, the protrusions 14810, 14812, 14814 are shape set to angle inwardly (shown in dashed lines in FIG. 148). The illustrated protrusions 14810, 14812, 14814 include respective eyelets 14811, 14813, 14815 that are oriented to provide a vertical aperture and that can be used to selectively release the protrusions from an undeployed state to a deployed state. For example, in certain embodiments of the disclosed technology and similar to the support stent 14400 illustrated in FIG. 144, the protrusions 14810, 14812, 14814 can be held in an undeployed state during delivery of the support stent (e.g., in a state in which the protrusions are held in the vertical (or cylindrical) plane or slightly outward of the vertical (or cylindrical) plane of the support stent, as shown in FIG. 148) by virtue of respective release wires being inserted through each of the eyelets 14811, 14813, 14815. When deployed, the inward-facing protrusions 14810, 14812, 14814 are configured to extend through apertures of and engage the frame of the prosthetic heart valve (e.g., the frame of the prosthetic heart valve 14000 at locations near or adjacent to the intermediate section 14022 of prosthetic heart valve) and thereby secure the support stent to the frame of the prosthetic valve and help prevent the undesired movement of the prosthetic valve (e.g., movement of the prosthetic heart valve during the diastolic phase of the patient's heart beat). The shape of the protrusions 14810, 14812, 14814 can vary from implementation to implementations. For example, the protrusions 14810, 14812, 14814 can be rectangular, hook-shaped, L-shaped, dorsal-fin shaped, or have some other shape. Furthermore, the protrusions 14810, 14812, 14814 can be angled slightly upwardly in order to more effectively resist movement of the prosthetic heart valve into the patient's left ventricle.

Figure 149:
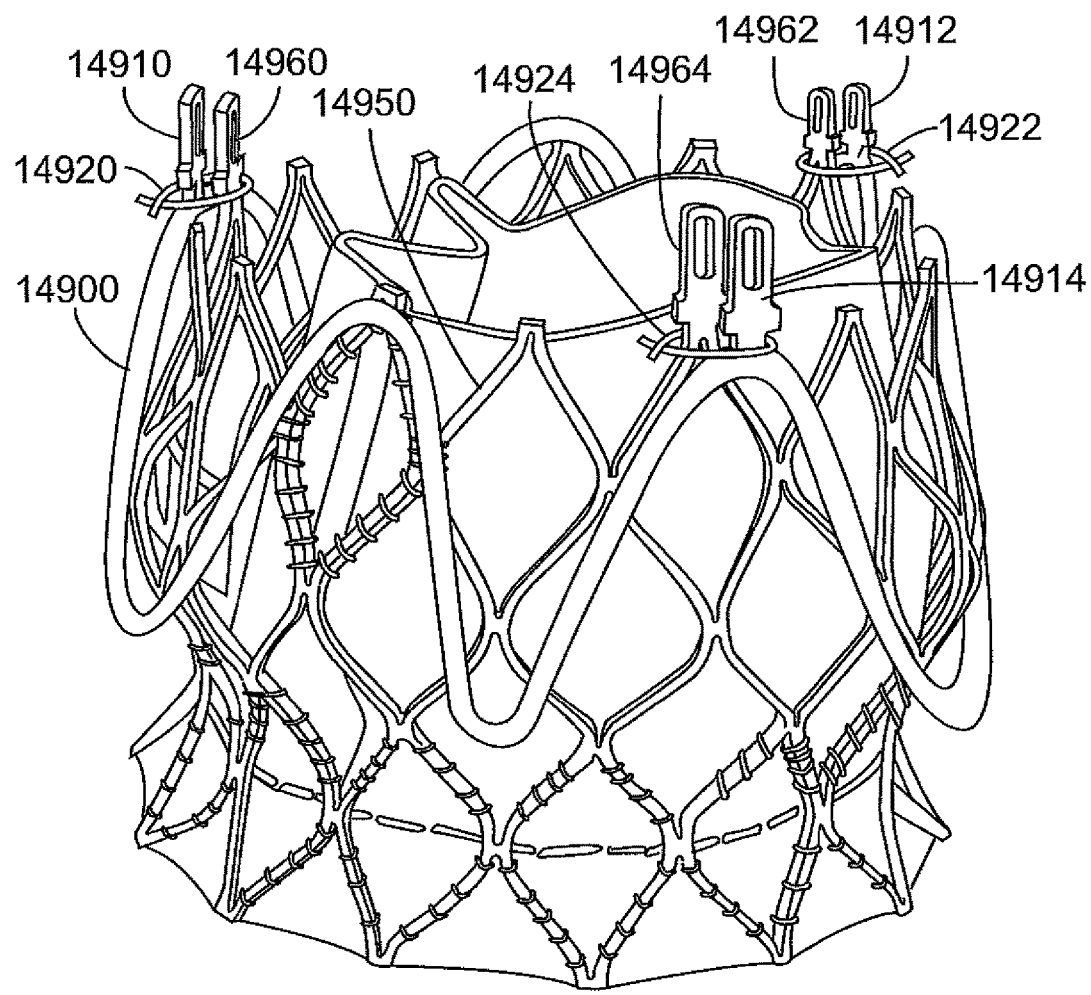
FIG. 149 is a perspective view of an exemplary support stent secured to an exemplary prosthetic heart valve by clips that couple respective retaining arms of the support stent and the prosthetic heart valve to one another.

Although the embodiments illustrated in FIGS. 144-148 illustrate retention mechanisms that are incorporated into the support stent, it is also possible for retention mechanisms to be delivered to the support stent and the prosthetic heart valve once they are deployed within a patient's heart valve. For example, FIG. 149 is a perspective view illustrating one example of a mechanism for further securing a support stent 14900 (illustrated as a support stent having six peaks and six valleys, although other numbers of peaks and valleys are possible) to the frame of a prosthetic heart valve 14950 (which has the same configuration as the prosthetic heart valve 14900). In the illustrated embodiment, the support stent 14900 includes three retaining arms 14910, 14912, 14914, which can be used to position and deploy the support stent to the appropriate location on the outflow side of the patient's heart valve using embodiments of the delivery systems described above. The prosthetic heart valve 14950 also has three retaining arms 14960, 14962, 14964, which can be used to position and deploy the prosthetic heart valve using embodiments of the delivery systems described above or systems described in U.S. Patent Application No. 2010/0049313 (U.S. application Ser. No. 12/429,040). In the illustrated embodiment, the retaining arms 14910, 14912, 14914 of the support stent 14900 are oriented so that they are adjacent to the retaining arms 14960, 14962, 14964 of the prosthetic heart valve 14950. This orientation can be achieved during delivery of the support stent using appropriate imaging techniques or by rotating the support stent until the operator feels the retaining arms 14910, 14912, 14914 "catch" or engage the retaining arms 14960, 14962, 14964 of the prosthetic heart valve 14950. Using a variety of mechanisms, the retaining arms 14910, 14912, 14914 of the support stent can be secured to the retaining arms 14960, 14962, 14964 of the prosthetic heart valve 14950. For example, in the illustrated embodiment, respective clips 14920, 14922, 14924 (or other fasteners) are delivered to the adjacent pairs of retaining arms and secure the pairs together. In the particular embodiment illustrated in FIG. 149, clips 14920, 14922, 14924 are clips that are crimped in place by a suitable crimping catheter. In other embodiments, the clips can be formed of a shape-memory alloy that self compresses once deployed around the respective pairs of retaining arms.

In other embodiments, the support stent is secured to the frame of the prosthetic heart valve prior to delivery. For example, any of the support stents can be secured to any of the prosthetic heart valve embodiments prior to deployment using any of the disclosed retention mechanisms. For instance, a portion of the support stent can be secured to a portion of the prosthetic heart valve at the time the prosthetic valve is compressed and loaded into the delivery system. In such embodiments, delivery of the support stent and the prosthetic heart valve typically involves delivering the support stent and the prosthetic heart valve using an integrated delivery system (such as any of the integrated delivery systems described herein). Furthermore, delivery can be performed in a multi-stage approach, whereby at least a portion of the support stent is expanded first, followed by expansion of the prosthetic heart valve.

Figure 150:
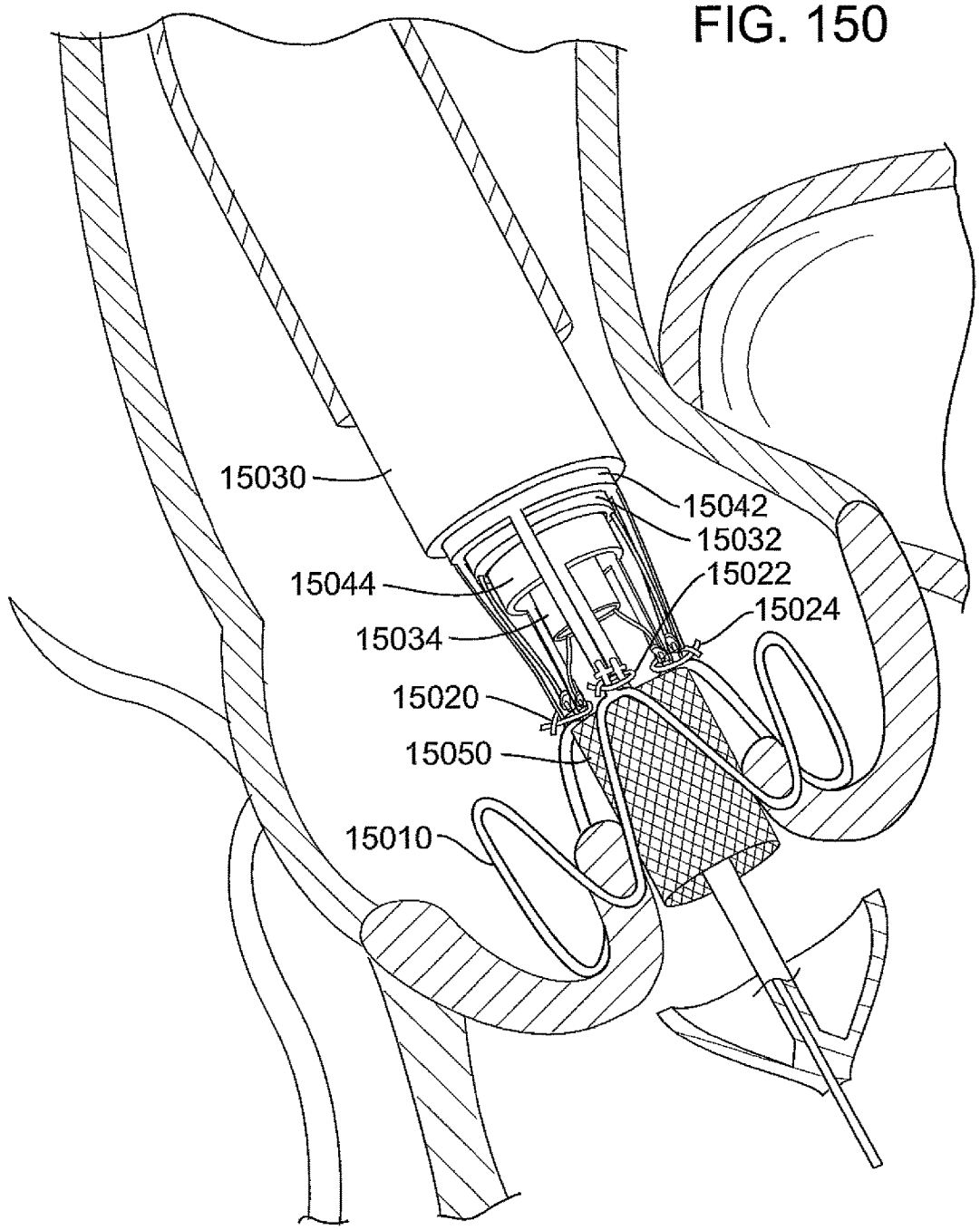
FIG. 150 is a cross-sectional side view of a patient's aortic valve in which a support stent coupled to a prosthetic heart valve at their retaining arms is deployed.

FIG. 150 is a perspective view illustrating an example of delivering a support stent that is at least partially locked to the prosthetic heart valve prior to valve deployment. In particular, the delivery system illustrated in FIG. 150 is similar to the delivery system described above with respect to FIGS. 56-61, but does not include a prosthetic valve sheath surrounding the prosthetic valve delivery catheters. It should be noted that the system illustrated in FIG. 150 is for illustrative purposes only, and other integrated delivery systems can be used. As shown in FIG. 150, the retaining arms of the support stent 15010 are secured to corresponding retaining arms of the prosthetic heart valve 15050 via one or more clips 15020, 15022, 15024. During delivery, an outer sheath 15030 of the delivery system can be retracted, thereby allowing the unsecured ends of the support stent 15010 to expand radially outwardly. The support stent 15010 and the prosthetic heart valve 15050 can then be advanced distally toward the native heart valve. To help properly position the native heart valve leaflets between the interior of the support stent frame and the exterior of the prosthetic heart valve 15050, a rapid pacing catheter (not shown) can be used to induce a rapid heart beat, thereby causing the native leaflets to flap open rapidly. With such rapid pacing, the support stent 15010 and the prosthetic heart valve 15050 can be advanced more reliably into the proper position (shown in FIG. 150). Furthermore, to help ensure that this position is maintained after deployment, inner prongs of support stent delivery inner catheter 15032 and inner prongs of prosthetic heart valve delivery inner catheter 15034 can be retracted during the rapid pacing, thereby allowing the retaining arms to be released from outer prongs of support stent delivery outer catheter 15042 and outer prongs of prosthetic heart valve delivery outer catheter 15044. The support stent 15010 and the prosthetic heart valve 15050 can then expand into their deployed state while remaining secured to one another via the clips 15020, 15022, 15024. The delivery system illustrated in FIG. 150 can be modified in a number of manners. For example, an extended hollow nose cone that is configured to partially enclose the compressed prosthetic heart valve 15050 up to a point at or near the retaining arms can be used. During delivery, the extended hollow nose cone can help maintain the prosthetic heart valve in its compressed state and allow the prosthetic heart valve to be reliably delivered to the interior of the native heart valves. The nose cone can then be advanced relative to the prosthetic heart valve, thereby revealing the valve and allowing it to expand into its deployed state.

It should be noted that a rapid pacing catheter can be used in conjunction with any of the support stent delivery techniques disclosed herein. Such rapid pacing can help reliably position the native heart valve leaflets into a position between the interior of the support stent and the exterior of the prosthetic heart valve by effectively forcing the leaflets to flap open rapidly.

Exemplary Prosthetic Heart Valve Modifications

Figure 151:
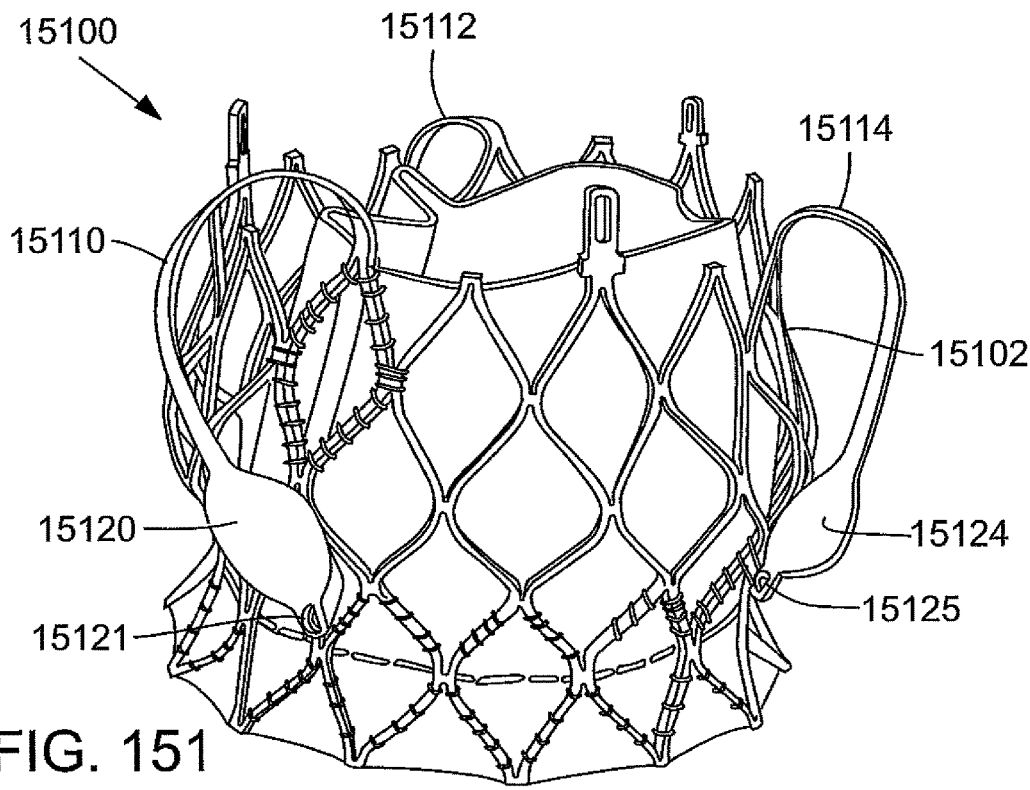
FIG. 151 is a perspective view of an exemplary prosthetic heart valve having one or more leaflet retaining arms that extend longitudinally along the body of the prosthetic heart valve.
Figure 152:
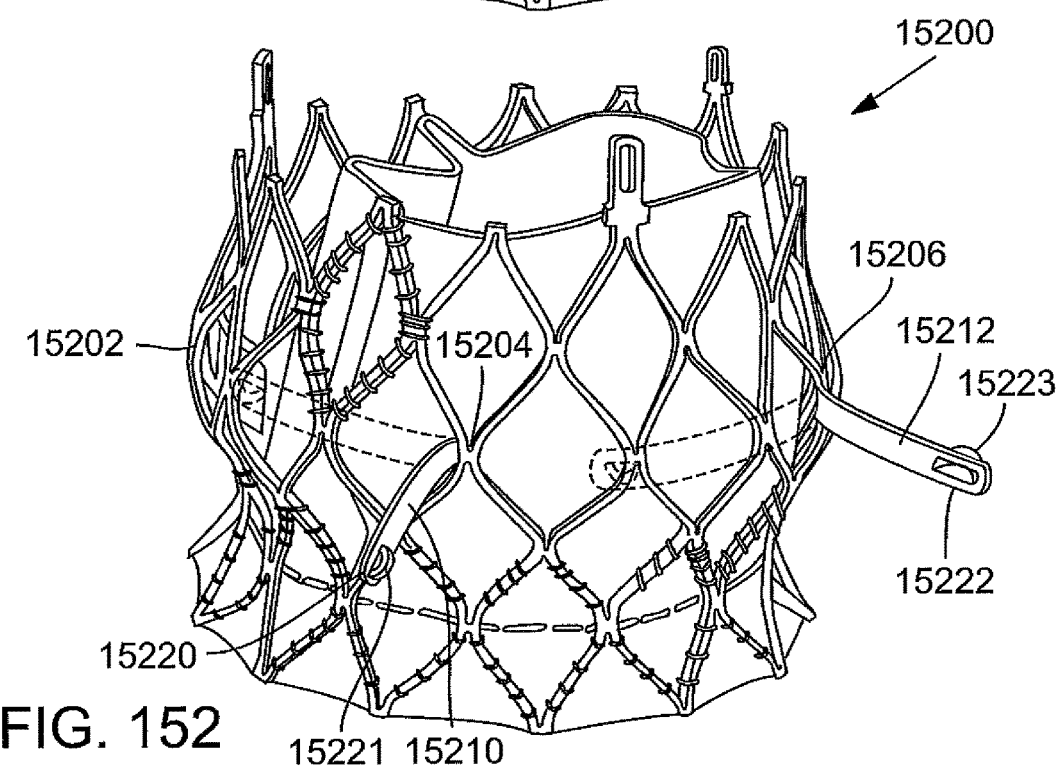
FIG. 152 is a perspective view of an exemplary prosthetic heart valve having one or more leaflet retaining arms that extend laterally across the body of the prosthetic heart valve.

Any of the prosthetic heart valves described herein can also include one or more mechanisms that help secure the prosthetic heart valve to the native heart valve leaflets. These additional retaining mechanisms can be integrally formed into the design of the prosthetic heart valve or can be part of a frame or other component that is attached to the prosthetic heart valve prior to being loaded into the delivery system. The retaining mechanisms can be include one or more retaining arms or prongs that are formed to press against the exterior of the prosthetic heart valve but which can be flexed outwardly from the prosthetic heart valve during deployment in order to capture the native valve leaflets. Representative examples of prosthetic heart valves that include native leaflet capturing mechanisms are shown in FIGS. 151 and 152. These embodiments should not be construed as limiting, however, as a wide variety of mechanisms can be used with a wide variety of prosthetic heart valves (e.g., any of the prosthetic heart valves described herein).

FIG. 151 is a perspective view of an exemplary prosthetic heart valve 15100 having a leaflet retaining mechanism. In particular, the exemplary prosthetic heart valve 15100 has a configuration similar to that of prosthetic heart valve 14000 but includes one or more leaflet retaining arms 15110, 15112, 15114. The leaflet retaining arms 15110, 15112, 15114 are configured to have base portions that extend radially outwardly from the main body of the prosthetic heart valve 15100 and to have distal end portions 15120, 15122 (not shown), 15124 that are shaped to loop back toward the main body so that the distal end portions press against the main body of the prosthetic heart valve. In the illustrated embodiment, the leaflet retaining arms 15110, 15112, 15114 extend outward from an edge of an outflow end portion 15102 of the prosthetic heart valve 15100, though the leaflet retaining arms can extend from other portions of the prosthetic heart valve. The leaflet retaining arms 15110, 15112, 15114 can be formed, for example, from a shape memory alloy or other flexible metal or metal alloy that is shape set into the desired shape. In the illustrated embodiment, the distal end portions 15120, 15122, 15124 are shaped to have a larger surface area than the remainder of the retaining arms 15110, 15112, 15114. In particular, the illustrated embodiment comprises spoon-shaped distal end portions 15120, 15122, 15124, though the distal end portions can have other shapes as well (e.g., a square shape, a diamond shape, a shape consistent with the remainder of the retaining arm, fork shape, and so on). In other embodiments, the leaflet retaining arms 15110, 15112, 15114 are formed to have a much wider cross-section than illustrated, and form wings or flaps that arch outwardly and loop back to the main body of the prosthetic heart valve. Additionally, the distal end portions 15120, 15122, 15124 can be at least partially covered with a cloth or other biocompatible material in order to reduce any trauma experienced by the native valve leaflets when the leaflets are secured by the leaflet retaining arms 15110, 15112, 15114. Furthermore, in the illustrated embodiment, the distal end portions 15120, 15122, 15124 include eyelets (or apertures) 15121, 15123 (not visible), 15125 that are configured to receive respective retaining wires that can extend proximally through the prosthetic heart valve delivery system. The retaining wires (not shown) can be configured to hold the leaflet retaining arms 15110, 15112, 15114 radially outward from the main body of the prosthetic heart valve during the valve delivery procedure. Once the valve is appropriately positioned within the annulus of the patient's aortic valve, the retaining wires can be retracted from the eyelets 15121, 15123 (not visible), 15125 (e.g., by an operator withdrawing the wires proximally), thereby releasing the leaflet retaining arms 15110, 15112, 15114 and causing them to move toward their natural state, thereby capturing the native heart valve leaflets and pressing the native leaflets against the exterior of the body of the prosthetic heart valve 15100. To help ensure that the native heart valve leaflets are properly disposed on the exterior of the prosthetic heart valve 15100, a rapid pacing catheter can be used to stimulate the heart beat of the patient prior to the retaining arms 15110, 15112, 151141 being released. In alternative embodiments, the distal end portions 15120, 15122, 15124 include retaining arms configured to be secured to corresponding outer and inner prongs of the prosthetic heart valve delivery system (e.g., in a fashion similar to the embodiments described above, such as the embodiment illustrated in FIGS. 4-6).

FIG. 152 is a perspective view of another exemplary prosthetic heart valve 15200 having a leaflet retaining mechanism. In particular, the exemplary prosthetic heart valve 15200 has a configuration similar to that of prosthetic heart valve 14000 but includes one or more leaflet retaining arms 15210, 15212. For instance, in the illustrated embodiment, the prosthetic heart valve 15200 has three leaflet retaining arms (one of which is not visible in FIG. 152), but more or fewer leaflet retaining arms can be present. The leaflet retaining arms 15210, 15212 are configured to extend laterally across the frame of the prosthetic heart valve and to press against the frame of the prosthetic heart valve 15200 along an intermediate portion 15202. This deployed state of the leaflet retaining arms 15210, 15212 is shown in dashed lines in FIG. 152. In particular, the illustrated leaflet retaining arms 15210, 15212 are formed to extend from or be attached to respective nodes 15204, 15206 of the main body portion. The leaflet retaining arms 15210, 15212 can be formed, for example, from a shape memory alloy or other flexible metal or metal alloy that is shape set into the desired shape. In the illustrated embodiment, the leaflet retaining arms 15210, 15212 have distal end portions 15220, 15222 that are shaped to have the same width as the remainder of the retaining arms. The distal end portions 15220, 15222 can have other shapes, however, that create a larger surface area to contact a native valve leaflet (e.g., a spoon shape, a square shape, a diamond shape, a fork shape, and so on). Additionally, the distal end portions 15120, 15122 can be at least partially covered with a cloth or other biocompatible material in order to reduce any trauma experienced by the native valve leaflets when the leaflets are secured by the retaining arms 15110, 15112. Furthermore, the distal end portions 15220, 15222, include eyelets (or apertures) 15221, 15223 that are configured to receive respective retaining wires that can extend proximally through the prosthetic heart valve delivery system. The retaining wires (not shown) can be configured to hold the leaflet retaining arms 15210, 15212 radially outward from the main body of the prosthetic heart valve during the valve delivery procedure. FIG. 152 illustrates the retaining arms 15210, 15212 being positioned in this pre-release or undeployed state, although the retaining wires for holding the arms in this state are not shown for ease of illustration. Once the valve is appropriately positioned within the annulus of the patient's aortic valve and oriented so that the native valve leaflets will be captured by the retaining arms 15210, 15212, the retaining wires can be retracted from the eyelets 15221, 15223 (e.g., by an operator withdrawing the wires proximally), thereby releasing the leaflet retaining arms 15210, 15212 and causing them to swing inward and capture the native heart valve leaflets against the exterior of the frame of the prosthetic heart valve 15200. To help ensure that the native heart valve leaflets are properly disposed on the exterior of the prosthetic heart valve 15200, a rapid pacing catheter can be used to stimulate the heart beat of the patient prior to the retaining arms 15210, 15212 being released. In alternative embodiments, the distal end portions 15220, 15222 include retaining arms configured to be secured to corresponding outer and inner prongs of the prosthetic heart valve delivery system (e.g., in a fashion similar to the embodiments described above, such as the embodiment illustrated in FIGS. 4-6).

Exemplary Dual System Delivery Methods

In several of the embodiments described above in which support stent delivery and prosthetic heart valve delivery are both performed transfemorally or both performed transapically, an integrated system is used. In other embodiments, however, two separate delivery systems can be used to at least partially simultaneously deliver the support stent and the prosthetic heart valve to the outflow side of the aortic arch. For illustrative purposes, such dual system approaches are described with respect to approaches that at least partially simultaneously approach the outflow side of the aortic valve (e.g., through the ascending aorta) and/or are simultaneously present in the ascending aorta during at least part of the delivery process, although similar techniques can be used to deploy the support stent and the prosthetic heart valve from the inflow side of the aortic valve.

When delivering the support stent and the prosthetic heart valve transfemorally using two separate delivery systems, access to the aortic valve can be obtained through different access routes or points. For example, the support stent delivery system can be delivered through the left femoral artery while the prosthetic heart valve delivery system can be delivered through the right femoral artery, or vice versa. In other embodiments, the support stent delivery system can be delivered through the carotid artery (e.g., through the right carotid artery and into the brachiocephalic artery or through the left carotid artery) or through the subclavian artery (e.g., through the right subclavian artery and into the brachiocephalic artery or through the left subclavian artery) and toward the outflow side of the aortic valve while the prosthetic heart valve delivery system can be delivered transfemorally (e.g., through the left or right femoral artery), or vice versa. Using the carotid or subclavian arteries can provide a more direct approach to the aortic valve than through a femoral artery over the aortic arch, thus making such an approach potentially more desirable for delivering the support stent or prosthetic heart valve.

Figure 153:
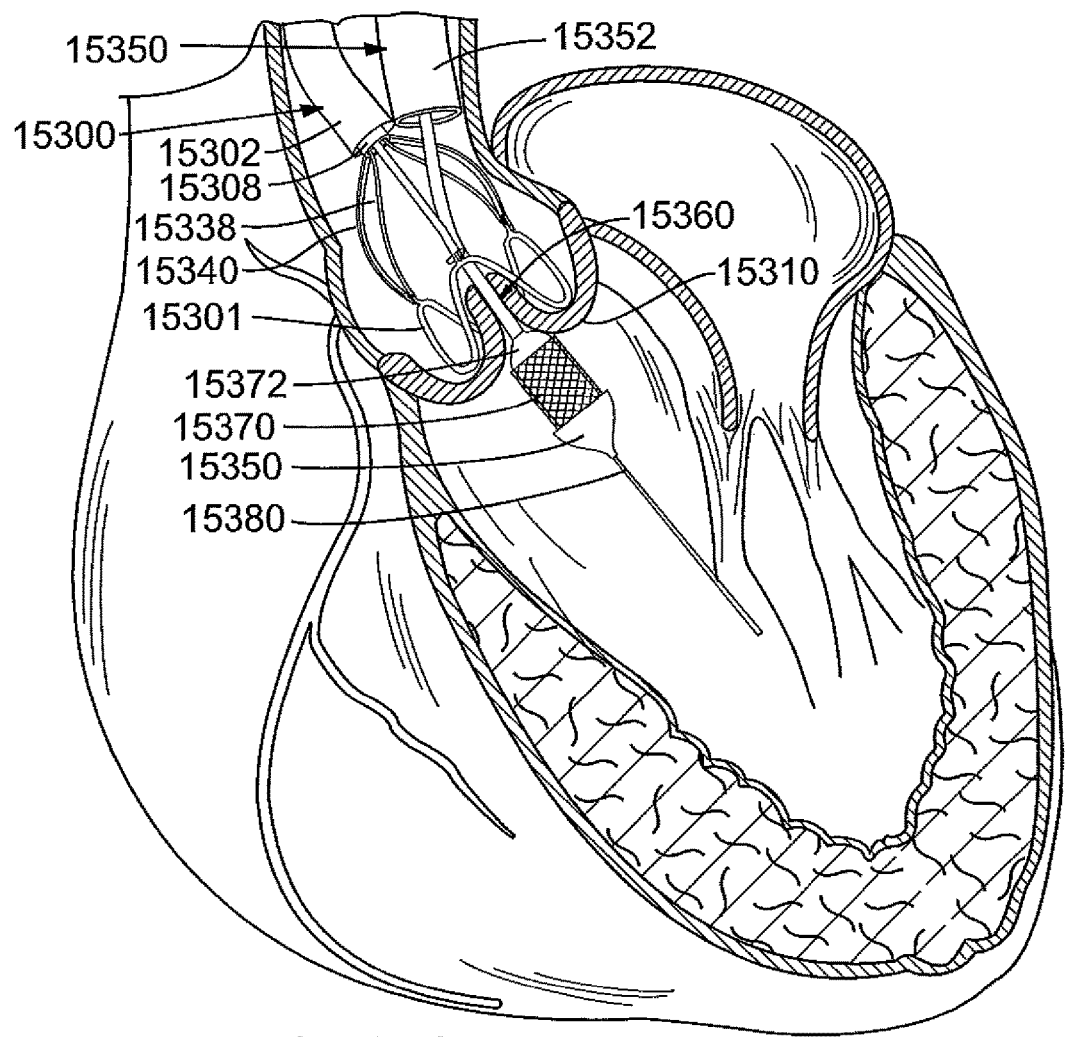
FIG. 153 is a cross-sectional side view of a patient's aortic valve illustrating an exemplary procedure for deploying a support stent around a prosthetic heart valve using a dual system approach.

When multiple delivery systems are used to deliver the support stent and the prosthetic heart valve, additional modifications to either the support stent delivery system or the prosthetic heart valve delivery system may be made. For example, FIG. 153 illustrates one exemplary system and procedure for deploying the support stent and securing a prosthetic valve to the support stent using a multi-system approach where the multiple delivery systems are at least partially simultaneously advanced toward the outflow side of the aortic valve (or are sequentially advanced but are simultaneously present in the aortic arch for at least part of the delivery process). In particular, FIG. 153 is a cross-sectional view through the left side of a patient's heart showing acts performed in delivering a support stent 15301 from the outflow side of the aortic valve.

FIG. 153 shows a main catheter 15302 of a support stent delivery system 15300 as it is advanced into a position near the surface of the outflow side of the aortic valve 15310. The support stent delivery system 15300 can be inserted through one of the femoral arteries of the patient or through one of the carotid or subclavian arteries and advanced into the aorta in the retrograde direction. FIG. 153 also shows a main catheter 15352 of a prosthetic heart valve delivery system 15350. The prosthetic valve delivery system 15350 can be inserted through another one of the femoral arteries of the patient or through the carotid or subclavian arteries (if the support stent delivery system 15300 is advanced transfemorally) and also advanced into the aorta in the retrograde direction. FIG. 153 additionally shows prongs (such as prong 15340) of the outer fork of a stent delivery outer catheter 15308 and prongs (such as prong 15338) of the inner fork of a stent delivery inner catheter (not visible) coupled to respective retaining arms of the support stent 15301. FIG. 153 further shows a prosthetic valve delivery catheter 15360 (a balloon catheter in the illustrated embodiment), nose cone 15350, and guidewire 15380, which is shown as being extended through the aortic valve 15310. In the illustrated embodiment, the prosthetic valve delivery catheter 15360 is advanced to the point where a balloon portion 15372 around which the prosthetic valve 15370 is compressed and nose cone 15350 are located adjacent to an inflow side of the native leaflets of the aortic valve. Furthermore, in FIG. 153, the main catheter 15302 is withdrawn from the stent delivery outer catheter 15308, the stent delivery inner catheter, and the support stent 15301, allowing the support stent to expand into its uncompressed, natural shape in a position above the aortic valve 15310.

During delivery, and in certain exemplary embodiments, the support stent delivery system 15300 is advanced into the aortic arch and the support stent 15301 is advanced into position at or above the outflow side of the aortic valve (e.g., to a position on the outflow side of the aortic valve or to a position between 0 and 50 mm from the aortic valve) before the prosthetic valve delivery system 15350 is advanced through aortic arch and/or before the prosthetic valve delivery catheter 15360 is advanced through the aortic valve. In order for the prosthetic valve delivery catheter 15360 to be advanced through the aortic valve as shown, the prongs (such as prong 15340) of the outer fork and the prongs (such as prong 15338) of the inner fork are desirably shaped so that they are bow-shaped and arch radially outward from the end of the main catheter 15302. Together, the prongs can be said to form a globe-like or pumpkin-like shape. This shape increases the space between the prongs, and creates a sufficient opening through which the nose cone 15350, balloon portion 15372, prosthetic valve 15370, and prosthetic valve delivery catheter 15360 can be advanced into the illustrated position.

Delivery of the support stent and the prosthetic heart valve can continue as described above (e.g., with respect to FIGS. 40-46) but with appropriate modification for two delivery systems.

It should be understood that the exemplary systems shown in FIG. 153 are by way of example and that any suitable support stent delivery system disclosed herein or suitable prosthetic heart valve delivery system disclosed herein can be used as part of a dual system delivery method.

As illustrated by the various delivery systems and approaches described in this disclosure, there are many delivery options available to both the patient and the physician for delivering a prosthetic heart valve secured by a support stent. In order to determine which of the systems and approaches is most suitable for a particular patient, the patient can be screened. For example, the patient can be screened for vasculature tortuosity and/or apical integrity. Depending on the patient etiology, a transfemoral approach may be a more appropriate mode of delivering the devices, or vice versa.

Considerations for Material Selection

For any of the systems described herein, the materials from which the support stent and the prosthetic heart valve are manufactured can impact whether and what type of additional retention mechanism is used. For example, in certain embodiments, if the support stent and the prosthetic heart valve are both manufactured of a shape memory alloy (e.g., Nitinol), then some form of additional retention mechanism is desirably used unless one of the devices has a significantly stronger radial force relative to the other. In other embodiments, one of the support stent or the prosthetic heart valve is manufactured from a stronger, less flexible, material, such as cobalt-chromium or stainless steel, whereas the other of the devices is manufactured of a more flexible material, such as a shape-memory alloy like Nitinol. In the case where the prosthetic heart valve is made of the more flexible material, the dictating shape of the combined system is the support stent. In the case where the prosthetic heart valve is made of the more rigid material, then the dictating shape of the combined system is the prosthetic heart valve. In either case, the frictional forces between the two devices are generally greater than situations where both devices are manufactured of the more flexible material (e.g., Nitinol). Consequently, in some embodiments, the devices do not include a further retention mechanism. Instead, the prosthetic heart valve is secured within the native heart valve only through the frictional engagement of the native heart valve leaflets and the support stent.

Further Examples of Prosthethic Heart Valve Embodiments

Particular examples of prosthetic heart valves that can be used in connection with embodiments of the disclosed technology include transcatheter heart valves ("THVs") available from Edwards Lifesciences. For example, a suitable THV includes a THV having a cobalt-chromium frame and that has a size of 23, 26, 29, or 31 mm OD (though other sizes are also possible). The 29 mm OD embodiment, for example, has a length of 19.3 mm and can be delivered with a 24 Fr. delivery system.

Other examples of suitable prosthetic valves include those described in U.S. Patent Application Publication No. 2010/0049313 (U.S. application Ser. No. 12/429,040). Embodiments of such valves can be about 20 mm in length and have a size of 23, 26, 29, or 31 mm OD (though other sizes are also possible). Such valves are similar to the prosthetic heart valve shown in FIG. 140 and have an anatomically correct hour glass shape at its inflow end portion that allows for a better fit within the aortic annulus. The valve can be delivered using a variety of delivery systems, including a 17 Fr. delivery system.

CONCLUSION

Having illustrated and described the principles of the disclosed technology, it will be apparent to those skilled in the art that the disclosed embodiments can be modified in arrangement and detail without departing from such principles. For example, any of the apparatus, associated components, or methods described in connection with the integrated delivery systems (e.g., the systems described in connection with FIGS. 40-70) can be used as part of a delivery system or method that involves a combination of a transapical approach and a transfemoral approach. For example, any of the apparatus, associated components, or methods described in connection with delivering a support stent transfemorally can be used in combination with apparatus and methods for delivering a prosthetic valve transapically or vice versa. In view of the many possible embodiments to which the principles of the disclosed technologies can be applied, it should be recognized that the illustrated embodiments are only preferred examples of the technologies and should not be taken as limiting the scope of the invention. Rather, the scope of the invention is defined by the following claims and their equivalents. We therefore claim all that comes within the scope and spirit of these claims.

What is claimed is:
1. A method, comprising:
advancing a self-expandable support structure and a self-expandable prosthetic heart valve into a patient's heart using a delivery apparatus and a transapical delivery approach, wherein the support structure and the prosthetic heart valve are in a radially compressed state;
positioning the support structure on or adjacent a surface of an outflow side of the patient's native aortic valve using the delivery apparatus;

radially expanding the support structure from the compressed state to a fully expanded state, the support structure having a support-structure interior;

positioning the prosthetic heart valve radially within the support-structure interior and within the patient's native aortic valve using the delivery apparatus;

radially expanding the prosthetic heart valve from the compressed state to an expanded state while the prosthetic heart valve is in the support-structure interior and while the support structure is in the fully expanded state; and releasing the support structure from the delivery apparatus after the prosthetic heart valve is radially expanded.

2. The method of claim 1, wherein the support structure comprises first and second end portions, and the first and second end portions of the support structure are in the fully expanded state in the act of radially expanding the support structure, and wherein the act of radially expanding the support structure occurs before the act of radially expanding the prosthetic heart valve.

3. The method of claim 1, wherein the support structure comprises a plurality of U-shaped portions that are connected together at apices of the U-shaped portions.

4. The method of claim 3, wherein the support structure includes a plurality of retaining arms extending from the apices of the U-shaped portions.

5. The method of claim 4, wherein the delivery apparatus comprises a plurality of flexible arms that are releasably coupled to the retaining arms of the support structure.

6. The method of claim 4, wherein the retaining arms comprise attachment apertures.

7. The method of claim 3, wherein the delivery apparatus comprises a plurality of flexible arms that are releasably coupled to the support structure during the acts of advancing the support structure and the prosthetic heart valve, positioning the support structure and the prosthetic heart valve, and radially expanding the support structure, and the flexible arms are released from the support structure after the prosthetic heart valve is radially expanded.

8. The method of claim 1, wherein the support structure and the prosthetic heart valve are axially spaced relative to each other along the delivery apparatus in the act of advancing the support structure and the prosthetic heart valve.

9. The method of claim 1, further comprising inserting a tube into a left ventricle of the patient's heart, and the act of advancing the support structure and the prosthetic heart valve comprises inserting the support structure and the prosthetic heart valve through the tube using the delivery apparatus.

10. The method of claim 1, wherein the act of radially expanding the prosthetic heart valve causes one or more native leaflets of the native aortic valve to be frictionally secured between the support structure and the prosthetic heart valve.

11. A method, comprising:

advancing an expandable support structure and an expandable prosthetic heart valve into a patient's heart using a single delivery apparatus, wherein the support structure and the prosthetic heart valve are in a radially compressed state;

positioning the support structure on or adjacent a surface of an outflow side of a native heart valve of the patient using the delivery apparatus;

radially expanding the support structure from the compressed state to a fully expanded state, the support structure having a support-structure interior, wherein the support structure is self-expandable;

positioning the prosthetic heart valve radially within the support-structure interior and within the patient's native heart valve using the delivery apparatus; and radially expanding the prosthetic heart valve from the compressed state to an expanded state while the prosthetic heart valve is in the support-structure interior and while the support structure is in the fully expanded state, wherein the prosthetic heart valve is self-expandable, and wherein the act of radially expanding the prosthetic heart valve causes one or more native leaflets of the native heart valve to be captured between the support structure and the prosthetic heart valve.

12. The method of claim 11, wherein the support structure comprises first and second end portions, and the first and second end portions of the support structure are in the fully expanded state in the act of radially expanding the support structure, and wherein the act of radially expanding the prosthetic heart valve occurs after the act of radially expanding the support structure.

13. The method of claim 11, wherein the support structure comprises a plurality of U-shaped portions that are connected together at apices of the U-shaped portions.

14. The method of claim 11, wherein the patient's native heart valve is a native aortic valve, and the support structure and the prosthetic heart valve are advanced into the patient's heart transapically.

15. The method of claim 11, wherein the patient's native heart valve is a native aortic valve, and the support structure and the prosthetic heart valve are advanced into the patient's heart transfemorally.

16. A method, comprising:

advancing a delivery apparatus into a patient's heart, wherein an expandable support structure and an expandable prosthetic heart valve are mounted at spaced-apart locations along a distal end portion of the delivery apparatus in a radially compressed state, wherein the support structure and the prosthetic heart valve are self-expandable and are advanced together in the same direction toward the patient's heart on the delivery apparatus;

positioning the support structure at or adjacent a native heart valve of the patient using the delivery apparatus;

radially expanding the support structure from the compressed state to a fully expanded state, wherein the support structure remains coupled to the delivery apparatus after the support structure is expanded;

positioning the prosthetic heart valve radially within the support structure and within the patient's native heart valve using the delivery apparatus;

radially expanding the prosthetic heart valve from the compressed state to an expanded state while the prosthetic heart valve is radially within the support structure and while the support structure is in the fully expanded state; and releasing the support structure from the delivery apparatus after the prosthetic heart valve is radially expanded.

17. The method of claim 16, wherein the support structure comprises a first end portion and a second end portion, and the first end portion and the second end portion of the support structure are in the fully expanded state in the act of radially expanding the support structure and before the act of radially expanding the prosthetic heart valve.

18. The method of claim 16, wherein the delivery apparatus comprises a first sheath and a second sheath, wherein the first sheath is configured to retain the support structure in the radially compressed state when the support structure is disposed radially within the first sheath, and the support structure is disposed radially within the first sheath in the act of advancing the delivery apparatus and in the act of positioning the support structure, and wherein the second sheath is configured to retain the prosthetic heart valve in the radially compressed state when the prosthetic heart valve is disposed radially within the second sheath, and the prosthetic heart valve is disposed within the second sheath in the act of advancing the delivery apparatus, in the act of positioning the support structure, and in the act of radially expanding the support structure.

19. The method of claim 18, wherein the act of radially expanding the support structure includes relative axial movement between the first sheath and the support structure to expose the support structure from the first sheath, and the act of radially expanding the prosthetic heart valve includes relative axial movement between the second sheath and the prosthetic heart valve to expose the prosthetic heart valve from the second sheath.

20. The method of claim 16, wherein one or more native leaflets of the patient's native heart valve are captured between the support structure and the prosthetic heart valve when the support structure is in the fully expanded state and the prosthetic heart valve is in the expanded state.

* * * * *